pustulosis US007029674B2

(12) United States Patent
Carreno et al.

(10) Patent No.: US 7,029,674 B2
(45) Date of Patent: Apr. 18, 2006

(54) METHODS FOR DOWNMODULATING IMMUNE CELLS USING AN ANTIBODY TO PD-1

(75) Inventors: Beatriz M. Carreno, Acton, MA (US); John Leonard, Manchester, NH (US)

(73) Assignee: Wyeth, Madison, NJ (US)

( * ) Notice: Subject to any disclaimer, the term of this patent is extended or adjusted under 35 U.S.C. 154(b) by 336 days.

(21) Appl. No.: 10/115,609

(22) Filed: Apr. 2, 2002

(65) Prior Publication Data

US 2006/0034826 A1 Feb. 16, 2006

Related U.S. Application Data

(60) Provisional application No. 60/281,541, filed on Apr. 2, 2001.

(51) Int. Cl.
*A61K 39/395* (2006.01)
*C07K 16/28* (2006.01)
*C12N 5/06* (2006.01)

(52) U.S. Cl. .............................. 424/130.1; 424/143.1; 424/144.1; 435/375; 435/377; 530/387.1; 530/388.22

(58) Field of Classification Search ............. 424/130.1, 424/143.1, 144.1; 435/375, 377; 530/387.1, 530/388.22
See application file for complete search history.

(56) References Cited

U.S. PATENT DOCUMENTS

| 5,580,756 A | 12/1996 | Linsley et al. ............. 435/69.7 |
| 5,698,520 A | 12/1997 | Honjo et al. .................. 514/12 |
| 2002/0160000 A1* | 10/2002 | Wood et al. ............. 424/144.1 |

FOREIGN PATENT DOCUMENTS

| WO | WO 95/03408 A1 | 2/1995 |
| WO | WO 01/14556 A1 | 3/2001 |
| WO | WO 01/14557 A1 | 3/2001 |

OTHER PUBLICATIONS

Huang, Pharmacol. Ther., 2000, 86: 201-215.*
Riley et al., Blood, 2005, 105: 13-21.*
Agata, Y. et al. Expression of the PD-1 antigen on the surface of stimulated mouse T and B lymphocytes. *Int. Immunol.* May 1996;8(5):765-72.
Dong, H. et al. B7-H1, a third member of the B7 family, co-stimulates T-cell proliferation and interleukin-10 secretion. *Nat. Med.* Dec. 1999;5(12):1365-9.
EST Database Acc. No.: AA292201; zt50f01.r1 Soares ovary tumor NbHOT *Homo sapiens* cDNA clone IMAGE:725785 5', mRNA sequence (1997).
EST Database Acc. No.: AA399416; zt50f01.s1 Soares ovary tumor NbHOT *Homo sapiens* cDNA clone IMAGE:725785 3', mRNA sequence (1997).
Freeman, G.J. et al. Engagement of the PD-1 immunoinhibitory receptor by a novel B7 family member leads to negative regulation of lymphocyte activation. *J. Exp. Med.* Oct. 2, 2000;192(7):1027-34.
Genbank Accession No. AF344424; *Homo sapiens* PD-1-ligand 2 protein (PDL2) mRNA, complete cds (2001).
Honjo, T. *Seppuku* and autoimmunity. *Science.* Oct. 23, 1992;258(5082):591-2.
Ishida, Y. et al. Induced expression of PD-1, a novel member of the immunoglobulin gene superfamily, upon programmed cell death. *EMBO J.* Nov. 1992;11(11):3887-95.
Krummel, M. F. et al. CTLA-4 engagement inhibits IL-2 accumulation and cell cycle progression upon activation of resting T cells. *J. Exp. Med.* Jun. 1, 1996;183(6):2533-40.
Latchman, Y. et al., PD-L2 is a second ligand for PD-1 and inhibits T cell activation. *Nat. Immunol.* Mar. 2001;2(3):261-8.
Nishimura, H. et al. Immunological studies on PD-1 deficient mice: implication of PD-1 as a negative regulator for B cell responses. *Int. Immunol.* Oct. 1998;10(10):1563-72.

(Continued)

*Primary Examiner*—Phillip Gambel
*Assistant Examiner*—Ilia Ouspenski
(74) *Attorney, Agent, or Firm*—Lahive & Cockfield LLP; Amy E. Mandragouras, Esq.

(57) ABSTRACT

Disclosed are methods for downmodulating an immune response comprising contacting an immune cell with an agent that modulates the interaction between PD-1 and a PD-1 ligand (e.g., soluble forms of PD-1 or PD-1 ligand or antibodies to PD-1) to thereby modulate the immune response.

7 Claims, 41 Drawing Sheets

OTHER PUBLICATIONS

Nishimura, H. et al. Developmentally regulated expression of the PD-1 protein on the surface of double-negative (CD4⁻CD8⁻) thymocytes. *Int. Immunol.* May 1996;8(5): 773-80.

Shinohara, T. et al. Structure and chromosomal localization of the human PD-1 gene (PDCD1). *Genomics.* Oct. 1994; 23(3):704-6.

Walunas, T. L. et al. CTLA-4 ligation blocks CD28-dependent T cell activation. *J. Exp. Med.* Jun. 1, 1996;183 (6):2541-50.

Woronicz, J. et al. Death genes in T cells. *Curr. Top. Microbiol. Immunol.* 1995;200:137-46.

Finger et al. "The human PD-1 gene: complete cDNA, genomic organization, and developmentally regulated expression in B cell progenitors." *Gene*, (1997), vol. 197, pp.: 177-187.

Henry et al. "Structure and evolution of the extended B7 family." *Immunology Today*, (1999), vol. 20, No. 6, pp.: 285-288.

Nishimura et al. "Developmental of Lupus-like Autoimmune Diseases by Disruption of the PD-1 Gene Encoding an ITM Motif-Carrying Immunoreceptor." *Immunity*, (1999), vol. 11, pp.: 141-151.

Nishimura et al. "PD-1 Regulates Self-Tolerance To Prevent Tissue Destruction." (1998), *Journal of Investigative Dermatology*, vol. 110, No. 4, p.: 477, Abstr. 25.

Nishimura et al. "Facilitation of β Selection and Modification of Positive Selection in the Thymus of PD-1-deficient Mice." *Journal of Experimental Medicine*, (2000), vol. 191, No. 5, pp.: 891-897.

Vibhakar et al. "Activation-Induced Expression of Human Programmed Death-1 Gene in T-Lymphocytes." *Experimental Cell Research*, (1997), vol. 232, pp.: 25-28.

Vivier et al. "Immunoreceptor tyosin-based inhibition motifs." *Immunology Today*, (1997), vol. 18, pp.: 286-291.

Genbank Acession No. AF177937; *Homo sapiens* B7-H1 mRNA, complete cds (1999).

Swissprot No. Q13410; Butyrophilin precursor (BT), (1997).

* cited by examiner

FIG. 1

```
GCTTCCCGAGGCTCCGCACCAGCCGCGGCCGCTTCTGTCCGCCTGCAGGGCATTCCA
GAAAGATGAGGATATTTGCTGTCTTTATTCATGACCTACTGGCATTTGCTG
AACGCATTTACTGTCACGGTTCCCAAGGACCTATATGTGGTAGAGTATGGTA
GCAATATGACAATTGAATGCAAATTCCCAGTAGAAAAACAATTAGACCTGGC
TGCACTAATTGTCTATTGGGAAATGGAGGATAAGAACATTATTCAATTGTGC
ATGGAGAGGAAGACCTGAAGGTTCAGCATAGTAGCTACAGACAGAGGGCCC
GGCTGTTGAAGGACCAGCTCTCCCTGGGAAATGCTGCACTTCAGATCACAGA
TGTGAAATTGCAGGATGCAGGGGTGTGAAAGTCCAGTCAGTCAGTATGGTGGT
GCCGACTACAAGCGAATTACTGTGAAGTCACCTCTGAACATGAACTGACATGT
ACCAAAGAATTTGGTGTGGATCCAGTCATCTGGACAAGCAGTGACCAGTGACCATC
CAGGCTGAGGGCTACCCCCAAGGCCGAAGTCATCTGGACAAGCAGTGACCATC
AAGTCCTGAGTGGTAAGACCACCACCACTGAGAATCAACACAACAACTAATGAGATTT
TTTTCAATGTGACCACTTTTAGGAGATTAGATCCTGAGGAAAACCATACAGCTGAATTG
CTACTGCACTTTAGGAGATTAGATCCTGAATGTCTCATTAAATATGTCTAACACTGTC
GTCATCCCAGTAATATTCTGAATGTCTCATTAAATATGTCTAACACTGTC
CCCTAGCACCTAGCAATGATGTCTGCCTATCATCATAGTCATTCAGTGATTGTTGAA
TAAATGAATGAATAACACTATGTTACAAATATATCCTAATTCCTCAC
CTCCATTCATCCAAACCATATTGTTACTTAATAACATTCAGCAGATATTTAT
GGAATAAAAAAAAAAAAAAA
```

FIG. 2

```
CGAGGCTCCGCACCAGCCGCGCTTCTGTCCGCCTGCAGGGCATTCCAGAAAGA
TGAGGATATTTGCTGTCTTTATATTCATGACCTACTGGCATTTGCTGAACGCATT
TACTGTCACGGTTCCCAAGGACCTATATGTGGTAGAGTATGGTAGCAATATGAC
AATTGAATGCAAATTCCCAGTAGAAAAACAATTAGACCTGGCTGCACTAATTGT
CTATTGGGAAATGGAGGATAAGAACATTATTCAATTTGTGCATGGAGAGGAAG
ACCTGAAGGTTCAGCATAGTAGCTACAGACAGAGGGCCCGGCTGTTGAAGGAC
CAGCTCTCCCTGGGAAATGCTGCACTTCAGATCACAGATGTGAAATTGCAGGAT
GCAGGGGTGTACCGCTGCATGATCAGCTATGGTGGTGCCGACTACAAGCGAAT
TACTGTGAAAGTCAATGCCCCATACAACAAAATCAACCAAAGAATTTTGGTTGT
GGATCCAGTCACCTCTGAACATGAACTGACATGTCAGGCTGAGGGCTACCCCA
AGGCCGAAGTCATCTGGACAAGCAGTGACCATCAAGTCCTGAGTGGTAAGACC
ACCACCACCAATTCCAAGAGAGAGGAGAAGCTTTTCAATGTGACCAGCACACT
GAGAATCAACACAACAACTAATGAGATTTTCTACTGCACTTTTAGGAGATTAGA
TCCTGAGGAAAACCATACAGCTGAATTGGTCATCCCAGAACTACCTCTGGCACA
TCCTCCAAATGAAAGGACTCACTTGGTAATTCTGGGAGCCATCTTATTATGCCTT
GGTGTAGCACTGACATTCATCTTCCGTTTAAGAAAAGGGAGAATGATGGATGT
GAAAAAATGTGGCATCCAAGATACAAACTCAAAGAAGCAAAGTGATACACATTT
GGAGGAGACGTAATCCAGCATTGGAACTTCTGATCTTCAAGCAGGGATTCTCA
ACCTGTGGTTTAGGGGTTCATCGGGGCTGAGCGTGACAAGAGGAAGGAATGG
GCCCGTGGGATGCAGGCAATGTGGGACTTAAAAGGCCCAAGCACTGAAAATG
GAACCTGGCGAAAGCAGAGGAGGAGAATGAAGAAAGATGGAGTCAAACAGGG
AGCCTGGAGGGAGACCTTGATACTTTCAAATGCCTGAGGGGCTCATCGACGCC
TGTGACAGGGAGAAAGGATACTTCTGAACAAGGAGCCTCCAAGCAAATCATCC
ATTGCTCATCCTAGGAAGACGGGTTGAGAATCCCTAATTTGAGGGTCAGTTCCT
GCAGAAGTGCCCTTTGCCTCCACTCAATGCCTCAATTTGTTTTCTGCATGACTGA
GAGTCTCAGTGTTGGAACGGGACAGTATTTATGTATGAGTTTTTCCTATTTATTT
TGAGTCTGTGAGGTCTTCTTGTCATGTGAGTGTGGTTGTGAATGATTTCTTTTGA
AGATATATTGTAGTAGATGTTACAATTTTGTCGCCAAACTAAACTTGCTGCTTAA
TGATTTGCTCACATCTAGTAAAACATGGAGTATTTGTAAAAAAAAAAAAAAAA
```

FIG. 3

292 secreted  (245 amino acids)

Signal/IgV/IgC/hydrophilic tail
 (a)   (b)  (c)       (d)
Ig cysteines in large bold MRIFAVFIFMTYWHLLNA  (signal)

FTVTVPKDLYVVEYGSNMTIECKFPVEKQLDLAALIVYWEMEDKN
IIQFVHGEEDLKVQHSSYRQRARLLKDQLSLGNAALQITDVKLQD
AGVYRCMISYGGADYKRITVKVNAPY  (IgV)

NKINQRILVVDPVTSEHELTCQAEGYPKAEVIWTSSDHQVLSGKT
TTTNSKREEKLFNVTSTLRINTTTNEIFYCTFRRLDPEENHTAEL
VIP  (IgC)

GNILNVSIKICLTLSPST  (hydrophilic tail)

FIG. 4

292 membrane    (290 amino acids)

Signal/IgV/IgC/transmembrane (underlined) plus cytoplasmic

Ig cysteines in large bold

MRIFAVFIFMTYWHLLNA   (signal)

FTVTVPKDLYVVEYGSNMTIECKFPVEKQLDLAALIVYWEMEDKN
IIQFVHGEEDLKVQHSSYRQRARLLKDQLSLGNAALQITDVKLQD
AGVYRCMISYGGADYKRITVKVNAPY   (IgV)

NKINQRILVVDPVTSEHELTCQAEGYPKAEVIWTSSDHQVLSGKT
TTTNSKREEKLFNVTSTLRINTTTNEIFYCTFRRLDPEENHTAEL
VIP   (IgC)

ELPLAHPPNER<u>THLVILGAILLCLGVALTFIF</u>RLRKGRMMDVKKC
GIQDTNSKKQSDTHLEET   (transmembrane plus cytoplasmic)

FIG. 5A

AGATAGTTCCCAAAACATGAGGATATTTGCTGGCATTATATTCACAGCCTGC
TGTCACTTGCTACGGGCGTTTACTATCACGGCTCCAAAGGACTTGTACGTG
GTGGAGTATGGCAGCAACGTCACGATGGAGTGCAGATTCCTGTAGAACG
GGAGCTGGACCTGCTTGCGTTAGTGGTGTACTGGGAAAAGGAAGATGAGC
AAGTGATTCAGTTTGTGGCAGGAGAGGAGGACCTTAAGCCTCAGCACAGCA
ACTTCAGGGGGAGAGCCTCGCTGCCAAAGGACCAGCTTTTGAAGGGAAAT
GCTGCCCTTCAGATCACAGACGTCAAGCTGCAGGACGCAGGCGTTTACTGC
TGCATAATCAGCTACGGTGGTGCGGACTACAAGCGAATCACGCTGAAAGTC
AATGCCCCATACCGCAAAATCAACCAGAGAATTTCCGTGGATCCAGCCACTT
CTGAGCATGAACTAATATGTCAGGCCGAGGGTTATCCAGAAGCTGAGGTAA
TCTGGACAAACAGTGACCACCAACCCGTGAGTGGGAAGAGAAGTGTCACCA
CTTCCCGGACAGAGGGGATGCTTCTCAATGTGACCAGCAGTCTGAGGGTCA
ACGCCACAGCGAATGATGTTTTCTACTGTACGTTTTGGAGATCACAGCCAG
GGCAAAACCACACAGCGGAGCTGATCATCCCAGAACTGCCTGCAACACATC
CTCCACAGAACAGGACTCACTGGGTGCTTCTGGGATCCATCCTGTTGTTCC
TCATTGTAGTGTCCACGGTCCTCCTCTTCTTGAGAAAACAAGTGAGAATGCT
AGATGTGGAGAAATGTGGCGTTGAAGATACAAGCTCAAAAAACCGAAATGA
TACACAATTCGAGGAGACGTAAGCAGTGTTGAACCCTCTGATCGTCGATTG
GCAGCTTGTGGTCTGTGAAAGAAAGGGCCCATGGGACATGAGTCCAAAGAC
TCAAGATGGAACCTGAGGGAGAGAACCAAGAAAGTGTTGGGAGAGGAGCC
TGGAACAACGGACATTTTTTCCAGGGAGACACTGCTAAGCAAGTTGCCCAT
CAGTCGTCTTGGGAAATGGATTGAGGGTTCCTGGCTTAGCAGCTGGTCCTT
GCACAGTGACCTTTTCCTCTGCTCAGTGCCGGGATGAGAGATGGAGTCATG
AGTGTTGAAGAATAAGTGCCTTCTATTTATTTTGAGTCTGTGTGTTCTCACTT
TGGGCATGTAATTATGACTGGTGAATTCTGACGACATGATAGATCTTAAGAT
GTAGTCACCAAACTCAACTGCTGCTTAGCATCCTCCGTAACTACTGATACAA
GCAGGGAACACAGAGGTCACCTGCTTGGTTTGACAGGCTCTTGCTGTCTGA
CTCAAATAATCTTTATTTTTCAGTCCTCAAGGCTCTTCGATAGCAGTTGTTCT
GTATCAGCCTTATAGGTGTCAGGTATAGCACTCAACATCTCATCTCATTACA
ATAGCAACCCTCATCACCATAGCAACAGCTAACCTCTGTTATCCTCACTTCA
TAGCCAGGAAGCTGAGCGACTAAGTCACTTGCCCACAGAGTATCAGCTCTC
AGATTTCTGTTCTTCAGCCACTGTCCTTTCAGGATAGAATTTGTCGTTAAGAA
ATTAATTTAAAAACTGATTATTGAGTAGCATTGTATATCAATCACAACATGCC
TTGTGCACTGTGCTGGCCTCTGAGCATAAAGATGTACGCCGGAGTACCGGT
CGGACATGTTTATGTGTGTTAAATACTCAGAGAAATGTTCATTAACAAGGAG
CTTGCATTTTAGAGACACTGGAAAGTAACTCCAGTTCATTGTCTAGCATTAC
ATTTACCTCATTTGCTATCCTTGCCATACAGTCTCTTGTTCTCCATGAAGTGT
CATGAATCTTGTTGAATAGTTCTTTTATTTTTTAAATGTTTCTATTTAAATGATA
TTGACATCTGAGGCGATAGCTCAGTTGGTAAAACCCTTTCCTCACAAGTGTG
AAACCCTGAGTCTTATCCCTAGAACCCACATAAAAAACAGTTGCGTATGTTT
GTGCATGCTTTTGATCCCAGCACTAGGGAGGCAGAGGCAGGCAGATCCTG
AGCTCTCATTGACCACCCAGCCTAGCCTACATGGTTAGCTCCAGGCCTACA
GGAGCTGGCAGAGCCTGAAAAACGATGCCTAGACACACACACACACACACA
CACACACACACACACACACACACCATGTACTCATAGACCTAAGTGCACC
CTCCTACACATGCACACACATACAATTCAAACACAAATCAACAGGGAATTGT

FIG. 5B

CTCAGAATGGTCCCCAAGACAAAGAAGAAGAAAAACACCAAACCAGCTCTA
TTCCCTCAGCCTATCCTCTCTACTCCTTCCTAGAAGCAACTACTATTGTTTTT
GTATATAAATTTACCCAACGACAGTTAATATGTAGAATATATATTAAAGTGTC
TGTCAATATATATTATCTCTTTCTTTCTTTCTTCCTTTCTTTCTTTCTTTCTTTC
TTTCTTTCTTTCTTTCTTTCTTTCTTTCTTTCTTCCTTCCTTCCTTCCTTCCTTC
CTTCCTTCCTTCCTTTCTTTCTTTCTTTCTTTTTTTCTGTCTATCTGTACCTAAA
TGGTTGCTCACTATGCATTTTCTGTGCTCTTCGCCCTTTTTATTTAATGTATG
GATATTTATGCTGCTTCCAGAATGGATCTAAAGCTCTTTGTTTCTAGGTTTTC
TCCCCCATCCTTCTAGGCATCTCTCACACTGTCTAGGCCAGACACCATGTCT
GCTGCCTGAATCTGTAGACACCATTTATAAAGCACGTACTCACCGAGTTTGT
ATTTGGCTTGTTCTGTGTCTGATTAAAGGGAGACCATGAGTCCCCAGGGTA
CACTGAGTTACCCCAGTACCAAGGGGGAGCCTTGTTTGTGTCTCCATGGCA
GAAGCAGGCCTGGAGCCATTTTGGTTTCTTCCTTGACTTCTCTCAAACACAG
ACGCCTCACTTGCTCATTACAGGTTCTCCTTTGGGAATGTCAGCATTGCTCC
TTGACTGCTGGCTGCCCTGGAAGGAGCCCATTAGCTCTGTGTGAGCCCTTG
ACAGCTACTGCCTCTCCTTACCACAGGGGCCTCTAAGATACTGTTACCTAGA
GGTCTTGAGGATCTGTGTTCTCTGGGGGGAGGAAAGGAGGAGGAACCCAG
AACTTTCTTACAGTTTTCCTTGTTCTGTCACATGTCAAGACTGAAGGAACAG
GCTGGGCTACGTAGTGAGATCCTGTCTCAAAGGAAAGACGAGCATAGCCGA
ACCCCCGGTGGAACCCCCTCTGTTACCTGTTCACACAAGCTTATTGATGAGT
CTCATGTTAATGTCTTGTTTGTATGAAGTTTAAGAAAATATCGGGTTGGGCAA
CACATTCTATTTATTCATTTTATTTGAAATCTTAATGCCATCTCATGGTGTTGG
ATTGGTGTGGCACTTTATTCTTTTGTGTTGTGTATAACCATAAATTTTATTTTG
CATCAGATTGTCAATGTATTGCATTAATTTAATAAATATTTTTATTTATTAAAAA
AAAAAAAAAAAAAAA

MRIFAGIIFTACCHLLRAFTITAPKDLYVVEYGSNVTMECRFPVERELDLLALVVYWEKEDEQVIQFVAGEE
DLKPQHSNFRGRASLPKDQLLKGNAALQITDVKLQDAGVYCCIISYGGADYKRITLKVNAPYRKINQRISV
DPATSEHELICQAEGYPEAEVIWTNSDHQPVSGKRSVTTSRTEGMLLNVTSSLRVNATANDVFYCTFWR
SQPGQNHTAELIIPELPATHPPQNRTHWVLLGSILLFLIVVSTVLLFLRKQVRMLDVEKCGVEDTSSKNRN
DTQFEET.

69% identity

```
mB7-4    1  MRIFAGIIFTACCHLLRAFTITAPKDLYVVEYGSNVTMECRFPVERELDLLALVVYWEKE  60
            MRIFA  IF   HLL AFT+T PKDLYVVEYGSN+T+EC+FPVE++LDL AL+VYWE E
hB7-4    1  MRIFAVFIFMTYWHLLNAFTVTVPKDLYVVEYGSNMTIECKFPVEKQLDLAALIVVWEME  60 mB7-4   61  DEQVIQFVAGEEDLKPQHSNFRGRASLPKDQLLKGNAALQITDVKLQDAGVYCCIISYGG 120
            D+ +IQFV GEEDLK QHS++R RA L KDQL GNAALQITDVKLQDAGVY C+ISYGG
hB7-4   61  DKNIIQFVHGEEDLKVQHSSYRQRARLLKDQLSLGNAALQITDVKLQDAGVYRCMISYGG 120 mB7-4  121  ADYKRITLKVNAPYRKINQRI-SVDPATSEHELICQAEGYPEAEVIWTNSDHQPVSGKRS 179
            ADYKRIT+KVNAPY KINQRI  VDP TSEHEL CQAEGYP +AEVIWT+SDHQ +SGK +
hB7-4  121  ADYKRITVKVNAPYNKINQRILVVDPVTSEHELTCQAEGYPKAEVIWTSSDHQVLSGKTT 180 mB7-4  180  VTTSRTEGMLLNVTSSLRVNATANDVFYCTFWRSQPGQNHTAELIIPELPATHPPQNRTH 239
            T S+ E  L NVTS+LR+N T N++FYCTF R  P +NHTAEL+IPELP  HPP  RTH
hB7-4  181  TTNSKREEKLFNVTSTLRINTTTNEIFYCTFRRLDPEENHTAELVIPELPLAHPPNERTH 240 mB7-4  240  WVLLGSILLFLIVVSTVLLFLRKQVRMLDVEKCGVEDTSSKNRNDTQFEET 290
            V+LG+ILL L V  T +  LRK   RM+DV+KCG++DT+SK ++DT  EET
hB7-4  241  LVILGAILLCLGVALTFIFRLRKG-RMMDVKKCGIQDTNSKKQSDTHLEET 290
```

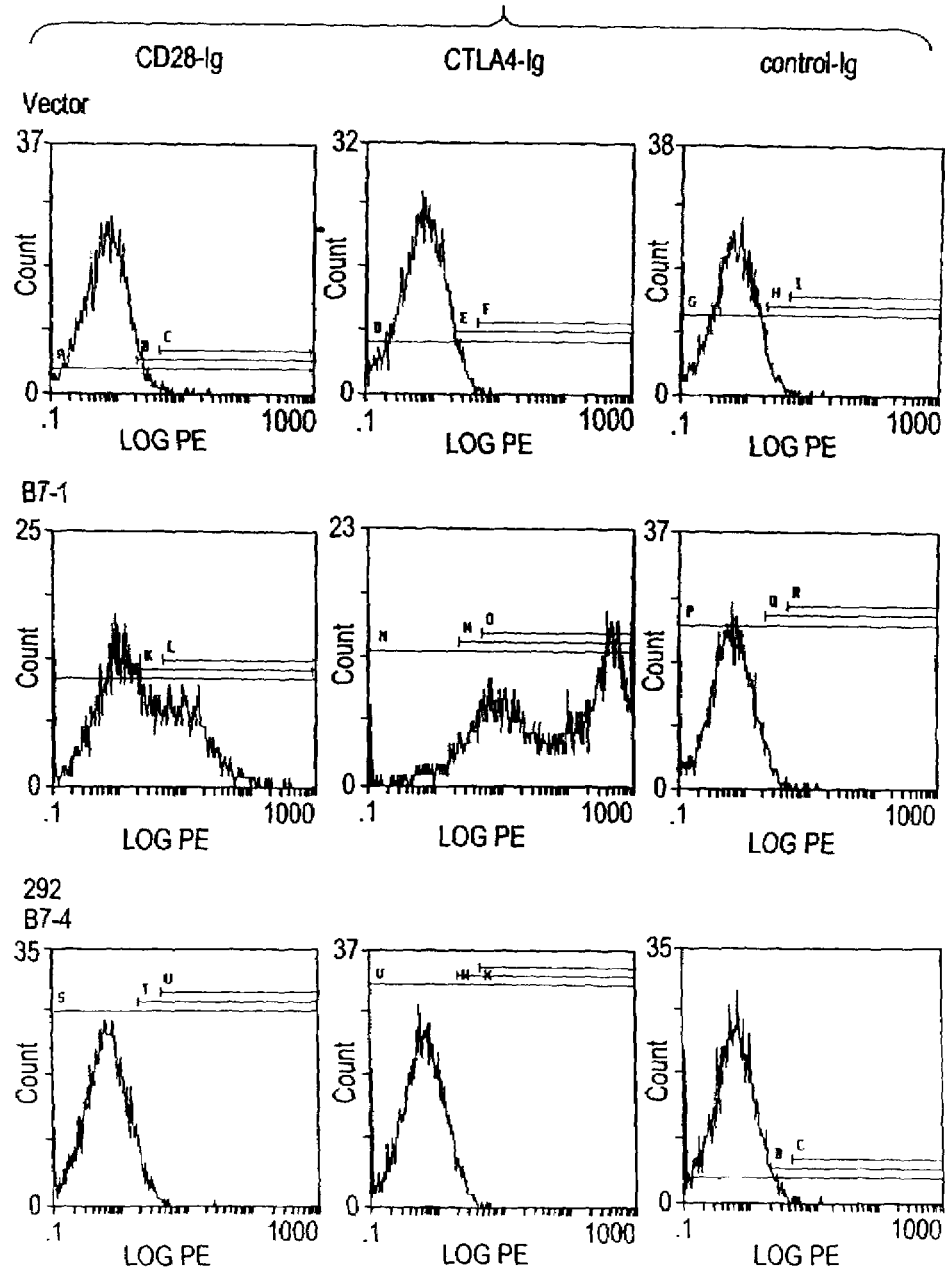

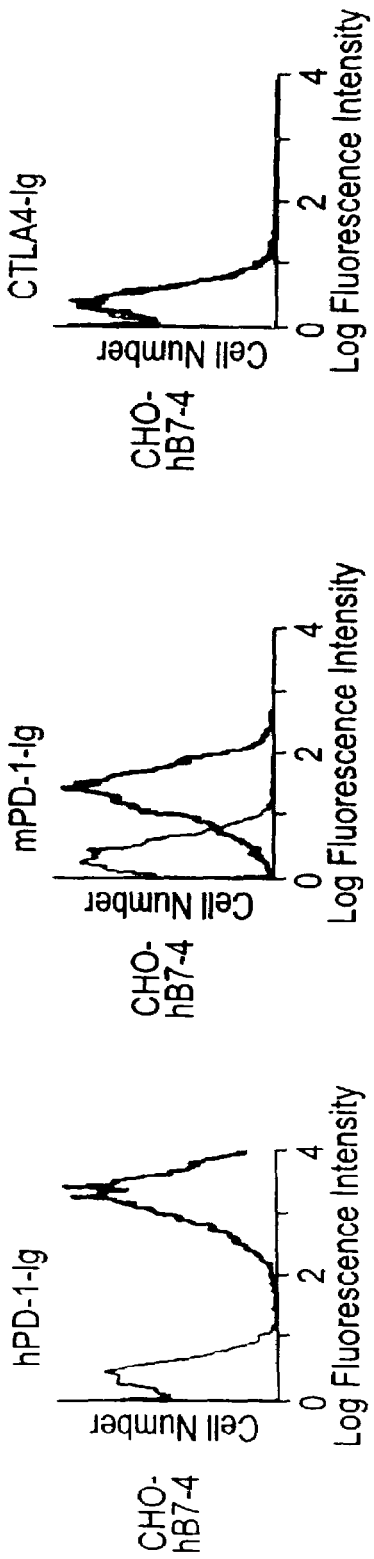
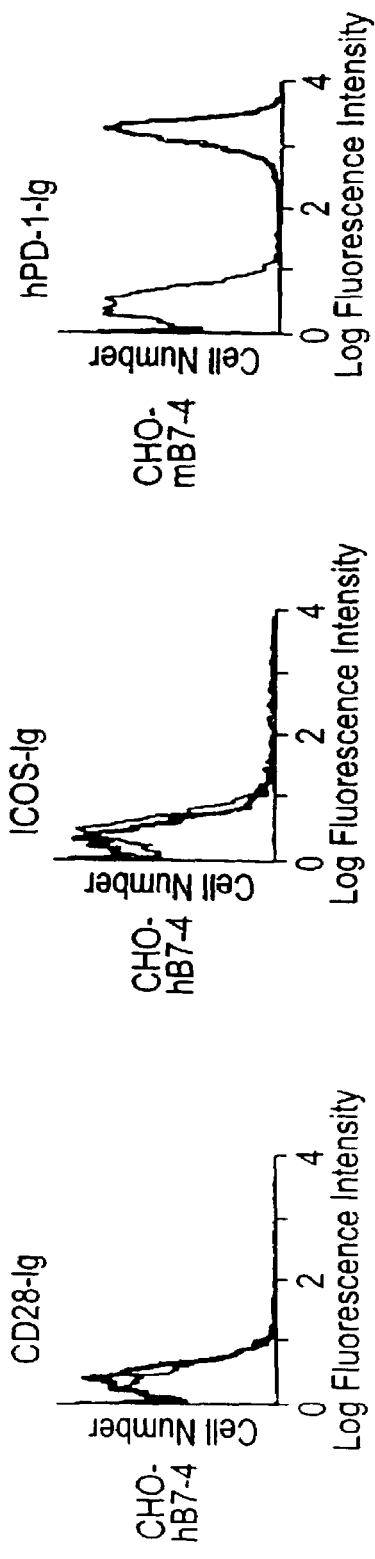
FIG. 15A  FIG. 15B  FIG. 15C
FIG. 15D  FIG. 15E  FIG. 15F

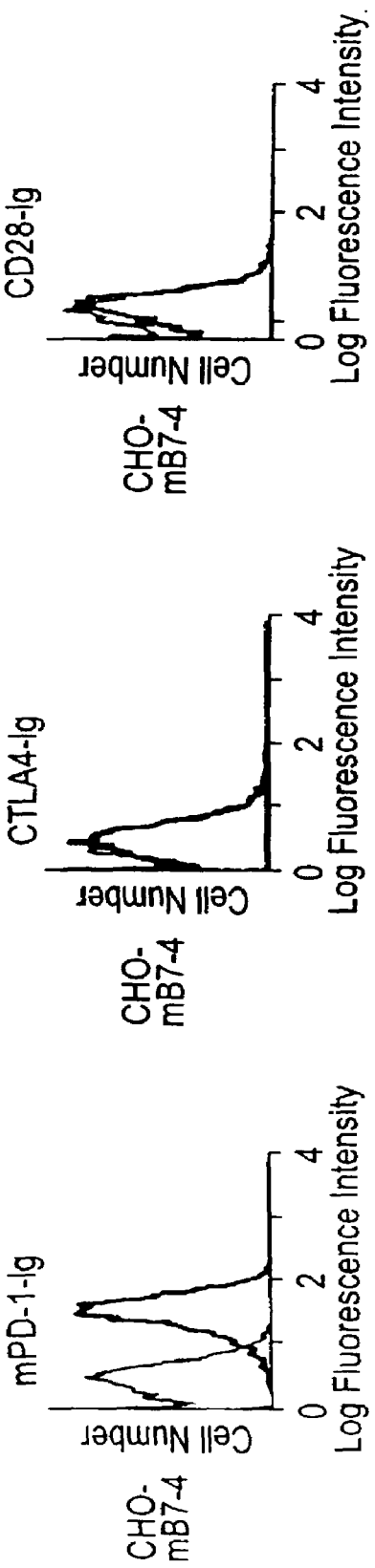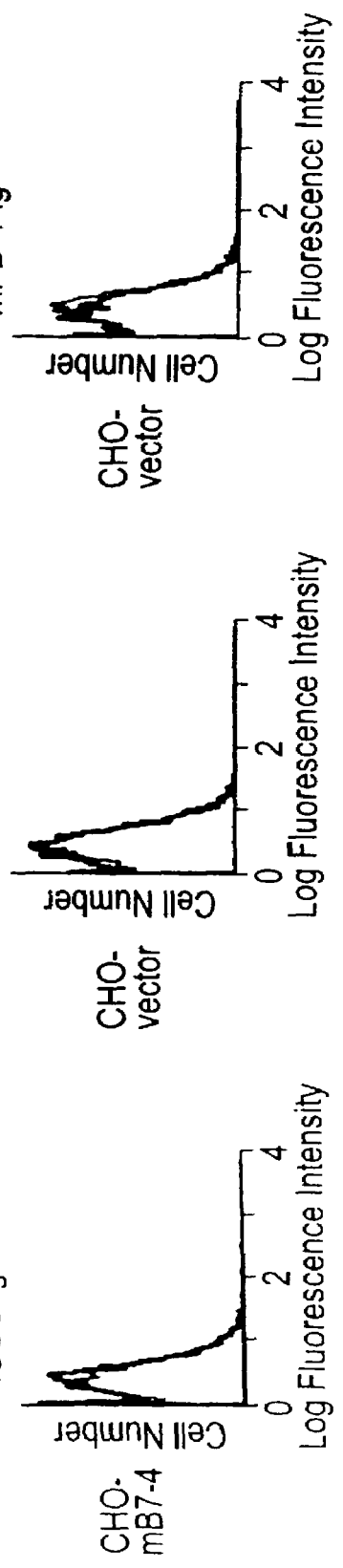

B7-4-COS Inhibits IL-2 Production by Jurkats

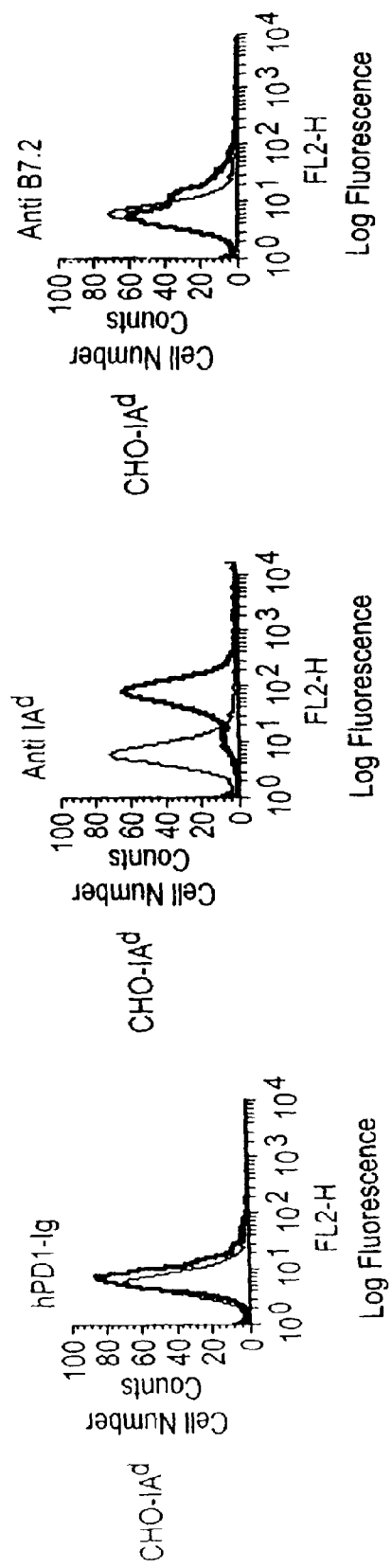

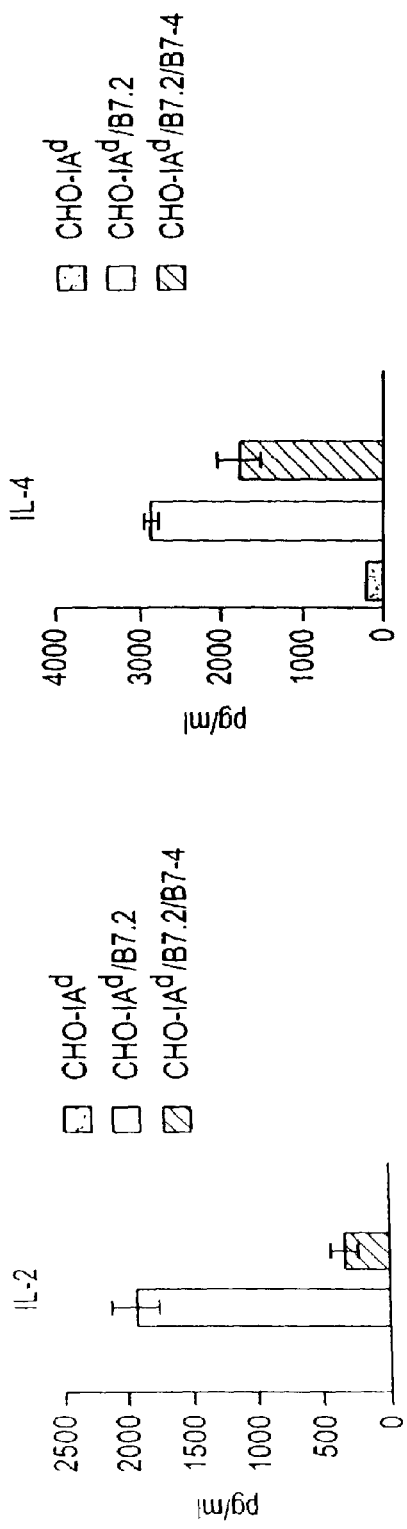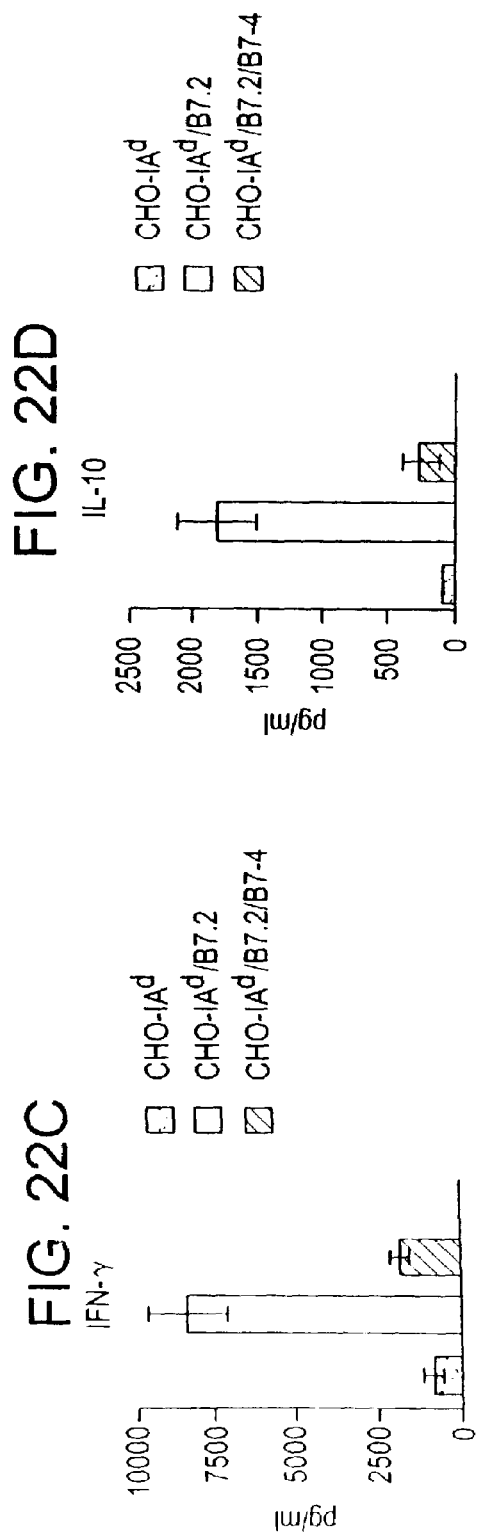

KM89 Binding curve of bio hB7-4.FC (TV2001) to hPD-1.FC

KM89 Binding curve of bio hB7-4.FC binding to hPD-1.FC by mAbs and B7-4 scFVs

| Inhibitor | IC50 |
|---|---|
| 10D9 | 0.5 |
| 11D12 | 0.7 |
| B7-4-1 | 4 |
| B7-4-6 | 19 |
| B7-4-12 | 24 |

Inhibition of B7-4 binding by PD-1 clone 17

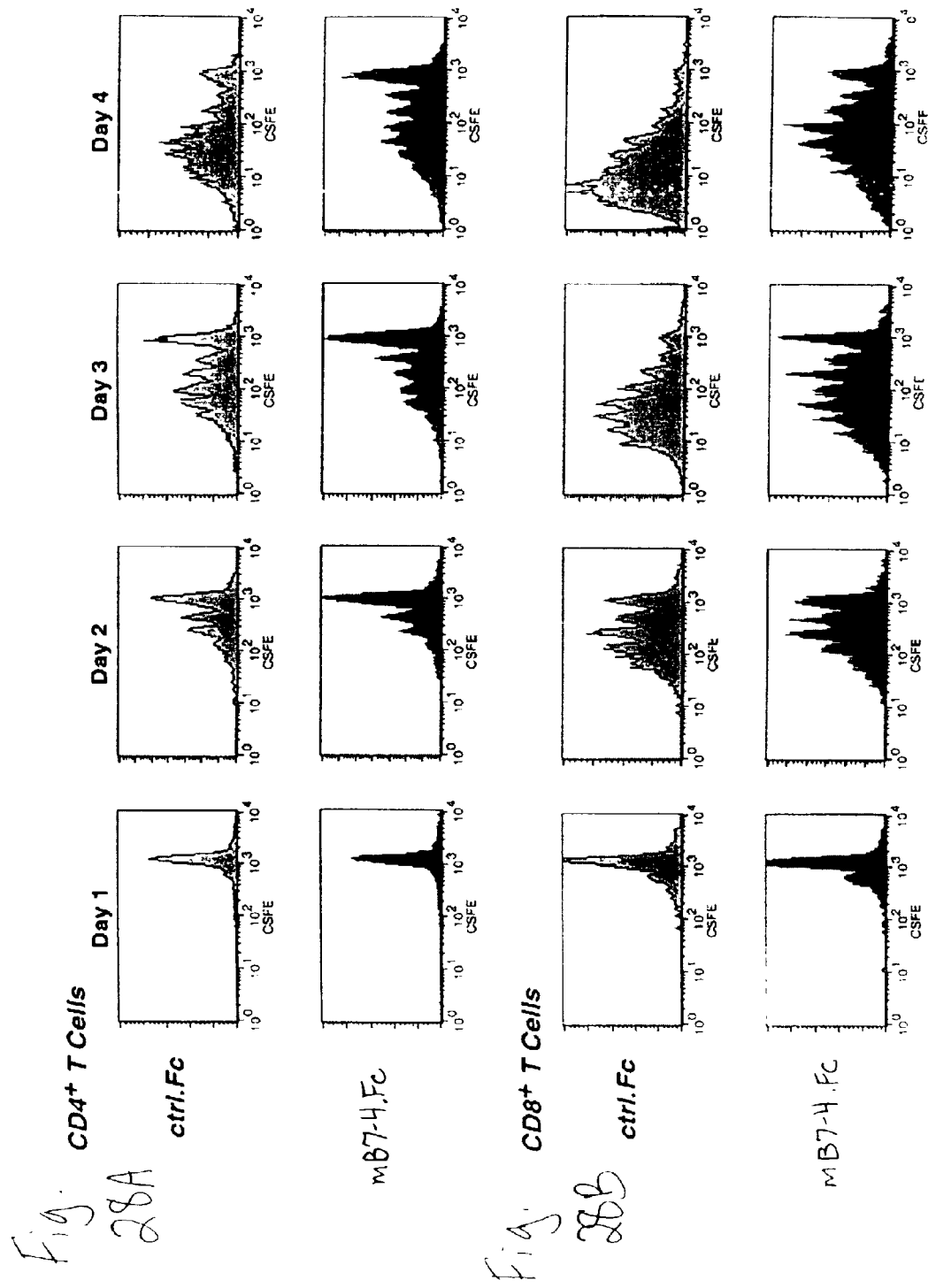

Fig. 31B

```
hPD-1  LVVGVVGGLLG. .SLVLLVWVL AVICSRAAARG TIGARRTGQP
mPD-1  MVIGIMSALVGI PVLLLLAWAL AVFCSTSMSE ARGAGSKDDT
                                                    Y(p)
                                                    Y
                                                    F hPD-1  LKEDPSAVPV FS....    DF QWREKTPEPP VPCVPEQ
mPD-1  LKEEPSAAPV PS....    DF QGREKTPELP TACV..H
            Y(p)
            Y
            F hPD-1  A...VFPSGMG TSSPARRGSA DGPRSAQPLR PEDGHCSWPL
mPD-1  A...VFTEGLG ASAMGRRGSA DGLQGPRPPR HEDGHCSWPL
```

ITIM Peptides
PD-1_pY1    biotin- KEDPSAVPVFSVDY(PO4)GELDFQWRE-amide
PD-1_Y1F    biotin- KEDPSAVPVFSVDFGELDFQWRE-amide
PD-1_Y1     biotin- KEDPSAVPVFSVDYGELDFQWRE-amide
PD-1_pY2    biotin- KTPEPPVPSVPEQTEY(PO4)ATIVFPSGMGTSS-amide
PD-1_Y2F    biotin- KTPEPPVPSVPEQTEFATIVFPSGMGTSS-amide
PD-1_Y2     biotin- KTPEPPVPSVPEQTEYATIVFPSGMGTSS-amide Other Peptides
PD-1_K212   biotin-RGTIGARRTGQP LKEDPSAVPVFS
PD-1_K212D  biotin-RGTIGARRTGQP LDEDPSAVPVFS
PD-1_K335   biotin-DFQWREKTPEPPVPCVPEQ
PD-1_K335D  biotin-DFQWREDTPEPPVPCVPEQ
PD-1_Ctail1 biotin-VFPSGMGTSSPARRGSADGPRSA
PD-1_Ctail2 biotin-ARRGSADGPRSAQPLRPEDGHCSWPL

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
      (A) LENGTH: 2373 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS (B) LOCATION: 1..2373

(xi) SEQUENCE DESCRIPTION: SEQ ID NO: 1:

```
ATG AAA CCA TTA CAA ATG CTC CCT ATC GCC GCG CTG GTC GGC AGT ATT       48
Met Lys Pro Leu Gln Met Leu Pro Ile Ala Ala Leu Val Gly Ser Ile
 1               5                  10                  15

TTC GGC AAT CCG GTC TTG GCA GCA GAT GAA GCT GCA ACT GAA ACC ACA       96
Phe Gly Asn Pro Val Leu Ala Ala Asp Glu Ala Ala Thr Glu Thr Thr
             20                  25                  30

CCC GTT AAG GCA GAG ATA AAA GCA GTG CGC GTT AAA GGT CAG CGC AAT      144
Pro Val Lys Ala Glu Ile Lys Ala Val Arg Val Lys Gly Gln Arg Asn
         35                  40                  45

GCG CCT GCG GCT GTG GAA CGC GTC AAC CTT AAC CGT ATC AAA CAA GAA      192
Ala Pro Ala Ala Val Glu Arg Val Asn Leu Asn Arg Ile Lys Gln Glu
     50                  55                  60

ATG ATA CGC GAC AAT AAA GAC TTG GTG CGC TAT TCC ACC GAT GTC GGC      240
Met Ile Arg Asp Asn Lys Asp Leu Val Arg Tyr Ser Thr Asp Val Gly
 65                  70                  75                  80

TTG AGC GAC AGC GGC CGC CAT CAA AAA GGC TTT GCT GTT CGC GGC GTG      288
Leu Ser Asp Ser Gly Arg His Gln Lys Gly Phe Ala Val Arg Gly Val
                 85                  90                  95

GAA GGC AAC CGT GTC GGC GTG AGC ATA GAC GGT GTA AAC CTG CCT GAT      336
Glu Gly Asn Arg Val Gly Val Ser Ile Asp Gly Val Asn Leu Pro Asp
            100                 105                 110

TCC GAA GAA AAC TCG CTG TAC GCC CGT TAT GGC AAC TTC AAC AGC TCG      384
Ser Glu Glu Asn Ser Leu Tyr Ala Arg Tyr Gly Asn Phe Asn Ser Ser
        115                 120                 125

CGT TTG TCT ATC GAC CCC GAA CTC GTA CGC AAT ATT GAA ATC GTG AAG      432
Arg Leu Ser Ile Asp Pro Glu Leu Val Arg Asn Ile Glu Ile Val Lys
    130                 135                 140

GGC GCA GAC TCT TTC AAT ACC GGC AGT GGT GCA TTG GGC GGC GGT GTG      480
Gly Ala Asp Ser Phe Asn Thr Gly Ser Gly Ala Leu Gly Gly Gly Val
145                 150                 155                 160

AAT TAC CAA ACG CTG CAA GGC CGT GAT TTG CTG TTG GAC GAC AGG CAA      528
Asn Tyr Gln Thr Leu Gln Gly Arg Asp Leu Leu Leu Asp Asp Arg Gln
                165                 170                 175

TTC GGC GTG ATG ATG AAA AAC GGT TAC AGC ACG CGT AAC CGT GAA TGG      576
Phe Gly Val Met Met Lys Asn Gly Tyr Ser Thr Arg Asn Arg Glu Trp
            180                 185                 190

ACA AAT ACC CTC GGT TTC GGT GTG AGT AAC GAC CGC GTG GAT GCT GCT      624
Thr Asn Thr Leu Gly Phe Gly Val Ser Asn Asp Arg Val Asp Ala Ala
        195                 200                 205

TTG CTG TAT TCG CAA CGG CGC GGC CAT GAA ACC GAA AGC GCG GGC AAC      672
Leu Leu Tyr Ser Gln Arg Arg Gly His Glu Thr Glu Ser Ala Gly Asn
    210                 215                 220

CGC GGC TAT CCG GTA GAA GGT GCG GGT AAA GAA ACG AAT ATC CGC GGT      720
Arg Gly Tyr Pro Val Glu Gly Ala Gly Lys Glu Thr Asn Ile Arg Gly
225                 230                 235                 240

TCC GCC CGC GGC ATC CCC GAT CCG TCC AAA CAC AAA TAC CAC AAC TTC      768
Ser Ala Arg Gly Ile Pro Asp Pro Ser Lys His Lys Tyr His Asn Phe
                245                 250                 255

TTG GGT AAG ATT GCT TAT CAA ATC AAC GAC AAC CAC CGC ATC GGC GCA      816
Leu Gly Lys Ile Ala Tyr Gln Ile Asn Asp Asn His Arg Ile Gly Ala
            260                 265                 270

TCG CTC AAC GGT CAG CAG GGG CAT AAT TAC ACG GTT GAA GAG TCT TAT      864
Ser Leu Asn Gly Gln Gln Gly His Asn Tyr Thr Val Glu Glu Ser Tyr
        275                 280                 285

AAC CTG ACC GCT TCT TCC TGG CGC GAA GCC GAT GAC GTA AAC AGA CGG      912
Asn Leu Thr Ala Ser Ser Trp Arg Glu Ala Asp Asp Val Asn Arg Arg
    290                 295                 300
```

```
                                                              -continued

CGC AAT GCC AAC CTC TTT TAC GAA TGG ATG CCT GAT TCA AAT TGG TTG      960
Arg Asn Ala Asn Leu Phe Tyr Glu Trp Met Pro Asp Ser Asn Trp Leu
305                 310                 315                 320

TCG TCT TTG AAG GCG GAC TTC GAT TAT CAG AAA ACC AAA GTG GCG GCG     1008
Ser Ser Leu Lys Ala Asp Phe Asp Tyr Gln Lys Thr Lys Val Ala Ala
                325                 330                 335

ATT AAC AAA GGT TCG TTC CCG ACG AAT TAC ACC ACA TGG GAA ACT GAG     1056
Ile Asn Lys Gly Ser Phe Pro Thr Asn Tyr Thr Thr Trp Glu Thr Glu
340                 345                 350

TAC CAT AAA AAG GAA GTT GGC GAA ATA TAC AAC CGC AGC ATG GAC ACC     1104
Tyr His Lys Lys Glu Val Gly Glu Ile Tyr Asn Arg Ser Met Asp Thr
            355                 360                 365

CGA TTC AAA CGT TTT ACT TTG CGT TTG GAC AGC CAT CCG TTG CAA CTC     1152
Arg Phe Lys Arg Phe Thr Leu Arg Leu Asp Ser His Pro Leu Gln Leu
370                 375                 380

GGG GGG GGG CGA CAC CGC CTG TCG TTT AAA ACT TTC GCC AGC CGC CGT     1200
Gly Gly Gly Arg His Arg Leu Ser Phe Lys Thr Phe Ala Ser Arg Arg
385                 390                 395                 400

GAT TTT GAA AAC CTA AAC CGC GAC GAT TAT TAC TTC AGC GGC CGT GTT     1248
Asp Phe Glu Asn Leu Asn Arg Asp Asp Tyr Tyr Phe Ser Gly Arg Val
                405                 410                 415

GTT CGA ACC ACC AGC AGT ATC CAG CAT CCG GTG AAA ACC ACC AAC TAC     1296
Val Arg Thr Thr Ser Ser Ile Gln His Pro Val Lys Thr Thr Asn Tyr
            420                 425                 430

GGT TTC TCA CTG TCT GAC CAA ATT CAA TGG AAC GAC GTG TTC AGT AGC     1344
Gly Phe Ser Leu Ser Asp Gln Ile Gln Trp Asn Asp Val Phe Ser Ser
                435                 440                 445

CGC GCA GGT ATC CGT TAC GAC CAC ACC AAA ATG ACG CCT CAG GAA TTG     1392
Arg Ala Gly Ile Arg Tyr Asp His Thr Lys Met Thr Pro Gln Glu Leu
450                 455                 460

AAT GCC GAG TGT CAT GCT TGT GAC AAA ACA CCA CCT GCA GCC AAC ACT     1440
Asn Ala Glu Cys His Ala Cys Asp Lys Thr Pro Pro Ala Ala Asn Thr
465                 470                 475                 480

TAT AAA GGC TGG AGC GGT TTT GTC GGC TTG GCG GCG CAA CTG AAT CAG     1488
Tyr Lys Gly Trp Ser Gly Phe Val Gly Leu Ala Ala Gln Leu Asn Gln
                485                 490                 495

GCT TGG CGT GTC GGT TAC GAC ATT ACT TCC GGC TAC CGT GTC CCC AAT     1536
Ala Trp Arg Val Gly Tyr Asp Ile Thr Ser Gly Tyr Arg Val Pro Asn
                500                 505                 510

GCG TCC GAA GTG TAT TTC ACT TAC AAC CAC GGT TCG GGT AAT TGG CTG     1584
Ala Ser Glu Val Tyr Phe Thr Tyr Asn His Gly Ser Gly Asn Trp Leu
            515                 520                 525

CCC AAT CCC AAC CTG AAA GCC GAG CGC AGC ACC ACC CAC ACC CTG TCT     1632
Pro Asn Pro Asn Leu Lys Ala Glu Arg Ser Thr Thr His Thr Leu Ser
530                 535                 540

CTG CAA GGC CGC AGC GAA AAA GGC ATG CTG GAT GCC AAC CTG TAT CAA     1680
Leu Gln Gly Arg Ser Glu Lys Gly Met Leu Asp Ala Asn Leu Tyr Gln
545                 550                 555                 560

AGC AAT TAC CGC AAT TTC CTG TCT GAA GAG CAG AAG CTG ACC ACC AGC     1728
Ser Asn Tyr Arg Asn Phe Leu Ser Glu Glu Gln Lys Leu Thr Thr Ser
                565                 570                 575

GGC ACT CCC GGC TGT ACT GAG GAA AAT GCT TAC TAC AGT ATA TGC AGC     1776
Gly Thr Pro Gly Cys Thr Glu Glu Asn Ala Tyr Tyr Ser Ile Cys Ser
            580                 585                 590

GAC CCC TAC AAA GAA AAA CTG GAT TGG CAG ATG AAA AAT ATC GAC AAG     1824
Asp Pro Tyr Lys Glu Lys Leu Asp Trp Gln Met Lys Asn Ile Asp Lys
                595                 600                 605

GCC AGA ATC CGC GGT ATC GAG CTG ACA GGC CGT CTG AAT GTG GAC AAA     1872
Ala Arg Ile Arg Gly Ile Glu Leu Thr Gly Arg Leu Asn Val Asp Lys
```

```
      610              615              620
GTA GCG TCT TTT GTT CCT GAG GGC TGG AAA CTG TTC GGC TCG CTG GGT     1920
Val Ala Ser Phe Val Pro Glu Gly Trp Lys Leu Phe Gly Ser Leu Gly
625              630              635              640

TAT GCG AAA AGC AAA CTG TCG GGC GAC AAC AGC CTG CTG TCC ACA CAG     1968
Tyr Ala Lys Ser Lys Leu Ser Gly Asp Asn Ser Leu Leu Ser Thr Gln
            645              650              655

CCG CTG AAA GTG ATT GCC GGT ATC GAC TAT GAA AGT CCG AGC GAA AAA     2016
Pro Leu Lys Val Ile Ala Gly Ile Asp Tyr Glu Ser Pro Ser Glu Lys
        660              665              670

TGG GGC GTA TTC TCC CGC CTG ACC TAT CTG GGC GCG AAA AAG GTC AAA     2064
Trp Gly Val Phe Ser Arg Leu Thr Tyr Leu Gly Ala Lys Lys Val Lys
    675              680              685

GAC GCG CAA TAC ACC GTT TAT GAA AAC AAG GGC TGG GGT ACG CCT TTG     2112
Asp Ala Gln Tyr Thr Val Tyr Glu Asn Lys Gly Trp Gly Thr Pro Leu
690              695              700

CAG AAA AAG GTA AAA GAT TAC CCG TGG CTG AAC AAG TCG GCT TAT GTG     2160
Gln Lys Lys Val Lys Asp Tyr Pro Trp Leu Asn Lys Ser Ala Tyr Val
705              710              715              720

TTC GAT ATG TAC GGC TTC TAC AAA CCG GTG AAA AAC CTG ACC CTG CGT     2208
Phe Asp Met Tyr Gly Phe Tyr Lys Pro Val Lys Asn Leu Thr Leu Arg
            725              730              735

GCG GGC GTG TAC AAC CTG TTC AAC CGC AAA TAC ACC ACT TGG GAT TCC     2256
Ala Gly Val Tyr Asn Leu Phe Asn Arg Lys Tyr Thr Thr Trp Asp Ser
        740              745              750

CTG CGC GGT TTA TAT AGC TAC AGC ACC ACC AAT GCG GTC GAC CGC GAT     2304
Leu Arg Gly Leu Tyr Ser Tyr Ser Thr Thr Asn Ala Val Asp Arg Asp
    755              760              765

GGC AAA GGC TTA GAT CGC TAC CGC GCC CCA GGC CGC AAT TAC GCC GTA     2352
Gly Lys Gly Leu Asp Arg Tyr Arg Ala Pro Gly Arg Asn Tyr Ala Val
770              775              780

TCG CTG GAA TGG AAG TTT TAA                                        2373
Ser Leu Glu Trp Lys Phe *
785              790
```

(2) INFORMATION FOR SEQ ID NO: 2:

(i) SEQUENCE CHARACTERISTICS:
        (A) LENGTH: 790 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Pro Leu Gln Met Leu Pro Ile Ala Ala Leu Val Gly Ser Ile
1               5                   10                  15

Phe Gly Asn Pro Val Leu Ala Ala Asp Glu Ala Ala Thr Glu Thr Thr
            20                  25                  30

Pro Val Lys Ala Glu Ile Lys Ala Val Arg Val Lys Gly Gln Arg Asn
        35                  40                  45

Ala Pro Ala Ala Val Glu Arg Val Asn Leu Asn Arg Ile Lys Gln Glu
    50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
            100                 105                 110
```

-continued

```
Ser Glu Glu Asn Ser Leu Tyr Ala Arg Tyr Gly Asn Phe Asn Ser Ser
        115                 120                 125

Arg Leu Ser Ile Asp Pro Glu Leu Val Arg Asn Ile Glu Ile Val Lys
130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Asp Asp Arg Gln
                165                 170                 175

Phe Gly Val Met Met Lys Asn Gly Tyr Ser Thr Arg Asn Arg Glu Trp
                180                 185                 190

Thr Asn Thr Leu Gly Phe Gly Val Ser Asn Asp Arg Val Asp Ala Ala
            195                 200                 205

Leu Leu Tyr Ser Gln Arg Arg Gly His Glu Thr Glu Ser Ala Gly Asn
        210                 215                 220

Arg Gly Tyr Pro Val Glu Gly Ala Gly Lys Glu Thr Asn Ile Arg Gly
225                 230                 235                 240

Ser Ala Arg Gly Ile Pro Asp Pro Ser Lys His Lys Tyr His Asn Phe
                245                 250                 255

Leu Gly Lys Ile Ala Tyr Gln Ile Asn Asp Asn His Arg Ile Gly Ala
                260                 265                 270

Ser Leu Asn Gly Gln Gln Gly His Asn Tyr Thr Val Glu Glu Ser Tyr
            275                 280                 285

Asn Leu Thr Ala Ser Ser Trp Arg Glu Ala Asp Asp Val Asn Arg Arg
        290                 295                 300

Arg Asn Ala Asn Leu Phe Tyr Glu Trp Met Pro Asp Ser Asn Trp Leu
305                 310                 315                 320

Ser Ser Leu Lys Ala Asp Phe Asp Tyr Gln Lys Thr Lys Val Ala Ala
                325                 330                 335

Ile Asn Lys Gly Ser Phe Pro Thr Asn Tyr Thr Thr Trp Glu Thr Glu
                340                 345                 350

Tyr His Lys Lys Glu Val Gly Glu Ile Tyr Asn Arg Ser Met Asp Thr
            355                 360                 365

Arg Phe Lys Arg Phe Thr Leu Arg Leu Asp Ser His Pro Leu Gln Leu
        370                 375                 380

Gly Gly Gly Arg His Arg Leu Ser Phe Lys Thr Phe Ala Ser Arg Arg
385                 390                 395                 400

Asp Phe Glu Asn Leu Asn Arg Asp Asp Tyr Tyr Phe Ser Gly Arg Val
                405                 410                 415

Val Arg Thr Thr Ser Ser Ile Gln His Pro Val Lys Thr Thr Asn Tyr
                420                 425                 430

Gly Phe Ser Leu Ser Asp Gln Ile Gln Trp Asn Asp Val Phe Ser Ser
            435                 440                 445

Arg Ala Gly Ile Arg Tyr Asp His Thr Lys Met Thr Pro Gln Glu Leu
450                 455                 460

Asn Ala Glu Cys His Ala Cys Asp Lys Thr Pro Ala Ala Asn Thr
465                 470                 475                 480

Tyr Lys Gly Trp Ser Gly Phe Val Gly Leu Ala Ala Gln Leu Asn Gln
                485                 490                 495

Ala Trp Arg Val Gly Tyr Asp Ile Thr Ser Gly Tyr Arg Val Pro Asn
            500                 505                 510

Ala Ser Glu Val Tyr Phe Thr Tyr Asn His Gly Ser Gly Asn Trp Leu
        515                 520                 525

Pro Asn Pro Asn Leu Lys Ala Glu Arg Ser Thr Thr His Thr Leu Ser
```

```
                530                 535                 540
Leu Gln Gly Arg Ser Glu Lys Gly Met Leu Asp Ala Asn Leu Tyr Gln
545                 550                 555                 560

Ser Asn Tyr Arg Asn Phe Leu Ser Glu Glu Gln Lys Leu Thr Thr Ser
                565                 570                 575

Gly Thr Pro Gly Cys Thr Glu Glu Asn Ala Tyr Tyr Ser Ile Cys Ser
                580                 585                 590

Asp Pro Tyr Lys Glu Lys Leu Asp Trp Gln Met Lys Asn Ile Asp Lys
                595                 600                 605

Ala Arg Ile Arg Gly Ile Glu Leu Thr Gly Arg Leu Asn Val Asp Lys
610                 615                 620

Val Ala Ser Phe Val Pro Glu Gly Trp Lys Leu Phe Gly Ser Leu Gly
625                 630                 635                 640

Tyr Ala Lys Ser Lys Leu Ser Gly Asp Asn Ser Leu Leu Ser Thr Gln
                645                 650                 655

Pro Leu Lys Val Ile Ala Gly Ile Asp Tyr Glu Ser Pro Ser Glu Lys
                660                 665                 670

Trp Gly Val Phe Ser Arg Leu Thr Tyr Leu Gly Ala Lys Lys Val Lys
                675                 680                 685

Asp Ala Gln Tyr Thr Val Tyr Glu Asn Lys Gly Trp Gly Thr Pro Leu
690                 695                 700

Gln Lys Lys Val Lys Asp Tyr Pro Trp Leu Asn Lys Ser Ala Tyr Val
705                 710                 715                 720

Phe Asp Met Tyr Gly Phe Tyr Lys Pro Val Lys Asn Leu Thr Leu Arg
                725                 730                 735

Ala Gly Val Tyr Asn Leu Phe Asn Arg Lys Tyr Thr Thr Trp Asp Ser
                740                 745                 750

Leu Arg Gly Leu Tyr Ser Tyr Ser Thr Thr Asn Ala Val Asp Arg Asp
                755                 760                 765

Gly Lys Gly Leu Asp Arg Tyr Arg Ala Pro Gly Arg Asn Tyr Ala Val
                770                 775                 780

Ser Leu Glu Trp Lys Phe
785                 790

(2) INFORMATION FOR SEQ ID NO: 3:

(i) SEQUENCE CHARACTERISTICS:
        (A) LENGTH: 2376 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2376

(xi) SEQUENCE DESCRIPTION: SEQ ID NO: 3:

ATG AAA CCA TTA CAA ATG CCC CCT ATC GCC GCG CTG CTC GGC AGT ATT       48
Met Lys Pro Leu Gln Met Pro Pro Ile Ala Ala Leu Leu Gly Ser Ile
 1               5                   10                  15

TTC GGC AAT CCG GTC TTT GCG GCA GAT GAA GCT GCA ACT GAA ACC ACA       96
Phe Gly Asn Pro Val Phe Ala Ala Asp Glu Ala Ala Thr Glu Thr Thr
                20                  25                  30

CCC GTT AAG GCA GAG GTA AAA GCA GTG CGC GTT AAA GGT CAG CGC AAT      144
Pro Val Lys Ala Glu Val Lys Ala Val Arg Val Lys Gly Gln Arg Asn
            35                  40                  45
```

```
GCG CCT GCG GCT GTG GAA CGC GTC AAC CTT AAC CGT ATC AAA CAA GAA        192
Ala Pro Ala Ala Val Glu Arg Val Asn Leu Asn Arg Ile Lys Gln Glu
 50              55                  60

ATG ATA CGC GAC AAT AAA GAC TTG GTG CGC TAT TCC ACC GAT GTC GGC        240
Met Ile Arg Asp Asn Lys Asp Leu Val Arg Tyr Ser Thr Asp Val Gly
 65              70                  75                  80

TTG AGC GAC AGG AGC CGT CAT CAA AAA GGC TTT GCC ATT CGC GGC GTG        288
Leu Ser Asp Arg Ser Arg His Gln Lys Gly Phe Ala Ile Arg Gly Val
                 85                  90                  95

GAA GGC GAC CGT GTC GGC GTT AGT ATT GAC GGC GTA AAC CTG CCT GAT        336
Glu Gly Asp Arg Val Gly Val Ser Ile Asp Gly Val Asn Leu Pro Asp
                100                 105                 110

TCC GAA GAA AAC TCG CTG TAC GCC CGT TAT GGC AAC TTC AAC AGC TCG        384
Ser Glu Glu Asn Ser Leu Tyr Ala Arg Tyr Gly Asn Phe Asn Ser Ser
            115                 120                 125

CGT CTG TCT ATC GAC CCC GAA CTC GTG CGC AAC ATC GAC ATC GTA AAA        432
Arg Leu Ser Ile Asp Pro Glu Leu Val Arg Asn Ile Asp Ile Val Lys
130                 135                 140

GGG GCG GAC TCT TTC AAT ACC GGC AGC GGC GCC TTG GGC GGC GGT GTG        480
Gly Ala Asp Ser Phe Asn Thr Gly Ser Gly Ala Leu Gly Gly Gly Val
145                 150                 155                 160

AAT TAC CAA ACC CTG CAA GGA CGT GAC TTA CTG TTG CCT GAA CGG CAG        528
Asn Tyr Gln Thr Leu Gln Gly Arg Asp Leu Leu Leu Pro Glu Arg Gln
                165                 170                 175

TTC GGC GTG ATG ATG AAA AAC GGT TAC AGC ACG CGT AAC CGT GAA TGG        576
Phe Gly Val Met Met Lys Asn Gly Tyr Ser Thr Arg Asn Arg Glu Trp
                180                 185                 190

ACA AAT ACC CTC GGT TTC GGC GTG AGC AAC GAC CGC GTG GAT GCC GCT        624
Thr Asn Thr Leu Gly Phe Gly Val Ser Asn Asp Arg Val Asp Ala Ala
            195                 200                 205

TTG CTG TAT TCG CAA CGG CGC GGC CAT GAA ACT GAA AGC GCG GGC AAG        672
Leu Leu Tyr Ser Gln Arg Arg Gly His Glu Thr Glu Ser Ala Gly Lys
210                 215                 220

CGT GGT TAT CCG GTA GAG GGT GCT GGT AGC GGA GCG AAT ATC CGT GGT        720
Arg Gly Tyr Pro Val Glu Gly Ala Gly Ser Gly Ala Asn Ile Arg Gly
225                 230                 235                 240

TCT GCG CGC GGT ATT CCT GAT CCG TCC CAA CAC AAA TAC CAC AGC TTC        768
Ser Ala Arg Gly Ile Pro Asp Pro Ser Gln His Lys Tyr His Ser Phe
                245                 250                 255

TTG GGT AAG ATT GCT TAT CAA ATC AAC GAC AAC CAC CGC ATC GGC GCA        816
Leu Gly Lys Ile Ala Tyr Gln Ile Asn Asp Asn His Arg Ile Gly Ala
                260                 265                 270

TCG CTC AAC GGT CAG CAG GGG CAT AAT TAC ACG GTT GAA GAG TCT TAC        864
Ser Leu Asn Gly Gln Gln Gly His Asn Tyr Thr Val Glu Glu Ser Tyr
            275                 280                 285

AAC CTG CTT GCT TCT TAT TGG CGT GAA GCT GAC GAT GTC AAC AGA CGG        912
Asn Leu Leu Ala Ser Tyr Trp Arg Glu Ala Asp Asp Val Asn Arg Arg
290                 295                 300

CGT AAC ACC AAC CTC TTT TAC GAA TGG ACG CCG GAA TCC GAC CGG TTG        960
Arg Asn Thr Asn Leu Phe Tyr Glu Trp Thr Pro Glu Ser Asp Arg Leu
305                 310                 315                 320

TCT ATG GTA AAA GCG GAT GTC GAT TAT CAA AAA ACC AAA GTA TCT GCG       1008
Ser Met Val Lys Ala Asp Val Asp Tyr Gln Lys Thr Lys Val Ser Ala
                325                 330                 335

GTC AAC TAC AAA GGT TCG TTC CCG ACG AAT TAC ACC ACA TGG GAA ACC       1056
Val Asn Tyr Lys Gly Ser Phe Pro Thr Asn Tyr Thr Thr Trp Glu Thr
            340                 345                 350

GAG TAC CAT AAA AAG GAA GTT GGC GAA ATC TAT AAC CGC AGC ATG GAT       1104
Glu Tyr His Lys Lys Glu Val Gly Glu Ile Tyr Asn Arg Ser Met Asp
            355                 360                 365
```

```
ACA ACC TTC AAA CGT ATT ACG CTG CGT ATG GAC AGC CAT CCG TTG CAA    1152
Thr Thr Phe Lys Arg Ile Thr Leu Arg Met Asp Ser His Pro Leu Gln
    370                 375                 380

CTC GGG GGG GGG CGA CAC CGC CTG TCG TTC AAA ACC TTT GCC GGG CAG    1200
Leu Gly Gly Gly Arg His Arg Leu Ser Phe Lys Thr Phe Ala Gly Gln
385                 390                 395                 400

CGT GAT TTT GAA AAC TTA AAC CGC GAC GAT TAC TAC TTC AGC GGC CGT    1248
Arg Asp Phe Glu Asn Leu Asn Arg Asp Asp Tyr Tyr Phe Ser Gly Arg
                405                 410                 415

GTT GTT CGA ACC ACC AAC AGT ATC CAG CAT CCG GTG AAA ACC ACC AAC    1296
Val Val Arg Thr Thr Asn Ser Ile Gln His Pro Val Lys Thr Thr Asn
            420                 425                 430

TAC GGT TTC TCG CTG TCC GAC CAA ATC CAA TGG AAC GAC GTG TTC AGT    1344
Tyr Gly Phe Ser Leu Ser Asp Gln Ile Gln Trp Asn Asp Val Phe Ser
                435                 440                 445

AGC CGC GCA GGT ATC CGT TAC GAC CAC ACC AAA ATG ACG CCT CAG GAA    1392
Ser Arg Ala Gly Ile Arg Tyr Asp His Thr Lys Met Thr Pro Gln Glu
        450                 455                 460

TTG AAT GCC GAC TGT CAT GCT TGT GAC AAA ACA CCG CCT GCA GCC AAC    1440
Leu Asn Ala Asp Cys His Ala Cys Asp Lys Thr Pro Pro Ala Ala Asn
465                 470                 475                 480

ACT TAT AAA GGC TGG AGC GGA TTT GTC GGC TTG GCG GCG CAG CTG AGC    1488
Thr Tyr Lys Gly Trp Ser Gly Phe Val Gly Leu Ala Ala Gln Leu Ser
                485                 490                 495

CAA ACA TGG CGT TTG GGT TAC GAT GTG ACC TCA GGT TTC CGC GTG CCG    1536
Gln Thr Trp Arg Leu Gly Tyr Asp Val Thr Ser Gly Phe Arg Val Pro
        500                 505                 510

AAT GCG TCT GAA GTG TAT TTC ACT TAC AAC CAC GGT TCG GGC ACT TGG    1584
Asn Ala Ser Glu Val Tyr Phe Thr Tyr Asn His Gly Ser Gly Thr Trp
            515                 520                 525

AAG CCT AAT CCT AAT TTG AAG GCA GAA CGC AGC ACC ACC CAC ACC CTG    1632
Lys Pro Asn Pro Asn Leu Lys Ala Glu Arg Ser Thr Thr His Thr Leu
        530                 535                 540

TCC TTG CAG GGG CGC GGC GAC AAA GGG ACA CTG GAT GCC AAC CTG TAT    1680
Ser Leu Gln Gly Arg Gly Asp Lys Gly Thr Leu Asp Ala Asn Leu Tyr
545                 550                 555                 560

CAA AGC AAT TAC CGA AAC TTC CTG TCG GAA GAG CAG AAT CTG ACT GTC    1728
Gln Ser Asn Tyr Arg Asn Phe Leu Ser Glu Glu Gln Asn Leu Thr Val
                565                 570                 575

AGC GGC ACA CCC GGC TGT ACT GAG GAG GAT GCT TAC TAC TAT AGA TGC    1776
Ser Gly Thr Pro Gly Cys Thr Glu Glu Asp Ala Tyr Tyr Tyr Arg Cys
        580                 585                 590

AGC GAC CCC TAC AAA GAA AAA CTG GAT TGG CAG ATG AAA AAT ATC GAC    1824
Ser Asp Pro Tyr Lys Glu Lys Leu Asp Trp Gln Met Lys Asn Ile Asp
    595                 600                 605

AAG GCC AGA ATC CGC GGT ATC GAG TTG ACA GGC CGT CTG AAT GTG GAC    1872
Lys Ala Arg Ile Arg Gly Ile Glu Leu Thr Gly Arg Leu Asn Val Asp
    610                 615                 620

AAA GTA GCG TCT TTT GTT CCT GAG GGT TGG AAA CTG TTC GGC TCG CTG    1920
Lys Val Ala Ser Phe Val Pro Glu Gly Trp Lys Leu Phe Gly Ser Leu
625                 630                 635                 640

GGT TAT GCG AAA AGC AAA CTG TCG GGC GAC AAC AGC CTG CTG TCC ACA    1968
Gly Tyr Ala Lys Ser Lys Leu Ser Gly Asp Asn Ser Leu Leu Ser Thr
                645                 650                 655

CAG CCG CTG AAA GTG ATT GCC GGT ATC GAC TAT GAA AGT CCG AGC GAA    2016
Gln Pro Leu Lys Val Ile Ala Gly Ile Asp Tyr Glu Ser Pro Ser Glu
        660                 665                 670

AAA TGG GGC GTA TTC TCC CGC CTG ACC TAT CTA GGC GCG AAA AAG GTC    2064
Lys Trp Gly Val Phe Ser Arg Leu Thr Tyr Leu Gly Ala Lys Lys Val
```

-continued

```
              675                 680                 685
AAA GAC GCG CAA TAC ACC GTT TAT GAA AAC AAG GGC TGG GGT ACG CCT    2112
Lys Asp Ala Gln Tyr Thr Val Tyr Glu Asn Lys Gly Trp Gly Thr Pro
        690                 695                 700

TTG CAG AAA AAG GTA AAA GAT TAC CCG TGG CTG AAC AAG TCG GCT TAT    2160
Leu Gln Lys Lys Val Lys Asp Tyr Pro Trp Leu Asn Lys Ser Ala Tyr
705                 710                 715                 720

GTG TTT GAT ATG TAC GGC TTC TAC AAA CCG GCT AAA AAC CTG ACT TTG    2208
Val Phe Asp Met Tyr Gly Phe Tyr Lys Pro Ala Lys Asn Leu Thr Leu
            725                 730                 735

CGT GCA GGC GTG TAC AAC CTG TTC AAC CGC AAA TAC ACC ACT TGG GAT    2256
Arg Ala Gly Val Tyr Asn Leu Phe Asn Arg Lys Tyr Thr Thr Trp Asp
        740                 745                 750

TCC CTG CGC GGT TTA TAT AGC TAC AGC ACC ACC AAT GCG GTC GAC CGC    2304
Ser Leu Arg Gly Leu Tyr Ser Tyr Ser Thr Thr Asn Ala Val Asp Arg
    755                 760                 765

GAT GGC AAA GGC TTA GAC CGC TAC CGC GCC CCA GGC CGC AAT TAC GCC    2352
Asp Gly Lys Gly Leu Asp Arg Tyr Arg Ala Pro Gly Arg Asn Tyr Ala
770                 775                 780

GTA TCG CTG GAA TGG AAG TTT TAA                                    2376
Val Ser Leu Glu Trp Lys Phe *
785                 790

(2) INFORMATION FOR SEQ ID NO: 4:

(i) SEQUENCE CHARACTERISTICS:
        (A) LENGTH: 791 amino acids
        (B) TYPE: amino acid
        (D) TOPOLOGY: linear (ii) MOLECULE TYPE: protein (xi) SEQUENCE DESCRIPTION: SEQ ID NO: 4:

Met Lys Pro Leu Gln Met Pro Pro Ile Ala Ala Leu Leu Gly Ser Ile
 1               5                  10                  15

Phe Gly Asn Pro Val Phe Ala Ala Asp Glu Ala Ala Thr Glu Thr Thr
                20                  25                  30

Pro Val Lys Ala Glu Val Lys Ala Val Arg Val Lys Gly Gln Arg Asn
            35                  40                  45

Ala Pro Ala Ala Val Glu Arg Val Asn Leu Asn Arg Ile Lys Gln Glu
        50                  55                  60

Met Ile Arg Asp Asn Lys Asp Leu Val Arg Tyr Ser Thr Asp Val Gly
65                  70                  75                  80

Leu Ser Asp Arg Ser Arg His Gln Lys Gly Phe Ala Ile Arg Gly Val
                85                  90                  95

Glu Gly Asp Arg Val Gly Val Ser Ile Asp Gly Val Asn Leu Pro Asp
                100                 105                 110

Ser Glu Glu Asn Ser Leu Tyr Ala Arg Tyr Gly Asn Phe Asn Ser Ser
            115                 120                 125

Arg Leu Ser Ile Asp Pro Glu Leu Val Arg Asn Ile Asp Ile Val Lys
        130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Pro Glu Arg Gln
                165                 170                 175

Phe Gly Val Met Met Lys Asn Gly Tyr Ser Thr Arg Asn Arg Glu Trp
            180                 185                 190

Thr Asn Thr Leu Gly Phe Gly Val Ser Asn Asp Arg Val Asp Ala Ala
```

```
                195                 200                 205
Leu Leu Tyr Ser Gln Arg Arg Gly His Glu Thr Glu Ser Ala Gly Lys
    210                 215                 220

Arg Gly Tyr Pro Val Glu Gly Ala Gly Ser Gly Ala Asn Ile Arg Gly
225                 230                 235                 240

Ser Ala Arg Gly Ile Pro Asp Pro Ser Gln His Lys Tyr His Ser Phe
                245                 250                 255

Leu Gly Lys Ile Ala Tyr Gln Ile Asn Asp Asn His Arg Ile Gly Ala
                260                 265                 270

Ser Leu Asn Gly Gln Gln Gly His Asn Tyr Thr Val Glu Glu Ser Tyr
            275                 280                 285

Asn Leu Leu Ala Ser Tyr Trp Arg Glu Ala Asp Asp Val Asn Arg Arg
        290                 295                 300

Arg Asn Thr Asn Leu Phe Tyr Glu Trp Thr Pro Glu Ser Asp Arg Leu
305                 310                 315                 320

Ser Met Val Lys Ala Asp Val Asp Tyr Gln Lys Thr Lys Val Ser Ala
                325                 330                 335

Val Asn Tyr Lys Gly Ser Phe Pro Thr Asn Tyr Thr Thr Trp Glu Thr
            340                 345                 350

Glu Tyr His Lys Lys Glu Val Gly Glu Ile Tyr Asn Arg Ser Met Asp
                355                 360                 365

Thr Thr Phe Lys Arg Ile Thr Leu Arg Met Asp Ser His Pro Leu Gln
    370                 375                 380

Leu Gly Gly Gly Arg His Arg Leu Ser Phe Lys Thr Phe Ala Gly Gln
385                 390                 395                 400

Arg Asp Phe Glu Asn Leu Asn Arg Asp Asp Tyr Tyr Phe Ser Gly Arg
                405                 410                 415

Val Val Arg Thr Thr Asn Ser Ile Gln His Pro Val Lys Thr Thr Asn
            420                 425                 430

Tyr Gly Phe Ser Leu Ser Asp Gln Ile Gln Trp Asn Asp Val Phe Ser
        435                 440                 445

Ser Arg Ala Gly Ile Arg Tyr Asp His Thr Lys Met Thr Pro Gln Glu
450                 455                 460

Leu Asn Ala Asp Cys His Ala Cys Asp Lys Thr Pro Pro Ala Ala Asn
465                 470                 475                 480

Thr Tyr Lys Gly Trp Ser Gly Phe Val Gly Leu Ala Ala Gln Leu Ser
                485                 490                 495

Gln Thr Trp Arg Leu Gly Tyr Asp Val Thr Ser Gly Phe Arg Val Pro
            500                 505                 510

Asn Ala Ser Glu Val Tyr Phe Thr Tyr Asn His Gly Ser Gly Thr Trp
        515                 520                 525

Lys Pro Asn Pro Asn Leu Lys Ala Glu Arg Ser Thr Thr His Thr Leu
    530                 535                 540

Ser Leu Gln Gly Arg Gly Asp Lys Gly Thr Leu Asp Ala Asn Leu Tyr
545                 550                 555                 560

Gln Ser Asn Tyr Arg Asn Phe Leu Ser Glu Glu Gln Asn Leu Thr Val
                565                 570                 575

Ser Gly Thr Pro Gly Cys Thr Glu Glu Asp Ala Tyr Tyr Arg Cys
            580                 585                 590

Ser Asp Pro Tyr Lys Glu Lys Leu Asp Trp Gln Met Lys Asn Ile Asp
        595                 600                 605

Lys Ala Arg Ile Arg Gly Ile Glu Leu Thr Gly Arg Leu Asn Val Asp
    610                 615                 620
```

-continued

```
Lys Val Ala Ser Phe Val Pro Glu Gly Trp Lys Leu Phe Gly Ser Leu
625                 630                 635                 640

Gly Tyr Ala Lys Ser Lys Leu Ser Gly Asp Asn Ser Leu Leu Ser Thr
                645                 650                 655

Gln Pro Leu Lys Val Ile Ala Gly Ile Asp Tyr Glu Ser Pro Ser Glu
                660                 665                 670

Lys Trp Gly Val Phe Ser Arg Leu Thr Tyr Leu Gly Ala Lys Lys Val
                675                 680                 685

Lys Asp Ala Gln Tyr Thr Val Tyr Glu Asn Lys Gly Trp Gly Thr Pro
690                 695                 700

Leu Gln Lys Lys Val Lys Asp Tyr Pro Trp Leu Asn Lys Ser Ala Tyr
705                 710                 715                 720

Val Phe Asp Met Tyr Gly Phe Tyr Lys Pro Ala Lys Asn Leu Thr Leu
                725                 730                 735

Arg Ala Gly Val Tyr Asn Leu Phe Asn Arg Lys Tyr Thr Thr Trp Asp
                740                 745                 750

Ser Leu Arg Gly Leu Tyr Ser Tyr Ser Thr Thr Asn Ala Val Asp Arg
                755                 760                 765

Asp Gly Lys Gly Leu Asp Arg Tyr Arg Ala Pro Gly Arg Asn Tyr Ala
770                 775                 780

Val Ser Leu Glu Trp Lys Phe
785                 790
```

(2) INFORMATION FOR SEQ ID NO: 5:

(i) SEQUENCE CHARACTERISTICS:
        (A) LENGTH: 2379 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2379

(xi) SEQUENCE DESCRIPTION: SEQ ID NO: 5:

```
ATG AAA CCA TTA CAA ATG CTC CCT ATC GCC GCG CTG GTC GGC AGT ATT        48
Met Lys Pro Leu Gln Met Leu Pro Ile Ala Ala Leu Val Gly Ser Ile
 1               5                  10                  15

TTC GGC AAT CCG GTC TTT GCG GCA GAT GAA GCT GCA ACT GAA ACC ACA        96
Phe Gly Asn Pro Val Phe Ala Ala Asp Glu Ala Ala Thr Glu Thr Thr
                20                  25                  30

CCC GTT AAG GCA GAG GTA AAA GCA GTG CGC GTT AAA GGC CAG CGC AAT       144
Pro Val Lys Ala Glu Val Lys Ala Val Arg Val Lys Gly Gln Arg Asn
            35                  40                  45

GCG CCT GCG GCT GTG GAA CGC GTC AAC CTT AAC CGT ATC AAA CAA GAA       192
Ala Pro Ala Ala Val Glu Arg Val Asn Leu Asn Arg Ile Lys Gln Glu
    50                  55                  60

ATG ATA CGC GAC AAC AAA GAC TTG GTG CGC TAT TCC ACC GAT GTC GGC       240
Met Ile Arg Asp Asn Lys Asp Leu Val Arg Tyr Ser Thr Asp Val Gly
65                  70                  75                  80

TTG AGC GAC AGC GGC CGC CAT CAA AAA GGC TTT GCT GTT CGC GGC GTG       288
Leu Ser Asp Ser Gly Arg His Gln Lys Gly Phe Ala Val Arg Gly Val
                85                  90                  95

GAA GGC AAC CGT GTC GGC GTG AGC ATA GAC GGC GTA AAC CTG CCT GAT       336
Glu Gly Asn Arg Val Gly Val Ser Ile Asp Gly Val Asn Leu Pro Asp
                100                 105                 110
```

-continued

| | | |
|---|---|---|
| TCC GAA GAA AAC TCG CTG TAC GCC CGT TAT GGC AAC TTC AAC AGC TCG<br>Ser Glu Glu Asn Ser Leu Tyr Ala Arg Tyr Gly Asn Phe Asn Ser Ser<br>    115                 120                 125 | 384 | |
| CGT CTG TCT ATC GAC CCC GAA CTC GTG CGC AAC ATC GAC ATC GTA AAA<br>Arg Leu Ser Ile Asp Pro Glu Leu Val Arg Asn Ile Asp Ile Val Lys<br>130                 135                 140 | 432 | |
| GGG GCG GAC TCT TTC AAT ACC GGC AGC GGC GCC TTG GGC GGC GGT GTG<br>Gly Ala Asp Ser Phe Asn Thr Gly Ser Gly Ala Leu Gly Gly Gly Val<br>145                 150                 155                 160 | 480 | |
| AAT TAC CAA ACC CTG CAA GGA CGT GAC TTA CTG TTG CCT GAA CGG CAG<br>Asn Tyr Gln Thr Leu Gln Gly Arg Asp Leu Leu Leu Pro Glu Arg Gln<br>                165                 170                 175 | 528 | |
| TTC GGC GTG ATG ATG AAA AAC GGT TAC AGC ACG CGT AAC CGT GAA TGG<br>Phe Gly Val Met Met Lys Asn Gly Tyr Ser Thr Arg Asn Arg Glu Trp<br>                180                 185                 190 | 576 | |
| ACA AAT ACC CTC GGT TTC GGC GTG AGC AAC GAC CGC GTG GAT GCC GCT<br>Thr Asn Thr Leu Gly Phe Gly Val Ser Asn Asp Arg Val Asp Ala Ala<br>                195                 200                 205 | 624 | |
| TTG CTG TAT TCG CAA CGG CGC GGC CAT GAA ACT GAA AGC GCG GGC AAG<br>Leu Leu Tyr Ser Gln Arg Arg Gly His Glu Thr Glu Ser Ala Gly Lys<br>    210                 215                 220 | 672 | |
| CGT GGT TAT CCG GTA GAG GGT GCT GGT AGC GGA GCG AAT ATC CGT GGT<br>Arg Gly Tyr Pro Val Glu Gly Ala Gly Ser Gly Ala Asn Ile Arg Gly<br>225                 230                 235                 240 | 720 | |
| TCT GCG CGC GGT ATT CCT GAT CCG TCC CAA CAC AAA TAC CAC AGC TTC<br>Ser Ala Arg Gly Ile Pro Asp Pro Ser Gln His Lys Tyr His Ser Phe<br>                245                 250                 255 | 768 | |
| TTG GGT AAG ATT GCT TAT CAA ATC AAC GAC AAC CAC CGC ATC GGC GCA<br>Leu Gly Lys Ile Ala Tyr Gln Ile Asn Asp Asn His Arg Ile Gly Ala<br>                260                 265                 270 | 816 | |
| TCG CTC AAC GGT CAG CAG GGG CAT AAT TAC ACG GTT GAA GAG TCT TAC<br>Ser Leu Asn Gly Gln Gln Gly His Asn Tyr Thr Val Glu Glu Ser Tyr<br>                275                 280                 285 | 864 | |
| AAC CTG CTT GCT TCT TAT TGG CGT GAA GCT GAC GAT GTC AAC AGA CGG<br>Asn Leu Leu Ala Ser Tyr Trp Arg Glu Ala Asp Asp Val Asn Arg Arg<br>    290                 295                 300 | 912 | |
| CGT AAC ACC AAC CTC TTT TAC GAA TGG ACG CCG GAA TCC GAC CGG TTG<br>Arg Asn Thr Asn Leu Phe Tyr Glu Trp Thr Pro Glu Ser Asp Arg Leu<br>305                 310                 315                 320 | 960 | |
| TCT ATG GTA AAA GCG GAT GTC GAT TAT CAA AAA ACC AAA GTA TCT GCG<br>Ser Met Val Lys Ala Asp Val Asp Tyr Gln Lys Thr Lys Val Ser Ala<br>                325                 330                 335 | 1008 | |
| GTC AAC TAC AAA GGT TCG TTC CCG ATA GAG GAT TCT TCC ACC TTG ACA<br>Val Asn Tyr Lys Gly Ser Phe Pro Ile Glu Asp Ser Ser Thr Leu Thr<br>                340                 345                 350 | 1056 | |
| CGT AAC TAC AAT CAA AAG GAC TTG GAT GAA ATC TAC AAC CGC AGT ATG<br>Arg Asn Tyr Asn Gln Lys Asp Leu Asp Glu Ile Tyr Asn Arg Ser Met<br>                355                 360                 365 | 1104 | |
| GAT ACC CGC TTC AAA CGC ATT ACC CTG CGT TTG GAC AGC CAT CCG TTG<br>Asp Thr Arg Phe Lys Arg Ile Thr Leu Arg Leu Asp Ser His Pro Leu<br>    370                 375                 380 | 1152 | |
| CAA CTC GGG GGG GGG CGA CAC CGC CTG TCG TTT AAA ACT TTC GCC AGC<br>Gln Leu Gly Gly Gly Arg His Arg Leu Ser Phe Lys Thr Phe Ala Ser<br>385                 390                 395                 400 | 1200 | |
| CGC CGT GAT TTT GAA AAC CTA AAC CGC GAC GAT TAT TAC TTC AGC GGC<br>Arg Arg Asp Phe Glu Asn Leu Asn Arg Asp Asp Tyr Tyr Phe Ser Gly<br>                405                 410                 415 | 1248 | |
| CGT GTT GTT CGA ACC ACC AGC AGT ATC CAG CAT CCG GTG AAA ACC ACC<br>Arg Val Val Arg Thr Thr Ser Ser Ile Gln His Pro Val Lys Thr Thr<br>                420                 425                 430 | 1296 | |

| | |
|---|---|
| AAC TAC GGT TTC TCA CTG TCT GAC CAA ATT CAA TGG AAC GAC GTG TTC<br>Asn Tyr Gly Phe Ser Leu Ser Asp Gln Ile Gln Trp Asn Asp Val Phe<br>                        435                     440                     445 | 1344 |
| AGT AGC CGC GCA GGT ATC CGT TAC GAT CAT ACC AAA ATG ACG CCT CAG<br>Ser Ser Arg Ala Gly Ile Arg Tyr Asp His Thr Lys Met Thr Pro Gln<br>      450                     455                     460 | 1392 |
| GAA TTG AAT GCC GAG TGT CAT GCT TGT GAC AAA ACA CCG CCT GCA GCC<br>Glu Leu Asn Ala Glu Cys His Ala Cys Asp Lys Thr Pro Pro Ala Ala<br>465                     470                     475                     480 | 1440 |
| AAC ACT TAT AAA GGC TGG AGC GGT TTT GTC GGC TTG GCG GCG CAA CTG<br>Asn Thr Tyr Lys Gly Trp Ser Gly Phe Val Gly Leu Ala Ala Gln Leu<br>                     485                     490                     495 | 1488 |
| AAT CAG GCT TGG CGT GTC GGT TAC GAC ATT ACT TCC GGC TAC CGT GTC<br>Asn Gln Ala Trp Arg Val Gly Tyr Asp Ile Thr Ser Gly Tyr Arg Val<br>      500                     505                     510 | 1536 |
| CCC AAT GCG TCC GAA GTG TAT TTC ACT TAC AAC CAC GGT TCG GGT AAT<br>Pro Asn Ala Ser Glu Val Tyr Phe Thr Tyr Asn His Gly Ser Gly Asn<br>                 515                     520                     525 | 1584 |
| TGG CTG CCC AAT CCC AAC CTG AAA GCC GAG CGC ACG ACC ACC CAC ACC<br>Trp Leu Pro Asn Pro Asn Leu Lys Ala Glu Arg Thr Thr Thr His Thr<br>530                     535                     540 | 1632 |
| CTC TCT CTG CAA GGC CGC AGC GAA AAA GGT ACT TTG GAT GCC AAC CTG<br>Leu Ser Leu Gln Gly Arg Ser Glu Lys Gly Thr Leu Asp Ala Asn Leu<br>545                     550                     555                     560 | 1680 |
| TAT CAA AGC AAT TAC CGC AAT TTC CTG TCT GAA GAG CAG AAG CTG ACC<br>Tyr Gln Ser Asn Tyr Arg Asn Phe Leu Ser Glu Glu Gln Lys Leu Thr<br>                     565                     570                     575 | 1728 |
| ACC AGC GGC GAT GTC AGC TGT ACT CAG ATG AAT TAC TAC TAC GGT ATG<br>Thr Ser Gly Asp Val Ser Cys Thr Gln Met Asn Tyr Tyr Tyr Gly Met<br>               580                     585                     590 | 1776 |
| TGT AGC AAT CCT TAT TCC GAA AAA CTG GAA TGG CAG ATG CAA AAT ATC<br>Cys Ser Asn Pro Tyr Ser Glu Lys Leu Glu Trp Gln Met Gln Asn Ile<br>                   595                     600                     605 | 1824 |
| GAC AAG GCC AGA ATC CGC GGT ATC GAG CTG ACG GGC CGT CTG AAT GTG<br>Asp Lys Ala Arg Ile Arg Gly Ile Glu Leu Thr Gly Arg Leu Asn Val<br>610                     615                     620 | 1872 |
| GAC AAA GTA GCG TCT TTT GTT CCT GAG GGC TGG AAA CTG TTC GGC TCG<br>Asp Lys Val Ala Ser Phe Val Pro Glu Gly Trp Lys Leu Phe Gly Ser<br>625                     630                     635                     640 | 1920 |
| CTG GGT TAT GCG AAA AGC AAA CTG TCG GGC GAC AAC AGC CTG CTG TCC<br>Leu Gly Tyr Ala Lys Ser Lys Leu Ser Gly Asp Asn Ser Leu Leu Ser<br>                     645                     650                     655 | 1968 |
| ACC CAG CCG TTG AAA GTG ATT GCC GGT ATC GAC TAT GAA AGT CCG AGC<br>Thr Gln Pro Leu Lys Val Ile Ala Gly Ile Asp Tyr Glu Ser Pro Ser<br>      660                     665                     670 | 2016 |
| GAA AAA TGG GGC GTG TTC TCC CGC CTG ACC TAT CTG GGC GCG AAA AAG<br>Glu Lys Trp Gly Val Phe Ser Arg Leu Thr Tyr Leu Gly Ala Lys Lys<br>               675                     680                     685 | 2064 |
| GTC AAA GAC GCG CAA TAC ACC GTT TAT GAA AAC AAG GGC TGG GGT ACG<br>Val Lys Asp Ala Gln Tyr Thr Val Tyr Glu Asn Lys Gly Trp Gly Thr<br>      690                     695                     700 | 2112 |
| CCT TTG CAG AAA AAG GTA AAA GAT TAC CCG TGG CTG AAC AAG TCG GCT<br>Pro Leu Gln Lys Lys Val Lys Asp Tyr Pro Trp Leu Asn Lys Ser Ala<br>705                     710                     715                     720 | 2160 |
| TAT GTG TTC GAT ATG TAC GGC TTC TAC AAA CCG GTG AAA AAC CTG ACT<br>Tyr Val Phe Asp Met Tyr Gly Phe Tyr Lys Pro Val Lys Asn Leu Thr<br>                     725                     730                     735 | 2208 |
| TTG CGT GCA GGC GTA TAT AAT GTG TTC AAC CGC AAA TAC ACC ACT TGG<br>Leu Arg Ala Gly Val Tyr Asn Val Phe Asn Arg Lys Tyr Thr Thr Trp | 2256 |

```
                    740                 745                 750
GAT TCC CTG CGC GGC CTG TAT AGC TAC AGC ACC ACC AAC TCG GTC GAC         2304
Asp Ser Leu Arg Gly Leu Tyr Ser Tyr Ser Thr Thr Asn Ser Val Asp
        755                 760                 765

CGC GAT GGC AAA GGC TTA GAC CGC TAC CGC GCC CCA AGC CGT AAT TAC         2352
Arg Asp Gly Lys Gly Leu Asp Arg Tyr Arg Ala Pro Ser Arg Asn Tyr
        770                 775                 780

GCC GTA TCG CTG GAA TGG AAG TTT TAA                                     2379
Ala Val Ser Leu Glu Trp Lys Phe  *
785                 790
```

(2) INFORMATION FOR SEQ ID NO: 6:

(i) SEQUENCE CHARACTERISTICS:
        (A) LENGTH: 792 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Lys Pro Leu Gln Met Leu Pro Ile Ala Ala Leu Val Gly Ser Ile
1               5                   10                  15

Phe Gly Asn Pro Val Phe Ala Ala Asp Glu Ala Ala Thr Glu Thr Thr
                20                  25                  30

Pro Val Lys Ala Glu Val Lys Ala Val Arg Val Lys Gly Gln Arg Asn
            35                  40                  45

Ala Pro Ala Ala Val Glu Arg Val Asn Leu Asn Arg Ile Lys Gln Glu
        50                  55                  60

Met Ile Arg Asp Asn Lys Asp Leu Val Arg Tyr Ser Thr Asp Val Gly
65                  70                  75                  80

Leu Ser Asp Ser Gly Arg His Gln Lys Gly Phe Ala Val Arg Gly Val
                85                  90                  95

Glu Gly Asn Arg Val Gly Val Ser Ile Asp Gly Val Asn Leu Pro Asp
                100                 105                 110

Ser Glu Glu Asn Ser Leu Tyr Ala Arg Tyr Gly Asn Phe Asn Ser Ser
            115                 120                 125

Arg Leu Ser Ile Asp Pro Glu Leu Val Arg Asn Ile Asp Ile Val Lys
        130                 135                 140

Gly Ala Asp Ser Phe Asn Thr Gly Ser Gly Ala Leu Gly Gly Gly Val
145                 150                 155                 160

Asn Tyr Gln Thr Leu Gln Gly Arg Asp Leu Leu Pro Glu Arg Gln
                165                 170                 175

Phe Gly Val Met Met Lys Asn Gly Tyr Ser Thr Arg Asn Arg Glu Trp
                180                 185                 190

Thr Asn Thr Leu Gly Phe Gly Val Ser Asn Asp Arg Val Asp Ala Ala
            195                 200                 205

Leu Leu Tyr Ser Gln Arg Arg Gly His Glu Thr Glu Ser Ala Gly Lys
        210                 215                 220

Arg Gly Tyr Pro Val Glu Gly Ala Gly Ser Ala Asn Ile Arg Gly
225                 230                 235                 240

Ser Ala Arg Gly Ile Pro Asp Pro Ser Gln His Lys Tyr His Ser Phe
                245                 250                 255

Leu Gly Lys Ile Ala Tyr Gln Ile Asn Asp Asn His Arg Ile Gly Ala
                260                 265                 270

Ser Leu Asn Gly Gln Gln Gly His Asn Tyr Thr Val Glu Glu Ser Tyr
            275                 280                 285
```

```
Asn Leu Leu Ala Ser Tyr Trp Arg Glu Ala Asp Asp Val Asn Arg Arg
    290                 295                 300
Arg Asn Thr Asn Leu Phe Tyr Glu Trp Thr Pro Glu Ser Asp Arg Leu
305                 310                 315                 320
Ser Met Val Lys Ala Asp Val Asp Tyr Gln Lys Thr Lys Val Ser Ala
                325                 330                 335
Val Asn Tyr Lys Gly Ser Phe Pro Ile Glu Asp Ser Ser Thr Leu Thr
            340                 345                 350
Arg Asn Tyr Asn Gln Lys Asp Leu Asp Glu Ile Tyr Asn Arg Ser Met
        355                 360                 365
Asp Thr Arg Phe Lys Arg Ile Thr Leu Arg Leu Asp Ser His Pro Leu
    370                 375                 380
Gln Leu Gly Gly Gly Arg His Arg Leu Ser Phe Lys Thr Phe Ala Ser
385                 390                 395                 400
Arg Arg Asp Phe Glu Asn Leu Asn Arg Asp Asp Tyr Tyr Phe Ser Gly
                405                 410                 415
Arg Val Val Arg Thr Thr Ser Ser Ile Gln His Pro Val Lys Thr Thr
            420                 425                 430
Asn Tyr Gly Phe Ser Leu Ser Asp Gln Ile Gln Trp Asn Asp Val Phe
        435                 440                 445
Ser Ser Arg Ala Gly Ile Arg Tyr Asp His Thr Lys Met Thr Pro Gln
    450                 455                 460
Glu Leu Asn Ala Glu Cys His Ala Cys Asp Lys Thr Pro Pro Ala Ala
465                 470                 475                 480
Asn Thr Tyr Lys Gly Trp Ser Gly Phe Val Gly Leu Ala Ala Gln Leu
                485                 490                 495
Asn Gln Ala Trp Arg Val Gly Tyr Asp Ile Thr Ser Gly Tyr Arg Val
            500                 505                 510
Pro Asn Ala Ser Glu Val Tyr Phe Thr Tyr Asn His Gly Ser Gly Asn
        515                 520                 525
Trp Leu Pro Asn Pro Asn Leu Lys Ala Glu Arg Thr Thr Thr His Thr
    530                 535                 540
Leu Ser Leu Gln Gly Arg Ser Glu Lys Gly Thr Leu Asp Ala Asn Leu
545                 550                 555                 560
Tyr Gln Ser Asn Tyr Arg Asn Phe Leu Ser Glu Glu Gln Lys Leu Thr
                565                 570                 575
Thr Ser Gly Asp Val Ser Cys Thr Gln Met Asn Tyr Tyr Gly Met
            580                 585                 590
Cys Ser Asn Pro Tyr Ser Glu Lys Leu Glu Trp Gln Met Gln Asn Ile
        595                 600                 605
Asp Lys Ala Arg Ile Arg Gly Ile Glu Leu Thr Gly Arg Leu Asn Val
    610                 615                 620
Asp Lys Val Ala Ser Phe Val Pro Glu Gly Trp Lys Leu Phe Gly Ser
625                 630                 635                 640
Leu Gly Tyr Ala Lys Ser Lys Leu Ser Gly Asp Asn Ser Leu Leu Ser
                645                 650                 655
Thr Gln Pro Leu Lys Val Ile Ala Gly Ile Asp Tyr Glu Ser Pro Ser
            660                 665                 670
Glu Lys Trp Gly Val Phe Ser Arg Leu Thr Tyr Leu Gly Ala Lys Lys
        675                 680                 685
Val Lys Asp Ala Gln Tyr Thr Val Tyr Glu Asn Lys Gly Trp Gly Thr
    690                 695                 700
```

```
Pro Leu Gln Lys Lys Val Lys Asp Tyr Pro Trp Leu Asn Lys Ser Ala
705                 710                 715                 720

Tyr Val Phe Asp Met Tyr Gly Phe Tyr Lys Pro Val Lys Asn Leu Thr
                725                 730                 735

Leu Arg Ala Gly Val Tyr Asn Val Phe Asn Arg Lys Tyr Thr Thr Trp
            740                 745                 750

Asp Ser Leu Arg Gly Leu Tyr Ser Tyr Thr Thr Asn Ser Val Asp
        755                 760                 765

Arg Asp Gly Lys Gly Leu Asp Arg Tyr Arg Ala Pro Ser Arg Asn Tyr
    770                 775                 780

Ala Val Ser Leu Glu Trp Lys Phe
785                 790
```

(2) INFORMATION FOR SEQ ID NO: 7:

(i) SEQUENCE CHARACTERISTICS:
        (A) LENGTH: 2378 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..2373

(xi) SEQUENCE DESCRIPTION: SEQ ID NO: 7:

```
ATG AAA CCA TTA CAC ATG CTT CCT ATT GCC GCG CTG GTC GGC AGT ATT        48
Met Lys Pro Leu His Met Leu Pro Ile Ala Ala Leu Val Gly Ser Ile
1               5                   10                  15

TTC GGC AAT CCG GTC TTG GCA GCG GAT GAA GCT GCA ACC GAA ACC ACA        96
Phe Gly Asn Pro Val Leu Ala Ala Asp Glu Ala Ala Thr Glu Thr Thr
                20                  25                  30

CCC GTT AAA GCA GAG ATA AAA GAA GTG CGC GTT AAA GAC CAG CTT AAT       144
Pro Val Lys Ala Glu Ile Lys Glu Val Arg Val Lys Asp Gln Leu Asn
            35                  40                  45

GCG CCT GCA ACC GTG GAA CGT GTC AAC CTC GGC CGC ATT CAA CAG GAA       192
Ala Pro Ala Thr Val Glu Arg Val Asn Leu Gly Arg Ile Gln Gln Glu
        50                  55                  60

ATG ATA CGC GAC AAC AAA GAC TTG GTG CGT TAC TCC ACC GAC GTC GGC       240
Met Ile Arg Asp Asn Lys Asp Leu Val Arg Tyr Ser Thr Asp Val Gly
65                  70                  75                  80

TTG AGC GAT AGC GGC CGC CAT CAA AAA GGC TTT GCT GTG CGC GGC GTG       288
Leu Ser Asp Ser Gly Arg His Gln Lys Gly Phe Ala Val Arg Gly Val
                85                  90                  95

GAA GGC AAC CGT GTC GGT GTC AGC ATT GAC GGC GTG AGC CTG CCT GAT       336
Glu Gly Asn Arg Val Gly Val Ser Ile Asp Gly Val Ser Leu Pro Asp
                100                 105                 110

TCG GAA GAA AAC TCA CTG TAT GCA CGT TAT GGC AAC TTC AAC AGC TCG       384
Ser Glu Glu Asn Ser Leu Tyr Ala Arg Tyr Gly Asn Phe Asn Ser Ser
            115                 120                 125

CGC CTG TCT ATC GAC CCC GAA CTC GTG CGC AAC ATC GAA ATC GCG AAG       432
Arg Leu Ser Ile Asp Pro Glu Leu Val Arg Asn Ile Glu Ile Ala Lys
        130                 135                 140

GGC GCT GAC TCT TTC AAT ACC GGT AGC GGC GCA TTG GGT GGC GGC GTG       480
Gly Ala Asp Ser Phe Asn Thr Gly Ser Gly Ala Leu Gly Gly Gly Val
145                 150                 155                 160

AAT TAC CAA ACC CTG CAA GGA CAT GAT TTG CTG TTG GAC GAC AGG CAA       528
Asn Tyr Gln Thr Leu Gln Gly His Asp Leu Leu Leu Asp Asp Arg Gln
                165                 170                 175
```

```
                                                -continued

TTC GGC GTG ATG ATG AAA AAC GGT TAC AGC AGC CGC AAC CGC GAA TGG           576
Phe Gly Val Met Met Lys Asn Gly Tyr Ser Ser Arg Asn Arg Glu Trp
            180                 185                 190

ACA AAT ACA CTC GGT TTC GGT GTG AGC AAC GAC CGC GTG GAT GCC GCT           624
Thr Asn Thr Leu Gly Phe Gly Val Ser Asn Asp Arg Val Asp Ala Ala
            195                 200                 205

TTG CTG TAT TCG CAA CGT CGC GGT CAT GAG ACC GAA AGC GCG GGC GAG           672
Leu Leu Tyr Ser Gln Arg Arg Gly His Glu Thr Glu Ser Ala Gly Glu
            210                 215                 220

CGT GGC TAT CCG GTA GAG GGT GCT GGC AGC GGA GCA ATT ATC CGT GGT           720
Arg Gly Tyr Pro Val Glu Gly Ala Gly Ser Gly Ala Ile Ile Arg Gly
225                 230                 235                 240

TCG TCA CGC GGT ATC CCT GAT CCG TCC AAA CAC AAA TAC CAC AAC TTC           768
Ser Ser Arg Gly Ile Pro Asp Pro Ser Lys His Lys Tyr His Asn Phe
            245                 250                 255

TTG GGT AAG ATT GCT TAT CAA ATC AAC GAC AAG CAC CGC ATC GGC CCA           816
Leu Gly Lys Ile Ala Tyr Gln Ile Asn Asp Lys His Arg Ile Gly Pro
            260                 265                 270

TCG TTT AAC GGC CAG CAG GGG CAT AAT TAC ACG ATT GAA GAG TCT TAT           864
Ser Phe Asn Gly Gln Gln Gly His Asn Tyr Thr Ile Glu Glu Ser Tyr
            275                 280                 285

AAC CTG ACC GCT TCT TCC TGG CGC GAA GCC GAT GAC GTA AAC AGA CGG           912
Asn Leu Thr Ala Ser Ser Trp Arg Glu Ala Asp Asp Val Asn Arg Arg
            290                 295                 300

CGC AAT GCC AAC CTC TTT TAC GAA TGG ACG CCT GAT TCA AAT TGG CTG           960
Arg Asn Ala Asn Leu Phe Tyr Glu Trp Thr Pro Asp Ser Asn Trp Leu
305                 310                 315                 320

TCG TCT TTG AAG GCG GAC TTC GAT TAT CAG ACA ACC AAA GTG GCG GCG          1008
Ser Ser Leu Lys Ala Asp Phe Asp Tyr Gln Thr Thr Lys Val Ala Ala
            325                 330                 335

GTT AAC AAC AAA GGC TCG TTC CCG ACG GAT TAT TCC ACC TGG ACG CGC          1056
Val Asn Asn Lys Gly Ser Phe Pro Thr Asp Tyr Ser Thr Trp Thr Arg
            340                 345                 350

AAC TAT AAT CAG AAG GAT TTG GAG AAT ATA TAC AAC CGC AGC ATG GAC          1104
Asn Tyr Asn Gln Lys Asp Leu Glu Asn Ile Tyr Asn Arg Ser Met Asp
            355                 360                 365

ACC CGA TTC AAA CGT TTT ACT TTG CGT ATG GAC AGC CAA CCG TTG CAA          1152
Thr Arg Phe Lys Arg Phe Thr Leu Arg Met Asp Ser Gln Pro Leu Gln
            370                 375                 380

CTG GGC GGC CAA CAT CGC TTG TCG CTT AAA ACT TTC GCC AGT CGG CGT          1200
Leu Gly Gly Gln His Arg Leu Ser Leu Lys Thr Phe Ala Ser Arg Arg
385                 390                 395                 400

GAG TTT GAA AAC TTA AAC CGC GAC GAT TAT TAC TTC AGC GAA AGA GTA          1248
Glu Phe Glu Asn Leu Asn Arg Asp Asp Tyr Tyr Phe Ser Glu Arg Val
            405                 410                 415

TCC CGT ACT ACC AGC TCG ATT CAA CAC CCC GTG AAA ACC ACT AAT TAT          1296
Ser Arg Thr Thr Ser Ser Ile Gln His Pro Val Lys Thr Thr Asn Tyr
            420                 425                 430

GGT TTC TCA CTG TCT GAT CAA ATC CAA TGG AAC GAC GTG TTC AGC AGC          1344
Gly Phe Ser Leu Ser Asp Gln Ile Gln Trp Asn Asp Val Phe Ser Ser
            435                 440                 445

CGT GCA GAT ATC CGT TAC GAT CAT ACC AAA ATG ACG CCT CAG GAA TTG          1392
Arg Ala Asp Ile Arg Tyr Asp His Thr Lys Met Thr Pro Gln Glu Leu
450                 455                 460

AAT GCC GAG TGT CAT GCT TGT GAC AAA ACA CCG CCT GCA GCC AAT ACT          1440
Asn Ala Glu Cys His Ala Cys Asp Lys Thr Pro Pro Ala Ala Asn Thr
            465                 470                 475                 480

TAT AAA GGC TGG AGC GGA TTT GTC GGT TTG GCG GCG CAA CTG AAT CAG          1488
Tyr Lys Gly Trp Ser Gly Phe Val Gly Leu Ala Ala Gln Leu Asn Gln
            485                 490                 495
```

```
GCT TGG CAT GTC GGT TAC GAC ATT ACT TCC GGC TAC CGT GTC CCC AAT      1536
Ala Trp His Val Gly Tyr Asp Ile Thr Ser Gly Tyr Arg Val Pro Asn
            500                 505                 510

GCG TCC GAA GTG TAT TTC ACT TAC AAC CAC GGT TCG GGT AAT TGG CTG      1584
Ala Ser Glu Val Tyr Phe Thr Tyr Asn His Gly Ser Gly Asn Trp Leu
            515                 520                 525

CCC AAT CCC AAC CTG AAA GCC GAG CGC AGC ACC ACC CAC ACC CTG TCT      1632
Pro Asn Pro Asn Leu Lys Ala Glu Arg Ser Thr Thr His Thr Leu Ser
            530                 535                 540

CTG CAA GGC CGC AGC GAA AAA GGT ACT TTG GAT GCC AAC CTG TAT CAA      1680
Leu Gln Gly Arg Ser Glu Lys Gly Thr Leu Asp Ala Asn Leu Tyr Gln
545                 550                 555                 560

AAC AAT TAC CGC AAC TTC TTG TCT GAA GAG CAG AAG CTG ACC ACC AGC      1728
Asn Asn Tyr Arg Asn Phe Leu Ser Glu Glu Gln Lys Leu Thr Thr Ser
                565                 570                 575

GGC GAT GTC GGC TGT ACT CAG ATG AAT TAC TAC TAC GGT ATG TGT AGC      1776
Gly Asp Val Gly Cys Thr Gln Met Asn Tyr Tyr Tyr Gly Met Cys Ser
            580                 585                 590

AAT CCT TAT TCC GAA AAA CCG GAA TGG CAG ATG CAA AAT ATC GAT AAG      1824
Asn Pro Tyr Ser Glu Lys Pro Glu Trp Gln Met Gln Asn Ile Asp Lys
            595                 600                 605

GCC CGA ATC CGT GGT CTT GAG CTG ACA GGC CGT CTG AAT GTG ACA AAA      1872
Ala Arg Ile Arg Gly Leu Glu Leu Thr Gly Arg Leu Asn Val Thr Lys
610                 615                 620

GTA GCG TCT TTT GTT CCT GAG GGC TGG AAA TTG TTC GGC TCG CTG GGT      1920
Val Ala Ser Phe Val Pro Glu Gly Trp Lys Leu Phe Gly Ser Leu Gly
625                 630                 635                 640

TAT GCG AAA AGC AAA CTG TCG GGC GAC AAC AGC CTG CTG TCC ACA CAG      1968
Tyr Ala Lys Ser Lys Leu Ser Gly Asp Asn Ser Leu Leu Ser Thr Gln
                645                 650                 655

CCG CCG AAA GTG ATT GCC GGT GTC GAC TAC GAA AGC CCG AGC GAA AAA      2016
Pro Pro Lys Val Ile Ala Gly Val Asp Tyr Glu Ser Pro Ser Glu Lys
            660                 665                 670

TGG GGT GTG TTC TCC CGC CTG ACT TAT CTG GGT GCG AAA AAG GCC AAA      2064
Trp Gly Val Phe Ser Arg Leu Thr Tyr Leu Gly Ala Lys Lys Ala Lys
            675                 680                 685

GAC GCG CAA TAC ACC GTT TAT GAA AAC AAG GGC CGG GGT ACG CCT TTG      2112
Asp Ala Gln Tyr Thr Val Tyr Glu Asn Lys Gly Arg Gly Thr Pro Leu
690                 695                 700

CAG AAA AAG GTA AAA GAT TAC CCG TGG CTG AAC AAG TCG GCT TAT GTG      2160
Gln Lys Lys Val Lys Asp Tyr Pro Trp Leu Asn Lys Ser Ala Tyr Val
705                 710                 715                 720

TTT GAT ATG TAC GGC TTC TAC AAA CTG GCT AAA AAC CTG ACT TTG CGT      2208
Phe Asp Met Tyr Gly Phe Tyr Lys Leu Ala Lys Asn Leu Thr Leu Arg
                725                 730                 735

GCA GGC GTA TAT AAT GTG TTC AAC CGC AAA TAC ACC ACT TGG GAT TCC      2256
Ala Gly Val Tyr Asn Val Phe Asn Arg Lys Tyr Thr Thr Trp Asp Ser
            740                 745                 750

CTG CGC GGT TTG TAT AGC TAC AGC ACC ACC AAC GCG GTC GAC CGA GAT      2304
Leu Arg Gly Leu Tyr Ser Tyr Ser Thr Thr Asn Ala Val Asp Arg Asp
            755                 760                 765

GGC AAA GGC TTA GAC CGC TAC CGC GCC TCA GGC CGT AAT TAC GCC GTA      2352
Gly Lys Gly Leu Asp Arg Tyr Arg Ala Ser Gly Arg Asn Tyr Ala Val
770                 775                 780

TCG CTG GAT TGG AAG TTT TGA ATTCC                                    2378
Ser Leu Asp Trp Lys Phe  *
785                 790
```

(2) INFORMATION FOR SEQ ID NO: 8:

-continued

```
    (i) SEQUENCE CHARACTERISTICS:
        (A) LENGTH: 790 amino acids
        (B) TYPE: amino acid
        (D) TOPOLOGY: linear (ii) MOLECULE TYPE: protein (xi) SEQUENCE DESCRIPTION: SEQ ID NO: 8:
```

| | | | | | | | | | | | | | | |
|---|---|---|---|---|---|---|---|---|---|---|---|---|---|---|
| Met | Lys | Pro | Leu | His | Met | Leu | Pro | Ile | Ala | Ala | Leu | Val | Gly | Ser | Ile |
| 1 | | | | 5 | | | | | 10 | | | | | 15 | |
| Phe | Gly | Asn | Pro | Val | Leu | Ala | Ala | Asp | Glu | Ala | Ala | Thr | Glu | Thr | Thr |
| | | | 20 | | | | | 25 | | | | | 30 | | |
| Pro | Val | Lys | Ala | Glu | Ile | Lys | Glu | Val | Arg | Val | Lys | Asp | Gln | Leu | Asn |
| | | 35 | | | | | 40 | | | | | 45 | | | |
| Ala | Pro | Ala | Thr | Val | Glu | Arg | Val | Asn | Leu | Gly | Arg | Ile | Gln | Gln | Glu |
| | 50 | | | | | 55 | | | | | 60 | | | | |
| Met | Ile | Arg | Asp | Asn | Lys | Asp | Leu | Val | Arg | Tyr | Ser | Thr | Asp | Val | Gly |
| 65 | | | | | 70 | | | | | 75 | | | | | 80 |
| Leu | Ser | Asp | Ser | Gly | Arg | His | Gln | Lys | Gly | Phe | Ala | Val | Arg | Gly | Val |
| | | | | 85 | | | | | 90 | | | | | 95 | |
| Glu | Gly | Asn | Arg | Val | Gly | Val | Ser | Ile | Asp | Gly | Val | Ser | Leu | Pro | Asp |
| | | | 100 | | | | | 105 | | | | | 110 | | |
| Ser | Glu | Glu | Asn | Ser | Leu | Tyr | Ala | Arg | Tyr | Gly | Asn | Phe | Asn | Ser | Ser |
| | | 115 | | | | | 120 | | | | | 125 | | | |
| Arg | Leu | Ser | Ile | Asp | Pro | Glu | Leu | Val | Arg | Asn | Ile | Glu | Ile | Ala | Lys |
| | 130 | | | | | 135 | | | | | 140 | | | | |
| Gly | Ala | Asp | Ser | Phe | Asn | Thr | Gly | Ser | Gly | Ala | Leu | Gly | Gly | Gly | Val |
| 145 | | | | | 150 | | | | | 155 | | | | | 160 |
| Asn | Tyr | Gln | Thr | Leu | Gln | Gly | His | Asp | Leu | Leu | Asp | Asp | Arg | Gln | |
| | | | | 165 | | | | | 170 | | | | | 175 | |
| Phe | Gly | Val | Met | Met | Lys | Asn | Gly | Tyr | Ser | Ser | Arg | Asn | Arg | Glu | Trp |
| | | | | 180 | | | | | 185 | | | | | 190 | |
| Thr | Asn | Thr | Leu | Gly | Phe | Gly | Val | Ser | Asn | Asp | Arg | Val | Asp | Ala | Ala |
| | | | 195 | | | | | 200 | | | | | 205 | | |
| Leu | Leu | Tyr | Ser | Gln | Arg | Arg | Gly | His | Glu | Thr | Glu | Ser | Ala | Gly | Glu |
| | 210 | | | | | 215 | | | | | 220 | | | | |
| Arg | Gly | Tyr | Pro | Val | Glu | Gly | Ala | Gly | Ser | Gly | Ala | Ile | Ile | Arg | Gly |
| 225 | | | | | 230 | | | | | 235 | | | | | 240 |
| Ser | Ser | Arg | Gly | Ile | Pro | Asp | Pro | Ser | Lys | His | Lys | Tyr | His | Asn | Phe |
| | | | | 245 | | | | | 250 | | | | | 255 | |
| Leu | Gly | Lys | Ile | Ala | Tyr | Gln | Ile | Asn | Asp | Lys | His | Arg | Ile | Gly | Pro |
| | | | 260 | | | | | 265 | | | | | 270 | | |
| Ser | Phe | Asn | Gly | Gln | Gln | Gly | His | Asn | Tyr | Thr | Ile | Glu | Glu | Ser | Tyr |
| | | 275 | | | | | 280 | | | | | 285 | | | |
| Asn | Leu | Thr | Ala | Ser | Ser | Trp | Arg | Glu | Ala | Asp | Asp | Val | Asn | Arg | Arg |
| | 290 | | | | | 295 | | | | | 300 | | | | |
| Arg | Asn | Ala | Asn | Leu | Phe | Tyr | Glu | Trp | Thr | Pro | Asp | Ser | Asn | Trp | Leu |
| 305 | | | | | 310 | | | | | 315 | | | | | 320 |
| Ser | Ser | Leu | Lys | Ala | Asp | Phe | Asp | Tyr | Gln | Thr | Thr | Lys | Val | Ala | Ala |
| | | | | 325 | | | | | 330 | | | | | 335 | |
| Val | Asn | Asn | Lys | Gly | Ser | Phe | Pro | Thr | Asp | Tyr | Ser | Thr | Trp | Thr | Arg |
| | | | 340 | | | | | 345 | | | | | 350 | | |
| Asn | Tyr | Asn | Gln | Lys | Asp | Leu | Glu | Asn | Ile | Tyr | Asn | Arg | Ser | Met | Asp |
| | | 355 | | | | | 360 | | | | | 365 | | | |

-continued

```
Thr Arg Phe Lys Arg Phe Thr Leu Arg Met Asp Ser Gln Pro Leu Gln
370                 375                 380
Leu Gly Gly Gln His Arg Leu Ser Leu Lys Thr Phe Ala Ser Arg Arg
385                 390                 395                 400
Glu Phe Glu Asn Leu Asn Arg Asp Asp Tyr Tyr Phe Ser Glu Arg Val
                405                 410                 415
Ser Arg Thr Thr Ser Ser Ile Gln His Pro Val Lys Thr Thr Asn Tyr
            420                 425                 430
Gly Phe Ser Leu Ser Asp Gln Ile Gln Trp Asn Asp Val Phe Ser Ser
                435                 440                 445
Arg Ala Asp Ile Arg Tyr Asp His Thr Lys Met Thr Pro Gln Glu Leu
450                 455                 460
Asn Ala Glu Cys His Ala Cys Asp Lys Thr Pro Pro Ala Ala Asn Thr
465                 470                 475                 480
Tyr Lys Gly Trp Ser Gly Phe Val Gly Leu Ala Ala Gln Leu Asn Gln
                485                 490                 495
Ala Trp His Val Gly Tyr Asp Ile Thr Ser Gly Tyr Arg Val Pro Asn
                500                 505                 510
Ala Ser Glu Val Tyr Phe Tyr Asn His Gly Ser Gly Asn Trp Leu
            515                 520                 525
Pro Asn Pro Asn Leu Lys Ala Glu Arg Ser Thr Thr His Thr Leu Ser
530                 535                 540
Leu Gln Gly Arg Ser Glu Lys Gly Thr Leu Asp Ala Asn Leu Tyr Gln
545                 550                 555                 560
Asn Asn Tyr Arg Asn Phe Leu Ser Glu Glu Gln Lys Leu Thr Thr Ser
                565                 570                 575
Gly Asp Val Gly Cys Thr Gln Met Asn Tyr Tyr Gly Met Cys Ser
            580                 585                 590
Asn Pro Tyr Ser Glu Lys Pro Glu Trp Gln Met Gln Asn Ile Asp Lys
                595                 600                 605
Ala Arg Ile Arg Gly Leu Glu Leu Thr Gly Arg Leu Asn Val Thr Lys
610                 615                 620
Val Ala Ser Phe Val Pro Glu Gly Trp Lys Leu Phe Gly Ser Leu Gly
625                 630                 635                 640
Tyr Ala Lys Ser Lys Leu Ser Gly Asp Asn Ser Leu Leu Ser Thr Gln
                645                 650                 655
Pro Pro Lys Val Ile Ala Gly Val Asp Tyr Glu Ser Pro Ser Glu Lys
                660                 665                 670
Trp Gly Val Phe Ser Arg Leu Thr Tyr Leu Gly Ala Lys Lys Ala Lys
            675                 680                 685
Asp Ala Gln Tyr Thr Val Tyr Glu Asn Lys Gly Arg Gly Thr Pro Leu
690                 695                 700
Gln Lys Lys Val Lys Asp Tyr Pro Trp Leu Asn Lys Ser Ala Tyr Val
705                 710                 715                 720
Phe Asp Met Tyr Gly Phe Tyr Lys Leu Ala Lys Asn Leu Thr Leu Arg
                725                 730                 735
Ala Gly Val Tyr Asn Val Phe Asn Arg Lys Tyr Thr Thr Trp Asp Ser
            740                 745                 750
Leu Arg Gly Leu Tyr Ser Tyr Ser Thr Thr Asn Ala Val Asp Arg Asp
            755                 760                 765
Gly Lys Gly Leu Asp Arg Tyr Arg Ala Ser Gly Arg Asn Tyr Ala Val
770                 775                 780
Ser Leu Asp Trp Lys Phe
```

```
785                790
```

(2) INFORMATION FOR SEQ ID NO: 9:

(i) SEQUENCE CHARACTERISTICS:
        (A) LENGTH: 600 amino acids
        (B) TYPE: amino acid
        (D) TOPOLOGY: linear (ii) MOLECULE TYPE: protein (xi) SEQUENCE DESCRIPTION: SEQ ID NO: 9:

```
Met Gln Gln Gln His Leu Phe Arg Leu Asn Ile Leu Cys Leu Ser Leu
1               5                   10                  15

Met Thr Ala Leu Pro Val Tyr Ala Glu Asn Val Gln Ala Glu Gln Ala
            20                  25                  30

Gln Glu Lys Gln Leu Asp Thr Ile Val Lys Ala Lys Lys Gln Lys Thr
        35                  40                  45

Arg Arg Asp Asn Glu Val Thr Gly Leu Gly Lys Leu Val Lys Ser Ser
50                  55                  60

Asp Thr Leu Ser Lys Glu Gln Val Leu Asn Ile Arg Asp Leu Thr Arg
65                  70                  75                  80

Tyr Asp Pro Gly Ile Ala Val Val Glu Gln Gly Arg Gly Ala Ser Ser
                85                  90                  95

Gly Tyr Ser Ile Arg Gly Met Asp Lys Asn Arg Val Ser Leu Thr Val
            100                 105                 110

Asp Gly Val Ser Gln Ile Gln Ser Tyr Thr Ala Gln Ala Ala Leu Gly
        115                 120                 125

Gly Thr Arg Thr Ala Gly Ser Ser Gly Ala Ile Asn Glu Ile Glu Tyr
130                 135                 140

Glu Asn Val Lys Ala Val Glu Ile Ser Lys Gly Ser Asn Ser Ser Glu
145                 150                 155                 160

Tyr Gly Asn Gly Ala Leu Ala Gly Ser Val Ala Phe Gln Thr Lys Thr
                165                 170                 175

Ala Ala Asp Ile Ile Gly Glu Gly Lys Gln Trp Gly Ile Gln Ser Lys
            180                 185                 190

Thr Ala Tyr Ser Gly Lys Asp His Ala Leu Thr Gln Ser Leu Ala Leu
        195                 200                 205

Ala Gly Arg Ser Gly Gly Ala Glu Ala Leu Leu Ile Tyr Thr Lys Arg
210                 215                 220

Arg Gly Arg Glu Ile His Ala His Lys Asp Ala Gly Lys Gly Val Gln
225                 230                 235                 240

Ser Phe Asn Arg Leu Pro Ile Cys Arg Phe Gly Asn Asn Thr Tyr Thr
                245                 250                 255

Asp Cys Thr Pro Arg Asn Ile Gly Gly Asn Gly Tyr Tyr Ala Ala Val
            260                 265                 270

Gln Asp Asn Val Arg Leu Gly Arg Trp Ala Asp Val Gly Ala Gly Ile
        275                 280                 285

Arg Tyr Asp Tyr Arg Ser Thr His Ser Glu Asp Lys Ser Val Ser Thr
290                 295                 300

Gly Thr His Arg Asn Leu Ser Trp Asn Ala Gly Val Val Leu Lys Pro
305                 310                 315                 320

Phe Thr Trp Met Asp Leu Thr Tyr Arg Ala Ser Thr Gly Phe Arg Leu
                325                 330                 335

Pro Ser Phe Ala Glu Met Tyr Gly Trp Arg Ala Gly Glu Ser Leu Lys
            340                 345                 350
```

```
Thr Leu Asp Leu Lys Pro Glu Lys Ser Phe Asn Arg Glu Ala Gly Ile
            355                 360                 365

Val Phe Lys Gly Asp Phe Gly Asn Leu Glu Ala Ser Tyr Phe Asn Asn
        370                 375                 380

Ala Tyr Arg Asp Leu Ile Ala Phe Gly Tyr Glu Thr Arg Thr Gln Asn
385                 390                 395                 400

Gly Gln Thr Ser Ala Ser Gly Asp Pro Gly Tyr Arg Asn Ala Gln Asn
                405                 410                 415

Ala Arg Ile Ala Gly Ile Asn Ile Leu Gly Lys Ile Asp Trp His Gly
                420                 425                 430

Val Trp Gly Gly Leu Pro Asp Gly Leu Tyr Ser Thr Leu Ala Tyr Asn
            435                 440                 445

Arg Ile Lys Val Lys Asp Ala Asp Arg Ala Asp Arg Thr Phe Val Thr
            450                 455                 460

Ser Tyr Leu Phe Asp Ala Val Gln Pro Ser Arg Tyr Val Leu Gly Leu
465                 470                 475                 480

Gly Tyr Asp His Pro Asp Gly Ile Trp Gly Ile Asn Thr Met Phe Thr
                485                 490                 495

Tyr Ser Lys Ala Lys Ser Val Asp Glu Leu Leu Gly Ser Gln Ala Leu
                500                 505                 510

Leu Asn Gly Asn Ala Asn Ala Lys Lys Ala Ala Ser Arg Arg Thr Arg
            515                 520                 525

Pro Trp Tyr Val Thr Asp Val Ser Gly Tyr Tyr Asn Ile Lys Lys His
        530                 535                 540

Leu Thr Leu Arg Ala Gly Val Tyr Asn Leu Leu Asn Tyr Arg Tyr Val
545                 550                 555                 560

Thr Trp Glu Asn Val Arg Gln Thr Ala Gly Ala Val Asn Gln His
                565                 570                 575

Lys Asn Val Gly Val Tyr Asn Arg Tyr Ala Ala Pro Gly Arg Asn Tyr
                580                 585                 590

Thr Phe Ser Leu Glu Met Lys Phe
            595                 600

(2) INFORMATION FOR SEQ ID NO: 10:

(i) SEQUENCE CHARACTERISTICS:
        (A) LENGTH: 607 amino acids
        (B) TYPE: amino acid
        (D) TOPOLOGY: linear (ii) MOLECULE TYPE: protein (xi) SEQUENCE DESCRIPTION: SEQ ID NO: 10:

Met Asn Lys Lys His Gly Phe Gln Leu Thr Leu Thr Ala Leu Ala Val
1               5                   10                  15

Ala Ala Ala Phe Pro Ser Tyr Ala Ala Asn Pro Glu Thr Ala Ala Pro
            20                  25                  30

Asp Ala Ala Gln Thr Gln Ser Leu Lys Glu Val Thr Val Arg Ala Ala
            35                  40                  45

Lys Val Gly Arg Arg Ser Lys Glu Ala Thr Gly Leu Gly Lys Ile Ala
        50                  55                  60

Lys Thr Ser Glu Thr Leu Asn Lys Glu Gln Val Leu Gly Ile Arg Asp
65                  70                  75                  80

Leu Thr Arg Tyr Asp Pro Gly Val Ala Val Glu Gln Gly Asn Gly
                85                  90                  95
```

```
Ala Ser Gly Gly Tyr Ser Ile Arg Gly Val Asp Lys Asn Arg Val Ala
            100                 105                 110

Val Ser Val Asp Gly Val Ala Gln Ile Gln Ala Phe Thr Val Gln Gly
            115                 120                 125

Ser Leu Ser Gly Tyr Gly Arg Gly Gly Ser Gly Ala Ile Asn Glu
            130                 135                 140

Ile Glu Tyr Glu Asn Ile Ser Thr Val Glu Ile Asp Lys Gly Ala Gly
145                 150                 155                 160

Ser Ser Asp His Gly Ser Gly Ala Leu Gly Gly Ala Val Ala Phe Arg
                165                 170                 175

Thr Lys Glu Ala Ala Asp Leu Ile Ser Asp Gly Lys Ser Trp Gly Ile
                180                 185                 190

Gln Ala Lys Thr Ala Tyr Gly Ser Lys Asn Arg Gln Phe Met Lys Ser
                195                 200                 205

Leu Gly Ala Gly Phe Ser Lys Asp Gly Trp Glu Gly Leu Leu Ile Arg
                210                 215                 220

Thr Glu Arg Gln Gly Arg Glu Thr His Pro His Gly Asp Ile Ala Asp
225                 230                 235                 240

Gly Val Ala Tyr Gly Ile Asn Arg Leu Ser Val Cys Gly Tyr Ile Glu
                245                 250                 255

Thr Leu Arg Ser Arg Lys Cys Val Pro Arg Lys Ile Asn Gly Ser Asn
                260                 265                 270

Ile His Ile Ser Leu Asn Asp Arg Phe Ser Ile Gly Lys Tyr Phe Asp
                275                 280                 285

Phe Ser Leu Gly Gly Arg Tyr Asp Arg Lys Asn Phe Thr Thr Ser Glu
                290                 295                 300

Glu Leu Val Arg Ser Gly Arg Tyr Val Asp Arg Ser Trp Asn Ser Gly
305                 310                 315                 320

Ile Val Phe Lys Pro Asn Arg His Phe Ser Leu Ser Tyr Arg Ala Ser
                325                 330                 335

Ser Gly Phe Arg Thr Pro Ser Phe Gln Glu Leu Phe Gly Ile Asp Ile
                340                 345                 350

Tyr His Asp Tyr Pro Lys Gly Trp Gln Arg Pro Ala Leu Lys Ser Glu
                355                 360                 365

Lys Ala Ala Asn Arg Glu Ile Gly Leu Gln Trp Lys Gly Asp Phe Gly
                370                 375                 380

Phe Leu Glu Ile Ser Ser Phe Arg Asn Arg Tyr Thr Asp Met Ile Ala
385                 390                 395                 400

Val Ala Asp His Lys Thr Lys Leu Pro Asn Gln Ala Gly Gln Leu Thr
                405                 410                 415

Glu Ile Asp Ile Arg Asp Tyr Tyr Asn Ala Gln Asn Met Ser Leu Gln
                420                 425                 430

Gly Val Asn Ile Leu Gly Lys Ile Asp Trp Asn Gly Val Tyr Gly Lys
                435                 440                 445

Leu Pro Glu Gly Leu Tyr Thr Thr Leu Ala Tyr Asn Arg Ile Lys Pro
                450                 455                 460

Lys Ser Val Ser Asn Arg Pro Gly Leu Ser Leu Arg Ser Tyr Ala Leu
465                 470                 475                 480

Asp Ala Val Gln Pro Ser Arg Tyr Val Leu Gly Phe Gly Tyr Asp Gln
                485                 490                 495

Pro Glu Gly Lys Trp Gly Ala Asn Ile Met Leu Thr Tyr Ser Lys Gly
                500                 505                 510

Lys Asn Pro Asp Glu Leu Ala Tyr Leu Ala Gly Asp Gln Lys Arg Tyr
```

```
                515                 520                 525
Ser Thr Lys Arg Ala Ser Ser Trp Ser Thr Ala Asp Val Ser Ala
    530                 535                 540

Tyr Leu Asn Leu Lys Lys Arg Leu Thr Leu Arg Ala Ala Ile Tyr Asn
545                 550                 555                 560

Ile Gly Asn Tyr Arg Tyr Val Thr Trp Glu Ser Leu Arg Gln Thr Ala
                565                 570                 575

Glu Ser Thr Ala Asn Arg His Gly Gly Asp Ser Asn Tyr Gly Arg Tyr
                580                 585                 590

Ala Ala Pro Gly Arg Asn Phe Ser Leu Ala Leu Glu Met Lys Phe
                595                 600                 605
```

(2) INFORMATION FOR SEQ ID NO: 11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

```
AAACAGGTCT CGGCATAG                                            18
```

(2) INFORMATION FOR SEQ ID NO: 12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

```
CGCGAATTCA AACAGGTCTC GGCATAG                                  27
```

(2) INFORMATION FOR SEQ ID NO: 13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

```
CGCGAATTCA AAAACTTCCA TTCCAGCGAT ACG                           33
```

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

```
TAAAACTTCC ATTCCAGCGA TACG                                     24
```

(2) INFORMATION FOR SEQ ID NO: 15:

```
    (i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

AAACAGGTCT CGGCATAG                                                  18

(2) INFORMATION FOR SEQ ID NO: 16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

CGCGAATTCA AACAGGTCTC GGCATAG                                        27

(2) INFORMATION FOR SEQ ID NO: 17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

CGCGAATTCA AAAACTTCCA TTCCAGCGAT ACG                                 33

(2) INFORMATION FOR SEQ ID NO: 18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

TAAAACTTCC ATTCCAGCGA TACG                                           24
```

US 7,029,674 B2

METHODS FOR DOWNMODULATING IMMUNE CELLS USING AN ANTIBODY TO PD-1

RELATED APPLICATIONS

This claims priority to U.S. Ser. No. 60/281,541 filed on Apr. 2, 2001. This application is incorporated herein in its entirety by this reference.

BACKGROUND OF THE INVENTION

In order for T cells to respond to foreign proteins, two signals must be provided by antigen-presenting cells (APCs) to resting T lymphocytes (Jenkins, M. and Schwartz, R. (1987) *J. Exp. Med.* 165:302–319; Mueller, D. L. et al. (1990) *J. Immunol.* 144:3701–3709). The first signal, which confers specificity to the immune response, is transduced via the T cell receptor (TCR) following recognition of foreign antigenic peptide presented in the context of the major histocompatibility complex (MHC). The second signal, termed costimulation, induces T cells to proliferate and become functional (Lenschow et al. (1996) *Annu. Rev. Immunol.* 14:233). Costimulation is neither antigen-specific, nor MHC restricted and is thought to be provided by one or more distinct cell surface molecules expressed by APCs (Jenkins, M. K. et al. (1988) *J. Immunol.* 140:3324–3330; Linsley, P. S. et al. (1991) *J. Exp. Med.* 173:721–730; Gimmi, C. D. et al. 1991 *Proc. Natl. Acad. Sci. USA* 88:6575–6579; Young, J. W. et al. (1992) *J. Clin. Invest.* 90:229–237; Koulova, L. et al. (1991) *J. Exp. Med.* 173: 759–762; Reiser, H. et al. (1992) *Proc. Natl. Acad. Sci. USA* 89:271–275; van-Seventer, G. A. et al. (1990) *J. Immunol.* 144:4579–4586; LaSalle, J. M. et al. (1991) *J. Immunol.* 147:774–80; Dustin, M. I. et al. (1989) *J. Exp. Med.* 169: 503; Armitage, R. J. et al. (1992) *Nature* 357:80–82; Liu, Y. et al. (1992) *J. Exp. Med.* 175:437–445).

The CD80 (B7-1) and CD86 (B7-2) proteins, expressed on APCs, are critical costimulatory molecules (Freeman et al. (1991) *J. Exp. Med.* 174:625; Freeman et al. (1989) *J. Immunol.* 143:2714; Azuma et al. (1993) *Nature* 366:76; Freeman et al. (1993) *Science* 262:909). B7-2 appears to play a predominant role during primary immune responses, while B7-1, which is upregulated later in the course of an immune response, may be important in prolonging primary T cell responses or costimulating secondary T cell responses (Bluestone (1995) *Immunity* 2:555).

One receptor to which B7-1 and B7-2 bind, CD28, is constitutively expressed on resting T cells and increases in expression after activation. After signaling through the T cell receptor, ligation of CD28 and transduction of a costimulatory signal induces T cells to proliferate and secrete IL-2 (Linsley, P. S. et al. (1991) *J. Exp. Med.* 173:721–730; Gimmi, C. D. et al. (1991) *Proc. Natl. Acad. Sci. USA* 88:6575–6579; June, C. H. et al. (1990) *Immunol. Today,* 11:211–6; Harding, F. A. et al. (1992) *Nature* 356:607–609). A second receptor, termed CTLA4 (CD152) is homologous to CD28 but is not expressed on resting T cells and appears following T cell activation (Brunet, J. F. et al. (1987) *Nature* 328:267–270). CTLA4 appears to be critical in negative regulation of T cell responses (Waterhouse et al. (1995) *Science* 270:985). Blockade of CTLA4 has been found to remove inhibitory signals, while aggregation of CTLA4 has been found to provide inhibitory signals that downregulate T cell responses (Allison and Krummel (1995) *Science* 270:932). The B7 molecules have a higher affinity for CTLA4 than for CD28 (Linsley, P. S. et al. (1991) *J. Exp. Med.* 174:561–569) and B7-1 and B7-2 have been found to bind to distinct regions of the CTLA4 molecule and have different kinetics of binding to CTLA4 (Linsley et al. (1994) *Immunity* 1:793). A new molecule related to CD28 and CTLA4, ICOS, has been identified and seems to be important in IL-10 production (Hutloff et al. (1999) *Nature* 397: 263; WO 98/38216), as has its ligand, which is a new B7 family member (Aicher A. et al. (2000) *J. Immunol.* 164: 4689–96; Mages H. W. et al. (2000) *Eur. J. Immunol.* 30:1040–7; Brodie D. et al. (2000) *Curr. Biol.* 10:333–6; Ling V. et al. (2000) *J. Immunol.* 164:1653–7; Yoshinaga S. K. et al. (1999) *Nature* 402:827–32). If T cells are only stimulated through the T cell receptor, without receiving an additional costimulatory signal, they become nonresponsive, anergic, or die, resulting in downmodulation of the immune response.

The importance of the B7:CD28/CTLA4 costimulatory pathway has been demonstrated in vitro and in several in vivo model systems. Blockage of this costimulatory pathway results in the development of antigen specific tolerance in murine and human systems (Harding, F. A. et al. (1992) *Nature* 356:607–609; Lenschow, D. J. et al. (1992) *Science* 257:789–792; Turka, L. A. et al. (1992) *Proc. Natl. Acad. Sci. USA* 89:11102–11105; Gimmi, C. D. et al. (1993) *Proc. Natl. Acad. Sci. USA* 90:6586–6590; Boussiotis, V. et al. (1993) *J. Exp. Med.* 178:1753–1763). Conversely, expression of B7 by B7 negative murine tumor cells induces T-cell mediated specific immunity accompanied by tumor rejection and long lasting protection to tumor challenge (Chen, L. et al. (1992) *Cell* 71:1093–1102; Townsend, S. E. and Allison, J. P. (1993) *Science* 259:368–370; Baskar, S. et al. (1993) *Proc. Natl. Acad. Sci.* 90:5687–5690.). Therefore, manipulation of the costimulatory pathways offers great potential to stimulate or suppress immune responses in humans.

SUMMARY OF THE INVENTION

The present invention is based, at least in part, on the discovery that agents that modulate the interaction between PD-1 and its ligands (PD-L1 and PD-L2) are useful in the downmodulation of the immune response, e.g., in autoimmune disease. PD-1 is a receptor for PD-L1 and PD-L2 molecules expressed on antigen presenting cells. PD-1 transmits a negative signal to immune cells, similar to CTLA4. PD-1 ligands (e.g., PD-L1 and PD-L2) are expressed on the surface of antigen presenting cells and provide a costimulatory signal to immune cells and can transmit downmodulatory signals to immune cells, depending upon the molecule to which they bind. Thus, modulation of PD-1 or PD-L1/PD-L2, and/or the interaction between PD-1 and PD-L1 and/or PD-L2 results in modulation of the immune response.

Accordingly, in one aspect, the invention pertains to a method for downmodulating activation of an immune cell, comprising contacting an immune cell, at the time of contact with antigen, with an agent that modulates signaling via PD-1 to thereby downmodulate activation of an immune cell.

In one embodiment, the agent is selected from the group consisting of: an antibody that transmits an inhibitory signal via PD-1, a soluble form of PD-1, a soluble form of PD-L1, a soluble form of PD-L2, a soluble form of PD-L1 and a soluble form of PD-L2, an antibody to PD-L1, an antibody to PD-L2, an antibody to PD-L1 and an antibody PD-L2, and a small molecule that transmits an inhibitory signal via PD-1.

In one embodiment, the agent is selected from the group consisting of: a soluble form of PD-L1, a soluble form of PD-L2, and a combination of a soluble form of PD-L1 and PD-L2.

In one embodiment, the antibody that transmits an inhibitory signal via PD-1 is a bivalent antibody that also recognizes an activating receptor.

In another embodiment, the immune cell is a T cell. In one embodiment, the T cell is a naïve T cell.

In another embodiment, the immune cell is a T cell and the activating receptor is a T cell receptor.

In one embodiment, anergy is induced in the immune cell.

In another embodiment, the method further comprises contacting the immune cell with an additional agent that downregulates an immune response.

In one embodiment, the step of contacting occurs in vivo.

In another embodiment, the step of contacting occurs in vitro.

In another aspect, the invention pertains to a method of downmodulating activation of an activated T cell from a subject having an autoimmune disorder mediated by activated T cells, comprising contacting a T cell from the subject with an antibody that binds to PD-1 such that activation of an activated T cell from a subject having an autoimmune disorder mediated by activated T cells is downmodulated.

In one embodiment, the antibody transmits an inhibitory signal via PD-1.

In one embodiment, the antibody that transmits an inhibitory signal via PD-1 is a bivalent antibody that also recognizes the T cell receptor.

In another embodiment, the autoimmune disorder is multiple sclerosis.

In yet another embodiment, the method further comprises contacting an immune cell from the subject with an additional agent that downregulates an immune response.

In one embodiment, the step of contacting occurs in vivo. In another embodiment, the step of contacting occurs in vitro.

BRIEF DESCRIPTION OF THE DRAWINGS

FIG. 1 depicts the nucleotide sequence encoding a human secreted PD-L1, PD-L1S (SEQ ID NO: 1).

FIG. 2 depicts the nucleotide sequence encoding a human PD-L1, PD-L1M (SEQ ID NO: 3).

FIG. 3 depicts the amino acid sequence of human PD-L1S (SEQ ID NO: 2) and illustrates the signal, IgV, IgC, and hydrophilic tail domains.

FIG. 4 depicts the amino acid sequence of human PD-L1M (SEQ ID NO: 4) and illustrates the signal, IgV, IgC, and transmembrane and cytoplasmic domains.

FIGS. 5A–5B depict the nucleotide sequence of murine PD-L1 (SEQ ID NO: 22).

FIG. 6 depicts the amino acid sequence of murine PD-L1 (SEQ ID NO: 23).

FIG. 7 depicts an alignment of the human PD-L1M and murine PD-L1 amino acid sequences (SEQ ID NO: 4 and 23, respectively).

FIG. 8 illustrates the results of FACS analysis of binding of CD28Ig, CTLA4-Ig, and control Ig by PD-L1M-transfected COS cells.

FIGS. 15A–15L illustrate the ability of PD-1 to bind to PD-L1 transfected CHO cells, as determined by flow cytometry.

FIGS. 20A–20I illustrate the binding of PD-1 to CHO cells expressing PD-L1.

FIGS. 22A–22D illustrate the inhibition of cytokine production by the PD-1:PD-L1 pathway, as measured by cytokine ELISA.

FIGS. 28A–28B illustrate the effect of PD-1:PD-L1 interaction on mitotic cell division. T cells were labeled with CSFE and stimulated with ctrl.Fc or mPD-L1.Fc beads. At the indicated time points, FACS analysis was done. Live-gated events are depicted. FIG. 28A: CD4+ T cells. FIG. 28B: CD8+ T cells. PD-1:PD-L1 interaction results in decreased mitotic divisions of both CD4+ and CD8+ T cells.

FIG. 29A illustrates schematically the cell lines and the experimental design. Stable antigen presenting cell (APC) lines were engineered to express GFP or mPD-L 1/GFP using retroviral technology. $5 \times 10^4$ purified LN T cells from TCR transgenic (Tg) mice were stimulated with APC plus peptide for 2, 2–3, 3, or 4 days. For experiments involving CD4+ T cells, the APC:T cell ratio was 1:10 with 10 μM PCCF peptide. For experiments involving CD8+ T cells, the APC:T cell ration was 1:1 with 1 mM p2Ca peptide. FIG. 29B illustrates the inhibition of proliferation of CD4+ T cells by PD-1:PD-L1 interaction. FIG. 29C illustrates the inhibition of proliferation of CD8+ T cells by PD-1:PD-L1 interaction.

FIG. 30A: CD4+ T cells. FIG. 30B: CD8+ T cells.

FIGS. 31A–31B illustrate schematically a screening assay used to identify proteins involved in the PD-1 signaling pathway. FIG. 31A depicts a schematic of the steps of the assay. FIG. 31B depicts the sequences of a fragment of human PD-1 (SEQ ID NO: 24), a fragment of mouse PD-1 (SEQ ID NO: 25) and the peptides used in the assay. Peptides used in the assay were the ITIM peptides: PD-1_Py1 (SEQ ID NO: 26); PD-1_Y1F (SEQ ID NO: 27); PD-1_Yi (SEQ ID NO: 28); PD-1 Py2 (SEQ ID NO: 29); PD-1_Y2F (SEQ ID NO: 30); PD-1_Y2 (SEQ ID NO: 31); and Other Peptides: PD-1_K212_(SEQ ID NO: 32); PD-1_K212D (SEQ ID NO: 33); PD-1_K335 (SEQ ID NO: 34); PD-1_K335D (SEQ ID NO: 35); PD-1_Ctail1 (SEQ ID NO: 36); and PD-1_Ctail2 (SEQ ID NO: 37).

DETAILED DESCRIPTION OF THE INVENTION

Figure 9:
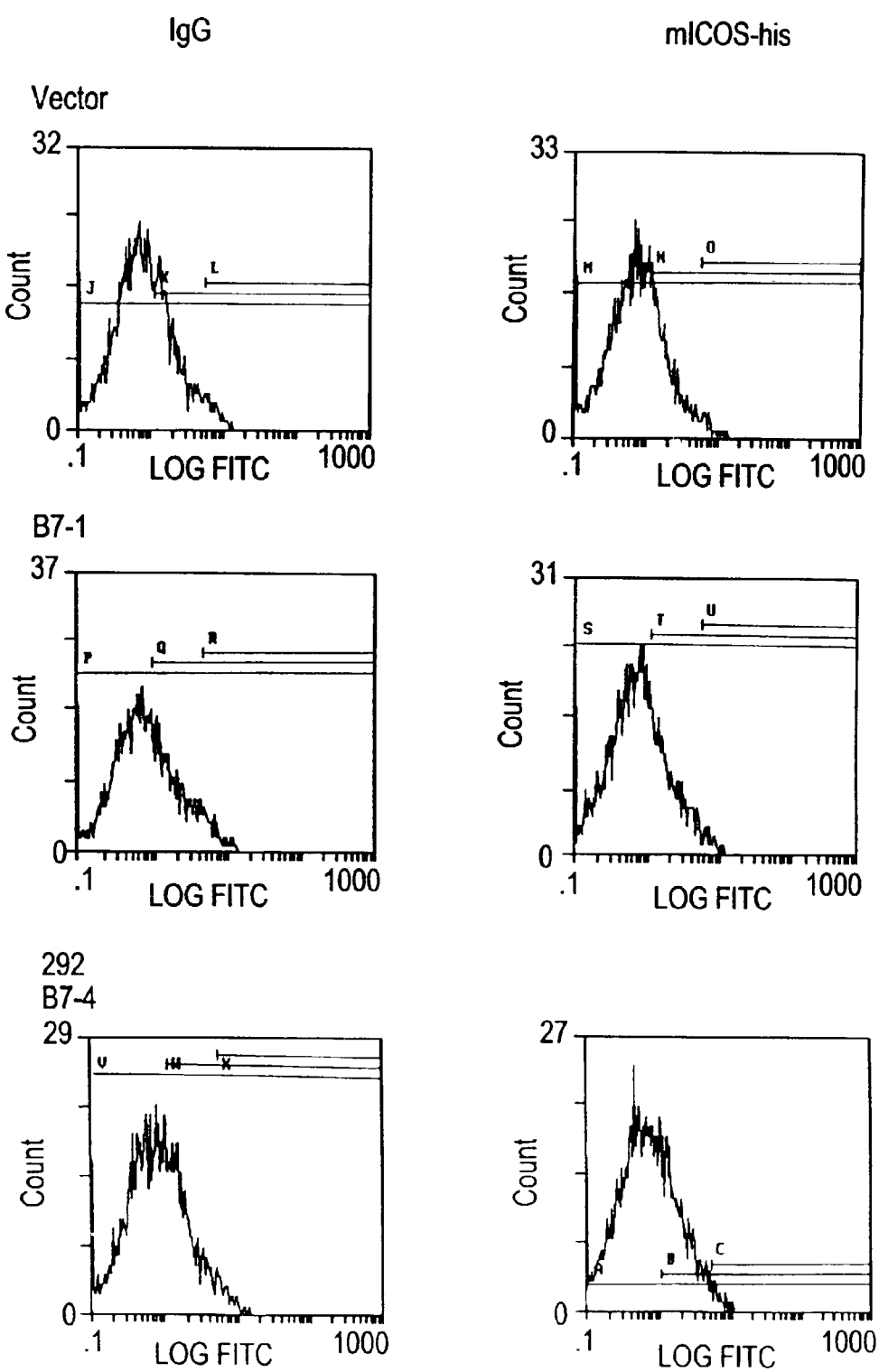
FIG. 9 illustrates the results of FACS analysis of binding of IgG and murine ICOS-his fusion protein by PD-L1M-transfected COS cells.

In addition to the previously characterized B lymphocyte activation antigens, e.g., B7-1 and B7-2, there are other antigens on the surface of antigen presenting cells which modulate costimulation of immune cells. For example, PD-L1 and PD-L2 have been identified as ligands for PD-1 (Freeman et al. 2000, J. Exp. Med. 192:1027; Latchman et al. 2001. Nature Immunology 2: 261–268).

Immune cells have receptors that transmit activating signals. For example, T cells have T cell receptors and the CD3 complex, B cells have B cell receptors, and myeloid cells have Fc receptors. In addition, immune cells bear receptors that transmit signals that provide costimulatory signals or receptors that transmit signals that inhibit receptor-mediated signaling. For example, CD28 transmits a costimulatory signal to T cells. After ligation of the T cell receptor, ligation of CD28 results in a costimulatory signal characterized by, e.g., upregulation of IL-2rα, IL-2rβ, and IL-2rγ receptor, increased transcription of IL-2 messenger RNA, and increased expression of cytokine genes (including IL-2, IFN-γ, GM-CSF, and TNF-α). Transmission of a costimulatory signal allows the cell to progress through the cell cycle and, thus, increases T cell proliferation (Greenfield et al. (1998) Crit. Rev. Immunol. 18:389). Binding of a receptor on a T cell which transmits a costimulatory signal to the cell (e.g., ligation of a costimulatory receptor that leads to cytokine secretion and/or proliferation of the T cell) by a B7 family molecule, such as PD-L1, results in costimulation. Thus, inhibition of an interaction between a B7 family molecule, such as PD-L1, and a receptor that transmits a costimulatory signal on an immune cell results in a downmodulation of the immune response and/or specific unresponsiveness, termed immune cell anergy. Inhibition of this interaction can be accomplished using, e.g., soluble forms of PD-1 ligands, anti-CD28 Fab fragments, antibodies to B7-1 and/or B7-2, antibodies to PD-L2 and/or PD-L1, or by using a soluble form of a receptor to which a B7 family member molecule can bind as a competitive inhibitor (e.g., PD-1 Ig, CTLA4Ig). As shown herein, agents that inhibit or reduce the interaction between B7 family molecules (e.g., B7-1, B7-2, PD-L1 and PD-L2) and costimulatory molecules (e.g., CD28 or a costimulatory molecule that binds to PD-L1 and/or PD-L2) decrease immune response and are particularly effective when used at the time of priming.

Inhibitory receptors that bind to costimulatory molecules have also been identified on immune cells. Activation of CTLA4, for example, transmits a negative signal to a T cell. Engagement of CTLA4 inhibits IL-2 production and can induce cell cycle arrest (Krummel and Allison (1996) J. Exp. Med. 183:2533). In addition, mice that lack CTLA4 develop lymphoproliferative disease (Tivol et al. (1995) Immunity 3:541; Waterhouse et al. (1995) Science 270:985). The blockade of CTLA4 with antibodies may remove an inhibitory signal, whereas aggregation of CTLA4 with antibody transmits an inhibitory signal. Therefore, depending upon the receptor to which a costimulatory molecule binds (i.e., a costimulatory receptor such as CD28 or an inhibitory receptor such as CTLA4), certain B7 molecules including PD-L1 can promote T cell costimulation or inhibition.

PD-1 is a member of the immunoglobulin family of molecules (Ishida et al. (1992) EMBO J. 11:3887; Shinohara et al. (1994) Genomics 23:704). PD-1 was previously identified using a subtraction cloning based approach designed to identify modulators of programmed cell death (Ishida et al. (1992) EMBO J. 11:3887–95; Woronicz et al. (1995) Curr. Top. Microbiol. Immunol. 200:137). PD-1 is believed to play a role of lymphocyte survival, e.g., during clonal selection (Honjo (1992) Science 258:591; Agata et al. (1996) Int. Immunology 8:765; Nishimura et al. (1996) Int. Immunology 8:773). PD-1 was also implicated as a regulator of B cell responses (Nishimura (1998) Int. Immunology 10:1563). Unlike CTLA4, which is found only on T cells, PD-1 is also found on B cells and myeloid cells.

The fact that PD-1 binds to PD-L1/PD-L2 places PD-1 in a family of inhibitory receptors with CTLA4. While engagement (to produce activation) of a costimulatory receptor results in a costimulatory signal in an immune cell, engagement of an inhibitory receptor, e.g., CTLA4 or PD-1 (for example by crosslinking or by aggregation, e.g., using an antibody), leads to the transmission of an inhibitory signal in an immune cell, resulting in downmodulation of immune cell responses and/or in immune cell anergy. As shown herein, Agents that inhibit or reduce the interaction between B7 family members (e.g., B7-1, B7-2, PD-L1 and/or PD-L2) and inhibitory molecules (e.g., CTLA4 or PD-1) also modulate immune responses. While transmission of an inhibitory signal leads to downmodulation in immune cell responses (and a resulting downmodulation in the overall immune response), the prevention of an inhibitory signal (e.g., by using a non-activating antibody against PD-1, i.e. an antibody that does not transmit an inhibitory signal via PD-1, for example because it does not cross-link PD-1) in immune cells leads to upmodulation of immune cell responses (and a resulting upmodulation of an immune response).

The instant invention makes available agents useful for modulating the interaction between PD-1 and its natural ligand(s) (e.g., PD-L2 and/or PD-L1), and agents for modulating the immune response via modulation of the interaction between PD-L2 and/or PD-L1 and PD-1. Exemplary modulatory agents for use in these methods are described further as follows.

PD-1 Ligands and PD-1: Nucleic Acid and Polypeptide Molecules

In one embodiment, a modulatory agent useful for modulating the activity and/or expression of PD-1 is a PD-L2 and/or PD-L1 and/or PD-1 nucleic acid molecule, preferably a human PD-L2 and/or PD-L1 and/or PD-1 nucleic acid molecule.

In one embodiment, the isolated nucleic acid molecules of the present invention encode eukaryotic PD-L2, PD-L1 or PD-1 polypeptides. The PD-1 ligands, PD-L2/PD-L1 molecules, are members of the B7 family of molecules and share a number of conserved regions, including signal domains, IgV domains and the IgC domains. IgV domains and the IgC domains are art recognized Ig superfamily member domains. These domains correspond to structural units that have distinct folding patterns called Ig folds. Ig folds are comprised of a sandwich of two β sheets, each consisting of antiparallel β strands of 5–10 amino acids with a conserved disulfide bond between the two sheets in most, but not all, domains. IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than C-domains and form an additional pair of β strands.

Two forms of human PD-L1 molecules have been identified. PD-L1 is described in (Freeman et al. *J. Exp. Med.* 2000. 192:1027; Dong et al. 1999. *Nature Medicine.* 5:1365). One form is a naturally occurring PD-L1 soluble polypeptide, i.e., having a short hydrophilic domain and no transmembrane domain, and is referred to herein as PD-L1S (shown in SEQ ID NO:2). The second form is a cell-associated polypeptide, i.e., having a transmembrane and cytoplasmic domain, referred to herein as PD-L1M (shown in SEQ ID NO:4).

PD-L1 proteins comprise a signal sequence, and an IgV domain and an IgC domain. The signal sequence of SEQ ID NO:2 is shown from about amino acid 1 to about amino acid 18. The signal sequence of SEQ ID NO:4 is shown from about amino acid 1 to about amino acid 18. The IgV domain of SEQ ID NO:2 is shown from about amino acid 19 to about amino acid 134 and the IgV domain of SEQ ID NO:4 is shown from about amino acid 19 to about amino acid 134. The IgC domain of SEQ ID NO:2 is shown from about amino acid 135 to about amino acid 227 and the IgC domain of SEQ ID NO:4 is shown from about amino acid 135 to about amino acid 227. The hydrophilic tail of the PD-L1 exemplified in SEQ ID NO:2 comprises a hydrophilic tail shown from about amino acid 228 to about amino acid 245. The PD-L1 polypeptide exemplified in SEQ ID NO:4 comprises a transmembrane domain shown from about amino acids 239 to about amino acid 259 of SEQ ID NO:4 and a cytoplasmic domain shown from about amino acid 260 to about amino acid 290 of SEQ ID NO:4.

Murine PD-L1 molecules were also identified. The murine cDNA sequence is presented in FIGS. 5A–5B and the murine PD-L1 amino acid sequence is presented in FIG. 6. The present invention also pertains to these murine PD-L1 molecules.

PD-L2 molecules have also been identified. (Latchman et al. 2001. *Nature Immunology.* 2:1). The nucleotide sequence of a cDNA encoding human PD-L2 is provided as SEQ ID NO: 38, and the amino acid sequence of human PD-L2 is provided as SEQ ID NO: 39. These are also available as Genbank Accession number AF344424, disclosed in Latchman et al. (2001. *Nature Immunology.* 2: 261–268).

PD-1 molecules are members of the immunoglobulin gene superfamily. PD-1 (Ishida et al. (1992) *EMBO J.* 11:3887; Shinohara et al. (1994) *Genomics* 23:704; U.S. Pat. No. 5,698,520) has an extracellular region containing immunoglobulin superfamily domain, a transmembrane domain, and an intracellular region including an immunoreceptor tyrosine-based inhibitory motif (ITIM). These features also define a larger family of molecules, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM motif of these receptors interacts with SH2-domain containing phosphatases, which leads to inhibitory signals. A subset of these immunoinhibitory receptors bind to MHC molecules, for example the KIRs, and CTLA4 bind to B7-1 and B7-2. It has been proposed that there is a phylogenetic relationship between the MHC and B7 genes (Henry et al. (1999) *Immunol. Today* 20(6):285–8).

The nucleotide sequence of PD-1 is shown in SEQ ID NO:10 and 11 and the amino acid sequence of PD-1 is shown in SEQ ID NO:12 (see also Ishida et al. (1992) *EMBO J.* 11:3887; Shinohara et al. (1994) *Genomics* 23:704; U.S. Pat. No. 5,698,520). PD-1 was previously identified using a subtraction cloning based approach to select for proteins involved in apoptotic cell death. PD-1 is identified herein as a member of the CD28/CTLA-4 family of molecules based on its ability to bind to PD-L1. Like CTLA4, PD-1 is rapidly induced on the surface of T-cells in response to anti-CD3 (Agata et al. (1996) *Int. Immunol.* 8:765). In contrast to CTLA4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

Various aspects of the invention are described in further detail in the following subsections:

I. Definitions

As used herein, the term "immune cell" includes cells that are of hematopoietic origin and that play a role in the immune response. Immune cells include lymphocytes, such as B cells and T cells; natural killer cells; myeloid cells, such as monocytes, macrophages, eosinophils, mast cells, basophils, and granulocytes.

As used herein, the term "T cell" includes cells bearing a T cell receptor (TCR). Preferably, the term "T cell" includes CD4+ T cells and/or CD8+ T cells. The term T cell also includes both T helper 1 type T cells and T helper 2 type T cells. In one embodiment, a T cell of the invention is a naïve T cell, i.e., not an activated or memory T cell. In one embodiment, a T cell of the invention is an activated or memory T cell. These cells can be distinguished using cell markers known in the art. For example, activated T cells express markers such as CD152 and CD154. Activated T cells also can be characterized by their enhanced ability to produce cytokines, proliferate, or perform certain effector functions.

The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "priming" includes exposing an immune cell, e.g., a T cell, to an antigen to produce an activated T cell (a memory-effector cell) that is capable of a heightened response upon reexposure to the antigen. Naïve T cells express high levels of L-selectin, which causes them to recirculate through lymph nodes. Naïve T cells specific for any given antigen are few in number, do not exhibit high antigen responsiveness, and do not express surface markers found only on activated T cells.

As used herein, the term "immune response" includes T cell mediated and/or B cell mediated immune responses that are influenced by modulation of T cell costimulation. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "costimulatory receptor" includes receptors which transmit a costimulatory signal to a immune cell, e.g., CD28. As used herein, the term "inhibitory receptors" includes receptors which transmit a negative signal to an immune cell (e.g., CTLA4 or PD-1). An inhibitory signal as transduced by an inhibitory receptor can occur even if a costimulatory receptor (such as CD28) in not present on the immune cell and, thus, is not simply a function of competition between inhibitory receptors and costimulatory receptors for binding of costimulatory molecules (Fallarino et al. (1998) *J. Exp. Med.* 188:205). Transmission of an inhibitory signal to an immune cell can result in unresponsiveness or anergy or programmed cell death in the immune cell. Preferably transmission of an inhibitory signal operates through a mechanism that does not involve apoptosis. As used herein the term "apoptosis" includes programmed cell death which can be characterized using techniques which are known in the art. Apoptotic cell death can be characterized, e.g., by cell shrinkage, membrane blebbing and chromatin condensation culminating in cell fragmentation. Cells undergoing apoptosis also display a characteristics pattern of internucleosomal DNA cleavage.

Depending upon the form of the PD-1 ligand molecule that binds to a receptor, either a signal can be transmitted or stimulated (e.g., by a multivalent form of a PD-1 ligand molecule that results in crosslinking of receptor) or a signal can be inhibited (e.g., by a soluble, monovalent form of a PD-1 ligand), e.g., by competing with activating forms PD-1 ligands for binding to the receptor. However, there are instances in which a soluble molecule can be stimulatory. The effects of the various modulatory agents can be easily demonstrated using routine screening assays as described herein.

As used herein, the term "costimulate" with reference to immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

As used herein, the term "activating receptor" includes immune cell receptors that bind antigen, complexed antigen (e.g., in the context of MHC molecules), or bind to antibodies. Such activating receptors include T cell receptors (TCR), B cell receptors (BCR), cytokine receptors, LPS receptors, complement receptors, and Fc receptors.

For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription change, protein synthesis changes, and cell volume changes.

B cell receptors are present on B cells. B cell antigen receptors are a complex between membrane Ig (mIg) and other transmembrane polypeptides (e.g., Igα and Igβ). The signal transduction function of mIg is triggered by crosslinking of receptor molecules by oligomeric or multimeric antigens. B cells can also be activated by anti-immunoglobulin antibodies. Upon BCR activation, numerous changes occur in B cells, including tyrosine phosphorylation.

Fc receptors are found on many cells which participate in immune responses. Fc receptors (FcRs) are cell surface receptors for the Fc portion of immunoglobulin molecules (Igs). Among the human FcRs that have been identified so far are those which recognize IgG (designated Fcγ R), IgE (Fcε R1), IgA (Fcα), and polymerized IgM/A (Fcμα R). FcRs are found in the following cell types: Fcε R I (mast cells), Fcε R.II (many leukocytes), Fcα R (neutrophils), and Fcμα R (glandular epithelium, hepatocytes) (Hogg, N. (1988) *Immunol. Today* 9:185–86). The widely studied FcγRs are central in cellular immune defenses, and are responsible for stimulating the release of mediators of inflammation and hydrolytic enzymes involved in the pathogenesis of autoimmune disease (Unkeless, J. C. et al. (1988) *Annu. Rev. Immunol.* 6:251–81). The FcγRs provide a crucial link between effector cells and the lymphocytes that secrete Ig, since the macrophage/monocyte, polymorphonuclear leukocyte, and natural killer (NK) cell FcγRs confer an element of specific recognition mediated by IgG. Human leukocytes have at least three different receptors for IgG: h Fcγ RI (found on monocytes/macrophages), hFcγ RII (on monocytes, neutrophils, eosinophils, platelets, possibly B cells, and the K562 cell line), and Fcγ III (on NK cells, neutrophils, eosinophils, and macrophages).

With respect to T cells, transmission of a costimulatory signal to a T cell involves a signaling pathway that is not inhibited by cyclosporine A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

As used herein, the term "inhibitory signal" refers to a signal transmitted via an inhibitory receptor (e.g., CTLA4 or PD-1) for a molecule on a immune cell. Such a signal antagonizes a signal produced by an activating receptor (e.g., via TCR, CD3, BCR, or Fc molecule) and can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule)

results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

The PD-1 ligand protein and nucleic acid molecules comprise a family of molecules having certain conserved structural and functional features. Similarly, the PD-1 protein and nucleic acid molecules are members of a family of molecules having conserved structural and functional features. The term "family" when referring to the protein and nucleic acid molecules is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. The PD-1 ligands described herein are members of the B7 family of molecules. The term "B7 family" or "B7 molecules" as used herein includes costimulatory molecules that share sequence homology with B7 polypeptides, e.g., with B7-1, B7-2, B7-3 (recognized by the antibody BB-1), B7h (Swallow et al. (1999) *Immunity* 11:423), and/or PD-1 ligand. For example, human B7-1 and B7-2 share approximately 26% amino acid sequence identity when compared using the BLAST program at NCBI with the default parameters (Blosum62 matrix with gap penalties set at existence 11 and extension 1 (See the NCBI website)).

Preferred B7 polypeptides are capable of providing costimulatory or inhibitory signals to immune cells to thereby promote or inhibit immune cell responses. For example, when bound to a costimulatory receptor, PD-1 ligand can induce costimulation of immune cells or can inhibit immune cell costimulation, e.g., when present in soluble form. When bound to an inhibitory receptor, PD-1 ligands can transmit an inhibitory signal to an immune cell. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

Preferred PD-1 molecules are capable of transmitting an inhibitory signal to an immune cell to thereby inhibit immune cell effector function or are capable of promoting costimulation (e.g., by competitive inhibition) of immune cells, e.g., when present in soluble, monomeric form. Preferred PD-1 family members bind to one or more receptors, e.g., B7-1, B7-2, PD-1 ligand, and/or other molecules on antigen presenting cells, and share sequence identity with PD-1.

In addition, in one embodiment, proteins that are members of a protein family are bound by antibodies generated against one or more other family member proteins.

As used herein, the term "activity" with respect to a PD-1 ligand or PD-1 polypeptide includes activities which are inherent in the structure of a PD-1 ligand or PD-1 protein. With regard to PD-1 ligand, the term "activity" includes the ability to modulate immune cell costimulation, e.g., by modulating a costimulatory signal in an immune cell, or to modulate inhibition by modulating an inhibitory signal in an immune cell, e.g., by engaging a natural receptor on a immune cell. When an activating form of the PD-1 ligand binds to a costimulatory receptor, a costimulatory signal is generated in the immune cell. When an activating form of the PD-1 ligand binds to an inhibitory receptor, an inhibitory signal is generated in the immune cell.

Modulation of a costimulatory signal results in modulation of effector function of an immune cell. Thus, the term "PD-1 ligand activity" includes the ability of a PD-1 ligand polypeptide to bind its natural receptor(s), the ability to modulate immune cell costimulatory or inhibitory signals, and the ability to modulate the immune response.

With respect to PD-1, the term "activity" includes the ability of a PD-1 polypeptide to modulate an inhibitory signal in an immune cell, e.g., by engaging a natural ligand on an antigen presenting cell. PD-1 transmits an inhibitory signal to an immune cell in a manner similar to CTLA4. Modulation of an inhibitory signal in an immune cell results in modulation of proliferation of and/or cytokine secretion by an immune cell. PD-1 can also modulate a costimulatory signal by competing with a costimulatory receptor for binding of a B7 molecule. Thus, the term "PD-1 activity" includes the ability of a PD-1 polypeptide to bind its natural ligand(s), the ability to modulate immune cell costimulatory or inhibitory signals, and the ability to modulate the immune response.

As used herein, a "naturally-occurring" nucleic acid molecule refers to an RNA or DNA molecule having a nucleotide sequence that occurs in nature (e.g., encodes a natural protein).

As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can hydrogen bond to a sense nucleic acid molecule.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

As used herein, the term "vector" refers to a nucleic acid molecule capable of transporting another nucleic acid molecule to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid molecule of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" refers to a protein that is substantially free of other proteins, cellular material and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the PD-1 ligand or PD-1 protein is derived, or substantially free from chemical precursors or other chemicals when chemically synthesized. The language "substantially free of cellular material" includes preparations of PD-1 ligand or PD-1 protein in which the protein is separated from cellular components of the cells from which it is isolated or recombinantly produced. In one embodiment, the language "substantially free of cellular material" includes preparations of PD-1 ligand or PD-1 protein having less than about 30% (by dry weight) of non-PD-1 ligand or PD-1 protein (also referred to herein as a "contaminating protein"), more preferably less than about 20% of non-PD-1 ligand or PD-1 protein, still more preferably less than about 10% of non-PD-1 ligand or PD-1 protein, and most preferably less than about 5% non-PD-1 ligand or PD-1 protein. When the PD-1 ligand or PD-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of PD-1 ligand or PD-1 protein in which the protein is separated from chemical precursors or other chemicals which are involved in the synthesis of the protein. In one embodiment, the language "substantially free of chemical precursors or other chemicals" includes preparations of PD-1 ligand or PD-1 protein having less than about 30% (by dry weight) of chemical precursors or non-PD-1 ligand or PD-1 chemicals, more preferably less than about 20% chemical precursors or non-PD-1 ligand or PD-1 chemicals, still more preferably less than about 10% chemical precursors or non-PD-1 ligand or PD-1 chemicals, and most preferably less than about 5% chemical precursors or non-PD-1 ligand or PD-1 chemicals.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., PD-1 ligand). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883; and Osbourn et al. (1998) *Nat. Biotechnol.* 16:778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG molecules or other isotypes. VH and Vl can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P. et al. (1993) *Proc. Natl. Acad. Sci. USA* 90:6444–6448; Poljak, R. J. et al. (1994) *Structure* 2:1121–1123).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93–101) and use of a cysteine residue, a marker peptide and a C-terminal poly-histidine tag to make bivalent and biotinylated scFv molecules (Kipriyanov, S. M., et al. (1994) *Mol. Immunol.* 31:1047–1058). Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

Antibodies may be polyclonal or monoclonal; xenogeneic, allogeneic, or syngeneic; or modified forms thereof, e.g., humanized, chimeric, etc. Preferably, antibodies of the invention bind specifically or substantially specifically to PD-1 ligands. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacting with a particular antigen. A monoclonal antibody composition, typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds PD-1 ligand is substantially free of antibodies that specifically bind antigens other than PD-1 ligand). Moreover, an isolated antibody may be substantially free of other cellular material and/or chemicals.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a PD-1 ligand or PD-1 polypeptide of the invention (or any portion thereof) can be used to derive the PD-1 ligand or PD-1 amino acid sequence, using the genetic code to translate the DNA or RNA molecule into an amino acid sequence. Likewise, for any PD-1 ligand or PD-1-amino acid sequence, corresponding nucleotide sequences that can encode PD-1 ligand or PD-1 protein can be deduced from the genetic code (which, because of its redundancy, will produce multiple nucleic acid sequences for any given amino acid sequence). Thus, description and/or disclosure herein of a PD-1 ligand or PD-1 nucleotide sequence should be considered to also include description and/or disclosure of the amino acid sequence encoded by the nucleotide sequence. Similarly, description and/or disclosure of a PD-1 ligand or PD-1 amino acid sequence herein should be considered to also include description and/or disclosure of all possible nucleotide sequences that can encode the amino acid sequence.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. *Science* 282:63), and natural product extract libraries. In another embodiment, the compounds are small, organic non-peptidic compounds. In a further embodiment, a small molecule is not biosynthetic.

II. Isolated Nucleic Acid Molecules

In one embodiment, modulating agents for use in the claimed methods comprise isolated nucleic acid molecules that encode PD-1 ligand or PD-1 proteins or biologically active portions thereof. Nucleic acid fragments sufficient for use as hybridization probes to identify PD-1 ligand or PD-1-encoding nucleic acids (e.g., PD-1 ligand or PD-1 mRNA) and fragments for use as PCR primers for the amplification or mutation of PD-1 ligand or PD-1 nucleic acid molecules are also provided. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. For example, with regards to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule (i.e., sequences located at the 5' and 3' ends of the nucleic acid) in the genomic DNA of the organism from which the nucleic acid molecule is derived. For example, in various embodiments, the isolated PD-1 ligand or PD-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. An "isolated" PD-1 ligand or PD-1 nucleic acid molecule may, however, be linked to other nucleotide sequences that do not normally flank the PD-1 ligand or PD-1 sequences in genomic DNA (e.g., the PD-1 ligand or PD-1 nucleotide sequences may be linked to vector sequences). In certain preferred embodiments, an "isolated" nucleic acid molecule, such as a cDNA molecule, also may be free of other cellular material. However, it is not necessary for the PD-1 ligand or PD-1 nucleic acid molecule to be free of other cellular material to be considered "isolated" (e.g., a PD-1 ligand or PD-1 DNA molecule separated from other mammalian DNA and inserted into a bacterial cell would still be considered to be "isolated").

A nucleic acid molecule of the present invention, e.g., a nucleic acid molecule having the nucleotide sequence of SEQ ID NO:1, 3, 10, 11, or 38 or a portion thereof, can be isolated using standard molecular biology techniques and the sequence information provided herein. For example, using all or portion of the nucleic acid sequence of SEQ ID NO:1, 3, 10, 11, or 38, as a hybridization probe, PD-1 ligand or PD-1 nucleic acid molecules can be isolated using standard hybridization and cloning techniques (e.g., as described in Sambrook, J. et al. *Molecular Cloning: A Laboratory Manual. 2nd, ed., Cold Spring Harbor Laboratory,* Cold Spring Harbor Laboratory Press, Cold Spring Harbor, N.Y., 1989).

Moreover, a nucleic acid molecule encompassing all or a portion of SEQ ID NO:1, 3, 10, 11, or 38 can be isolated by the polymerase chain reaction (PCR) using synthetic oligonucleotide primers designed based upon the sequence of SEQ ID NO:1, 3, 10, 11, or 38, respectively.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to PD-1 ligand or PD-1 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1, 3, 10, 11, or 38.

In another preferred embodiment, an isolated nucleic acid molecule of the invention comprises a nucleic acid molecule which is a complement of the nucleotide sequence shown in SEQ ID NO:1, 3, 10, 11, or 38, or a portion of any of these nucleotide sequences. A nucleic acid molecule which is complementary to the nucleotide sequence shown in SEQ ID NO:1, 3, 10, 11, or 38, is one which is sufficiently complementary to the nucleotide sequence shown in SEQ ID NO:1, 3, 10, 11, or 38, respectively, such that it can hybridize to the nucleotide sequence shown in SEQ ID NO:1, 3, 10, 11, or 38, respectively, thereby forming a stable duplex. An exact complement is 100% complementary to a specified nucleotide sequence. In still another preferred embodiment, an isolated nucleic acid molecule of the present invention comprises a nucleotide sequence which is at least about 50%, 55%, 60%, 65%, 70%, 75%, 80%, 85%, 90%, 95%, 98% or more homologous to the nucleotide sequence (e.g., to the entire length of the nucleotide sequence) shown in SEQ ID NO:1, 3, 10, 11, or 38, or a portion of any of these nucleotide sequences.

Moreover, the nucleic acid molecule of the invention can comprise only a portion of the nucleic acid sequence of SEQ ID NO:1, 3, 10, 11, or 38, for example a fragment which can be used as a probe or primer or a fragment encoding a biologically active portion of a PD-1 ligand or PD-1 protein. The nucleotide sequence determined from the cloning of the PD-1 ligand or PD-1 genes allows for the generation of probes and primers designed for use in identifying and/or cloning other PD-1 ligand or PD-1 family members, as well as PD-1 ligand or PD-1 family homologues from other species. The probe/primer typically comprises a substantially purified oligonucleotide. The oligonucleotide typically comprises a region of nucleotide sequence that hybridizes under stringent conditions to at least about 12 or 15, preferably about 20 to 25, more preferably about 30, 35, 40, 45, 50, 55, 60, 65, or 75 consecutive nucleotides of a sense sequence of SEQ ID NO:1, 3, 10, 11, or 38, or of a naturally occurring allelic variant or mutant of SEQ ID NO:1, 3, 10, 11, or 38. In an exemplary embodiment, a nucleic acid molecule of the present invention comprises a nucleotide sequence which is at least 350, 400, 450, 500, 550, 600, 650, 700, 750, or 800 nucleotides in length and hybridizes under stringent hybridization conditions to a nucleic acid molecule of SEQ ID NO:1, 3, 10, 11, or 38.

In another embodiment, a second nucleic acid molecule comprises at least about 500, 600, 700, 800, 900, or 1000 contiguous nucleotides of SEQ ID NO:1, 3, 10, 11, or 38.

In one embodiment, a nucleic acid molecule of the invention, e.g., for use as a probe, does not include the portion of SEQ ID NO:1 from about nucleotides 815 to about 850 of SEQ ID NO:1 or about nucleotides 320 to 856 of SEQ ID NO:1. In another embodiment, a nucleic acid molecule of the invention does not include the portion of SEQ ID NO:3 from about nucleotides 314 to about 734, or from about nucleotides 835 to about 860, or from about nucleotides 1085 to about 1104 or from about nucleotides 1286 to about 1536 of SEQ ID NO:3.

In one embodiment, a nucleic acid molecule of the invention comprises at least about 500 contiguous nucleotides of SEQ ID NO:1 or SEQ ID NO:3. In a preferred embodiment, a nucleic acid molecule of the invention comprises at least about 600, at least about 700, at least about 800, at least about 900 or at least about 950 contiguous nucleotides of SEQ ID NO:1 or about 1000 contiguous nucleotides of SEQ ID NO:3. In another embodiment, a nucleic acid molecule of the invention comprises at least about 1500 or 1550 nucleotides of SEQ ID NO:3.

Preferably, an isolated nucleic acid molecule of the invention comprises at least a portion of the coding region of SEQ ID NO:1 (shown in nucleotides 59–793) or SEQ ID NO:3 (shown in nucleotides 53–922). In another embodiment, a PD-1 ligand nucleic acid molecule comprises from about nucleotide 1 to about nucleotide 319 of SEQ ID NO:1. In another embodiment, a PD-1 ligand nucleic acid molecule comprises from about nucleotide 855 to about nucleotide 968 of SEQ ID NO:1. In another embodiment, a PD-1 ligand nucleic acid molecule comprises from about nucleotide 1 to about nucleotide 314 of SEQ ID NO:3. In another embodiment, a PD-1 ligand nucleic acid molecule comprises from about nucleotide 955 to about nucleotide 1285 of SEQ ID NO:3. In another embodiment, a PD-1 ligand nucleic acid molecule comprises from about nucleotide 1535 to about nucleotide 1552 of SEQ ID NO:3.

In other embodiments, a nucleic acid molecule of the invention has at least 70% identity, more preferably 80% identity, and even more preferably 90% identity with a nucleic acid molecule comprising: at least about 500, at least about 600, at least about 700, at least about 800, at least about 900 or at least about 1000 contiguous nucleotides of SEQ ID NO:1 or SEQ ID NO:3.

Probes based on the PD-1 ligand or PD-1 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissues which misexpress a PD-1 ligand or PD-1 protein, such as by measuring a level of a PD-1 ligand or PD-1-encoding nucleic acid in a sample of cells from a subject e.g., detecting PD-1 ligand or PD-1 mRNA levels or determining whether a genomic PD-1 ligand or PD-1 gene has been mutated or deleted.

A nucleic acid fragment encoding a "biologically active portion of a PD-1 ligand or PD-1 protein" can be prepared by isolating a portion of the nucleotide sequence of SEQ ID NO:1, 3, 10, 11, or 38 which encodes a polypeptide having a PD-1 ligand or PD-1 biological activity (the biological activities of the PD-1 ligand or PD-1 proteins are described herein), expressing the encoded portion of the PD-1 ligand or PD-1 protein (e.g., by recombinant expression in vitro) and assessing the activity of the encoded portion of the PD-1 ligand or PD-1 protein.

Nucleic acid molecules that differ from SEQ ID NO:1, 3, 10, 11, or 38 due to degeneracy of the genetic code, and thus encode the same PD-1 ligand or PD-1 protein as that encoded by SEQ ID NO:1, 3, 10, 11, or 38, are encompassed by the invention. Accordingly, in another embodiment, an isolated nucleic acid molecule of the invention has a nucleotide sequence encoding a protein having an amino acid sequence shown in SEQ ID NO:2, 4, 12, or 39. In another embodiment, an isolated nucleic acid molecule of the invention has a nucleotide sequence encoding a PD-1 ligand or PD-1 protein.

In addition to the PD-1 ligand or PD-1 nucleotide sequences shown in SEQ ID NO:1, 3, 10, 11, or 38 it should be appreciated by those skilled in the art that DNA sequence polymorphisms that lead to changes in the amino acid sequences of the PD-1 ligand or PD-1 proteins may exist within a population (e.g., the human population). Such genetic polymorphism in the PD-1 ligand or PD-1 genes may exist among individuals within a population due to natural allelic variation. As used herein, the terms "gene" and "recombinant gene" refer to nucleic acid molecules which include an open reading frame encoding a PD-1 ligand or PD-1 protein, preferably a mammalian PD-1 ligand or PD-1 protein, and can further include non-coding regulatory sequences, and introns. Such natural allelic variations include both functional and non-functional PD-1 ligand or PD-1 proteins and can typically result in 1–5% variance in the nucleotide sequence of a PD-1 ligand or PD-1 gene. Such nucleotide variations and resulting amino acid polymorphisms in PD-1 ligand or PD-1 genes that are the result of natural allelic variation and that do not alter the functional activity of a PD-1 ligand or PD-1 protein are intended to be within the scope of the invention.

Moreover, nucleic acid molecules encoding other PD-1 ligand or PD-1 family members and, thus, which have a nucleotide sequence which differs from the PD-1 ligand or PD-1 family sequences of SEQ ID NO:1, 3, 10, 11, or 38 are intended to be within the scope of the invention. For example, another PD-1 ligand or PD-1 cDNA can be identified based on the nucleotide sequence of human PD-1 ligand or PD-1. Moreover, nucleic acid molecules encoding PD-1 ligand or PD-1 proteins from different species, and thus which have a nucleotide sequence which differs from the PD-1 ligand or PD-1 sequences of SEQ ID NO:1, 3, 10, 11, or 38 are intended to be within the scope of the invention. For example, a mouse PD-1 ligand or PD-1 cDNA can be identified based on the nucleotide sequence of a human PD-1 ligand or PD-1 molecule.

Nucleic acid molecules corresponding to natural allelic variants and homologues of the PD-1 ligand or PD-1 cDNAs of the invention can be isolated based on their homology to the PD-1 ligand or PD-1 nucleic acids disclosed herein using the cDNAs disclosed herein, or a portion thereof, as a hybridization probe according to standard hybridization techniques. For example, a PD-1 ligand or PD-1 DNA can be isolated from a human genomic DNA library using all or portion of SEQ ID NO:1, 3, 10, 11, or 38 as a hybridization probe and standard hybridization techniques (e.g., as described in Sambrook, J., et al. *Molecular Cloning: A Laboratory Manual.* 2nd, ed., Cold Spring Harbor Laboratory, Cold Spring Harbor, N.Y., 1989). Moreover, a nucleic acid molecule encompassing all or a portion of a PD-1 ligand or PD-1 gene can be isolated by the polymerase chain reaction using oligonucleotide primers designed based upon the sequence of SEQ ID NO:1, 3, 10, 11, or 38. For example, mRNA can be isolated from cells (e.g., by the guanidinium-thiocyanate extraction procedure of Chirgwin et al. (1979) *Biochemistry* 18:5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed based upon the nucleotide sequence shown in SEQ ID NO:1, 3, 10, 11, or 38. A nucleic acid molecule of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a PD-1 ligand or PD-1 nucleotide sequence can be prepared by standard synthetic techniques, e.g., using an automated DNA synthesizer.

In another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, 3, 10, 11, or 38. In other embodiment, the nucleic acid molecule is at least 30, 50, 100, 150, 200, 250, 300, 350, 400, 450, 500, 550, or 600 nucleotides in length. As used herein, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washed in 0.2×SSC, 0.1% SDS at 50–65° C. Preferably, an isolated nucleic acid molecule of the invention that hybridizes under stringent conditions to the sequence of SEQ ID NO:1, 3, 10, 11, or 38 corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein). In addition to the PD-1 ligand or PD-1 nucleotide sequences shown in SEQ ID NO:1, 3, 10, and 11, it should be appreciated by those skilled in the art that DNA sequence polymorphisms that lead to minor changes in the nucleotide or amino acid sequences of a PD-1 ligand or PD-1 may exist within a population. Such genetic polymorphism in a PD-1 ligand or PD-1 gene may exist among individuals within a population due to natural allelic variations. Such natural allelic variations can typically result in 1–2% variance in the nucleotide sequence of the gene. Such nucleotide variations and resulting amino acid polymorphisms in a PD-1 ligand or PD-1 that are the result of natural allelic variation and that do not alter the functional activity of a PD-1 ligand or PD-1 polypeptide are within the scope of the invention.

In addition to naturally-occurring allelic variants of PD-1 ligand or PD-1 sequences that may exist in the population, the skilled artisan will further appreciate that minor changes may be introduced by mutation into nucleotide sequences, e.g., of SEQ ID NO:1, 3, 10, 11, or 38, thereby leading to changes in the amino acid sequence of the encoded protein, without altering the functional activity of a PD-1 ligand or PD-1 protein. For example, nucleotide substitutions leading to amino acid substitutions at "non-essential" amino acid residues may be made in the sequence of SEQ ID NO:1, 3, 10, 11, or 38. A "non-essential" amino acid residue is a residue that can be altered from the wild-type sequence of a PD-1 ligand nucleic acid molecule (e.g., the sequence of SEQ ID NO:1, 3, 10, 11, or 38) without altering the functional activity of a PD-1 ligand or PD-1 molecule. Preferably, residues in the extracellular domain of PD-1 ligand or PD-1 which are found to be required for binding of PD-1 ligand to a receptor or PD-1 to a natural ligand (e.g., identified using an alanine scanning mutagenesis screen or other art recognized screening assay) are not altered. For PD-1 ligands, exemplary residues which are non-essential and, therefore, amenable to substitution, can be identified by one of ordinary skill in the art by performing an amino acid alignment of B7 family members (or of PD-1 family members) and determining residues that are not conserved. Such residues, because they have not been conserved, are more likely amenable to substitution.

Accordingly, another aspect of the invention pertains to nucleic acid molecules encoding PD-1 ligand or PD-1 proteins that contain changes in amino acid residues that are not essential for a PD-1 ligand or PD-1 activity. Such PD-1 ligand or PD-1 proteins differ in amino acid sequence from SEQ ID NO:2, 4, 12, or 39 yet retain an inherent PD-1 ligand activity or, in the case of PD-1, retain the ability to bind to PD-1 ligand. An isolated nucleic acid molecule encoding a non-natural variant of a PD-1 ligand or PD-1 protein can be created by introducing one or more nucleotide substitutions, additions or deletions into the nucleotide sequence of SEQ ID NO:1, 3, 10, 11, or 38 such that one or more amino acid substitutions, additions or deletions are introduced into the encoded protein. Mutations can be introduced into SEQ ID NO:1, 3, 10, 11, or 38 by standard techniques, such as site-directed mutagenesis and PCR-mediated mutagenesis. Preferably, conservative amino acid substitutions are made at one or more non-essential amino acid residues. A "conservative amino acid substitutions" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tryosine, phenylalanine, tryptophan, histidine). Thus, a nonessential amino acid residue in a PD-1 ligand or PD-1 is preferably replaced with another amino acid residue from the same side chain family.

Alternatively, in another embodiment, mutations can be introduced randomly along all or part of a PD-1 ligand or PD-1 coding sequence, such as by saturation mutagenesis, and the resultant mutants can be screened for their ability to bind to DNA and/or activate transcription, to identify mutants that retain functional activity. Following mutagenesis, the encoded PD-1 ligand or PD-1 mutant protein can be expressed recombinantly in a host cell and the functional activity of the mutant protein can be determined using assays available in the art for assessing a PD-1 ligand or PD-1 activity.

Accordingly, another aspect of the invention pertains to nucleic acid molecules encoding PD-1 ligand or PD-1 proteins that contain changes in amino acid residues that are not essential for activity.

Yet another aspect of the invention pertains to isolated nucleic acid molecules encoding a PD-1 ligand or PD-1 fusion proteins. Such nucleic acid molecules, comprising at least a first nucleotide sequence encoding a PD-1 ligand or PD-1 protein, polypeptide or peptide operatively linked to a second nucleotide sequence encoding a non- a PD-1 ligand or PD-1 protein, polypeptide or peptide, can be prepared by standard recombinant DNA techniques.

In a preferred embodiment, a mutant PD-1 ligand protein can be assayed for the ability to: 1) costimulate (or inhibit the costimulation of, e.g., in soluble form) the proliferation and/or effector function of immune cells; 2) bind to an anti-B7 family- or anti-PD-1 ligand-antibody; and/or 3) bind to a natural receptor(s) of PD-1 ligand (e.g., PD-1).

In a preferred embodiment, a mutant PD-1 protein can be assayed for the ability to: 1) inhibit the costimulation of (e.g., in soluble form) the proliferation and/or effector function of immune cells; 2) bind to an anti-PD-1 antibody; and/or 3) bind to a natural ligand(s) of PD-1 (e.g., PD-1 ligand).

In addition to the nucleic acid molecules encoding PD-1 ligand or PD-1 proteins described above, isolated nucleic acid molecules which are antisense thereto can be used as modulating agents. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PD-1 ligand or PD-1 coding strand, or only to a portion thereof. In one embodiment, an antisense nucleic acid molecule is antisense to a "coding region" of the coding strand of a nucleotide sequence encoding PD-1 ligand or PD-1. The term "coding region" refers to the region of the nucleotide sequence comprising codons which are translated into amino acid residues. In another embodiment, the antisense nucleic acid molecule is antisense to a "noncoding region" of the coding strand of a nucleotide sequence encoding PD-1 ligand or PD-1. The term "noncoding region" refers to 5' and 3' sequences which flank the coding region that are not translated into amino acids (i.e., also referred to as 5' and 3' untranslated regions).

Given the coding strand sequences encoding PD-1 ligand or PD-1 disclosed herein, antisense nucleic acids of the invention can be designed according to the rules of Watson and Crick base pairing. The antisense nucleic acid molecule can be complementary to the entire coding region of PD-1 ligand or PD-1 mRNA, but more preferably is an oligonucleotide which is antisense to only a portion of the coding or noncoding region of PD-1 ligand or PD-1 mRNA. For example, the antisense oligonucleotide can be complementary to the region surrounding the translation start site of PD-1 ligand or PD-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid molecule (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid is of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a PD-1 ligand or PD-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an $\alpha$-anomeric nucleic acid molecule. An $\alpha$-anomeric nucleic acid molecule forms specific double-stranded hybrids with complementary RNA in which, contrary to the usual $\beta$-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid molecule of the invention is a ribozyme. Ribozymes are catalytic RNA molecules with ribonuclease activity which are capable of cleaving a single-stranded nucleic acid molecule, such as an mRNA, to which they have a complementary region. Thus, ribozymes (e.g., hammerhead ribozymes (described in Haseloff and Gerlach (1988) *Nature* 334: 585–591)) can be used to catalytically cleave PD-1 ligand or PD-1 mRNA transcripts to thereby inhibit translation of PD-1 ligand or PD-1 mRNA. A ribozyme having specificity for a PD-1 ligand or PD-1-encoding nucleic acid can be designed based upon the nucleotide sequence of a PD-1 ligand or PD-1 cDNA disclosed herein (i.e., SEQ ID NO:1, 3, 10, 11, or 38). For example, a derivative of a Tetrahymena L-19 IVS RNA can be constructed in which the nucleotide sequence of the active site is complementary to the nucleotide sequence to be cleaved in a PD-1 ligand or PD-1 encoding mRNA. See, e.g., Cech et al. U.S. Pat. No. 4,987,071; and Cech et al. U.S. Pat. No. 5,116,742. Alternatively, PD-1 ligand or PD-1 mRNA can be used to select a catalytic RNA having a specific ribonuclease activity from a pool of RNA molecules. See, e.g., Bartel, D. and Szostak, J. W. (1993) Science 261:1411–1418.

Alternatively, PD-1 ligand or PD-1 gene expression can be inhibited by targeting nucleotide sequences complementary to the regulatory region of the PD-1 ligand or PD-1 (e.g., the PD-1 ligand or PD-1 promoter and/or enhancers) to form triple helical structures that prevent transcription of the PD-1 ligand or PD-1 gene in target cells. See generally, Helene, C. (1991) Anticancer Drug Des. 6(6):569–84; Helene, C. et al. (1992) Ann. N.Y. Acad. Sci. 660:27–36; and Maher, L. J. (1992) Bioessays 14(12):807–15.

In yet another embodiment, the PD-1 ligand or PD-1 nucleic acid molecules of the present invention can be modified at the base moiety, sugar moiety, or phosphate backbone to improve, e.g., the stability, hybridization, or solubility of the molecule. For example, the deoxyribose phosphate backbone of the nucleic acid molecules can be modified to generate peptide nucleic acids (see Hyrup, B. and Nielsen, P. E. (1996) Bioorg. Med. Chem. 4(1):5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup and Nielsen (1996) supra and Perry-O'Keefe et al. (1996) Proc. Natl. Acad. Sci. USA 93:14670–675.

PNAs of PD-1 ligand or PD-1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of PD-1 ligand or PD-1 nucleic acid molecules can also be used in the analysis of single base pair mutations in a gene, (e.g., by PNA-directed PCR clamping); as 'artificial restriction enzymes' when used in combination with other enzymes. (e.g., S1 nucleases (Hyrup and Nielsen (1996) supra)); or as probes or primers for DNA sequencing or hybridization (Hyrup B. and Nielsen (1996) supra; Perry-O'Keefe et al. (1996) supra).

In another embodiment, PNAs of PD-1 ligand or PD-1 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of PD-1 ligand or PD-1 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. and Nielsen (1996) supra). The synthesis of PNA-DNA chimeras can be performed as described in Hyrup B. and Nielsen (1996) supra and Finn P. J. et al. (1996) Nucleic Acids Res. 24(17):3357–63. For example, a DNA chain can be synthesized on a solid support using standard phosphoramidite coupling chemistry. Modified nucleoside analogs, (e.g., 5'-(4-methoxytrityl)amino-5'-deoxythymidine phosphoramidite), can be used as a linker between the PNA and the 5' end of DNA (Mag, M. et al. (1989) Nucleic Acids Res. 17:5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) Bioorganic Med. Chem. Lett. 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Biotechniques 6:958–976) or intercalating agents (See, e.g., Zon (1988) Pharm. Res. 5:539–549). To this end, the oligonucleotide can be conjugated to another molecule, (e.g., a peptide, hybridization triggered cross-linking agent, transport agent, or hybridization-triggered cleavage agent).

III. Isolated PD-1 Ligand or PD-1 Proteins and Anti-PD-1 Ligand or PD-1 Antibodies In addition, isolated PD-1 ligand or PD-1 proteins, and biologically active portions thereof, as well as anti-PD-1 ligand or PD-1 antibodies can be used as modulating agents. In one embodiment, native PD-1 ligand or PD-1 proteins can be isolated from cells or tissue sources by an appropriate purification scheme using standard protein purification techniques. In another embodiment, PD-1 ligand or PD-1 proteins are produced by recombinant DNA techniques. Alternative to recombinant expression, a PD-1 ligand or PD-1 protein or polypeptide can be synthesized chemically using standard peptide synthesis techniques.

Another aspect of the invention pertains to isolated PD-1 ligand or PD-1 proteins. Preferably, the PD-1 ligand or PD-1 proteins comprise the amino acid sequence encoded by SEQ ID NO:1, 3, 10 or 11. In another preferred embodiment, the protein comprises the amino acid sequence of SEQ ID NO:2, 4, 12, or 39. In other embodiments, the protein has at least 50%, at least 60% amino acid identity, more preferably 70% amino acid identity, more preferably 80%, and even more preferably, 90% or 95% amino acid identity with the amino acid sequence shown in SEQ ID NO:2, 4, 12, or 39.

In other embodiments, the invention provides isolated portions of a PD-1 ligand or PD-1 protein. For example, PD-1 ligand proteins comprise a signal sequence, and an IgV domain and an IgC domain. The signal sequence of SEQ ID NO:2 is shown from about amino acid 1 to about amino acid 18. The signal sequence of SEQ ID NO:4 is shown from about amino acid 1 to about amino acid 18. The IgV domain of SEQ ID NO:2 is shown from about amino acid 19 to about amino acid 134 and the IgV domain of SEQ ID NO:4 is shown from about amino acid 19 to about amino acid 134. The IgC domain of SEQ ID NO:2 is shown from about amino acid 135 to about amino acid 227 and the IgC domain of SEQ ID NO:4 is shown from about amino acid 135 to about amino acid 227. The hydrophilic tail of the PD-1 ligand exemplified in SEQ ID NO:2 comprises a hydrophilic tail shown from about amino acid 228 to about amino acid 245. The PD-1 ligand polypeptide exemplified in SEQ ID NO:4 comprises a transmembrane domain shown from about amino acid 239 to about amino acid 259 of SEQ ID NO:4 and a cytoplasmic domain shown from about amino acid 260 to about amino acid 290 of SEQ ID NO:4.

The human PD-L2 gene, which is approximately 1223 nucleotides in length, encodes a polypeptide having a molecular weight of approximately 30.0 kD and which is approximately 273 amino acid residues in length. Amino acids residues 1–219 of the native human PD-L2 polypeptide, and amino acid residues 1–200 of the predicted mature polypeptide, are predicted to comprise extracellular domains. mino acid residues 244–273 of the native human PD-L2 polypeptide, and amino acid residues 225–273 of the predicted mature polypeptide, are predicted to comprise cytoplasmic domains. The nucleic acid sequence of PD-L2 is shown in SEQ ID NO: 38 and the amino acid sequence of PD-L2 is shown in SEQ ID NO:39.

The PD-1 polypeptide is 288 amino acids in length and its domain structure is known in the art (Shinohara et al. (1994) *Genomics* 23:704). The predicted mature form of the protein contains about 268 amino acids and comprises an extracellular domain (147 amino acids), a transmembrane domain (27 amino acids), a transmembrane region (27 amino acids) and a cytoplasmic domain (94 amino acids). Four potential N-glycosylation sites are found in the extracellular domain (U.S. Pat. No. 5,698,520). The 68 amino acid residues between two cysteine residues (cys 54 and cys 123) bear resemblance to a disulfide-linked immunoglobulin domain of the V-set sequences (U.S. Pat. No. 5,698,520).

The invention further pertains to soluble forms of PD-1 ligand or PD-1 proteins. As used herein, the term "soluble" includes molecules that are not expressed on the surface of a cell and which are soluble under physiological conditions. Such forms can be naturally occurring, e.g., as shown in SEQ ID NO:2 or can be engineered and can comprise, e.g., an extracellular domain of aPD-1 ligand or PD-1 protein. Exemplary PD-1 ligand extracellular domains comprise from about amino acids 19–238 of SEQ ID NO:4. Exemplary PD-1 extracellular domains comprise from about amino acids 21–288 of SEQ ID NO:12.

In one embodiment, the extracellular domain of a PD-1 ligand polypeptide comprises the mature form of a PD-1 ligand polypeptide, e.g., the IgV and IgC domains, but not the transmembrane and cytoplasmic domains of a PD-1 ligand polypeptide (e.g., from about amino acid 19 to amino acid 238 of SEQ ID NO:4) or from about amino acid 19 to amino acid 245 of SEQ ID NO:2.

In one embodiment, the extracellular domain of a PD-1 polypeptide comprises the mature form of a PD-1 polypeptide, e.g., immunoglobulin superfamily domains (e.g., V-set sequences), but not the transmembrane and cytoplasmic domains of a PD-1 polypeptide (e.g., from about amino acid 21–288 of SEQ ID NO:12).

Biologically active portions of a PD-1 ligand or PD-1 protein include peptides comprising amino acid sequences sufficiently homologous to or derived from the amino acid sequence of the PD-1 ligand or PD-1 protein, which include less amino acids than the full length PD-1 ligand or PD-1 proteins, and exhibit at least one activity of a PD-1 ligand or PD-1 protein, preferably the ability to bind to a natural binding partner. Typically, biologically active portions comprise a domain or motif with at least one activity of the PD-1 ligand or PD-1 protein. A biologically active portion of a PD-1 ligand or PD-1 protein can be a polypeptide which is, for example, at least 10, 25, 50, 100, 150, 200 or more amino acids in length.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The residues or nucleic acids at corresponding positions are then compared and when a position in one sequence is occupied by the same residue or nucleic acid as the corresponding position in the other sequence, then the molecules are identical at that position. The percent identity between two sequences, therefore, is a function of the number of identical positions shared by two sequences (i.e., % identity=# of identical positions/total # of positions× 100). The percent identity between the two sequences is a function of the number of identical positions shared by the sequences, taking into account the number of gaps, and the length of each gap, which need to be introduced for optimal alignment of the two sequences. As used herein amino acid or nucleic acid "identity" is equivalent to amino acid or nucleic acid "homology".

The comparison of sequences and determination of percent identity between two sequences can be accomplished using a mathematical algorithm. In a preferred embodiment, the percent identity between two amino acid sequences is determined using the GAP program in the GCG software package (available at the GCG website), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCCG software package (available at the GCG website), using a NWSgapdna.CMP matrix and a gap weight of 40, 50, 60, 70, or 80 and a length weight of 1, 2, 3, 4, 5, or 6.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to PD-1 ligand or PD-1 nucleic acid molecules of the invention. BLAST protein searches can be performed with the XBLAST program, score=50, wordlength=3 to obtain amino acid sequences homologous to PD-1 ligand or PD-1 protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. For example, the nucleotide sequences of the invention were analyzed using the default Blastn matrix 1–3 with gap penalties set at: existence 11 and extension 1. The amino acid sequences of the invention were analyzed using the default settings: the Blosum 62 matrix with gap penalties set at existence 11 and extension 1. See the NCBI website.

The invention also provides PD-1 ligand or PD-1 chimeric or fusion proteins. As used herein, a PD-1 ligand or PD-1 "chimeric protein" or "fusion protein" comprises a PD-1 ligand or PD-1 polypeptide operatively linked to a non-PD-1 ligand or PD-1 polypeptide. A "PD-1 ligand or PD-1 polypeptide" refers to a polypeptide having an amino acid sequence corresponding to PD-1 ligand or PD-1 polypeptide, whereas a "non-PD-1 ligand or PD-1 polypeptide" refers to a polypeptide having an amino acid sequence corresponding to a protein which is not substantially homologous to the PD-1 ligand or PD-1 protein, e.g., a protein which is different from the PD-1 ligand or PD-1 protein and which is derived from the same or a different organism. Within a PD-1 ligand or PD-1 fusion protein the PD-1 ligand or PD-1 polypeptide can correspond to all or a portion of a PD-1 ligand or PD-1 protein. In a preferred embodiment, a PD-1 ligand or PD-1 fusion protein comprises at least one biologically active portion of a PD-1 ligand or PD-1 protein, e.g., an extracellular domain of a PD-1 ligand or PD-1 protein. Within the fusion protein, the term "operatively linked" is intended to indicate that the PD-1 ligand or PD-1 polypeptide and the non-PD-1 ligand or PD-1 polypeptide are fused in-frame to each other. The non-PD-1 ligand or PD-1 polypeptide can be fused to the N-terminus or C-terminus of the PD-1 ligand or PD-1 polypeptide.

For example, in one embodiment, the fusion protein is a GST-PD-1 ligand or GST-PD-1 fusion protein in which the PD-1 ligand or PD-1 sequences are fused to the C-terminus of the GST sequences. In another embodiment, the fusion protein is a PD-1 ligand or PD-1-HA fusion protein in which the PD-1 ligand or PD-1 nucleotide sequence is inserted in a vector such as pCEP4-HA vector (Herrscher, R. F. et al. (1995) *Genes Dev.* 9:3067–3082) such that the PD-1 ligand or PD-1 sequences are fused in frame to an influenza hemagglutinin epitope tag. Such fusion proteins can facilitate the purification of a recombinant PD-1 ligand or PD-1 protein.

A PD-1 ligand or PD-1 fusion protein can be produced by recombinant expression of a nucleotide sequence encoding a first peptide having B7-4 activity and a nucleotide sequence encoding a second peptide corresponding to a moiety that alters the solubility, affinity, stability or valency of the first peptide, for example, an immunoglobulin constant region. Preferably, the first peptide consists of a portion of the PD-1 ligand polypeptide (e.g., a portion of amino acid residues 1–238 or 19–238 (after cleavage of the signal sequence) of the sequence shown in SEQ ID NO:4 that is sufficient to modulate costimulation or inhibition of immune cells). In another preferred embodiment, the first peptide consists of a portion of a PD-1 polypeptide (e.g., a portion of amino acid residues 1–288 (or 21–288 after cleavage of the signal peptide) of the sequence shown in SEQ ID NO:12 that is sufficient to modulate costimulation or inhibition of immune cells) The second peptide can include an immunoglobulin constant region, for example, a human Cγ1 domain or Cγ4 domain (e.g., the hinge, CH2 and CH3 regions of human IgCγ1, or human IgCγ4, see e.g., Capon et al. U.S. Pat. Nos. 5,116,964; 5,580,756; 5,844,095 and the like, incorporated herein by reference). A resulting fusion protein may have altered PD-1 ligand or PD-1 solubility, binding affinity, stability and/or valency (i.e., the number of binding sites available per molecule) and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Particularly preferred PD-1 ligand or PD-1 Ig fusion proteins include the extracellular domain portion or variable region-like domain of a human PD-1 ligand or PD-1 coupled to an immunoglobulin constant region (e.g., the Fc region). The immunoglobulin constant region may contain genetic modifications which reduce or eliminate effector activity inherent in the immunoglobulin structure. For example, DNA encoding the extracellular portion of a PD-1 ligand or PD-1 polypeptide can be joined to DNA encoding the hinge, CH2 and CH3 regions of human IgGγ1 and/or IgGγ4 modified by site directed mutagenesis, e.g., as taught in WO 97/28267. Fusion proteins of, e.g., PD-1 ligand and an immunoglobulin fusion protein may be referred to interchangeably herein as "PD-1 ligand.Ig" or "PD-1 ligand.Fc". Other variations which incorporate the terms "Ig" or "Fc" may be used.

Preferably, a PD-1 ligand or PD-1 fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide or an HA epitope tag). A PD-1 ligand or PD-1 encoding nucleic acid can be cloned into such an expression vector such that the fusion moiety is linked in-frame to the PD-1 ligand or PD-1 protein.

In another embodiment, the fusion protein is PD-1 ligand or PD-1 protein containing a heterologous signal sequence at its N-terminus. In certain host cells (e.g., mammalian host cells), expression and/or secretion of PD-1 ligand or PD-1 can be increased through use of a heterologous signal sequence.

The PD-1 ligand or PD-1 fusion proteins of the invention can be incorporated into pharmaceutical compositions and administered to a subject in vivo. PD-1 ligand or PD-1 fusion proteins are useful for therapeutic modulation of an mmune response to, for instance in the treatment of immunological disorders, e.g., autoimmune diseases, or in the case of inhibiting rejection of transplants. Moreover, the PD-1 ligand or PD-1 fusion proteins of the invention, (e.g., full length protein or portions thereof) can be used as immunogens to produce anti-PD-1 ligand or PD-1 antibodies in a subject, to purify PD-1 ligand or PD-1 and in screening assays to identity molecules which inhibit the interaction of PD-1 ligand with a PD-1 ligand receptor, e.g., PD-1.

Preferably, a PD-1 ligand or PD-1 chimeric or fusion protein of the invention is produced by standard recombinant DNA techniques. For example, DNA fragments coding for the different polypeptide sequences are ligated together in-frame in accordance with conventional techniques, for example by employing bluntended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of nucleic acid (e.g., gene) fragments can be carried out using anchor primers which give rise to complementary overhangs between two consecutive nucleic acid fragments which can subsequently be annealed and reamplified to generate a chimeric nucleic acid sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A PD-1 ligand or PD-1-encoding nucleic acid can be cloned into such an expression vector such that the fusion moiety is linked in-frame to the PD-1 ligand or PD-1 protein.

The present invention also pertains to variants of the PD-1 ligand or PD-1 proteins which function as either PD-1 ligand or PD-1 agonists (mimetics) or as PD-1 ligand or PD-1 antagonists. Variants of the PD-1 ligand or PD-1 proteins can be generated by mutagenesis, e.g., discrete point mutation or truncation of a PD-1 ligand or PD-1 protein. An agonist of the PD-1 ligand or PD-1 proteins can retain substantially the same, or a subset, of the biological activities of the naturally occurring form of a PD-1 ligand or PD-1 protein. An antagonist of a PD-1 ligand or PD-1 protein can inhibit one or more of the activities of the naturally occurring form of the PD-1 ligand or PD-1 protein by, for example, competitively modulating a cellular activity of a PD-1 ligand or PD-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the PD-1 ligand or PD-1 protein.

In one embodiment, variants of a PD-1 ligand or PD-1 protein which function as either PD-1 ligand or PD-1 agonists (mimetics) or as PD-1 ligand or PD-1 antagonists can be identified by screening combinatorial libraries of mutants, e.g., point mutants or truncation mutants, of a PD-1 ligand or PD-1 protein for PD-1 ligand or PD-1 protein agonist or antagonist activity. In one embodiment, a variegated library of PD-1 ligand or PD-1 variants is generated by combinatorial mutagenesis at the nucleic acid level and is encoded by a variegated gene library. A variegated library of PD-1 ligand or PD-1 variants can be produced by, for example, enzymatically ligating a mixture of synthetic oligonucleotides into gene sequences such that a degenerate set of potential PD-1 ligand or PD-1 sequences is expressible as individual polypeptides, or alternatively, as a set of larger fusion proteins (e.g., for phage display) containing the set of PD-1 ligand or PD-1 sequences therein. There are a variety of methods which can be used to produce libraries of potential PD-1 ligand or PD-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential PD-1 ligand or PD-1 sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323: Itakura et al. (1984) *Science* 198:1056; Ike et al. (1983) *Nucleic Acids Res.* 11:477.

In addition, libraries of fragments of a PD-1 ligand or PD-1 protein coding sequence can be used to generate a variegated population of PD-1 ligand or PD-1 fragments for screening and subsequent selection of variants of a PD-1 ligand or PD-1 protein. In one embodiment, a library of coding sequence fragments can be generated by treating a double stranded PCR fragment of a PD-1 ligand or PD-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PD-1 ligand or PD-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PD-1 ligand or PD-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify PD-1 ligand or PD-1 variants (Arkin and Youvan (1992) *Proc. Natl. Acad. Sci. USA* 89:7811–7815; Delagrave et al. (1993) *Protein Eng.* 6(3):327–331).

In one embodiment, cell based assays can be exploited to analyze a variegated PD-1 ligand or PD-1 library. For example, a library of expression vectors can be transfected into a cell line which ordinarily synthesizes and secretes PD-1 ligand or PD-1. The transfected cells are then cultured such that PD-1 ligand or PD-1 and a particular mutant PD-1 ligand or PD-1 are secreted and the effect of expression of the mutant on PD-1 ligand or PD-1 activity in cell supernatants can be detected, e.g., by any of a number of functional assays. Plasmid DNA can then be recovered from the cells which score for inhibition, or alternatively, potentiation of PD-1 ligand or PD-1 activity, and the individual clones further characterized.

In addition to PD-1 ligand or PD-1 polypeptides consisting only of naturally-occurring amino acids, PD-1 ligand or PD-1 peptidomimetics are also provided. Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15:29; Veber and Freidinger (1985) TINS p. 392; and Evans et al. (1987) *J. Med. Chem.* 30:1229, which are incorporated herein by reference) and are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as human PD-1 ligand or PD-1, but have one or more peptide linkages optionally replaced by a linkage selected from the group consisting of: —CH2NH—, —CH2S—, —CH2—CH2—, —CH=CH— (cis and trans), —COCH2—, —CH(OH)CH2—, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463–468 (general review); Hudson, D. et al. (1979) *Int. J. Pept. Prot. Res.* 14:177–185 (—CH2NH—, CH2CH2—); Spatola, A. F. et al. (1986) *Life Sci.* 38:1243–1249 (—CH2—S); Hann, M. M. (1982) *J. Chem. Soc. Perkin Trans. I.* 307–314 (—CH—CH—, cis and trans); Almquist, R. G. et al. (190) *J. Med. Chem.* 23:1392–1398 (—COCH2—); Jennings-White, C. et al. (1982) *Tetrahedron Lett.* 23:2533 (—COCH2—); Szelke, M. et al. European Appln. EP 45665 (1982) CA: 97:39405 (1982)(—CH (OH)CH2—); Holladay, M. W. et al. (1983) *Tetrahedron Lett.* (1983) 24:4401–4404 (—C(OH)CH2—); and Hruby, V. J. (1982) *Life Sci.* (1982) 31:189–199 (—CH2—S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labeling) of peptidomimetics should not substantially interfere with the desired biological or pharmacological activity of the peptidomimetic.

Systematic substitution of one or more amino acids of a PD-1 ligand or PD-1 amino acid sequence with a D-amino acid of the same type (e.g., D-lysine in place of L-lysine) can be used to generate more stable peptides. In addition, constrained peptides comprising a PD-1 ligand or PD-1 amino acid sequence or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences of PD-1 ligand or PD-1 polypeptides identified herein will enable those of skill in the art to produce polypeptides corresponding to PD-1 ligand or PD-1 peptide sequences and sequence variants thereof. Such polypeptides can be produced in prokaryotic or eukaryotic host cells by expression of polynucleotides encoding a PD-1 ligand or PD-1 peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins,* Wiley Publishing, which are incorporated herein by reference).

Peptides can be produced, typically by direct chemical synthesis, and used e.g., as agonists or antagonists of a PD-1 ligand/PD-1 interaction. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides can be used therapeutically to treat disease, e.g., by altering costimulation in a patient.

An isolated PD-1 ligand or PD-1 protein, or a portion or fragment thereof (or a nucleic acid molecule encoding such a polypeptide), can be used as an immunogen to generate antibodies that bind PD-1 ligand or PD-1 using standard techniques for polyclonal and monoclonal antibody preparation. A full-length PD-1 ligand or PD-1 protein can be used, or alternatively, the invention provides antigenic peptide fragments of PD-1 ligand or PD-1 for use as immunogens. The antigenic peptide of PD-1 ligand or PD-1 comprises at least 8 amino acid residues and encompasses an epitope of PD-1 ligand or PD-1 such that an antibody raised against the peptide forms a specific immune complex with PD-1 ligand or PD-1. Preferably, the antigenic peptide comprises at least 10 amino acid residues, more preferably at least 15 amino acid residues, even more preferably at least 20 amino acid residues, and most preferably at least 30 amino acid residues.

Alternatively, an antigenic peptide fragment of a PD-1 ligand or PD-1 polypeptide can be used as the immunogen. An antigenic peptide fragment of a PD-1 ligand or PD-1 polypeptide typically comprises at least 8 amino acid residues of the amino acid sequence shown in SEQ ID NO:2, 4, 12, or 39 and encompasses an epitope of a PD-1 ligand or PD-1 polypeptide such that an antibody raised against the peptide forms an immune complex with a PD-1 ligand or PD-1 molecule. Preferred epitopes encompassed by the antigenic peptide are regions of PD-1 ligand or PD-1 that are located on the surface of the protein, e.g., hydrophilic regions. In one embodiment, an antibody binds substantially specifically to a molecule which contains a portion of a B7-4 or PD-1 molecule (e.g., the extracellular portion).PD-1 ligand or PD-1 molecule. In another embodiment, an antibody binds specifically to a PD-1 ligand or PD-1 polypeptide.

Preferably, the antigenic peptide comprises at least about 10 amino acid residues, more preferably at least about 15 amino acid residues, even more preferably at least about 20 amino acid residues, and most preferably at least about 30 amino acid residues. Preferred epitopes encompassed by the antigenic peptide are regions of a PD-1 ligand or PD-1 polypeptide that are located on the surface of the protein, e.g., hydrophilic regions, and that are unique to a PD-1 ligand or PD-1 polypeptide. In one embodiment such epitopes can be specific for a PD-1 ligand or PD-1 proteins from one species, such as mouse or human (i.e., an antigenic peptide that spans a region of a PD-1 ligand or PD-1 polypeptide that is not conserved across species is used as immunogen; such non conserved residues can be determined using an alignment such as that provided herein). A standard hydrophobicity analysis of the PD-1 ligand or PD-1 protein can be performed to identify hydrophilic regions.

A PD-1 ligand or PD-1 immunogen typically is used to prepare antibodies by immunizing a suitable subject, (e.g., rabbit, goat, mouse or other mammal) with the immunogen. An appropriate immunogenic preparation can contain, for example, a recombinantly expressed PD-1 ligand or PD-1 protein or peptide fragment, or a chemically synthesized PD-1 ligand or PD-1 peptide fragment. The preparation can further include an adjuvant, such as Freund's complete or incomplete adjuvant, or similar immunostimulatory agent. Immunization of a suitable subject with an immunogenic PD-1 ligand or PD-1 preparation induces a polyclonal anti-PD-1 ligand or PD-1 antibody response.

In another embodiment, nucleic acid vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. (1996) *J. Biotechnol.* 44:37)). Alternatively, nucleic acid vaccines can be administered by non-invasive means. For example, pure or lipid-formulated DNA can be delivered to the respiratory system or targeted elsewhere, e.g., Peyers patches by oral delivery of DNA (Schubert (1997) *Proc. Natl. Acad. Sci. USA* 94:961). Attenuated microorganisms can be used for delivery to mucosal surfaces. (Sizemore et al. (1995) *Science* 270:29).

Yet another aspect of the invention pertains to anti-PD-1 ligand antibodies or anti-PD-1 antibodies. Such antibodies are, for instance, generated by immunizing an animal with an immunogenic PD-1 ligand or PD-1 protein, or an immunogenic portion thereof which is unique to a PD-1 ligand or PD-1 polypeptide, and then isolating antibodies from the animal that specifically bind to the PD-1 ligand or PD-1 protein, or a fragment thereof.

Polyclonal anti-PD-1 ligand or PD-1 antibodies can be prepared as described above by immunizing a suitable subject with a PD-1 ligand or PD-1 immunogen. The anti-PD-1 ligand or PD-1 antibody titer in the immunized subject can be monitored over time by standard techniques, such as with an enzyme linked immunosorbent assay (ELISA) using immobilized a PD-1 ligand or PD-1 polypeptide. If desired, the antibody molecules directed against a PD-1 ligand or PD-1 polypeptide can be isolated from the mammal (e.g., from the blood) and further purified by well known techniques, such as protein A chromatography to obtain the IgG fraction. At an appropriate time after immunization, e.g., when the anti-PD-1 ligand or PD-1 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also Brown et al. (1981) *J. Immunol.* 127:539–46; Brown et al. (1980) *J. Biol. Chem.* 255:4980–83; Yeh et al. (1976) *Proc. Natl. Acad. Sci.* 76:2927–31; and Yeh et al. (1982) *Int. J. Cancer* 29:269–75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77–96) or trioma techniques. The technology for producing monoclonal antibody hybridomas is well known (see generally Kenneth, R. H. in *Monoclonal Antibodies: A New Dimension In Biological Analyses*. Plenum Publishing Corp., New York, N.Y. (1980); Lerner, E. A. (1981) *Yale J. Biol. Med.* 54:387–402; Gefter, M. L. et al. (1977) *Somatic Cell Genet.* 3:231–36). Briefly, an immortal cell line (typically a myeloma) is fused to lymphocytes (typically splenocytes) from a mammal immunized with a PD-1 ligand or PD-1 immunogen as described above, and the culture supernatants of the resulting hybridoma cells are screened to identify a hybridoma producing a monoclonal antibody that binds to a PD-1 ligand or PD-1 polypeptide, preferably specifically.

Any of the many well known protocols used for fusing lymphocytes and immortalized cell lines can be applied for the purpose of generating an anti-PD-1 ligand or PD-1 monoclonal antibody (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a PD-1 ligand or PD-1 molecule, e.g., using a standard ELISA assay.

As an alternative to preparing monoclonal antibody-secreting hybridomas, a monoclonal anti-PD-1 ligand or PD-1 antibody can be identified and isolated by screening a recombinant combinatorial immunoglobulin library (e.g., an antibody phage display library) with a PD-1 ligand or PD-1 to thereby isolate immunoglobulin library members that bind a PD-1 ligand or PD-1 polypeptide. Kits for generating and screening phage display libraries are commercially available (e.g., the Pharmacia *Recombinant Phage Antibody System,* Catalog No. 27-9400-01; and the Stratagene *SurfZAP™ Phage Display Kit,* Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Brietling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology (NY)* 9:1369–1372; Hay et al. (1992) *Hum. Antibod. Hybridomas* 3:81–85; Huse et al. (1989) *Science* 246:1275–1281; Griffiths et al. (1993) *EMBO J.* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrard et al. (1991) *Biotechnology (NY)* 9:1373–1377; Hoogenboom et al. (1991) *Nucleic Acids Res.* 19:4133–4137; Barbas et al. (1991) *Proc. Natl. Acad. Sci. USA* 88:7978–7982; and McCafferty et al. (1990) *Nature* 348:552–554.

Additionally, recombinant anti-PD-1 ligand or PD-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci.* 84:214–218; Nishimura et al. (1987) *Cancer Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *Biotechniques* 4:214; Winter U.S. Pat. No. 5,225,539; Jones et al. (1986) *Nature* 321:552–525; Verhoeyen et al. (1988) *Science* 239:1534; and Beidler et al. (1988) *J. Immunol.* 141:4053–4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable genetic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638–2646; Biocca, S. et al. (1990) *EMBO J.* 9:101–108; Werge, T. M. et al. (1990) *FEBS Lett.* 274:193–198; Carlson, J. R. (1993) *Proc. Natl. Acad. Sci. USA* 90:7427–7428; Marasco, W. A. et al. (1993) *Proc. Natl. Acad. Sci. USA* 90:7889–7893; Biocca, S. et al. (1994) *Biotechnology (NY)* 12:396–399; Chen, S-Y. et al. (1994) *Hum. Gene Ther.* 5:595–601; Duan, L. et al. (1994) *Proc. Natl. Acad. Sci. USA* 91:5075–5079; Chen, S-Y. et al. (1994) *Proc. Natl. Acad. Sci. USA* 91:5932–5936; Beerli, R. R. et al. (1994) *J. Biol. Chem.* 269:23931–23936; Beerli, R. R. et al. (1994) *Biochem. Biophys. Res. Commun.* 204:666–672; Mhashilkar, A. M. et al. (1995) *EMBO J.* 14:1542–1551; Richardson, J. H. et al. (1995) *Proc. Natl. Acad. Sci. USA* 92:3137–3141; PCT Publication No. WO 94/02610 by Marasco et al.; and PCT Publication No. WO 95/03832 by Duan et al.).

In one embodiment, an antibody for use in the instant invention is a bispecific antibody. A bispecific antibody has binding sites for two different antigens within a single antibody molecule. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to PD-1 or PD-1 ligand.

An anti-PD-1 ligand or PD-1 antibody (e.g., monoclonal antibody) can be used to isolate a PD-1 ligand or PD-1 polypeptide by standard techniques, such as affinity chromatography or immunoprecipitation. Anti-PD-1 ligand or PD-1 antibodies can facilitate the purification of natural PD-1 ligand or PD-1 polypeptides from cells and of recombinantly produced PD-1 ligand or PD-1 polypeptides expressed in host cells. Moreover, an anti-PD-1 ligand or PD-1 antibody can be used to detect a PD-1 ligand or PD-1 protein (e.g., in a cellular lysate or cell supernatant). Detection can be facilitated by coupling (i.e., physically linking) the antibody to a detectable substance. Accordingly, in one embodiment, an anti-PD-1 ligand or PD-1 antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S, and $^3$H.

IV. Recombinant Expression Vectors and Host Cells

Nucleic acid molecules encoding a PD-1 ligand or PD-1 family protein (or a portion thereof) can be contained in vectors, preferably expression vectors. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Recombinant expression vectors can comprise a nucleic acid molecule of the invention in a form suitable for expression, e.g., constitutive or inducible expression, of a PD-1 or PD-1 ligand in the indicator cell(s) of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" includes promoters, enhancers and other expression control elements (e.g., polyadenylation signals). Such regulatory sequences are described, for example, in Goeddel (1990) *Methods Enzymol.* 185:3–7. Regulatory sequences include those which direct constitutive expression of a nucleotide sequence in many types of host cell and those which direct expression of the nucleotide sequence only in certain host cells (e.g., tissue-specific regulatory sequences). It should be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., PD-1 ligand or PD-1 family proteins, mutant forms of PD-1 ligand or PD-1 proteins, fusion proteins, and the like).

The recombinant expression vectors of the invention can be designed for expression of PD-1 ligand or PD-1 proteins in prokaryotic or eukaryotic cells. For example, PD-1 ligand or PD-1 proteins can be expressed in bacterial cells such as *E. coli*, insect cells (using baculovirus expression vectors) yeast cells or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in PD-1 ligand or PD-1 activity assays, (e.g., direct assays or competitive assays described in detail below), or to generate antibodies specific for PD-1 ligand or PD-1 proteins, for example.

Examples of suitable inducible non-fusion *E. coli* expression vectors include pTrc (Amann et al., (1988) *Gene* 69:301–315) and pET 11d (Studier et al. (1990) *Methods Enzymol.* 185:60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S. (1990) *Methods Enzymol.* 185:119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the PD-1 ligand or PD-1 expression vector is a yeast expression vector. Examples of vectors for expression in yeast *S. cerevisiae* include pYepSec1 (Baldari, et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and picZ (Invitrogen Corp, San Diego, Calif.).

Alternatively, a PD-1 ligand or PD-1 polypeptide can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow, V. A. and Summers, M. D. (1989) *Virology* 170:31–39).

In yet another embodiment, a nucleic acid of the invention is expressed in mammalian cell using a mammalian expression vector. Examples of mammalian expression vectors include pMex-NeoI, pCDM8 (Seed, B. (1987) *Nature* 329: 840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al. *Molecular Cloning: A Laboratory Manual. 2nd, ed., Cold Spring Harbor Laboratory,* Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Moreover, inducible regulatory systems for use in mammalian cells are known in the art, for example systems in which gene expression is regulated by heavy metal ions (see e.g., Mayo et al. (1982) *Cell* 29:99–108; Brinster et al. (1982) *Nature* 296:39–42; Searle et al. (1985) *Mol. Cell. Biol.* 5:1480–1489), heat shock (see e.g., Nouer et al. (1991) in *Heat Shock Response,* ed. Nouer, L., CRC, Boca Raton, Fla., pp 167–220), hormones (see e.g., Lee et al. (1981) *Nature* 294:228–232; Hynes et al. (1981) *Proc. Natl. Acad. Sci. USA* 78:2038–2042; Klock et al. (1987) *Nature* 329: 734–736; Israel and Kaufman (1989) *Nucleic Acids Res.* 17:2589–2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547–5551; Gossen, M. et al. (1995) *Science* 268:1766–1769; PCT Publication No. WO 94/29442; and PCT Publication No. WO 96/01313). Accordingly, in another embodiment, the invention provides a recombinant expression vector in which a PD-1 ligand or PD-1 DNA is operatively linked to an inducible eukaryotic promoter, thereby allowing for inducible expression of a PD-1 ligand or PD-1 protein in eukaryotic cells.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to PD-1 ligand or PD-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al. (1986) "Antisense RNA as a molecular tool for genetic analysis" *Reviews—Trends in Genetics,* Vol. 1(1).

The invention further pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PD-1 ligand or PD-1 protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a PD-1 ligand or PD-1 protein or can be introduced on a separate vector. Cells stably transfected with the introduced nucleic acid can be identified by drug selection (e.g., cells that have incorporated the selectable marker gene will survive, while the other cells die).

A host cell of the invention, such as prokaryotic or eukaryotic host cell in culture, can be used to produce (i.e., express) a PD-1 ligand or PD-1 protein. Accordingly, the invention further provides methods for producing a PD-1 ligand or PD-1 protein using the host cells of the invention. In one embodiment, the method comprises culturing the host cell (into which a recombinant expression vector encoding a PD-1 ligand or PD-1 protein has been introduced) in a suitable medium such that a PD-1 ligand or PD-1 protein is produced. In another embodiment, the method further comprises isolating a PD-1 ligand or PD-1 protein from the medium or the host cell.

Certain host cells can also be used to produce non-human transgenic animals. For example, in one embodiment, a host cell is a fertilized oocyte or an embryonic stem cell into which a PD-1 ligand or PD-1 coding sequences have been introduced. Such host cells can then be used to create non-human transgenic animals in which exogenous PD-1 ligand or PD-1 sequences have been introduced into their genome or homologous recombinant animals in which endogenous PD-1 ligand or PD-1 sequences have been altered. Such animals are useful for studying the function and/or activity of a PD-1 ligand or PD-1 polypeptide and for identifying and/or evaluating modulators of PD-1 ligand or PD-1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous PD-1 ligand or PD-1 gene has been altered by homologous recombination between the endogenous gene and an exogenous DNA molecule introduced into a cell of the animal, e.g., an embryonic cell of the animal, prior to development of the animal.

A transgenic animal can be created by introducing a PD-1 ligand or PD-1-encoding nucleic acid molecule into the male pronucleus of a fertilized oocyte, e.g., by microinjection, retroviral infection, and allowing the oocyte to develop in a pseudopregnant female foster animal. The PD-1 ligand or PD-1 cDNA sequence of SEQ ID NO:1, 3, 10, 11, or 38 can be introduced as a transgene into the genome of a non-human animal. Alternatively, a nonhuman homologue of a human PD-1 ligand or PD-1 gene, such as a mouse or rat PD-1 ligand or PD-1 gene, can be used as a transgene. Alternatively, a PD-1 ligand or PD-1 gene homologue, such as another PD-1 ligand or PD-1 family member, can be isolated based on hybridization to the PD-1 ligand or PD-1 family cDNA sequences of SEQ ID NO:1, 3, 10, 11, or 38 (described further in subsection I above) and used as a transgene. Intronic sequences and polyadenylation signals can also be included in the transgene to increase the efficiency of expression of the transgene. A tissue-specific regulatory sequence(s) can be operably linked to a PD-1 ligand or PD-1 transgene to direct expression of a PD-1 ligand or PD-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B. *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of a PD-1 ligand or PD-1 transgene in its genome and/or expression of PD-1 ligand or PD-1 mRNA in tissues or cells of the animals. A transgenic founder animal can then be used to breed additional animals carrying the transgene. Moreover, transgenic animals carrying a transgene encoding a PD-1 ligand or PD-1 protein can further be bred to other transgenic animals carrying other transgenes.

To create a homologous recombinant animal, a vector is prepared which contains at least a portion of a PD-1 ligand or PD-1 gene into which a deletion, addition or substitution has been introduced to thereby alter, e.g., functionally disrupt, the PD-1 ligand or PD-1 gene. The PD-1 ligand or PD-1 gene can be a human gene (e.g., the SEQ ID NO:1, 3, 10, 11, or 38), but more preferably, is a non-human homologue of a human PD-1 ligand or PD-1 gene (e.g., a cDNA isolated by stringent hybridization with the nucleotide sequence of SEQ ID NO:1, 3, 10, 11, or 38). For example, a mouse PD-1 ligand or PD-1 gene can be used to construct a homologous recombination vector suitable for altering an endogenous PD-1 ligand or PD-1 gene in the mouse genome. In a preferred embodiment, the vector is designed such that, upon homologous recombination, the endogenous PD-1 ligand or PD-1 gene is functionally disrupted (i.e., no longer encodes a functional protein; also referred to as a "knock out" vector). Alternatively, the vector can be designed such that, upon homologous recombination, the endogenous PD-1 ligand or PD-1 gene is mutated or otherwise altered but still encodes a functional protein (e.g., the upstream regulatory region can be altered to thereby alter the expression of the endogenous PD-1 ligand or PD-1 protein). In the homologous recombination vector, the altered portion of the PD-1 ligand or PD-1 gene is flanked at its 5' and 3' ends by additional nucleic acid sequence of the PD-1 ligand or PD-1 gene to allow for homologous recombination to occur between the exogenous PD-1 ligand or PD-1 gene carried by the vector and an endogenous PD-1 ligand or PD-1 gene in an embryonic stem cell. The additional flanking PD-1 ligand or PD-1 nucleic acid sequence is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced PD-1 ligand or PD-1 gene has homologously recombined with the endogenous PD-1 ligand or PD-1 gene are selected (see, e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach,* Robertson, E. J., ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Curr. Opin. Biotechnol.* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In addition to the foregoing, the skilled artisan will appreciate that other approaches known in the art for homologous recombination can be applied to the instant invention. Enzyme-assisted site-specific integration systems are known in the art and can be applied to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucleic Acids Res.* 21:2025–2029; and Fukushige, S. and Sauer, B. (1992) *Proc. Natl. Acad. Sci. USA* 89:7905–7909) and the FLP recombinase-FRT target system (e.g., as described in Dang, D. T. and Perrimon, N. (1992) *Dev. Genet.* 13:367–375; and Fiering, S. et al. (1993) *Proc. Natl. Acad. Sci. USA* 90:8469–8473). Tetracycline-regulated inducible homologous recombination systems, such as described in PCT Publication No. WO 94/29442 and PCT Publication No. WO 96/01313, also can be used.

For example, in another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

V. Pharmaceutical Compositions

PD-1 ligand or PD-1 modulators (e.g., PD-1 ligand or PD-1 inhibitory or stimulatory agents, including PD-1 ligand or PD-1 nucleic acid molecules, proteins, antibodies described above, or compounds identified as modulators of a PD-1 ligand or PD-1 activity and/or expression or modulators of the interaction between PD-1 ligand and PD-1) can be incorporated into pharmaceutical compositions suitable for administration. Such composition typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PD-1 ligand or PD-1 protein or anti-PD-1 ligand or PD-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g.; a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polyactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

VI. Uses and Methods of the Invention

The PD-1 ligand and/or PD-1 modulatory agents, e.g., the nucleic acid molecules, proteins, protein homologues, and antibodies described herein, can be used in one or more of the following methods: a) methods of treatment, e.g., by down-modulating the immune response; b) screening assays; c) predictive medicine (e.g., diagnostic assays, prognostic assays, monitoring clinical trials, and pharmacogenetics). The isolated nucleic acid molecules of the invention can be used, for example, to express PD-1 ligand or PD-1 protein (e.g., via a recombinant expression vector in a host cell in gene therapy applications), to detect PD-1 ligand or PD-1 mRNA (e.g., in a biological sample) or a genetic alteration in a PD-1 ligand or PD-1 gene, and to modulate PD-1 ligand or PD-1 activity, as described further below. The PD-1 ligand or PD-1 proteins can be used to treat disorders characterized by insufficient or excessive production of PD-1 ligand or PD-1 protein. In addition, the PD-1 ligand or PD-1 proteins can be used to screen for naturally occurring PD-1 ligand or PD-1 binding partners, to screen for drugs or compounds which modulate PD-1 ligand or PD-1 activity, as well as to treat disorders characterized by insufficient or excessive production of PD-1 ligand or PD-1 protein or production of PD-1 ligand or PD-1 protein forms which have decreased or aberrant activity compared to PD-1 ligand or PD-1 wild type protein. Moreover, the anti-PD-1 ligand or PD-1 antibodies of the invention can be used to detect and isolated PD-1 ligand or PD-1 proteins, regulate the bioavailability of PD-1 ligand or PD-1 proteins, and modulate PD-1 ligand or PD-1 activity, e.g., by modulating the interaction of PD-1 ligand and PD-1.

A. Methods of Treatment:

The present invention provides for both prophylactic and therapeutic methods of treating a subject at risk of (or susceptible to) a disorder or having a disorder associated with aberrant PD-1 ligand or PD-1 expression or activity.

1. Prophylactic Methods

In one aspect, the invention provides a method for preventing in a subject, a disease or condition associated with an aberrant PD-1 ligand or PD-1 expression or activity, by administering to the subject a PD-1 ligand or PD-1 polypeptide or an agent which modulates PD-1 ligand or PD-1 polypeptide expression or at least one PD-1 ligand or PD-1 activity. Subjects at risk for a disease which is caused or contributed to by aberrant PD-1 ligand or PD-1 expression or activity can be identified by, for example, any or a combination of diagnostic or prognostic assays as described herein. Administration of a prophylactic agent can occur prior to the manifestation of symptoms characteristic of PD-1 ligand or PD-1 aberrancy, such that a disease or disorder is prevented or, alternatively, delayed in its progression. In another embodiment, an agent which modulates the interaction between PD-1 and a PD-1 ligand can be administered at the time of exposure to antigen. Depending on the type of PD-1 ligand or PD-1 aberrancy or condition, for example, a PD-1 ligand or PD-1 polypeptide, PD-1 ligand or PD-1 agonist or PD-1 ligand or PD-1 antagonist agent can be used for treating the subject. The appropriate agent can be determined based on clinical indication and can be identified, e.g., using screening assays described herein.

2. Therapeutic Methods

Another aspect of the invention pertains to methods of modulating PD-1 ligand or PD-1 expression or activity for therapeutic purposes. PD-1 ligand has been demonstrated to inhibit the costimulation and proliferation of immune cells and to transmit an inhibitory signal to immune cells via PD-1. Accordingly, the activity and/or expression of PD-1 ligand or PD-1 as well as the interaction between PD-1 ligand and PD-1 can be modulated in order to modulate the immune response. It should be understood that in embodiments where PD-1 ligand binds to a costimulatory receptor, upregulation of PD-1 ligand activity results in upregulation of immune responses, whereas downregulation of PD-1 ligand activity results in downregulation of immune responses. In embodiments where PD-1 ligand binds to inhibitory receptors, upregulation of PD-1 ligand activity results in downregulation of immune responses, whereas downregulation of PD-1 ligand activity results in upregulation of immune responses. In a preferred embodiment, PD-1 ligand binds to inhibitory receptors. In a particularly preferred embodiment, PD-1 ligand binds to PD-1.

Modulatory methods of the invention involve contacting a cell with a modulator of a PD-1 ligand or a PD-1 polypeptide, e.g., an agent that modulates expression or activity of PD-1 ligand and/or PD-1, or an agent that modulates the interaction of PD-1 ligand and PD-1.

An agent that modulates PD-1 ligand or PD-1 protein activity is an agent as described herein, such as a nucleic acid or a protein molecule, a naturally-occurring target molecule of a PD-1 ligand or PD-1 protein (e.g., PD-1 in the case of PD-1 ligand or PD-1 ligand in the case of PD-1), a PD-1 ligand or PD-1 antibody, a PD-1 ligand or PD-1 agonist or antagonist, a peptidomimetic of a PD-1 ligand or PD-1 agonist or antagonist, or other small molecule.

An agent that modulates the expression of PD-1 ligand or PD-1 is, e.g., an antisense nucleic acid molecule, triplex oligonucleotide, a ribozyme or a recombinant vector for expression of a PD-1 ligand or PD-1 protein. For example, an oligonucleotide complementary to the area around a PD-1 ligand or PD-1 polypeptide translation initiation site, can be synthesized and used. One or more antisense oligonucleotides can be added to cell media, typically at 200 μg/ml, or administered to a patient to prevent the synthesis of a PD-1 ligand or PD-1 polypeptide. The antisense oligonucleotide is taken up by cells and hybridizes to a PD-1 ligand or PD-1 mRNA to prevent translation. Alternatively, an oligonucleotide which binds double-stranded DNA to form a triplex construct to prevent DNA unwinding and transcription can be used. As a result of either, synthesis of a PD-1 ligand or PD-1 polypeptide is blocked. When PD-1 expression is modulated, preferably, such modulation occurs by a means other than by knocking out the PD-1 gene, i.e., cells in which PD-1 expression is modulated preferably comprise a nucleic acid molecule encoding PD-1.

Agents which modulate expression, by virtue of the fact that they control the amount of PD-1 or PD-1 ligand in a cell, also modulate the total amount of PD-1 or PD-1 ligand activity in a cell.

In one embodiment, an agent that stimulates an inhibitory activity of a PD-1 ligand or an inhibitory activity of PD-1 is an agonist of PD-1 ligand or PD-1. Examples of such agents include active PD-1 ligand or PD-1 protein and an expressible nucleic acid molecule encoding PD-1 ligand or PD-1 polypeptide that has been introduced into the cell. In another embodiment, the agent inhibits the costimulatory or inhibitory activity of a PD-1 ligand or inhibitory activity of PD-1 and is an antagonist of a PD-1 ligand or PD-1. Examples of such agents include antisense PD-1 ligand or PD-1 nucleic acid molecules, anti-PD-1 ligand or anti-PD-1 antibodies (e.g., non-activating antibodies), soluble, nonactivating forms of PD-1 ligand or PD-1 molecules, and PD-1 ligand or PD-1 inhibitors.

These modulatory agents can be administered in vitro (e.g., by contacting the cell with the agent) or, alternatively, in vivo (e.g., by administering the agent to a subject). As such, the present invention provides methods of treating an individual afflicted with a disease or disorder that would benefit from modulation of a PD-1 ligand or PD-1 protein, e.g., a disorder which would benefit from downmodulation of the immune response, or which is characterized by aberrant expression or activity of a PD-1 ligand or PD-1 protein or nucleic acid molecule. In one embodiment, the method involves administering an agent (e.g., an agent identified by a screening assay described herein), or combination of agents that modulates (e.g., upregulates or downregulates) PD-1 ligand or PD-1 expression or activity. In another embodiment, the method involves administering a PD-1 ligand or PD-1 protein or nucleic acid molecule as therapy to compensate for reduced or aberrant PD-1 ligand or PD-1 expression or activity.

Stimulation of PD-1 ligand or PD-1 activity is desirable in situations in which PD-1 ligand or PD-1 is abnormally downregulated and/or in which increased PD-1 ligand or PD-1 activity is likely to have a beneficial effect. Likewise, inhibition of PD-1 ligand or PD-1 activity is desirable in situations in which PD-1 ligand or PD-1 is abnormally upregulated and/or in which decreased PD-1 ligand or PD-1 activity is likely to have a beneficial effect. One of ordinary skill in the art should recognize that in embodiments where PD-1 ligand binds to a costimulatory receptor, stimulation of PD-1 ligand and stimulation of PD-1 have opposite effects on immune cell costimulation, and therefore, on the immune response. In such an instance, when stimulation of the activity of one molecule is desirable, suppression of the activity of the other molecule is desirable.

Exemplary agents for use in downmodulating PD-1 ligand (PD-1 ligand antagonists) include (for example): antisense molecules, antibodies that recognize PD-1 ligand, compounds that block interaction of PD-1 ligand and one of its naturally occurring receptors on a immune cell (e.g., soluble, monovalent PD-1 ligands, and soluble forms of PD-1 ligand ligands or compounds identified in the screening assays described herein). Exemplary agents for use in downmodulating PD-1 (PD-1 antagonists) include (for example): antisense molecules, antibodies that bind to PD-1, but do not transduce an inhibitory signal to the immune cell ("non-activating antibodies"), and soluble forms of PD-1.

Exemplary agents for use in upmodulating PD-1 ligand (PD-1 ligand agonists) include (for example): nucleic acid molecules encoding PD-1 ligand polypeptides, multivalent forms of PD-1 ligand, compounds that increase the expression of PD-1 ligand, and cells that express PD-1 ligand, etc. Exemplary agents for use in upmodulating PD-1 (PD-1 agonists) include (for example): antibodies that transmit an inhibitory signal via PD-1 by binding to and activating (e.g., crosslinking) the PD-1 molecule, compounds that enhance the expression of PD-1, nucleic acid molecules encoding PD-1, and forms of PD-1 ligand that transduce a signal via PD-1 (especially bivalent forms of B7-4).

3. Downregulation of Immune Responses by Modulation of PD-1 Ligand or PD-1

There are numerous embodiments of the invention for upregulating the inhibitory function or downregulating the costimulatory function of a PD-1 ligand polypeptide to thereby downregulate immune responses. Downregulation can be in the form of inhibiting or blocking an immune response already in progress or may involve preventing the induction of an immune response.

The functions of immune cells can be inhibited by downregulating immune cell responses or by inducing specific anergy in immune cells, or both.

For example, anti-PD-1 ligand antibodies or PD-1 ligand polypeptides (e.g., soluble, monomeric forms of a PD-1 ligand polypeptide such as PD-1 ligand-Ig), and/or anti-PD-1 ligand antibodies that block the interaction of PD-1 ligand with a costimulatory receptor can be used to inhibit a costimulatory signal and, thus, downmodulate the immune response.

In addition, in embodiments where PD-1 ligand binds to an inhibitory receptor, forms of PD-1 ligand that bind to the inhibitory receptor and activate it, e.g., multivalent PD-1 ligand on a cell surface, can be used to downmodulate the immune response.

Likewise, the PD-1 pathway can also be stimulated by the use of an agent to thereby downmodulate the immune response. This is accomplished via inhibition of the interaction of PD-1 ligand with a stimulatory receptor on an immune cell (e.g., by using a soluble form of PD-1 and/or CTLA4) or activation of PD-1 (e.g., using an activating antibody which crosslinks PD-1) to provide negative signals to immune cells.

In one embodiment of the invention, an activating antibody used to stimulate PD-1 activity is a bispecific antibody. For example, such an antibody can comprise a PD-1 binding site and another binding site which targets a cell surface receptor on an immune cell, e.g., on a T cell, a B cell, or a myeloid cell. In one embodiment, such an antibody, in addition to comprising a PD-1 binding site can further comprise a binding site which binds to a molecule which is in proximity to an activating or inhibitory receptor, e.g., B-cell antigen receptor, a T-cell antigen receptor, or an Fc receptor in order to target the molecule to a specific cell population. For example, a CD3 antigen, a T-cell receptor chain, LFA-1, CD2, CTLA-4, immunoglobulin, B cell receptor, Ig alpha, Ig beta, CD22, or Fc receptor could be used. Such antibodies (or other bispecific agents) are art recognized and can be produced, e.g., as described herein. Selection of this second antigen for the bispecific antibody provides flexibility in selection of cell population to be targeted for inhibition.

In another embodiment, co-ligation of PD-1 and an activating or inhibitory receptor on a cell can enhance the generation of a negative signal via PD-1. Such co-ligation can be accomplished e.g., by use of a bispecific agent, e.g., a bispecific antibody as described herein having specificity for both PD-1 and a molecule associated with a receptor. In another embodiment, the use of a multivalent form of an agent that transmits a negative signal via PD-1 can be used to enhance the transmission of a negative signal via PD-1, e.g., an agent presented on a bead or on a surface. In another embodiment, a such a multivalent agent can comprise two specificities to achieve co-ligation of PD-1 and a receptor or a receptor associated molecule (e.g., a bead comprising anti CD3 and PD-1 ligand).

Agents that block or inhibit interaction of PD-1 ligand with a costimulatory receptor (e.g., soluble forms of PD-1 ligand or blocking antibodies to PD-1 ligand) as well as agents that promote a PD-1 ligand-mediated inhibitory signal or agonists of PD-1 which activate PD-1 (e.g., PD-1 activating antibodies or PD-1 activating small molecules) can be identified by their ability to inhibit immune cell proliferation and/or effector function or to induce anergy when added to an in vitro assay. For example, cells can be cultured in the presence of an agent that stimulates signal transduction via an activating receptor. A number of art recognized readouts of cell activation can be employed to measure the inhibition, e.g., cell proliferation or effector function (e.g., antibody production, cytokine production, phagocytosis) in the presence of the activating agent. The ability of a test agent to block this activation can be readily determined by measuring the ability of the agent to affect a decrease in proliferation or effector function being measured.

In one embodiment of the invention, tolerance is induced against specific antigens by co-administering an antigen with a PD-1 agonist. For example, tolerance can be induced to specific proteins. In one embodiment, immune responses to allergens or foreign proteins to which an immune response is undesirable can be inhibited. For example, patients that receive Factor VIII frequently generate antibodies against this clotting factor. Co-administration of an agent that blocks a PD-1 ligand-mediated costimulatory signal or an agent that stimulates a PD-1 mediated inhibitory signal in combination with recombinant factor VIII (or by physically linked to Factor VIII, e.g., by cross-linking) can result in downmodulation.

In one embodiment, fusion proteins comprising a PD-1 ligand first peptide fused to a second peptide having an activity of another B lymphocyte antigen (e.g., B7-1 or B7-2), can be used to block interaction of PD-1 ligand with a costimulatory receptor on a immune cell to downmodulate immune responses. Alternatively, two separate peptides (for example, a PD-1 ligand polypeptide with B7-2 and/or B7-1), or a combination of blocking antibodies (e.g., antibodies against a PD-1 ligand polypeptide with anti-B7-2 and/or anti-B7-1 monoclonal antibodies) can be combined as a single composition or administered separately (simultaneously or sequentially) to downregulate immune cell mediated immune responses in a subject. Furthermore, a therapeutically active amount of one or more peptides having a PD-1 ligand polypeptide activity, with B7-1 and/or B7-2 activity can be used in conjunction with other downmodulating reagents to influence immune responses. Examples of other immunomodulating reagents include antibodies that block a costimulatory signal, (e.g., against CD28, ICOS), antibodies that activate an inhibitory signal via CTLA4, and/or antibodies against other immune cell markers (e.g., against CD40, against CD40 ligand, or against cytokines), fusion proteins (e.g., CTLA4-Fc, PD-1-Fc), and immunosuppressive drugs, (e.g., rapamycin, cyclosporine A or FK506).

The PD-1 ligand and/or PD-1 peptides may also be useful in the construction of therapeutic agents which block immune cell function by destruction of cells. For example, portions of a PD-1 ligand or PD-1 polypeptide can be linked to a toxin to make a cytotoxic agent capable of triggering the destruction of cells to which it binds.

For making cytotoxic agents, polypeptides of the invention may be linked, or operatively attached, to toxins using techniques that are known in the art, e.g., crosslinking or via recombinant DNA techniques. The preparation of immunotoxins is, in general, well known in the art (see, e.g., U.S. Pat. No. 4,340,535, and EP 44167, both incorporated herein by reference). Numerous types of disulfide-bond containing linkers are known which can successfully be employed to conjugate the toxin moiety with a polypeptide. In one embodiment, linkers that contain a disulfide bond that is sterically "hindered" are to be preferred, due to their greater stability in vivo, thus preventing release of the toxin moiety prior to binding at the site of action.

A wide variety of toxins are known that may be conjugated to polypeptides or antibodies of the invention. Examples include: numerous useful plant-, fungus- or even bacteria-derived toxins, which, by way of example, include various A chain toxins, particularly ricin A chain, ribosome inactivating proteins such as saporin or gelonin, .alpha.-sarcin, aspergillin, restrictocin, ribonucleases such as placental ribonuclease, angiogenic, diphtheria toxin, and pseudomonas exotoxin, etc. A preferred toxin moiety for use in connection with the invention is toxin A chain which has been treated to modify or remove carbohydrate residues, deglycosylated A chain (U.S. Pat. No. 5,776,427).

Infusion of one or a combination of such cytotoxic agents, (e.g., PD-1 ligand ricin (alone or in combination with B7-2-ricin or B7-1-ricin), into a patient may result in the death of immune cells, particularly in light of the fact that activated immune cells that express higher amounts of PD-1 ligand ligands. For example, because PD-1 is induced on the surface of activated lymphocytes, an antibody against PD-1 can be used to target the depletion of these specific cells by Fc-R dependent mechanisms or by ablation by conjugating a cytotoxic drug (e.g., ricin, saporin, or calicheamicin) to the antibody. In one embodiment, the antibody toxin can be a bispecific antibody. Such bispecific antibodies are useful for targeting a specific cell population, e.g., using a marker found only on a certain type of cell, e.g., a TCR, BCR, or FcR molecule.

Downregulating or preventing PD-1 ligand polypeptide costimulatory functions or activating a PD-1 ligand or a PD-1 inhibitory function (e.g., by stimulation of the negative signaling function of PD-1) is useful to downmodulate the immune response, e.g., in situations of tissue, skin and organ transplantation, in graft-versus-host disease (GVHD), or in autoimmune disease such as systemic lupus erythematosus, and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of a molecule which inhibits or blocks interaction of a B7 molecule with a costimulatory receptor(s) on immune cells (such as a soluble, monomeric form of a PD-1 ligand or PD-1 polypeptide) alone or in conjunction with another downmodulatory agent prior to or at the time of transplantation can inhibit the generation of a costimulatory signal. Moreover, inhibition of PD-1 ligand costimulatory signals, or promotion of a PD-1 ligand or PD-1 inhibitory signal may also be sufficient to anergize the immune cells, thereby inducing tolerance in a subject. Induction of long-term tolerance by blocking a PD-1 ligand mediated costimulatory signal may avoid the necessity of repeated administration of these blocking reagents.

To achieve sufficient immunosuppression or tolerance in a subject, it may also be desirable to block the costimulatory function of other molecules. For example, it may be desirable to block the function of B7-1 and PD-1 ligand, B7-2 and PD-1 ligand, or B7-1 and B7-2 and PD-1 ligand by administering a soluble form of a combination of peptides having an activity of each of these antigens or blocking antibodies against these antigens (separately or together in a single composition) prior to or at the time of transplantation. Alternatively, it may be desirable to promote inhibitory activity of PD-1 ligand or PD-1 and inhibit a costimulatory activity of B7-1 and/or B7-2. Other downmodulatory agents that can be used in connection with the downmodulatory methods of the invention include, for example, agents that transmit an inhibitory signal via CTLA4, soluble forms of CTLA4, antibodies that activate an inhibitory signal via CTLA4, blocking antibodies against other immune cell markers or soluble forms of other receptor ligand pairs (e.g., agents that disrupt the interaction between CD40 and CD40 ligand (e.g., anti CD40 ligand antibodies)), antibodies against cytokines, or immunosuppressive drugs. In another embodiment, a combination of at least two different PD-1 ligand antibodies can be administered to achieve optimal blocking activity.

Blocking PD-1 ligand polypeptide costimulation or activating a PD-1 ligand or PD-1 inhibitory function is also useful in treating autoimmune disease. Many autoimmune disorders are the result of inappropriate activation of immune cells that are reactive against self tissue and which promote the production of cytokines and autoantibodies involved in the pathology of the diseases. Preventing or downmodulating the activation of autoreactive immune cells may reduce or eliminate disease symptoms. Administration of reagents which block costimulation of immune cells by disrupting receptor:ligand interactions of B7 molecules with costimulatory receptors is useful to inhibit immune cells activation and prevent production of autoantibodies or cytokines which are involved in the disease process. Additionally, agents that promote an inhibitory function of PD-1 ligand or PD-1 may induce antigen-specific tolerance of autoreactive immune cells which could lead to long-term relief from the disease. The efficacy of reagents in preventing or alleviating autoimmune disorders can be determined using a number of well-characterized animal models of human autoimmune diseases. Examples include murine experimental autoimmune encephalitis, systemic lupus erythematosus in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840–856).

Inhibition of immune cell activation is useful therapeutically in the treatment of allergy and allergic reactions, e.g., by inhibiting IgE production. An agent that promotes a PD-1 ligand or PD-1 inhibitory function can be administered to an allergic subject to inhibit immune cell mediated allergic responses in the subject. Activating a PD-1 molecule is also useful in treating allergies. Inhibition of PD-1 ligand costimulation of immune cells or stimulation of a PD-1 ligand or PD-1 inhibitory pathway can be accompanied by exposure to allergen in conjunction with appropriate MHC molecules. Allergic reactions can be systemic or local in nature, depending on the route of entry of the allergen and the pattern of deposition of IgE on mast cells or basophils. Thus, inhibition of immune cell mediated allergic responses can be local or systemic by administration (e.g., either local or systemic, respectively) of an inhibitory form of an agent that inhibits the interaction of PD-1 ligand with a costimulatory receptor or an agent that promotes an inhibitory function of PD-1 ligand or PD-1.

Inhibition of immune cell activation through blockage of a PD-1 ligand costimulatory activity or stimulation of PD-1 inhibitory activity may also be important therapeutically in viral infections of immune cells. For example, in the acquired immune deficiency syndrome (AIDS), viral replication is stimulated by immune cell activation. Blocking a PD-1 ligand/costimulatory receptor interaction or stimulation of PD-1 ligand or PD-1 inhibitory function may result in inhibition of viral replication to thereby ameliorate the course of AIDS. Downregulation of an immune response via stimulation of PD-1 ligand activity or PD-1 ligand interaction with its natural binding partner(s), e.g., PD-1, may also be useful in promoting the maintenance of pregnancy. PD-1 ligand is normally highly expressed in placental trophoblasts, the layer of cells that forms the interface between mother and fetus and is thought to play a role in preventing maternal rejection of the fetus. Females at risk for spontaneous abortion (e.g., those identified by screening for PD-1 ligand activity, as described in the "Prognostic Assays" section, those who have previously had a spontaneous abortion or those who have had difficulty conceiving) because of immunologic rejection of the embryo or fetus can be treated with agents that stimulate the activity of PD-1 ligand or its interaction with its natural binding partner(s), e.g., PD-1.

Downregulation of an immune response via stimulation of PD-1 ligand activity or PD-1 ligand interaction with its natural binding partner(s), e.g., PD-1, is also useful in treating an autoimmune attack of autologous tissues. For example, PD-1 ligand is normally highly expressed in the heart and protects the heart from autoimmune attack. This is evidenced by the fact that the Balb/c PD-1 knockout mouse exhibits massive autoimmune attack on the heart with thrombosis. Thus, conditions that are caused or exacerbated by autoimmune attack (e.g., in this example, heart disease, myocardial infarction or atherosclerosis) may be ameliorated or improved by increasing PD-1 ligand activity or PD-1 ligand biding to its natural binding partner, e.g., PD-1. It is therefore within the scope of the invention to modulate conditions exacerbated by autoimmune attack, such as autoimmune disorders (as well as conditions such as heart disease, myocardial infarction, and atherosclerosis) by stimulating PD-1 ligand activity or PD-1 ligand interaction with PD-1 ligand.

B. Identification of Molecules which Modulate Expression of a PD-1 Ligand or PD-1 Polypeptide The antibodies produced using the proteins and peptides of the current invention can be used in a screening assay for molecules which modulate the expression of PD-1 ligand or PD-1 polypeptide on cells. For example, molecules which modulate intracellular signaling pathways that culminate in changes in expression of PD-1 ligand or PD-1 polypeptides (e.g., in response to activation signals), can be identified by assaying expression of one or more PD-1 ligand or PD-1 polypeptides on the cell surface. Reduced immunofluorescent staining by an appropriate antibody in the presence of the molecule would indicate that the molecule inhibits intracellular signals. Molecules which upregulate PD-1 ligand or PD-1 polypeptide expression result in an increased immunofluorescent staining. Alternatively, the effect of a molecule on expression of a polypeptide can be determined by detecting cellular mRNA levels using a probe of the invention. For example, a cell which expresses a PD-1 ligand or PD-1 polypeptide can be contacted with a molecule to be tested, and an increase or decrease in mRNA levels in the cell detected by standard techniques, such as Northern hybridization analysis or conventional dot blot of mRNA or total poly($A^+$)RNAs using a cDNA probe labeled with a detectable marker. Molecules which modulate expression of a PD-1 ligand or PD-1 polypeptide are useful therapeutically for either upregulating or downregulating immune responses alone or in conjunction with soluble blocking or stimulating reagents as described above. For instance, a molecule which inhibits expression of PD-1 ligand can be administered together with a second agent (e.g., an immunosuppressant) agent, e.g., an immunosuppressant or a molecule which inhibits expression of PD-1 can be given with an immunostimulant (e.g., an adjuvant). Exemplary molecules which can be tested for their ability to modulate PD-1 ligand or PD-1 include cytokines such as IL-4, γINF, IL-10, IL-12, GM-CSF and prostagladins.

C. Screening Assays

The invention provides a method (also referred to herein as a "screening assay") for identifying modulators, i.e., candidate or test compounds or agents (e.g., peptides, peptidomimetics, small molecules or other drugs) which bind to PD-1 ligand or PD-1 proteins, have a stimulatory or inhibitory effect on, for example, PD-ligand or PD-1 expression or PD-1 ligand or PD-1 activity. In one embodiment, the invention provides assays for screening candidate or test compounds which bind to, or modulate the activity of a PD-1 ligand or PD-1 protein or polypeptide or biologically active portion thereof, e.g., which modulate the ability of PD-1 ligand or PD-1 polypeptide to interact with its cognate biding partner or an interactor molecule (e.g., an intracellular interactor molecule).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) Angew. Chem. Int. Ed. Engl. 33:2061; and in Gallop et al. (1994) *J. Med. Chem.* 37:1233.

Libraries of compounds can be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci. USA* 87:6378–6382); (Felici (1991) *J. Mol. Biol.* 223:301–310); (Ladner supra.).

In another embodiment, an assay is a cell-based assay comprising contacting a cell expressing a PD-1 ligand target molecule (an intracellular interactor molecule or a PD-1 receptor) or PD-1 target molecule (e.g., a PD-1 ligand ligand or intracellular interactor molecule) with a test compound and determining the ability of the test compound to modulate (e.g., stimulate or inhibit) the activity of the PD-1 ligand or PD-1 target molecule. Determining the ability of the test compound to modulate the activity of a PD-1 ligand or PD-1 target molecule can be accomplished, for example, by determining the ability of the PD-1 ligand or PD-1 protein to bind to or interact with the PD-1 ligand or PD-1 target molecule, as molecules which bind to or interact with the target molecule are more likely to modulate activity. Determining the ability of the PD-1 ligand or PD-1 protein to bind to or interact with its binding partner can be accomplished, e.g., by measuring direct binding.

In a direct binding assay, the PD-1 ligand or PD-1 protein (or their respective target molecules) can be coupled with a radioisotope or enzymatic label such that binding of the PD-1 ligand or PD-1 protein to aPD-1 ligand or PD-1 target molecule can be determined by detecting the labeled protein in a complex. For example PD-1 ligand or PD-1 molecules, e.g., PD-1 ligand or PD-1 proteins, can be labeled with $^{125}I$, $^{35}S$, $^{14}C$, or $^{3}H$, either directly or indirectly, and the radioisotope detected by direct counting of radioemission or by scintillation counting. Alternatively, PD-1 ligand or PD-1 molecules can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interaction between PD-1 ligand or PD-1 and its target molecule, without the labeling of any of the interactants. For example, a microphysiometer can be used to detect the interaction of PD-1 ligand or PD-1 with its target molecule without the labeling of either PD-1 ligand or PD-1 or the target molecule (McConnell, H. M. et al. (1992) *Science* 257:1906–1912).

As used herein, a "microphysiometer" (e.g., Cystosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the PD-1 ligand or PD-1 protein to bind to or interact with a PD-1 ligand or PD-1 target molecule can be accomplished by determining the activity of the PD-1 ligand, PD-1 or the appropriate target molecule. For example, the activity of PD-1 ligand, PD-1 or the appropriate target molecule can be determined by detecting induction of a cellular second messenger (e.g., tyrosine kinase activity), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by PD-1 ligand, PD-1 or the appropriate target molecule. For example, determining the ability of the PD-1 ligand or PD-1 protein to bind to or interact with a PD-1 ligand or PD-1 target molecule can be accomplished, for example, by measuring the ability of a compound to modulate immune cell costimulation or inhibition in a proliferation assay, or by interfering with the ability of a PD-1 ligand or PD-1 polypeptide to bind to antibodies that recognize a portion of the PD-1 ligand or PD-1 polypeptide.

In yet another embodiment, an assay of the present invention is a cell-free assay in which a PD-1 ligand or PD-1 protein or biologically active portion thereof is contacted with a test compound and the ability of the test compound to bind to the PD-1 ligand or PD-1 protein or biologically active portion thereof is determined. Binding of the test compound to the PD-1 ligand or PD-1 protein can be determined either directly or indirectly as described above. In a preferred embodiment, the assay includes contacting the PD-1 ligand or PD-1 protein or biologically active portion thereof with a known compound which binds PD-1 ligand or PD-1 to form an assay mixture, contacting the assay mixture with a test compound, and determining the ability of the test compound to interact with a PD-1 ligand or PD-1 protein, wherein determining the ability of the test compound to interact with a PD-1 ligand or PD-1 protein comprises determining the ability of the test compound to preferentially bind to PD-1 ligand or PD-1 polypeptide or biologically active portion thereof as compared to the known compound.

In another embodiment, the assay is a cell-free assay in which a PD-1 ligand or PD-1 protein or biologically active portion thereof is contacted with a test compound and the ability of the test compound to modulate (e.g., stimulate or inhibit) the activity of the PD-1 ligand or PD-1 protein or biologically active portion thereof is determined. Determining the ability of the test compound to modulate the activity of a PD-1 ligand or PD-1 protein can be accomplished, for example, by determining the ability of the PD-1 ligand or PD-1 protein to bind to its binding partner (e.g., by determining the ability of the compound to inhibit the ability of PD-1 ligand to bind to PD-1) by one of the methods described above for determining direct binding. Determining the ability of the PD-1 ligand or PD-1 protein to bind to its binding partner can also be accomplished using a technology such as real-time Biomolecular Interaction Analysis (BIA) (Sjolander, S. and Urbaniczky, C. (1991) *Anal. Chem.* 63:2338–2345 and Szabo et al. (1995) *Curr. Opin. Struct. Biol.* 5:699–705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In yet another embodiment, the cell-free assay involves contacting a PD-1 ligand or PD-1 protein or biologically active portion thereof with a known compound which binds the PD-1 ligand or PD-1 protein (e.g., with its binding partner) to form an assay mixture, contacting the assay mixture with a test compound, and determining the ability of the test compound to prevent the interaction of PD-1 ligand or PD-1 protein with its binding partner, for example the ability of the test compound to preferentially interact with the PD-1 ligand or PD-1 protein at its binding site or the ability to modulate the activity of a PD-1 ligand or PD-1 target molecule can be tested. The cell-free assays of the present invention are amenable to use of both soluble and/or membrane-bound forms of proteins (e.g., PD-1 ligand or PD-1 proteins on biologically active portions thereof, or binding partners to which PD-1 ligand or PD-1 binds). In the case of cell-free assays in which a membrane-bound form of a protein is used (e.g., a cell surface PD-1 ligand or PD-1 receptor) it may be desirable to utilize a solubilizing agent such that the membrane-bound form of the protein is maintained in solution. Examples of such solubilizing agents include non-ionic detergents such as n-octylglucoside n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either PD-1 ligand or PD-1 or an appropriate target molecule to facilitate separation of complexed from uncomplexed forms of one or both of the proteins, as well as to accommodate automation of the assay. Binding of a test compound to a PD-1 ligand or PD-1 protein, or interaction of a PD-1 ligand or PD-1 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/PD-1 ligand or PD-1 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or PD-1 ligand or PD-1 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of PD-1 ligand or PD-1 binding or activity determined using standard techniques.

Other techniques for immobilizing proteins on matrices can also be used in the screening assays of the invention. For example, either a PD-1 ligand or PD-1 protein or a PD-1 ligand or PD-1 target molecule can be immobilized utilizing conjugation of biotin and streptavidin. Biotinylated PD-1 ligand or PD-1 protein or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with PD-1 ligand or PD-1 protein or target molecules but which do not interfere with binding of the PD-1 ligand or PD-1 protein to its target molecule can be derivatized to the wells of the plate, and unbound target or PD-1 ligand or PD-1 protein trapped in the wells by antibody conjugation. Methods for detecting such complexes, in addition to those described above for the GST-immobilized complexes, include immunodetection of complexes using antibodies reactive with the PD-1 ligand or PD-1 protein or target molecule, as well as enzyme-linked assays which rely on detecting an enzymatic activity associated with the PD-1 ligand or PD-1 protein or target molecule.

In an alternative embodiment, determining the ability of the test compound to modulate the activity of a PD-1 ligand or PD-1 protein can be accomplished by determining the ability of the test compound to modulate the activity of a molecule that functions downstream of PD-1 ligand, e.g., a molecule that interacts with PD-1 ligand, or a molecule that functions downstream of PD-1, e.g., by interacting with the cytoplasmic domain of PD-1. For example, levels of second messengers can be determined, the activity of the interactor molecule on an appropriate target can be determined, or the binding of the interactor to an appropriate target can be determined as previously described.

In another embodiment, modulators of PD-1 ligand or PD-1 expression are identified in a method wherein a cell is contacted with a candidate or test compound and the expression of PD-1 ligand or PD-1 mRNA or protein in the cell is determined. The level of expression of PD-1 ligand or PD-1 mRNA or protein in the presence of the candidate compound is compared to the level of expression of PD-1 ligand or PD-1 mRNA or protein in the absence of the candidate compound. The candidate compound can then be identified as a modulator of PD-1 ligand or PD-1 expression based on this comparison. For example, when expression of PD-1 ligand or PD-1 mRNA or protein is greater (e.g., reproducibly and statistically significantly greater) in the presence of the candidate compound than in its absence, the candidate compound is identified as a stimulator of PD-1 ligand or PD-1 mRNA or protein expression. Alternatively, when expression of PD-1 ligand or PD-1 mRNA or protein is less (e.g., reproducibly and statistically significantly less) in the presence of the candidate compound than in its absence, the candidate compound is identified as an inhibitor of PD-1 ligand or PD-1 mRNA or protein expression. The level of PD-1 ligand or PD-1 mRNA or protein expression in the cells can be determined by methods described herein for detecting PD-1 ligand or PD-1 mRNA or protein.

Figure 31A:
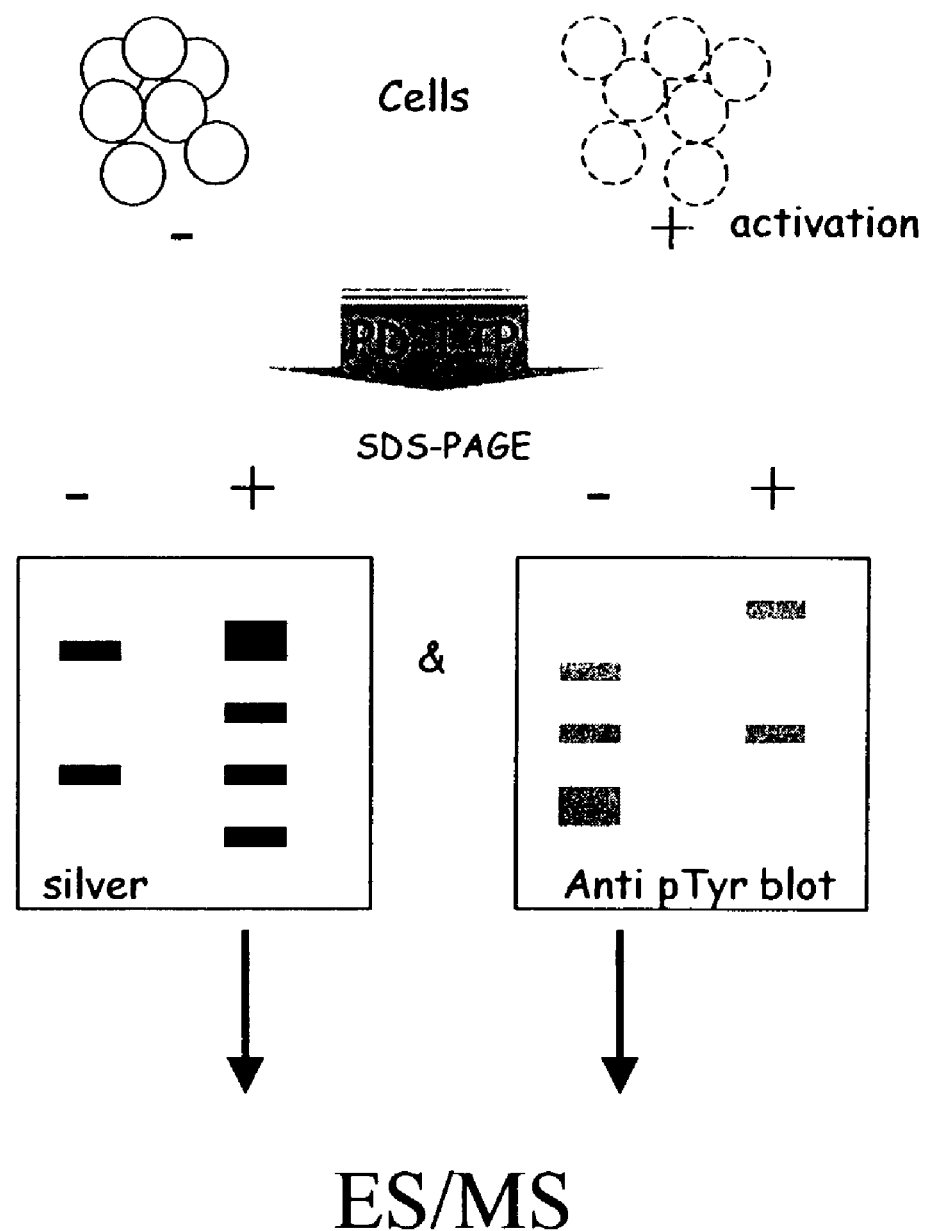
Figure 32:
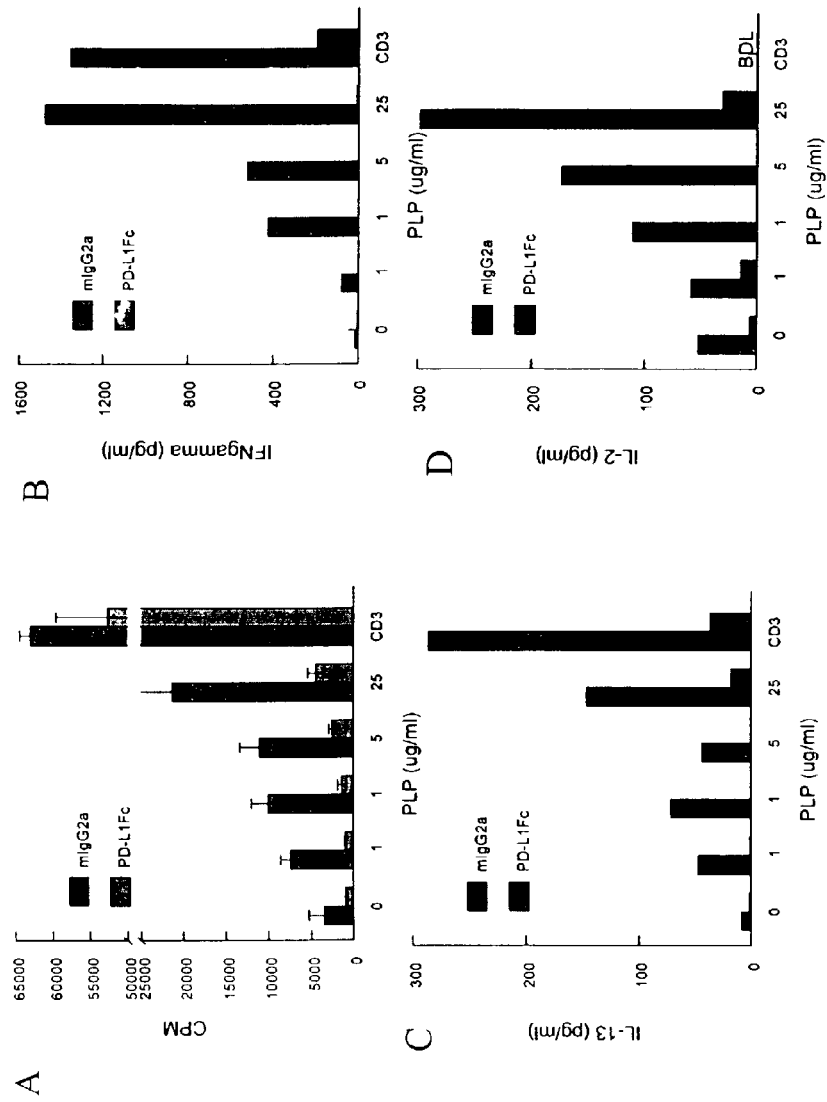
FIG. 32 A–D show that immunization of SJL/J mice with proteolipid protein (PLP) in complete Freund's adjuvant (CFA) and PD-L1Fc (on the day of immunization) attenuates proliferation and cytokine secretion by lymph node cells.
Figure 33:
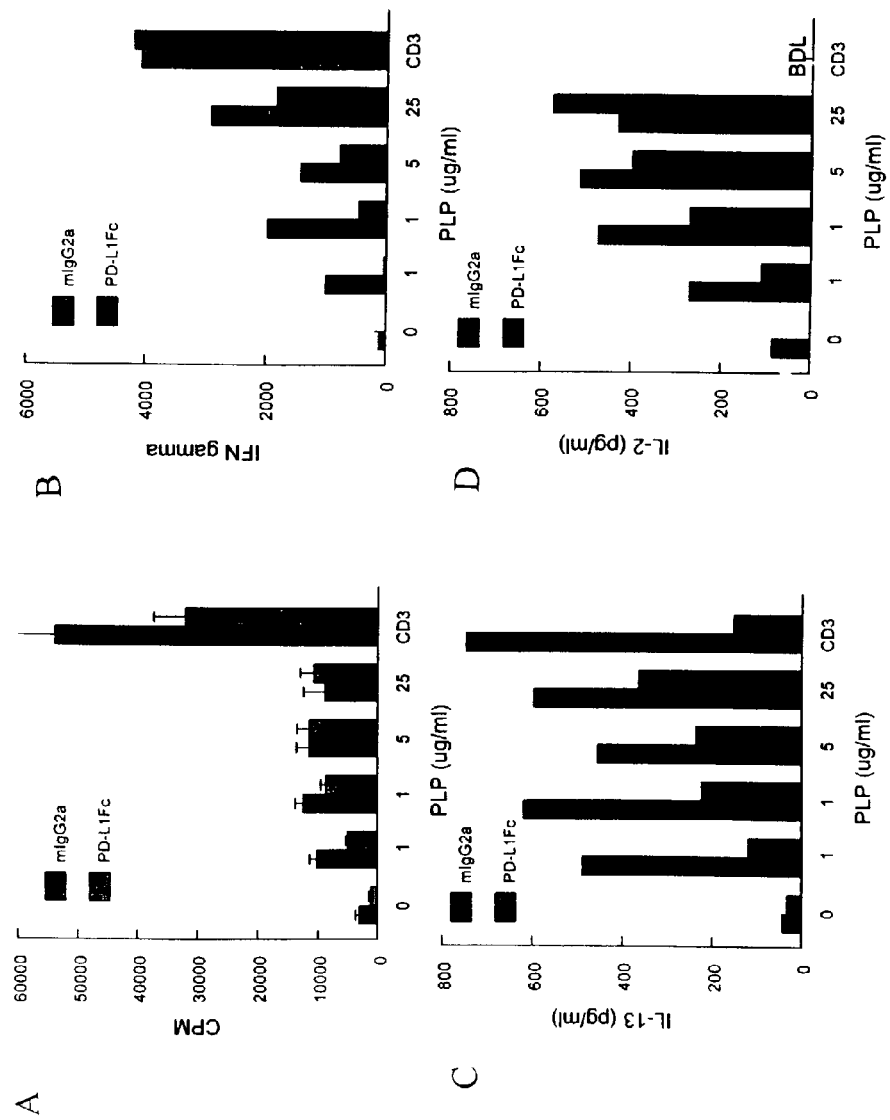
FIG. 33 A–D show that immunization of SJL/J mice with proteolipid protein (PLP) in complete Freund's adjuvant (CFA) and PD-L1Fc (on the day of immunization) attenuates proliferation and cytokine secretion by spleen cells.

In another embodiment of the invention, peptides and/or proteins which are involved in PD-1 signaling pathways (e.g., proteins which can act as PD-1:PD-1 ligand agonists or antagonists, proteins which are phosphorylated in response to PD-1 signaling, and/or proteins which bind PD-1) can be identified using a peptide binding/immunoprecipitation and mass spectrometry assay. For example, T cells (e.g., Jurkat T cells) can be activated in the presence or absence of PD-1 ligand, and in the presence or absence of pervanadate. Proteins can then be immunoprecipitated from lysates of the T cells using, e.g., anti-PD-1 antibodies, antiphosphotyrosine (Ptyr), or PD-1 peptides. The patterns of immunoprecipitated proteins and the changes in phosphorylation can then be compared using, e.g., SDS-PAGE (sodium dodecyl sulfate polyacrylamide gel electrophoresis). Proteins can then be analyzed and identified using ESI MS/MS (mass spectrometry). A schematic depicting the above described screening assay is shown in FIG. 31A.

Proteins identified using the above-described screening assay (e.g., in an assay using a Jurkat T cell) can then be used in analysis of human T cells. Such proteins can then be used in signaling-based screening assays to identify PD-1 agonists or antagonists, e.g., small molecule agonists or antagonists.

In yet another aspect of the invention, the PD-1 ligand or PD-1 proteins, preferably in membrane bound form, can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins ("PD-1 ligand or PD-1 binding proteins" or "PD-1 ligand or PD-1 bp"), which bind to or interact with PD-1 ligand or PD-1 and are involved in PD-1 ligand or PD-1 activity. Such PD-1 ligand-or PD-1 binding proteins are also likely to be involved in the propagation of signals by the PD-1 ligand or PD-1 proteins or PD-1 ligand or PD-1 targets as, for example, upstream or downstream elements of a PD-1 ligand or PD-1 mediated signaling pathway. Alternatively, such PD-1 ligand or PD-1 binding proteins may be PD-1 ligand or PD-1 inhibitors.

The two hybrid system is based on the modular nature of most transcription factors, which consist of separable DNA-binding and activation domains. Briefly, the assay utilizes two different DNA constructs. In one construct, the gene that codes for a PD-1 ligand or PD-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a PD-1 ligand-dependent complex, the DNA-binding and activation domains of the transcription factor are brought into close proximity. The proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the PD-1 ligand or PD-1 protein.

This invention further pertains to novel agents identified by the above-described screening assays. Accordingly, it is within the scope of this invention to further use an agent identified as described herein in an appropriate animal model. For example, an agent identified as described herein (e.g., a PD-1 ligand or PD-1 modulating agent, an antisense PD-1 ligand or PD-1 nucleic acid molecule, a PD-1 ligand- or PD-1 specific antibody, or a PD-1 ligand or PD-1 binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to use of novel agents identified by the above-described screening assays for treatments as described herein.

D. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Diagnostic Assays

An exemplary method for detecting the presence or absence of PD-1 ligand or PD-1 protein or nucleic acid in a biological sample involves obtaining a biological sample from a test subject and contacting the biological sample with a compound or an agent capable of detecting PD-1 ligand or PD-1 protein or nucleic acid (e.g., mRNA, genomic DNA) that encodes PD-1 ligand or PD-1 protein such that the presence of PD-1 ligand or PD-1 protein or nucleic acid is detected in the biological sample. A preferred agent for detecting PD-1 ligand or PD-1 mRNA or genomic DNA is a labeled nucleic acid probe capable of hybridizing to PD-1 ligand or PD-1 mRNA or genomic DNA. The nucleic acid probe can be, for example, a human PD-1 ligand or PD-1 nucleic acid, such as the nucleic acid of SEQ ID NO:1, 3, 10, 11, or 38 or a portion thereof, such as an oligonucleotide of at least 15, 30, 50, 100, 250 or 500 nucleotides in length and sufficient to specifically hybridize under stringent conditions to PD-1 ligand or PD-1 mRNA or genomic DNA. Other suitable probes for use in the diagnostic assays of the invention are described herein.

A preferred agent for detecting PD-1 ligand or PD-1 protein is an antibody capable of binding to PD-1 ligand or PD-1 protein, preferably an antibody with a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substrate to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect PD-1 ligand or PD-1 mRNA, protein, or genomic DNA in a biological sample in vitro as well as in vivo. For example, in vitro techniques for detection of PD-1 ligand or PD-1 mRNA include Northern hybridizations and in situ hybridizations. In vitro techniques for detection of PD-1 ligand or PD-1 protein include enzyme-linked immunosorbent assays (ELISAs), Western blots, immunoprecipitations and immunofluorescence. In vitro techniques for detection of PD-1 ligand or PD-1 genomic DNA include Southern hybridizations. Furthermore, in vivo techniques for detection of PD-1 ligand or PD-1 protein include introducing into a subject a labeled anti-PD-1 ligand or PD-1 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting PD-1 ligand or PD-1 protein, mRNA, or genomic DNA, such that the presence of PD-1 ligand or PD-1 protein, mRNA or genomic DNA is detected in the biological sample, and comparing the presence of PD-1 ligand or PD-1 protein, mRNA or genomic DNA in the control sample with the presence of PD-1 ligand or PD-1 protein, mRNA or genomic DNA in the test sample.

The invention also encompasses kits for detecting the presence of PD-1 ligand or PD-1 in a biological sample. For example, the kit can comprise a labeled compound or agent capable of detecting PD-1 ligand or PD-1 protein or mRNA in a biological sample; means for determining the amount of PD-1 ligand or PD-1 in the sample; and means for comparing the amount of PD-1 ligand or PD-1 in the sample with a standard. The compound or agent can be packaged in a suitable container. The kit can further comprise instructions for using the kit to detect PD-1 ligand or PD-1 protein or nucleic acid.

2. Prognostic Assays

The diagnostic methods described herein can furthermore be utilized to identify subjects having or at risk of developing a disease or disorder associated with aberrant PD-1 ligand or PD-1 expression or activity. For example, the assays described herein, such as the preceding diagnostic assays or the following assays, can be utilized to identify a subject having or at risk of developing a disorder associated with PD-1 ligand or PD-1 protein, expression or activity. Thus, the present invention provides a method for identifying a disease or disorder associated with aberrant PD-1 ligand or PD-1 expression or activity in which a test sample is obtained from a subject and PD-1 ligand or PD-1 protein or nucleic acid (e.g., mRNA, genomic DNA) is detected, wherein the presence of PD-1 ligand or PD-1 protein or nucleic acid is diagnostic for a subject having or at risk of developing a disease or disorder associated with aberrant PD-1 ligand or PD-1 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant PD-1 ligand or PD-1 expression or activity. Thus, the present invention provides methods for determining whether a subject can be effectively treated with an agent for a disorder associated with aberrant PD-1 ligand or PD-1 expression or activity in which a test sample is obtained and PD-1 ligand or PD-1 protein or nucleic acid expression or activity is detected (e.g., wherein the abundance of PD-1 ligand or PD-1 protein or nucleic acid expression or activity is diagnostic for a subject that can be administered the agent to treat a disorder associated with aberrant PD-1 ligand or PD-1 expression or activity).

The methods of the invention can also be used to detect genetic alterations in a PD-1 ligand or PD-1 gene, thereby determining if a subject with the altered gene is at risk for a disorder associated with the PD-1 ligand or PD-1 gene. In preferred embodiments, the methods include detecting, in a sample of cells from the subject, the presence or absence of a genetic alteration characterized by at least one of an alteration affecting the integrity of a gene encoding a PD-1 ligand or PD-1 protein, or the mis-expression of the PD-1 ligand or PD-1 gene. For example, such genetic alterations can be detected by ascertaining the existence of at least one of 1) a deletion of one or more nucleotides from a PD-1 ligand or PD-1 gene; 2) an addition of one or more nucleotides to a PD-1 ligand or PD-1 gene; 3) a substitution of one or more nucleotides of a PD-1 ligand or PD-1 gene, 4) a chromosomal rearrangement of a PD-1 ligand or PD-1 gene; 5) an alteration in the level of a messenger RNA transcript of a PD-1 ligand or PD-1 gene, 6) aberrant modification of a PD-1 ligand or PD-1 gene, such as of the methylation pattern of the genomic DNA, 7) the presence of a non-wild type splicing pattern of a messenger RNA transcript of a PD-1 ligand or PD-1 gene, 8) a non-wild type level of a PD-1 ligand or PD-1 protein, 9) allelic loss of a PD-1 ligand or PD-1 gene, and 10) inappropriate post-translational modification of a PD-1 ligand or PD-1 protein. As described herein, there are a large number of assay techniques known in the art which can be used for detecting alterations in a PD-1 ligand or PD-1 gene. A preferred biological sample is a tissue or serum sample isolated by conventional means from a subject, e.g., a cardiac tissue sample.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the PD-1 ligand or PD-1 gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to a PD-1 ligand or PD-1 gene under conditions such that hybridization and amplification of the PD-1 ligand or PD-1 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al. (1989) *Proc. Natl. Acad. Sci. USA* 86:1173–1177), Q-Beta Replicase (Lizardi, P. M. et al. (1988) *Biotechnology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a PD-1 ligand or PD-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in PD-1 ligand or PD-1 can be identified by hybridizing a sample and control nucleic acids, e.g., DNA or RNA, to high density arrays containing hundreds or thousands of oligonucleotides probes (Cronin, M. T. et al. (1996) *Hum. Mutat.* 7:244–255; Kozal, M. J. et al. (1996) *Nat. Med.* 2:753–759). For example, genetic mutations in PD-1 ligand or PD-1 can be identified in two dimensional arrays containing light-generated DNA probes as described in Cronin, M. T. et al. (1996) supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the PD-1 ligand or PD-1 gene and detect mutations by comparing the sequence of the sample PD-1 ligand or PD-1 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the PD-1 ligand or PD-1 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type PD-1 ligand or PD-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397; Saleeba et al. (1992) *Methods Enzymol.* 217: 286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in PD-1 ligand or PD-1 cDNAs obtained from samples of cells. For example, the inutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a PD-1 ligand sequence, e.g., a wild-type PD-1 ligand or PD-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility can be used to identify mutations in PD-1 ligand or PD-1 genes. For example, single strand conformation polymorphism (SSCP) can be used to detect differences in electrophoretic mobility between mutant and wild type nucleic acids (Orita et al. (1989) *Proc. Natl. Acad. Sci. USA:* 86:2766, see also Cotton (1993) *Mutat. Res.* 285:125–144; and Hayashi (1992) *Genet. Anal. Tech. Appl.* 9:73–79). Single-stranded DNA fragments of sample and control PD-1 ligand or PD-1 nucleic acids can be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA can be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification can be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner et al. (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving a PD-1 ligand or PD-1 gene.

Furthermore, any cell type or tissue in which PD-1 ligand or PD-1 is expressed can be utilized in the prognostic assays described herein.

VII. Administration of Modulating Agents for PD-1 Ligand or PD-1

PD-1 ligand or PD-1 modulating agents of the invention are administered to subjects in a biologically compatible form suitable for pharmaceutical administration in vivo to either enhance or suppress immune cell mediated immune responses. By "biologically compatible form suitable for administration in vivo" is meant a form of the protein to be administered in which any toxic effects are outweighed by the therapeutic effects of the protein. The term subject is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic compositions of the present invention is defined as an amount effective, at dosages and for periods of time necessary to achieve the desired result. For example, a therapeutically active amount of a PD-1 ligand or PD-1 polypeptide may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The PD-1 ligand or PD-1 modulating agent (e.g., a peptide, a nucleic acid molecule, antibody, peptidomimetic, or small molecule) can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, to administer PD-1 ligand or PD-1 modulating agent by other than parenteral administration, it may be desirable to coat the peptide with, or co-administer the peptide with, a material to prevent its inactivation.

A PD-1 ligand or PD-1 modulating agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating active compound (e.g., a PD-1 ligand or PD-1 polypeptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient (e.g., peptide) plus any additional desired ingredient from a previously sterile-filtered solution thereof.

When the active compound is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

In one embodiment of the present invention a therapeutically effective amount of an antibody to a PD-1 ligand or PD-1 protein is administered to a subject. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 or 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays as described herein.

Monitoring the influence of agents (e.g., drugs or compounds) on the expression or activity of a PD-1 ligand or PD-1 protein can be applied not only in basic drug screening, but also in clinical trials. For example, the effectiveness of an agent determined by a screening assay as described herein to increase PD-1 ligand or PD-1 gene expression, protein levels, or upregulate PD-1 ligand or PD-1 activity, can be monitored in clinical trials of subjects exhibiting decreased PD-1 ligand or PD-1 gene expression, protein levels, or downregulated PD-1 ligand or PD-1 activity. Alternatively, the effectiveness of an agent determined by a screening assay to decrease PD-1 ligand or PD-1 gene expression, protein levels, or downregulate PD-1 ligand or PD-1 activity, can be monitored in clinical trials of subjects exhibiting increased PD-1 ligand or PD-1 gene expression, protein levels, or upregulated PD-1 ligand or PD-1 activity. In such clinical trials, the expression or activity of a PD-1 ligand or PD-1 gene, and preferably, other genes that have been implicated in a disorder can be used as a "read out" or markers of the phenotype of a particular cell.

For example, and not by way of limitation, genes, including PD-1 ligand or PD-1, that are modulated in cells by treatment with an agent (e.g., compound, drug or small molecule) which modulates PD-1 ligand or PD-1 activity (e.g., identified in a screening assay as described herein) can be identified. Thus, to study the effect of agents on a PD-1 ligand or PD-1 associated disorder, for example, in a clinical trial, cells can be isolated and RNA prepared and analyzed for the levels of expression of PD-1 ligand or PD-1 and other genes implicated in the PD-1 ligand or PD-1 associated disorder, respectively. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of PD-1 ligand or PD-1 or other genes. In this way, the gene expression pattern can serve as a marker, indicative of the physiological response of the cells to the agent. Accordingly, this response state can be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of expression of a PD-1 ligand or PD-1 protein, mRNA, or genomic DNA in the pre-administration sample; (iii) obtaining one or more post-administration samples from the subject; (iv) detecting the level of expression or activity of the PD-1 ligand or PD-1 protein, mRNA, or genomic DNA in the post-administration samples; (v) comparing the level of expression or activity of the PD-1 ligand or PD-1 protein, mRNA, or genomic DNA in the pre-administration sample with the PD-1 ligand or PD-1 protein, mRNA, or genomic DNA in the post administration sample or samples; and (vi) altering the administration of the agent to the subject accordingly. For example, increased administration of the agent may be desirable to increase the expression or activity of PD-1 ligand or PD-1 to higher levels than detected, i.e., to increase the effectiveness of the agent. Alternatively, decreased administration of the agent may be desirable to decrease expression or activity of PD-1 ligand or PD-1 to lower levels than detected, i.e., to decrease the effectiveness of the agent. According to such an embodiment, PD-1 ligand or PD-1 expression or activity can be used as an indicator of the effectiveness of an agent, even in the absence of an observable phenotypic response.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Isolation of PD-L1 cDNA Molecules

The protein sequence of the extracellular domain of human B7-1 was used to search the public databases for nucleic acid molecules encoding homologous polypeptides. Two overlapping sequences in the EST database, AA292201 and AA399416, were identified. These sequences were used to isolate full-length PD-L1 cDNAs from human activated keratinocyte and placental cDNA libraries as follows.

Oligonucleotides with the sequence 5'-CAGCTATGGTG-GTGCCGACTACAA-3' (SEQ ID NO:5) and 5'-AGGT-GCTAGGGGACAGTGTTAGACA-3' (SEQ ID NO:6) from these ESTs were synthesized. These oligonucleotides were used to prime a PCR reaction using as template cDNA prepared by reverse transcription of mRNAs from the spleen of a case of follicular lymphoma, activated B cells, INF-γ activated keratinocytes, normal spleen, and placenta. Conditions were 94° C., 1 min; 94° C., 30 sec, 56° C., 30 sec, 68° C., 1 min for 35 cycles; 68° C., 3 min, hold 4° C. All templates gave a band of the expected size of 389 bp. The 389 bp product from the PCR of INF-γ activated keratinocytes was purified by agarose gel electrophoresis and 0.12 ng was used as a template in a PCR reaction containing 0.05 mM biotin-21-dUTP and the above primers. Conditions were 94° C., 1 min; 94° C., 30 sec, 56° C., 30 sec, 68° C., 2 min for 20 cycles; 68° C., 5 min, hold 4° C. The biotinylated PCR product was purified on a Nucleospin column (Clontech) and used as a probe in the ClonCapture cDNA selection procedure (Clontech). 60 ng of denatured, biotinylated PCR product was incubated with 2 mM $CoCl_2$, 1×RecA buffer, 1 μg of RecA protein, 1×ATP in a final volume of 30 μl. The reaction was incubated at 37° C. for 15 min. To that mixture, 0.7 μg of plasmid DNA of an activated keratinocyte cDNA library and 0.4 μg of a human placental cDNA library was added and incubation continued for 20 min. 50 ng of EcoRV digested lambda DNA was added to the reaction and incubated 5 min. 0.6 μl of 10% SDS and 5.6 μg of proteinase K were added and incubated at 37° C. for 10 min. Proteinase K was inactivated by adding 1 μl of 0.1 M PMSF. Streptavidin magnetic beads were preincubated with 5 μg of sheared salmon sperm DNA for 10 min and the beads captured with a magnet, the supernatant removed, and the beads resuspended in 30 μl of binding buffer (1 mM EDTA, 1 M NaCl, 10 mM Tris-HCl, pH 7.5). The beads were added to the reaction and the reaction incubated for 30 min at room temperature with gentle mixing. The beads were captured with a magnet and the supernatant removed. The beads were washed with 1 ml of washing buffer (1 mM EDTA, 2 M NaCl, 10 mM Tris-HCl, pH 7.5), beads were captured with a magnet and the supernatant removed. The wash procedure was repeated 3 times. One ml of sterile $H_2O$ was added to the washed beads, incubated 5 min at 37° C., beads were captured on a magnet and the supernatant removed. Captured DNA was eluted by adding 0.1 ml of elution buffer (1 mM EDTA, 0.1 N NaOH), incubating 5 min at room temperature, beads were captured with a magnet and the supernatant removed and saved in a new tube. 22.5 μl of precipitation mix containing carrier and pH neutralizers was added along with 2.5 volumes of ethanol. The plasmid DNA was concentrated by centrifugation and re-dissolved in $H_2O$. Plasmid DNA was re-introduced into E. coli DH10B/P3 by electroporation and selected on LB-agar plates containing 7.5 μg/ml tetracycline and 25 μg/ml ampicillin. Colonies were lifted onto Nytran filters and hybridized with $^{32}$P-labeled oligonucleotides with the sequence 5'-CAGCTATG-GTGGTGCCGACTACAA-3' (SEQ ID NO:5), 5'-AGGT-GCTAGGGGACAGTGTTAGACA-3' (SEQ ID NO:6), and 5'-TCGCTTGTAGTCGGCACCACCATA-3' (SEQ ID NO:9). All oligos are from AA292201 sequence. Final wash conditions were 2×SSC, 0.1% SDS at 55° for 20 min. The two hybridizing colonies were picked and the sequence of the cDNA inserts was determined.

Sequencing revealed two forms of PD-L1 molecules. The first form, PD-L1 secreted (PD-L1S) encodes a protein having a short hydrophilic domain without a membrane anchor. The nucleotide and amino acid sequences of this form are shown in SEQ ID NO:1 and 2, respectively. The second form, PD-L1 membrane (PD-L1M) encodes a protein having a transmembrane and short cytoplasmic domain. The nucleotide and amino acid sequences of this form are shown in SEQ ID NO:3 and 4, respectively. Both members of the PD-L1 family identified have signal, IgV, and IgC domains, as illustrated in FIGS. 3 and 4. The PD-L1M form has approximately 21% amino acid identity to human B7-1 and about 20% amino acid identity to human B7-2 as calculated using the default Blosum62 matrix with gap penalties set at existence 11 and extension 1 (See the NCBI website), under conditions where B7-1 and B7-2 have about 26% identity.

Example 2

Expression of PD-L1 mRNA: Northern Blot Analysis

An mRNA of the soluble form of PD-L1 is predicted to be about 1.2 kb though other sizes are possible. The mRNA of the second form is about 3.8 kb, with minor mRNAs of 1.6 and 6.5 kb.

Expression of PD-L1 polypeptides was analyzed. RNA was prepared by guanidine thiocyanate homogenization and cesium chloride centrifugation. Equal amounts of RNA (approximately 2 μg poly(A)+ RNA) were electrophoresed on agarose gel, blotted, and hybridized to a portion of $^{32}$P-labeled PD-L1 cDNA common to both the PD-L1S and PD-Li M forms. These PD-L1 mRNAs are highly expressed in placenta, lung, and heart and are moderately expressed in the thymus. In addition, these PD-L1 mRNAs are weakly expressed in skeletal muscle, kidney, pancreas, prostate, testis, ovary, small intestine, colon, and peripheral blood leukocytes. They were also found to be very weakly expressed in liver or brain. PD-L1 mRNAs were not expressed in unstimulated monocytes, but were strongly induced by IFN-γ. Similarly, the expression of these polypeptides was found to be induced in keratinocytes by TPA/IFN-γ and in dendritic cells by IFN-γ. These PD-L1 mRNAs were not expressed in unstimulated B cells, but were induced by Ig crosslinking.

Expression of these PD-L1 mRNAs was also examined in a variety of cell lines. They were not found to be expressed in B cell lines such as Raji, Ramos, LBL, Nalm 6, and DHL-4. They were also not expressed in T cell lines, such as Jurkat, Rex, CEM, HPB-ALL, Peer4, and H9 or in HTLV-1 transformed T cell lines such as SPP and MT2 or in the myeloid line U937.

Example 3

Further Characterization of PD-L1 mRNA Expression: Northern Blot Analysis

Mouse and human multiple tissue Northern blots (Clontech, Palo Alto, Calif.) were probed with $^{32}$P-dCTP radiolabeled cDNA probes in QuikHyb (Stratagene, La Jolla, Calif.) according to the manufacturer's instructions. The human PD-L1 probe consisted of a 1 kb BamHI/NotI fragment of the cDNA spanning the coding region and 3' untranslated region of SEQ ID NO:1. The mouse PD-L1 probe consisted of a 300 bp cDNA fragment from the coding region. Control actin probes were supplied by Clontech. Blots were washed twice at room temperature in 2×SSC, 0.1% SDS, followed by 0.2×SSC, 0.1% SDS at 65° C., and examined by autoradiography.

PD-L1 mRNA was expressed at high levels in heart, human placenta, and human fetal liver, and at lower levels in spleen, lymph nodes, thymus, and mouse liver.

PD-L1 mRNA was expressed in a variety of transformed mouse cell lines, including PU5-1.8, RAW 264.7, K-Balb, M-MSV-Balb/3T3, Hepa 1-6, R1.1, L1210, P38D1, P815, and NB41A3 cells.

Example 4

Further Characterization of PD-L1 mRNA Expression: Quantitative PCR, Genechip Hybridization, and RNA Blot Analysis PD-L1 mRNA expression on antigen presenting cells was examined and compared to the expression of B7-1 and B7-2 on those cells. For quantitative PCR analysis, cellular RNA was deoxyribonuclease-treated, re-extracted and converted to first strand cDNA. FAM (6-carboxyfluorescein)-labeled human PD-L1, B7-1, B7-2, and GAPDH probes were purchased from PE Biosystems PD-L1: primers 5'-GCCGAAGTCATCTGGACAAG-3' (SEQ ID NO:13) and 5'-TCTCAGTGTGCTGGTCACAT-3' (SEQ ID NO:14), probe 5'-FAM-CACCACCACCAATTCCAAGA-3' (SEQ ID NO:15); B7-1: primers 5'-ACGTGACCAAGGAAGTGAAAGAA-3' (SEQ ID NO:16) and 5'-TGCCAGCTCTTCAACAGAAACAT-3' (SEQ ID NO:17), probe 5'-FAM-TGGCAACGCTGTCCTGTGGTCAC-3' (SEQ ID NO:18); B7-2: primers 5'-GGGCCGCACAAGTTTTGAT-3' (SEQ ID NO:19) and 5'-GCCCTTGTCCTTGATCTGAAGA-3' (SEQ ID NO:20), probe 5'-FAM-CGGACAGTTGGACCCTGAGACTTCACA-3' (SEQ ID NO:21).

PCR reactions were set up in 96-well plates using reagents from the Perkin Elmer TaqMan™ EZ kit, according to the manufacturer's instructions. Standard curves were set up for each of the four genes analyzed. Forty cycles of PCR were run in an ABI Prism 7700 Sequence Detector and GAPDH was used to normalize the PD-L1, B7-1, and B7-2 results.

The Affymetrix Mu19KsubA chip was used for Genechip hybridization analysis. The sequence of a portion of murine PD-L1 is represented by expressed sequence tag TC17781 of The Institute for Genomic Research on this chip. RNA isolation, chip hybridization and scanning was performed as described in Byrne, M. C. et al. (2000) *Curr. Prot. Mol. Biol. Suppl.* 49:22.2.1–22.2.13.

For RNA blot hybridization, the 1.6 kb human and 3.6 kb murine PD-L1 cDNAs were excised by digestion with Xba I and labeled by random priming with γ-$^{32}$P-ATP and the Klenow fragment of DNA polymerase I. RNA blots were hybridized as described in Freeman, G. J. et al. (1992) *J. Immunol.* 149:3795–3801.

Human dendritic cells were derived from peripheral blood. Mononuclear cells were isolated after fractionation on a Ficoll gradient. Non-adherent cells were removed and the remaining cells cultured in 150 ng/ml human GM-CSF (R&D Systems) and 100 ng/ml human IL-4 (R&D Systems) for 2 days. The non-adherent dendritic cells were isolated (CD80$^+$ CD86$^+$ HLA-DR$^+$ CD54$^+$ CD58$^+$ CD1a$^+$) and cultured in GM-CSF alone or activated with GM-CSF, 2.5 µg/ml LPS (Sigma Chemicals), and 10 ng/ml human Interferon-γ. At 4 hours and 20 hours after activation, cells were harvested and RNA isolated using the RNeasy kit (Qiagen).

Murine bone marrow mononuclear cells were immunodepleted of granulocytes, lymphocytes and Ia$^+$ cells by magnetic activated cell sorting and cultured in petri dishes with GM-CSF and IL-4. Dendritic cells were harvested as the non-adherent population after 7 days of culture, and demonstrated to be 75–80% CD11c$^+$, high IA$^+$ cells. Cells were activated with LPS and human interferon-γ.

Analysis of expression in human blood monocytes by RNA blot hybridization demonstrated that B7-2 is not expressed by unstimulated monocytes, but is rapidly upregulated upon interferon-γ treatment. Treatment of monocytes with another pro-inflammatory cytokine, tumor necrosis factor (TNF)-α led to a low level induction similar to that found with medium alone, presumably as a result of activation by adherence to plastic. In addition to the major 4.2 kb PD-L1 mRNA, a minor 1.8 kb PD-L1 mRNA species was also observed in interferon-γ treated monocytes. Expression of PD-L1 by human B-cells activated by cell surface immunoglobulin cross-linking, but not by the Raji cell line, was also observed. Similarly, B7-1 is not expressed by unstimulated monocytes, but is upregulated in response to interferon-γ with kinetics similar to PD-L1 expression. In contrast, B7-2 mRNA is constitutively expressed in monocytes and levels are unaffected by interferon-γ or TNF-α treatment.

PD-L1, B7-1, and B7-2 mRNA expression by human dendritic cells was also examined by quantitative PCR. Human peripheral blood-derived dendritic cells were treated with granulocyte-macrophage colony stimulated factor (GM-CSF) alone or activated with GM-CSF, lipopolysaccharide (LPS), and interferon-γ. As a result of activation by LPS and interferon-γ, PD-L1 mRNA was rapidly induced with a 16-fold increase at 4 hours and a 34-fold increase at 20 hours, relative to non-induced cells. B7-1 and B7-2 mRNAs were also induced upon activation: B7-1 was induced 21-fold at 4 hours and 22-fold at 20 hours. B7-2 showed little induction at 4 hours; however, expression was induced 5-fold at 20 hours. Expression of PD-L1 by murine bone marrow-derived dendritic cells treated with LPS and interferon-γ was examined using Genechip™ hybridization. PD-L1 expression in these cells follows a pattern similar to that observed on human dendritic cells: a 5-fold induction of the PD-L1 mRNA relative to the uninduced cells at 6 and 20 hours after induction. These data demonstrate that PD-L1 is expressed by antigen presenting cells and lymphocytes, and it is induced on dendritic cells in a manner similar to B7-1 and B7-2. Treatment of human keratinocytes with phorbol ester and interferon-γ also induced PD-L1.

In murine tissues, an approximately 3.7 kb PD-L1 mRNA transcript was detected by northern blot hybridization. The distribution of the murine PD-L1 mRNA closely resembled that of the human PD-L1, with high levels in heart, thymus and lung, and low levels in kidney, spleen and liver.

Example 5

Chromosomal Localization of PD-L1

The chromosomal localization of the PD-L1 genes was determined using a monochromosomal blot kit commercially available from Quantum (Toronto, Canada). The blots were probed with a sequence that recognizes both PD-L1S and PD-L1M. Using this method, the PD-L1 polypeptides have been localized to human chromosome 9, whereas B7-1 and B7-2 have been localized to human chromosome 3. The butyrophilins, which also share limited amino acid sequence identity with the PD-L1 family have been localized to the major histocompatibility complex on chromosome 6. The chromosomal location of PD-L1 was confirmed using PD-L1 specific primers in PCR amplification of monochromosomal somatic cell hybrid DNA templates available from Quantum Technologies (Canada).

Example 6

Binding of PD-L1 Molecules to T Cell Ligands or Antibodies

COS cells were transfected with either vector DNA (pcDNAI), or an expression plasmid containing the PD-L1M cDNA. After 72 hours, the transfected COS cells were detached by incubation in PBS containing 0.5 mM EDTA for 30 min. at 37° C.

Figure 10:
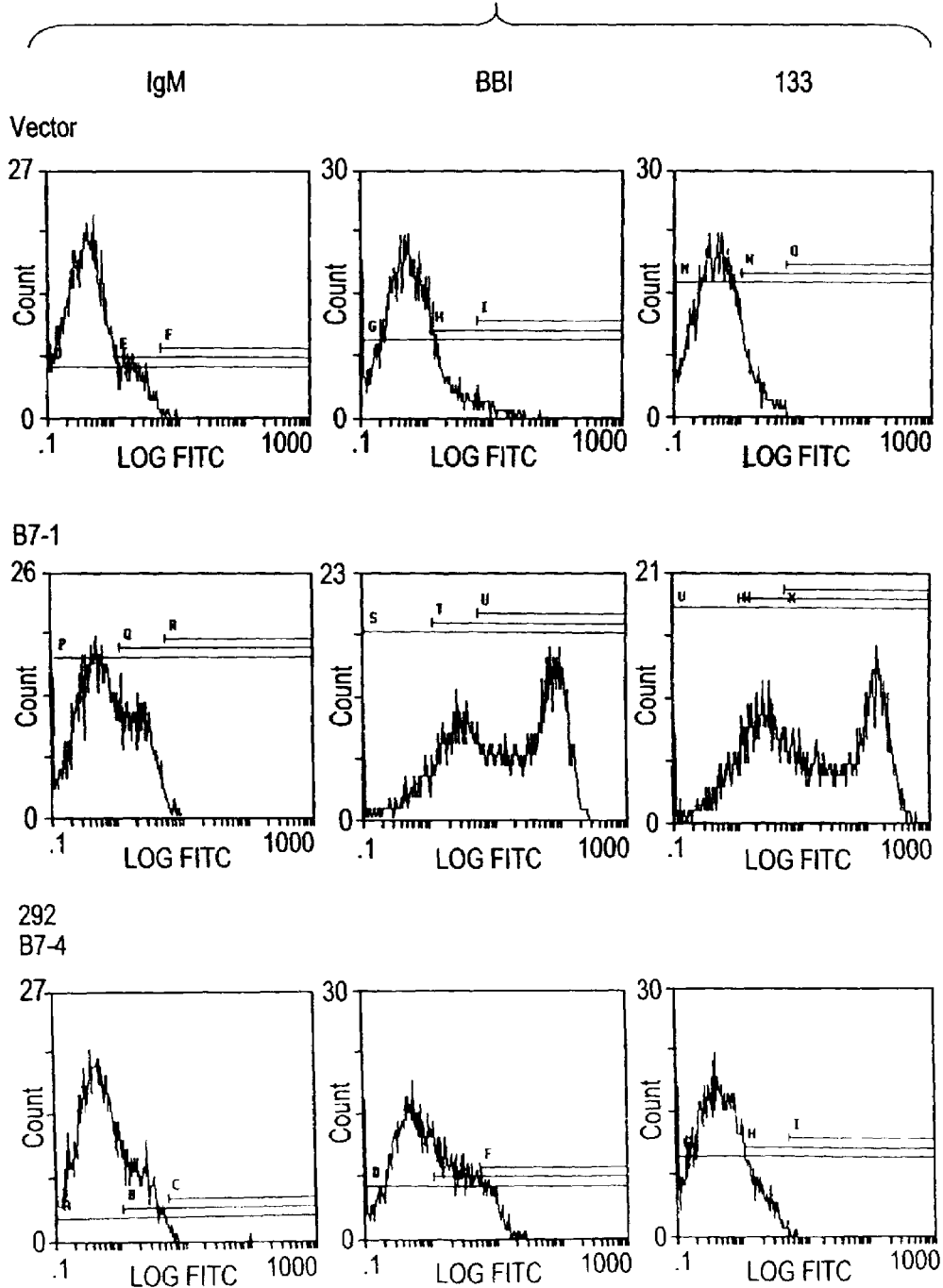
FIG. 10 illustrates the results FACS analysis of binding of IgM, BB1 and 133 antibodies to PD-L1M-transfected COS cells.

The ability of COS cells expressing PD-L1M to bind to various T cell receptors and antibodies was tested. FACS analysis of binding of CS28Ig, CTLA4-Ig, and control Ig by PD-L1-transfected COS cells showed that neither CD28Ig nor CTLA4-Ig was bound by PD-L1 (FIG. 8). The ability of COS cells expressing PD-L1M to bind to IgG and murine ICOS-his fusion protein was also tested. No binding of human PD-L1 to murine ICOS was detected (FIG. 9). As shown in FIG. 10, FACS analysis revealed binding of BB1 (anti B7-1 and anti B7-3), but not IgM or 133 (anti-B7) antibodies PD-L1-transfected COS cells.

Example 7

Costimulation of T Cell Proliferation by PD-L1 Molecules

The ability of PD-L1 polypeptides to costimulate human T cell proliferation was tested. Human CD28$^+$ T cells were isolated by immunomagnetic bead depletion using monoclonal antibodies directed against B cells, natural killer cells and macrophages as previously described (Gimmi, C. D. et al. (1993) *Proc. Natl. Acad. Sci. USA* 90:6586–6590). PD-L1 and vector transfected COS cells were harvested 72 hours after transfection, incubated with 25 µg/ml of mitomycin-C for 1 hour, and then extensively washed. 10$^5$ naïve T Cells were stimulated with plate bound anti-CD3 mAb plus 20,000 mitomycin-c treated COS cells transfected with the indicated DNA construct.

Figure 11:
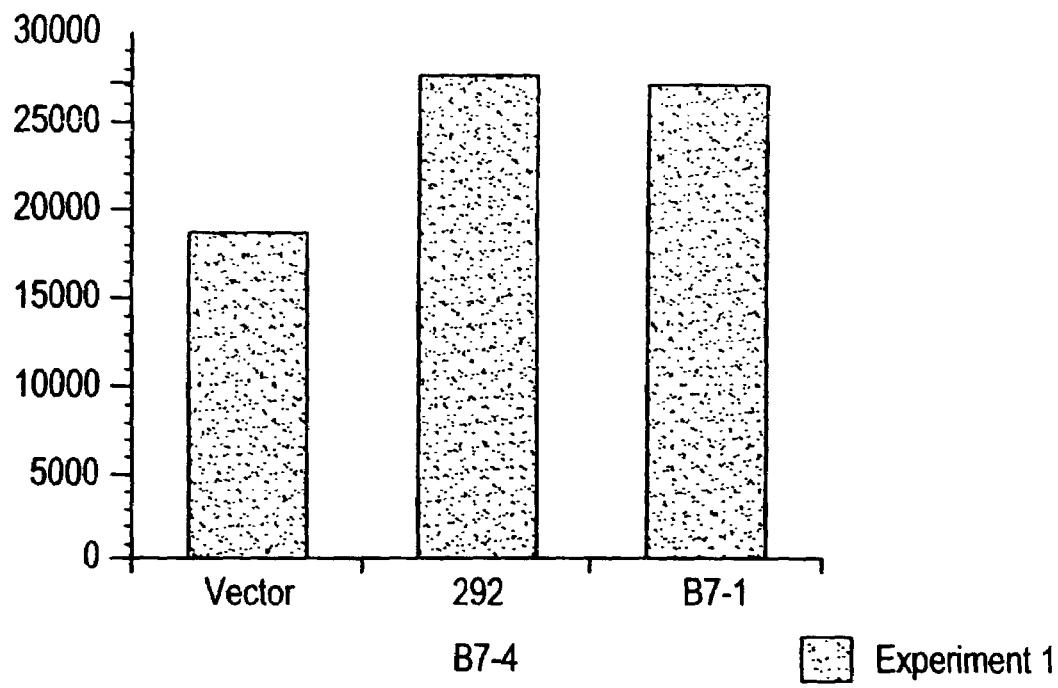
FIG. 11 illustrates that COS cells transfected with PD-L1M (292) can costimulate T cell proliferation.
Figure 12:
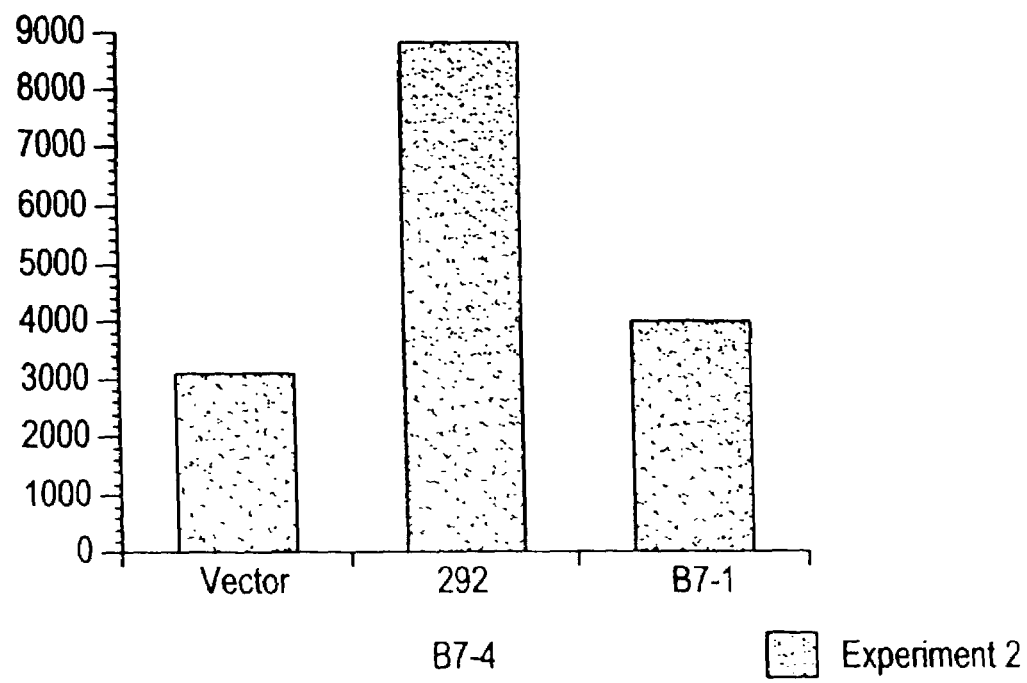
FIG. 12 illustrates that COS cells transfected with a PD-L1M (292) can costimulate T cell proliferation.
Figure 13A:
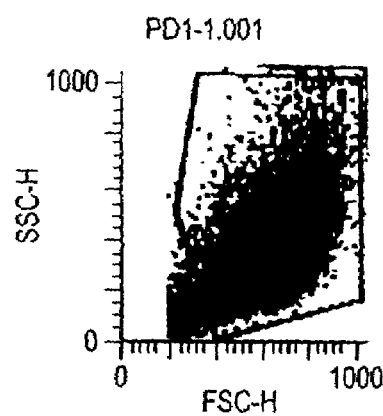
FIGS. 13A–13D illustrate the binding of PD-1 to PD-L1M transfected COS cells.
Figure 13B:
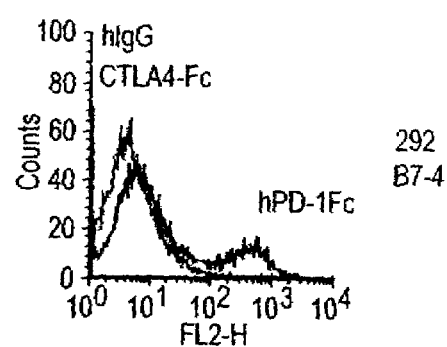
Figure 13C:
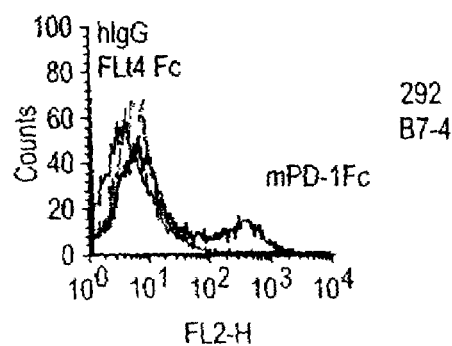
Figure 13D:
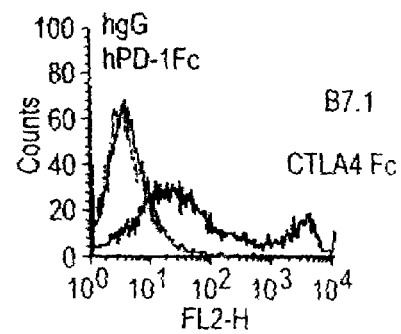
Figure 14A:
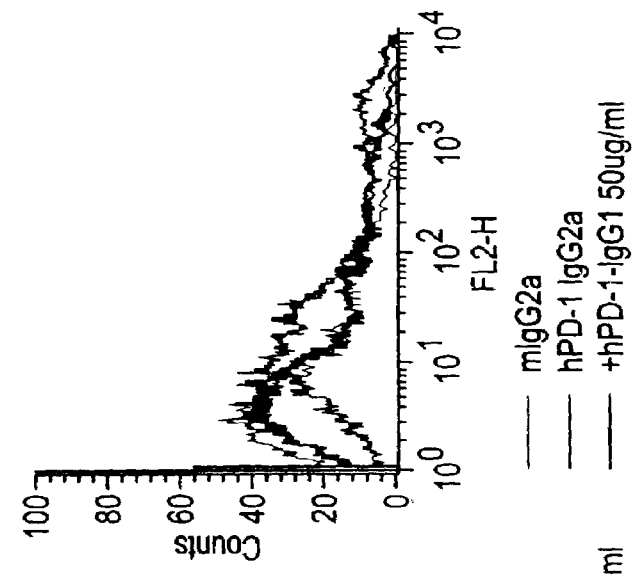
FIGS. 14A–14F illustrate the ability of added PD-1 and not Flt4 to compete for the binding of PD-1 to PD-L1M transfected COS cells.
Figure 14B:
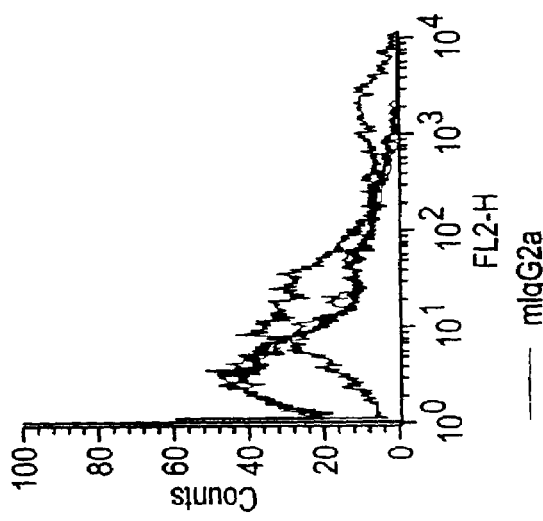
Figure 14C:
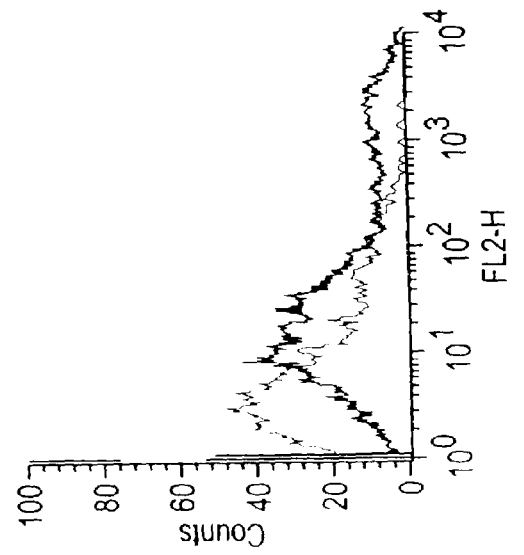
Figure 14D:
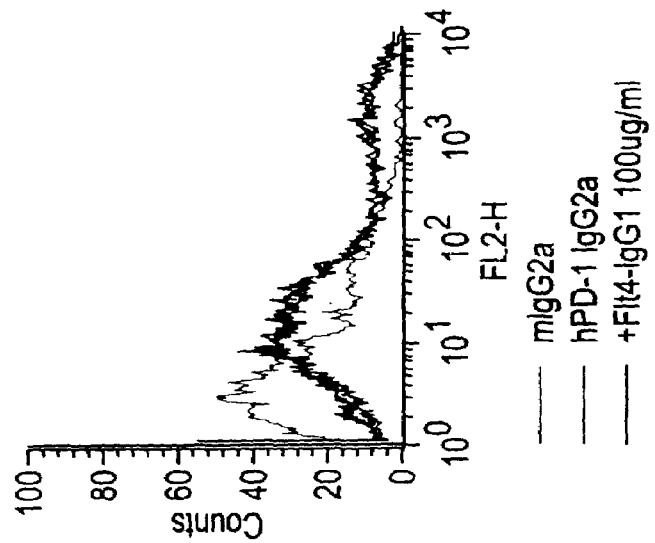
Figure 14E:
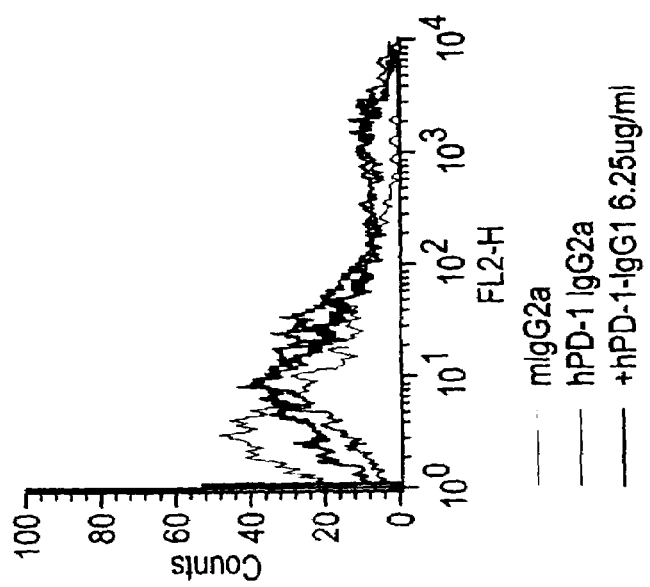
Figure 14F:
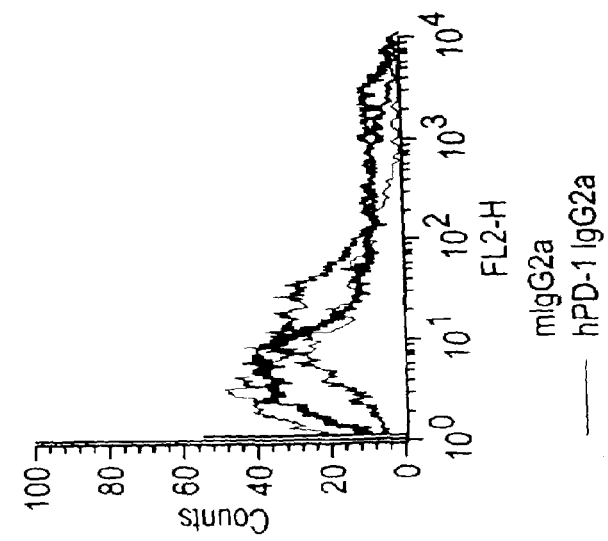

T cell proliferation, was measured by 3H-thymidine (1 µCi) incorporated for the last 12 hours of a 72 hour incubation. As shown in FIGS. 11 and 12, COS cells expressing PD-L1 can costimulate T cell proliferation.

Example 8

Generation of Murine Antibodies to PD-L1 and Use in Detecting Cell-Surface Expression of PD-L1

Mammalian expression vectors (pEF6 or pcDNA3.1 (Invitrogen)) were prepared comprising the entire murine or human PD-L1 cDNA. The cDNA/vector construct was dissolved in 0.9% saline at 1 mg/ml (not TE or PBS).

Before immunization, 78 µl of 1 mg/ml cardiotoxin (Sigma #C-1777) in 0.9% saline was injected into the tibialis anterior muscle of each hind limb of the mouse being immunized. Each mouse was then left alone for 5 days.

After anesthetizing the mice, 50 µl of 1 mg/ml purified PD-L1 cDNA/vector construct (in 0.9% saline) was injected into each regenerating tibialis anterior muscle.

Antibody titers were measured approximately six days after immunization using standard methods, for example, in an ELISA assay. The cDNA immunization was repeated every 2–4 weeks for three cycles (until the antibody titre was >1:10,000). Mice were then boosted with CHO cells transfected with PD-L1.

Spleen cells isolated from mice having appropriate antibody titers were harvested. The spleen cells were fused to fusion partners SP2-0) to make hybridomas. Hybridomas and antibodies were manipulated using standard methods (see, e.g., "Antibodies: A Laboratory Manual", Harlow, E. and Lane, D., Cold Spring Harbor Laboratory (1988), which is incorporated herein by reference).

Antibodies 2A3, 10D9, 5A9, and 11D12 were among those selected in screening assays. These antibodies were found to bind to COS or CHO cells transfected with human PD-L1 and not to mock transfected cells or to cells transfected with mouse PD-L1. The antibodies were used to detect the presence of PD-L1 on various cell populations. PD-L1 expression was observed, inter alia, on heart tissue, tumor cells (including some lung tumor cells, some ovarian tumor cells, some breast tumor cells, some epithelial tumor cells, and some squamous cell carcinomas), placenta, and thymic epithelium.

Another antibody, clone 29E.2A3.C6 (mouse IgG2bκ) was used to examine cell surface expression of PD-L1. PD-L1 is expressed on human breast cancer cell lines MDA-231, SKBR-3, and MCF-7.

Example 9

Generation of Fully Human Antibodies to PD-L1

In this example, fully human antibodies against PD-L1 or PD-1 are made in mice that are transgenic for human immunoglobulin genes. Transgenic mice are made using standard methods, e.g., according to Hogan, et al., "Manipulating the Mouse Embryo: A Laboratory Manual", Cold Spring Harbor Laboratory, which is incorporated herein by reference, or are purchased commercially. Embryonic stem cells are manipulated according to published procedures (Teratocarcinomas and embryonic stem cells: a practical approach, Robertson, E. J. ed., IRL Press, Washington, D.C., 1987; Zijlstra et al. (1989) *Nature* 342:435–438; and Schwartzberg et al. (1989) *Science* 246:799–803, each of which is incorporated herein by reference). DNA cloning procedures are carried out according to Sambrook, J. et al. in Molecular Cloning: A Laboratory Manual, 2d ed., 1989, Cold Spring Harbor Laboratory Press, Cold Spring Harbor, N.Y., which is incorporated herein by reference. Oligonucleotides are synthesized, e.g., on an Applied Bio Systems oligonucleotide synthesizer according to specifications provided by the manufacturer or are purchased commercially.

Transgenic mice are immunized using a purified or recombinant PD-L1 or PD-1 or a fusion protein comprising at least an immunogenic portion of the extracellular domain of PD-L1 or PD-1. Approximately four hundred µg of PD-L1 or PD-1 in 100 µL of phosphate buffered saline (PBS) is injected intraperitoneally into each mouse. Serum samples are collected approximately six days later by retro-orbital sinus bleeding.

Antibody reactivity and specificity for PD-L1 or PD-1 are assessed using an indirect enzyme-linked immunosorbent assay (ELISA). Several immunoglobulin superfamily molecules are tested as controls (e.g., CTLA4 and CD28) to analyze the antibody specificity of the antibody for D-L1 or PD-1. Antibodies having human variable regions which bind to PD-L1 or PD-1 are detected by enzyme conjugates specific for human IgM and human IgG sub-classes with no cross reactivity to mouse immunoglobulin. Briefly, PVC microtiter plates are coated with PD-L1 or PD-1 by coating wells overnight at 37° C. with 5 µg/mL PD-L1 in PBS. Serum samples are diluted in PBS, 5% serum, 0.5% Tween-20 and are incubated in the wells for 1 hour at room temperature, followed by anti-human IgG Fc and IgG F(ab')-horseradish peroxidase or anti-human IgM Fc-horseradish peroxidase in the same diluent. After 1 hour at room temperature enzyme activity is assessed by addition of ABTS substrate (Sigma, St. Louis, Mo.) and read after 30 minutes at 415–490 nm. In pre-immunization serum samples from the same mice, titers of human antibodies to the same target antigens are also tested.

Spleen cells isolated from mice having appropriate antibody titers are harvested. The spleen cells are fused to appropriate fusion partners (e.g., myeloma cells) to make hybridomas. Hybridomas and antibodies are manipulated according to "Antibodies: A Laboratory Manual", Ed Harlow and David Lane, Cold Spring Harbor Laboratory (1988), which is incorporated herein by reference.

The complementarity determining sequences of the murine VH and VL domains of a murine antibody could be used to graft into the framework of human immunoglobulins in order to generate a humanized antibody against PD-L1 or PD-1 (Riechmann et al. (1988) *Nature* 332:323; Verhoeyen et al. (1988) *Science* 239:1534).

Example 10

Generation of Human Single Chain Fvs Reactive with PD-L1 or PD-1

As an alternative to preparing monoclonal antibody-secreting hybridomas, anti PD-L1 or anti-PD-1 antibodies (single chain Fv-like portions of antibodies) were identified and isolated by screening a combinatorial library of human immunoglobulin sequences displayed on M13 bacteriophage from Cambridge Antibody Technology Ltd., Melbourn, UK (Winter et al. (1994) *Annu. Rev. Immunol.* 12:433; Hoogenboom et al. (1998) *Immunotechnology* 4:1). PD-1.Fc or PD-L1.Fc was used to thereby isolate immunoglobulin library members that bind a PD-L1 or PD-1 polypeptide. Kits for generating and screening phage display libraries are commercially available and standard methods were employed to generate the scFv (Helfrich et al. (2000) *J. Immunol. Methods* 237:131–45; Cardoso et al. (2000) *Scand. J. Immunol.* 51:337–44). PD-1.Fc or PD-L1.Fc were immobilized on plastic and phage expressing specific scFv were selected by panning and multiple rounds of enrichment (Griffiths et al. (1993) *EMBO J.* 12:725).

Example 11

Identification of a Receptor for PD-L1

Fusion proteins consisting of the extracellular region of human PD-1 fused to the hinge-CH2-CH3 domains of either human immunoglobulin gamma 1 or murine Ig gamma2a (with mutations blocking FcR and complement interaction) were used to search for a ligand that binds to PD-1. As part of this search, staining of the cell surface of monocytes stimulated with gamma-interferon was found. PD-L1 is induced in monocytes after stimulation with gamma-interferon, as observed by northern blot hybridization.

The binding of PD-1-Fc (human Ig gamma1) to the surface of COS cells transiently transfected with a PD-L1-expression vector was tested. COS cells were transfected with either PD-L1M or B7-1 using LipofectAMINE transfection reagent. After 48 hours, the cells were stained with human PD-1-Fc, murine PD-1-Fc, CTLA4-Fc, Flt4-Fc, or IgG followed by anti-IgG conjugated to phycoerythrin (PE). The cells were then analyzed by flow cytometry. As shown in FIGS. 13A–13D, COS cells expressing PD-L1 bound both human PD-1-Fc and murine PD-1-Fc, but did not bind CTLA4-Fc, Flt4-Fc, or human IgG. As a positive control, it was demonstrated that B7-1 expressing COS cells bound CTLA4-Fc, but not PD-1-Fc or IgG.

In addition, an in situ assay of transfected COS cell monolayers was performed. Monolayers were proved with PD-1Fc, CTLA4Fc or human IgG1 and binding was detected with a secondary antibody directed against the Fc portion and conjugated to alkaline phosphatase. Binding was visualized with chromogenic substrates 5-bromo-4-chloro-3-indolyl phosphate and nitro blue tetrazolium and light microscopy. In parallel, cells transfected with PD-L1 were found to bind to PD-1-Fc, and not CTLA4-Fc (human Ig gamma 1) or Flt4-Fc, the extracellular region of murine Flt4 linked to human Ig gamma 1. In parallel, PD-1Fc did not bind the surface of mock-transfected, B7-1 or B7-2 transfected COS cells.

In another experiment, no binding of PD-1-Fc to soluble forms of B7-1 or B7-2 and binding to PD-L1 was detected using a BIACORE-based assay. In parallel, hCTLA4 was shown to bind to B7-1 and not to PD-L1. PD-1-Fc or CTLA4-FC was immobilized and conditions were essentially as described by Fitz et al. (1997) *Oncogene* 15:613). Concentrated COS cell medium from cells that had been transfected with full length PD-L1M or PD-L1-Fc was injected and interactions were measured using real-time Biomolecular Interaction Analysis (BIA) (Sjolander, S. and Urbaniczky, C. (1991) *Anal. Chem.* 63:2338–2345 and Szabo et al. (1995) *Curr. Opin. Struct. Biol.* 5:699–705). Human PD-L1 was found to bind human and mouse PD-1 and this binding was inhibited by competition with a coinjected PD-1-Fc, but not CTLA4-Fc. These experiments demonstrate not only the binding of soluble pD-L1-Fc fusion protein to immobilized PD-1-Fc, but also demonstrate the presence of a soluble form of PD-L1 in the conditioned medium of PD-L1M cDNA transfected cells, presumably as a result of shedding.

FIGS. 14A–14F illustrate the ability of PD-1 and not Flt4 (the receptor for vascular endothelial growth factor C) to competitively inhibit the binding of PD-1 to PD-L1. The binding of human PD-1 gamma 2a fusion protein to COS cells expressing PD-L1M is shown in Panel A. The binding was detected with antigamma 2a specific reagents linked to PE. Human PD-1 linked to IgG1 was added at: 50 µg/ml, 6.25 µg/ml, 100 µg/ml, or 25 µg/ml and was found to compete for binding. As a control, Flt4IgG1 at 100 µg/ml was not found to compete for binding of PD-1 to PD-L1.

Figure 16:
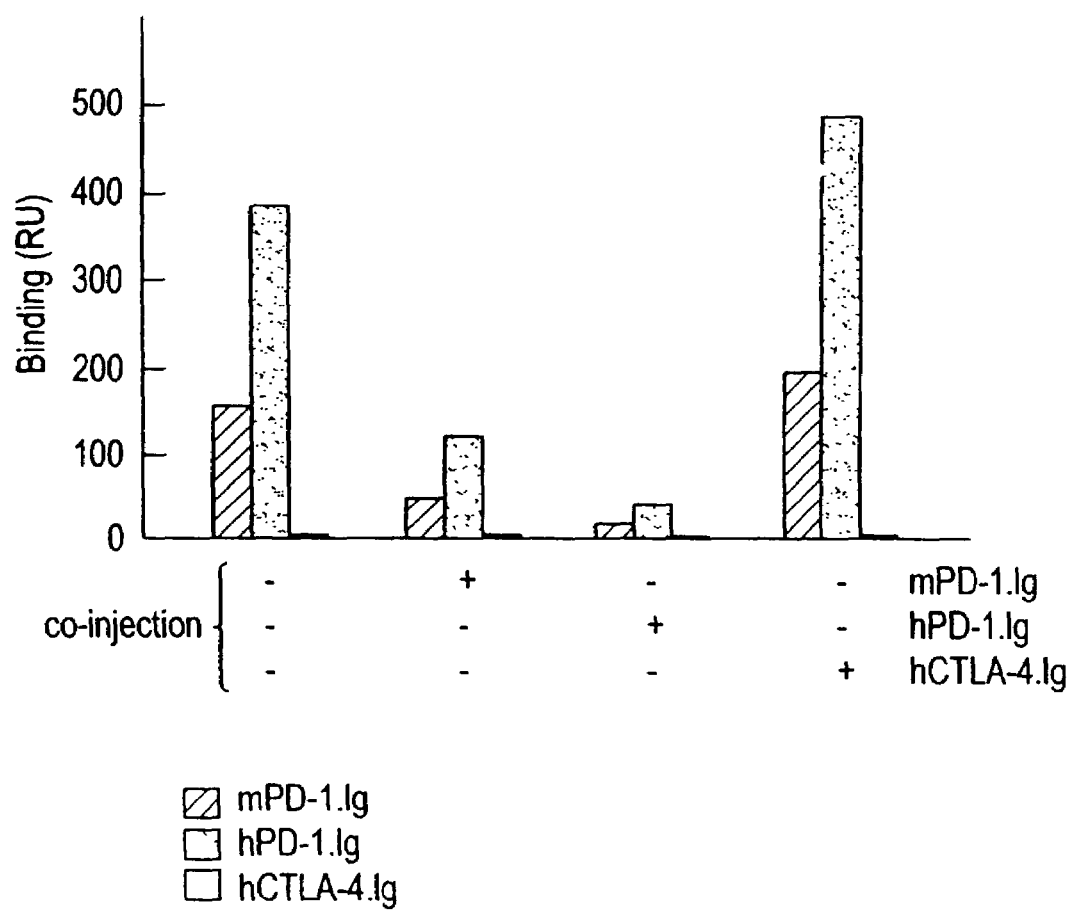
FIG. 16 illustrates the ability of PD-1 to bind to PD-L1 transfected CHO cells, as determined by BIACORE® analysis.

In yet another experiment, the ability of PD-L1 to bind to PD-1 was determined by flow cytometry and BIACORE-binding assays. Human and murine PD-1.Ig fusion proteins bound to both human and murine PD-L1 expressed on CHO cells, as detected by flow cytometry (FIGS. 15A–15F). However, neither human CTLA-4.Ig, human CD28.Ig, nor human ICOS.Ig bound to either PD-L1 expressing cell line. The PD-1 fusion proteins did not bind CHO cells transfected with vector alone. Further confirmation of the PD-1:PD-L1 interaction was obtained using surface plasmon resonance with a BIACORE instrument. The human and murine PD-1.Ig proteins and human CTLA-4.Ig were immobilized on the flow cell surfaces of a dextran chip and tested for binding to soluble human PD-L1.Ig. PD-L1.Ig bound to both human and murine PD-1.Ig, but not to human CTLA-4.Ig (FIG. 16). This binding was blocked by competition with co-injected soluble PD-1.Ig but not CTLA-4.Ig. Soluble forms of human B7-1 and B7-2 did not bind immobilized human PD-1.

BIACORE analysis was also used to analyze PD-1.Fc: PD-L1.Fc binding kinetics. A BIA 2000, CM5 sensor chip was used. NHS/EDC immobilization was used to bind 50–150 RU PD-1.Fc to the chip. The surface was conditioned with 20 injections of ionic regeneration buffer (30% 1.83 M $MgCl_2$, 0.46 M KSCN, 0.92 M Urea, 1.83 M guanidine-HCl). The running buffer was PBS (phosphate buffered saline) with 3.4 mM EDTA, 0.005% Tween-20, and 100 µg/ml BSA (bovine serum albumin) at 25° C. The reference surfaces used were (1) blank activation (NHS/EDC) followed by ethanolamine block and (2) mutated mIgG2a. The concentration of PD-L1.Fc used (undetectable multimer, determined by SEC) was determined by ELISA and BCA protein assay (Pierce). The range of PD-L1.mFc used was 20 nM to 2 µM. The flow rate was 60 µl/minute. Association was for 3–4 minutes with 4 minutes dissociation. Injections were done in triplicate and randomized. Analysis was done using BIAevaluation software, with 1:1 Langmuir and global analysis. The results of the analysis showed that PD-1.Fc:hPD-L1.Fc binding fit a 1:1 model. The kinetic rate constant ($K_D$) calculated for PD-1.Fc:hPD-L1.Fc was 186 nM ($k_{on}$=6.57±1.2 Xe4 $M^{-1}s^{-1}$; $k_{off}$=0.122±0.0007 $s^{-1}$).

These data demonstrate that PD-1 binds PD-L1, and that this interaction may regulate the action of PD-1.

Example 12

PD-L1 can Transmit a Negative Signal to Immune Cells

Figure 17:
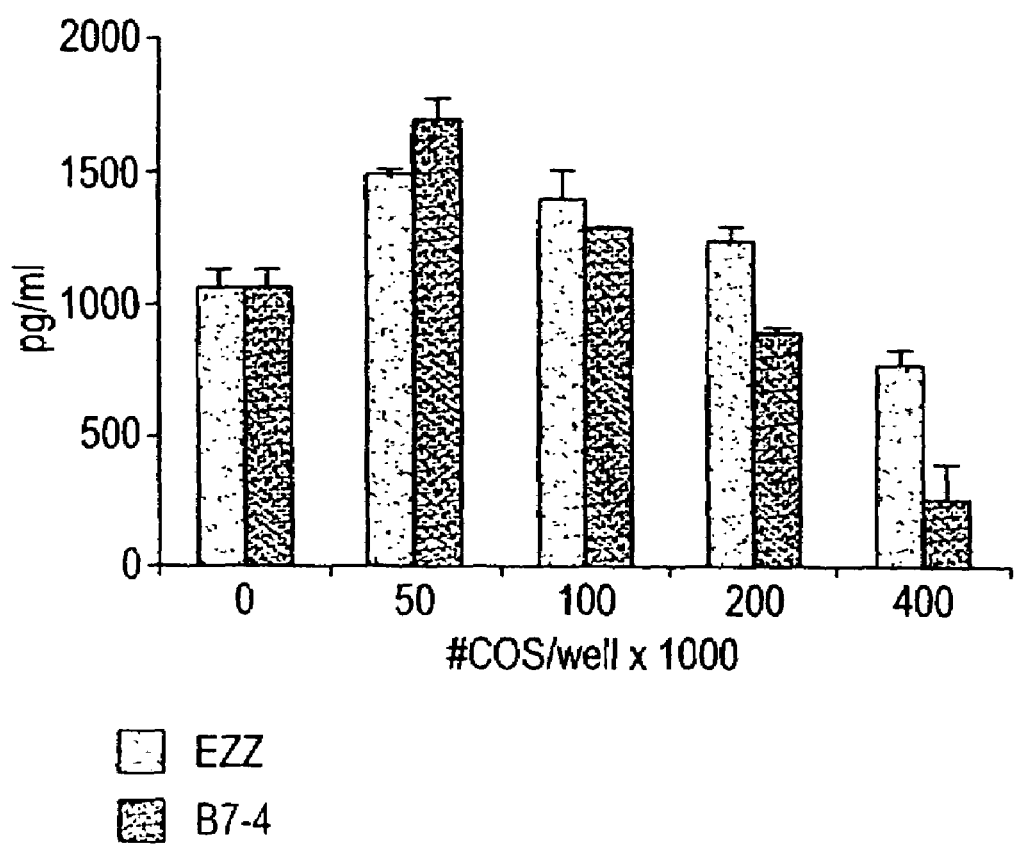
FIG. 17 illustrates the ability of PD-L1M to transmit a negative signal to T cells.

In this example, $5 \times 10^5$ Jurkat T cells per well were stimulated with anti-CD3 coated beads (at a 1:1 ratio) and soluble anti-CD28. COS cells expressing PD-L1 or a negative control, called EZZ, were titrated into the wells. Supernatants were harvested at 48 hours and assayed by ELISA for human IL-2. FIG. 17 shows that increasing numbers of COS PD-L1 cells (bars on the right in the figure) lead to a decrease in IL-2 production.

Using similar assay formats, for example, in which human PHA-blasts from PBMCs were stimulated with immobilized anti-CD3 and soluble anti-CD28, a decrease in T-cell proliferation was observed by titrating in COS cells expressing PD-L1.

Example 13

The PD-1:PD-L1 Interaction Inhibits CD3-mediated T-Cell Proliferation, Cytokine Production, and Expression of T Cell Activation Markers To examine the functional significance of the PD-1:PD-L1 interaction, the functional consequences of PD-L1 interaction with its receptor were also examined using human T-cells. Peripheral blood mononuclear cells were isolated by Ficoll-Hypaque gradient centrifugation. $CD4^+$ T cell populations (85–90% purity) were purified by negative selection using a cocktail of monoclonal antibodies and immunomagnetic beads (PerspectiveBiosystems). Anti-CD3, control IgG and fusion protein were covalently attached to polyurethane-coated tosyl activated DYNABEADS® (Dynal) according to manufacturer's instructions and as described previously (Blair, P. J. et al. (1998) *J. Immunol.* 160:12–15). Anti-CD3 antibody (UCHT1, Pharmingen) at the indicated concentration was added to $1 \times 10^7$ beads/ml 0.1 M phosphate buffer pH 7.4. Control IgG was added to the bead suspension in order to maintain a constant total Ig concentration of 5 µg/ml during binding. Similarly, anti-CD3/PD-L1.Ig(γ2a) beads were prepared with the indicated anti-CD3 antibody concentration, a constant concentration of either PD-L1.Ig representing 40% of the total bound protein (2 µg/$10^7$ beads), and control IgG to make up the remaining total bound protein. $10^5$ T cells were cultured in 96 well flat-bottom plates, and beads were added at a 1 bead to 1 cell ratio in the presence or absence of the indicated concentrations of anti-CD28 antibody (CD28.2, Pharmingen). Proliferation was determined by labeling cultures for the last 6 hr of a 4-day assay with 1 µCi $^3$H-thymidine/well. For analysis by cytokine ELISAs, cultures were set up as described above and supernatants harvested at the indicated times. Interferon-γ, IL-10 and IL-2 concentrations were determined using commercially available ELISA kits (Genzyme, Framingham, Mass.).

Figure 18A:
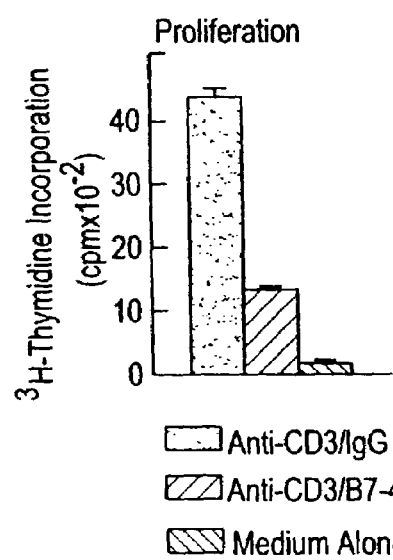
FIGS. 18A–18C illustrate the inhibition of T cell proliferation and cytokine production in human T cell stimulated in the presence of PD-L1.

Purified $CD4^+$ T-cells obtained from peripheral blood mononuclear cells (PBMC) were activated with beads coated with anti-CD3 mAb and either human PD-L1.Ig or a control Ig. Proliferation and cytokine production was assessed 96 hours after stimulation. Cells activated with anti-CD3 mAb/PD-L1.Ig coated beads showed a 69% decrease in proliferation relative to anti-CD3 mAb/control Ig activated cells (FIG. 18A). Proliferation was inhibited in a dose dependent manner when different concentrations of PD-L1.Ig coated beads were used (0.25, 0.5, 1, and 2 µgPD-L1.Ig/$10^7$ beads).

Figure 18B:
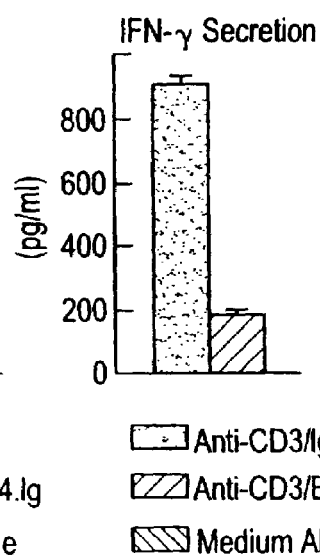
Figure 18C:
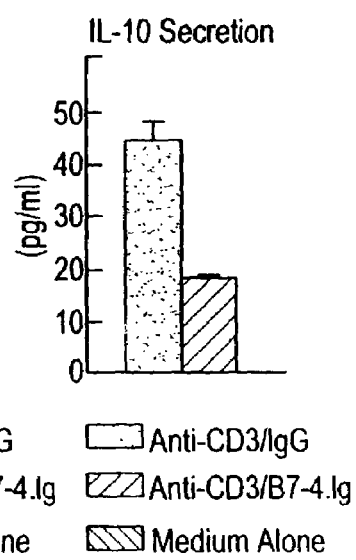

Furthermore, activation of cells in the presence of PD-L1 also impaired cytokine secretion. In the presence of PD-L1, interferon-γ (FIG. 18B) and IL-10 (FIG. 18C) secretions were decreased by approximately 80% and 60%, respectively. IL-2 production was below detection under these activation conditions at both 24 and 96 hr. However, activation of T cells using beads as in Example 14 below showed that PD-L1 could inhibit IL-2 production at 2, 3, and 4 days of stimulation. PD-L1 also inhibited IL-2 production in Jurkat T cells at beads:cell ratios of 1:1, 2:1, and 4:1. Furthermore, under conditions in which costimulation in the form of soluble anti-CD28 was provided, activation of cells in the presence of PD-L1 also led to a decrease in IL-2 production. PD-1:PD-L1 interaction also led to a decrease in both IL-10 and IFN-γ production. Thus, activation of murine and human T-cells in the presence of PD-L1 leads to inhibition of both proliferation and cytokine secretion.

Further experiments showed that activation of T cells in the presence of PD-L1 results in decreased expression of T cell activation markers. For example, when T cells were activated in the presence of PD-L1, and the expression of the early activation marker CD69 examined by flow cytometry, the results were as follows (% positive for CD69 expression):

|  | anti-CD3 | anti-CD3/PD-L1.Fc | Media |
|---|---|---|---|
| % CD69+ |  |  |  |
| 24 hours | 26% | 26% | 1% |
| 48 hours | 46% | 36% | 2% |
| 72 hours | 63% | 42% | 5% |

When T cells were activated in the presence of PD-L1, and the expression of IL-2R (CD25) examined by flow cytometry, the results were as follows (% positive for IL-2R expression);

|  | anti-CD3 | anti-CD3/PD-L1.Fc | Media |
|---|---|---|---|
| % IL-2R+ |  |  |  |
| 24 hours | 17% | 12% | 2% |
| 48 hours | 29% | 17% | 4% |
| 79 hours | 54% | 15% | 5% |

Example 14

PD-1:PD-L1 Inhibition Kinetics Correlate with PD-1 Expression

This example describes the correlation between the timing of PD-1 expression during T cell activation and the ability of PD-L1 to inhibit T cell proliferation. T cell activation was achieved using tosyl-activated beads ($10^7$) coated with 3 μg anti-CD3 and 2 μg of either control Fc (ctrl.Fc) or PD-L1.Fc fusion protein. $5\times10^4$ purified Balb/c LN T cells were stimulated with $1\times10^5$ beads in a 96 well plate format. For proliferation, plates were pulsed for the final ~10 hours of the culture period. For IL-2 ELISAs, supernatants were harvested from parallel wells.

To determine the kinetics of PD-1 expression during T cell activation, purified Balb/c LN T cells were stimulated with anti-CD3/ctrl.Fc beads. At 0, 1, 2, 3, 4, and 5 days of stimulation, cells were harvested, washed, and stained using biotinylated anti-murine PD-1 (made from monoclonal antibody J43, described in Agata, Y. et al. (1996) *Int. Immunol.* 8:765–72) or biotinylated hamster control, followed by PE-Streptavidin. Data were calculated for live-gated cells, and the percent positive were calculated relative to isotype control. PD-1 expression increased over the course of time during T cell activation as follows: Day 0 (0%); Day 1 (27%); Day 2 (37%); Day 3 (40%); Day 4 (74%); and Day 5 (83%).

When proliferation of Balb/c LN T cells activated using either anti-CD3/ctrl.Fc beads or anti-CD3/mPD-L1.Fc is compared, the kinetics of the PD-L1 inhibition of T cell proliferation correlates with the expression kinetics of PD-1, providing further evidence that PD-L1 acts to inhibit T cell activation via its interaction with PD-1.

Example 15

Figure 19A:
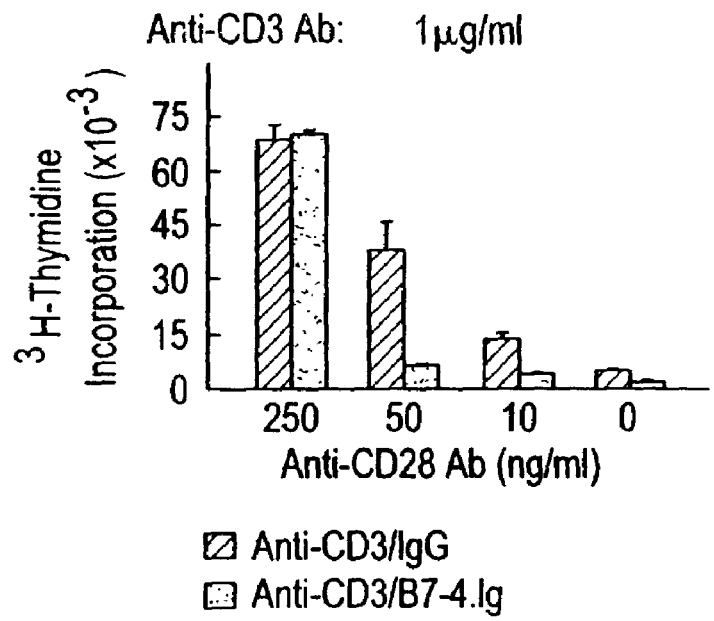
FIGS. 19A–19B illustrate that T cell receptor/PD-L1 activation in the presence of CD28 costimulation results in inhibition of T cell proliferation.
Figure 19B:
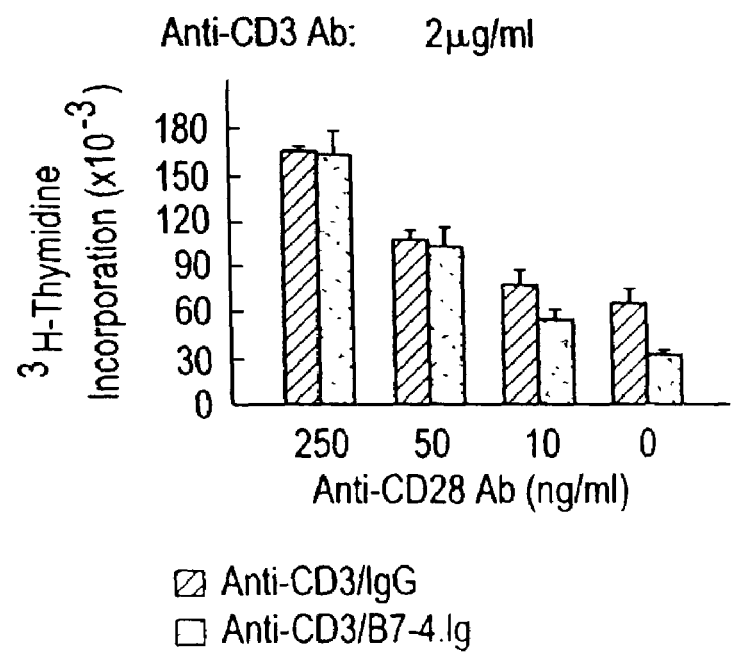
Figure 20E:
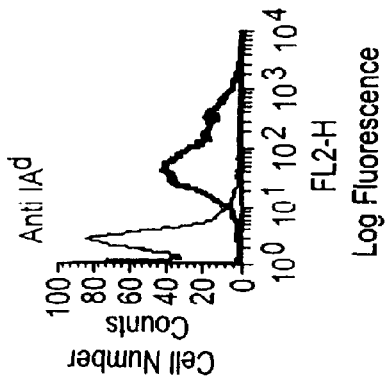
Figure 20D:
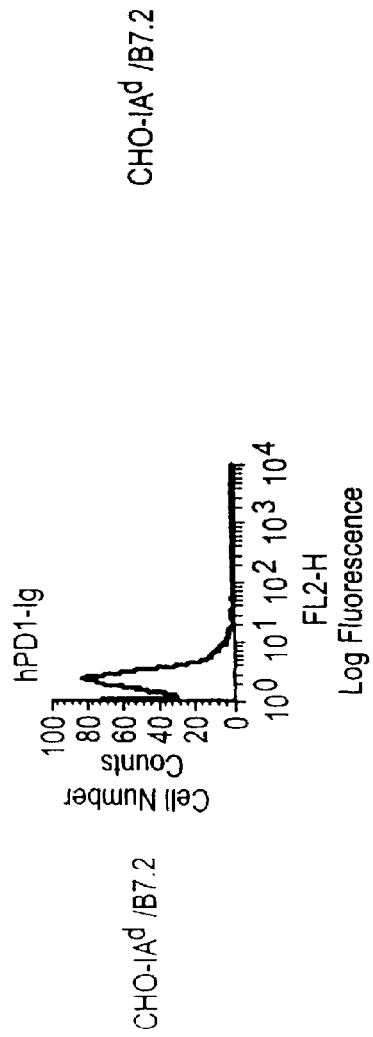
Figure 20G:
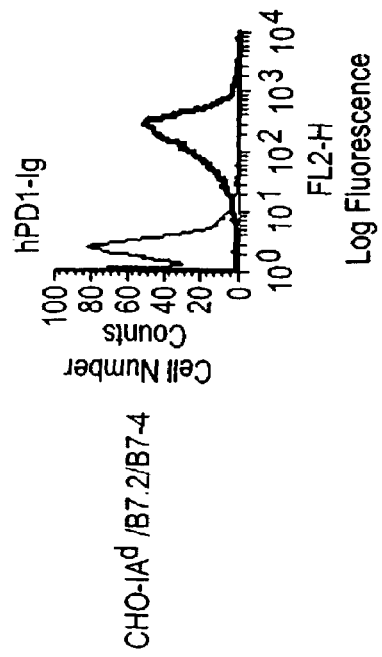
Figure 20F:
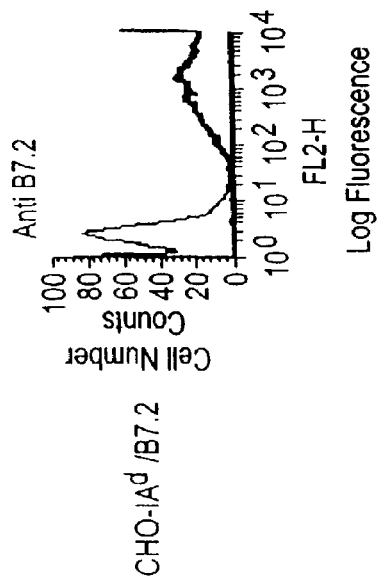
Figure 20I:
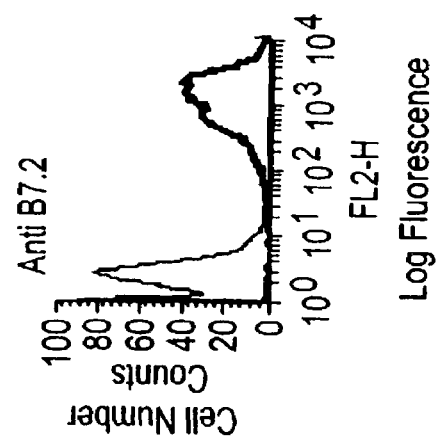
Figure 20H:
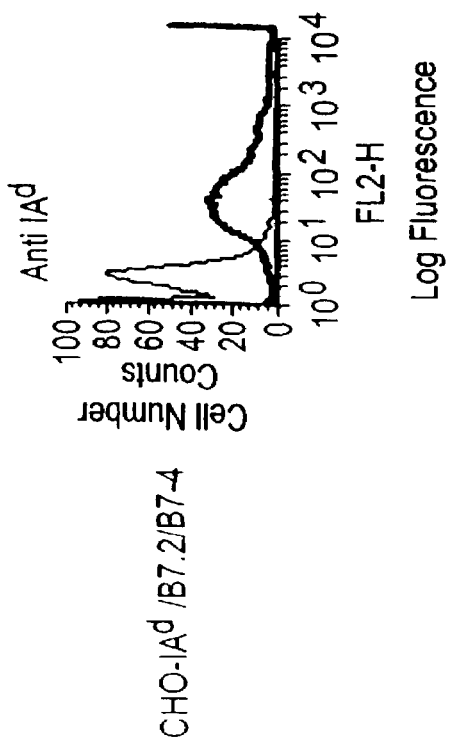

The Outcome of PD-1:PD-L1 Interaction Depends on the Strength of T-cell Receptor and CD28 Signals To examine the relationship between T-cell receptor, CD28 and PD-1 mediated signals, human CD4+ T-cells were stimulated with suboptimal or optimal concentrations of anti-CD3 mAb, a fixed concentration of PD-L1.Ig and increasing concentrations of soluble anti-CD28 mAb. Using anti-CD3 mAb-coated beads, the concentrations required for suboptimal and optimal T-cell stimulation were established. Under conditions of suboptimal T-cell receptor engagement (anti-CD3 mAb at 1 μg/ml), minimal proliferation was observed in the absence of costimulation (FIG. 19A). Addition of increasing concentrations of soluble anti-CD28 mAb led to an up to 30-fold increase in proliferation. Under these conditions, activation of T cells in the presence of PD-L1 resulted in an 80% reduction in proliferation (FIG. 19A). A maximal level of costimulation (anti-Cd28 at 250 ng/ml) was required to rescue the inhibition of proliferation mediated by PD-L1 stimulation. In contrast, under saturating conditions of T-cell receptor activation (anti-CD3 mAb at 2 μg/ml), PD-L1 mediated inhibition of T-cell proliferation was only observed in the absence of CD28 costimulation (FIG. 19B).

To examine the ability of costimulation to rescue the PD-1:PD-L1 mediated inhibition of proliferation at different time points during T cell activation, Balb/c LN T cells were stimulated as in Example 14 in the presence or absence of 1 μg/ml soluble anti-CD28. Proliferation was measured on days 2, 3, and 4. Anti-CD28 reverses PD-1:PD-L1.Fc mediated inhibition at early (day 2), but not late (days 3 and 4) timepoints of T cell activation. Reversal of inhibition was dose-dependent and seen across a range of anti-CD28 concentrations (160 ng/ml, 800 ng/ml, 1 μg/ml, 4 μg/ml, and 20 μg/ml). Under the same conditions of strong costimulation (1 μg/ml anti-CD28), however, PD-L1.Fc inhibits IL-2 production at all time points examined (days 2, 3, and 4). PD-L1.Fc also inhibits IL-2 production across a broad range of soluble anti-CD28 costimulation (100 ng/ml, 160 ng/ml, 500 ng/ml, 800 ng/ml, 4 μg/ml, 5 μg/ml, 10 μg/ml, and 20 μg/ml).

ICOS mediated costimulation also rescues PD-1:PD-L1 mediated inhibition of proliferation.

Example 16

Ability of PD-L1 to Inhibit CD28 Signals and Cytokine Production

The inhibitory effects of the PD-1:PD-L1 pathway appear to be determined by the strength of signal through the TCR and CD28 (see previous example), whereby weak CD3/CD28-mediated responses are easily downregulated. To study the interaction of the CD28 signal and the PD-1:PD-L1 pathway, pre-activated DO11.10 CD4+ T cells were activated with OVA peptide presented by CHO-IA$^d$/B7.2 or CHO-IA$^d$/B7.2/PD-L1.

For detection of PD-L1, $5\times10^4$ CHO transfectants cells were incubated with 5 μg/ml of human PD-1Ig (hPD-1-Ig) (Genetics Institute, Cambridge, Mass.) and developed with goat anti-murine IgG2a-phycoerythrin (PE) (Southern Biotechnology Associates Inc., Birmingham, Ala.). In addition, cells were stained separately with 5 µg/ml anti-IA$^d$-PE or B7.2-PE (Pharmingen, San Diego, Calif.). Following each step, cells were washed three times with PBS/1% BSA/ 0.02% sodium azide. After the final incubation, cells were fixed with 1% paraformaldehyde. Ten thousand events were analyzed on a FACSCalibar (Becton Dickinson, Mountain View, Calif.). All isotype controls were obtained from Pharmingen.

Splenocytes were prepared from DO11.10 mice and treated with Tris-NH$_4$Cl to deplete erythrocytes. Cells were cultured with 1 µg/ml of OVA peptide for 72 hours (Analytical Biotechnology Services, Boston, Mass.) in RPMI 1640 (Life Technologies, Grand Island, N.Y.) supplemented with 10% FCS (Sigma, St Louis, Mo.), 2 mM L-glutamine, 100 U/ml penicillin, 100 µg/ml streptomycin, 250 ng/ml amphotericin B, 10 mM HEPES, 50 µM 2-ME (all from Life Technologies) and 15 mg/ml of gentamicin (BioWhittaker, Walkersville, Md.). CD4$^+$ T cells were purified by positive selection using magnetic-activated cell sorting separation columns (Miltenyi Biotec, Auburn, Calif.) with resulting purity of >98%. Cells were rested overnight before re-stimulation.

Proliferation of CHO cells was inhibited by incubation with 50 µg/ml of mitomycin C (Bristol Laboratories, Princeton, N.J.) for 16 hours at 37° C. At the end of the incubation period, the cells were harvested with 10 mM EDTA in PBS, washed twice and left on ice for 1 hour. The cells were subsequently washed three times and resuspended in culture medium. $10^5$ pre-activated CD4$^+$ T cells were cultured with varying concentrations of OVA peptide and $10^4$ mitomycin C-treated CHO transfectants in 96 well plates. To assay proliferation, cultures were incubated for 48 hrs and pulsed with 1 µCi/well of [$^3$H] thymidine (New England Nuclear, Boston, Mass.) for the last 6 hours of the incubation period.

Figure 21B:
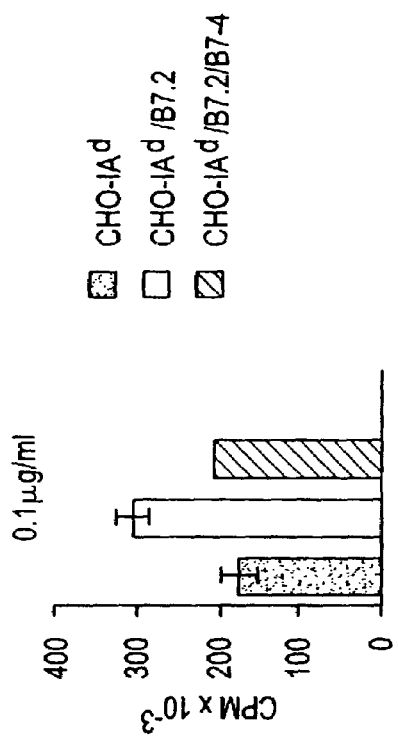
FIGS. 21A–21D illustrate the action of PD-L1 in the inhibition of CD28 signals.
Figure 21D:
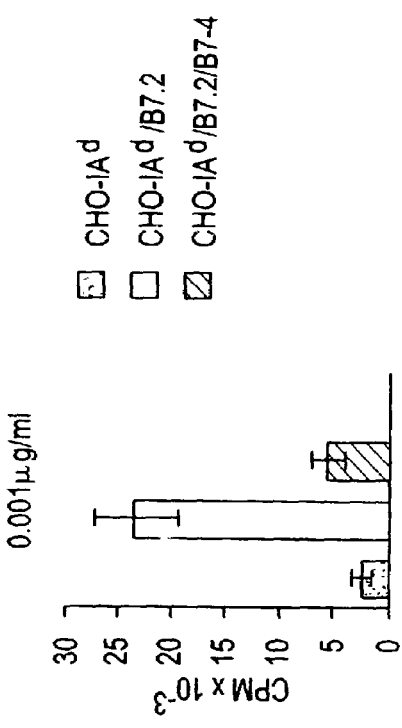
Figure 21A:
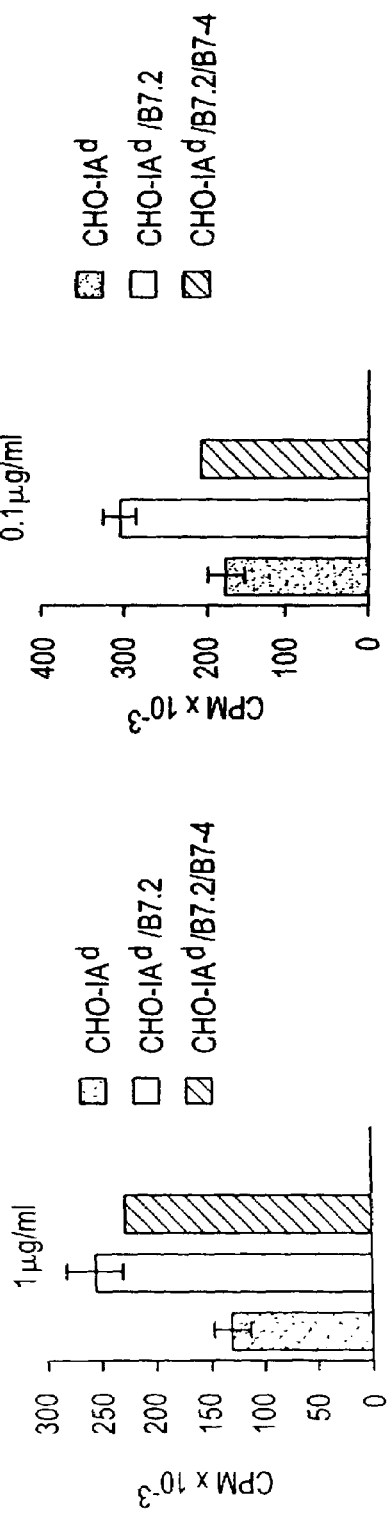
Figure 21C:
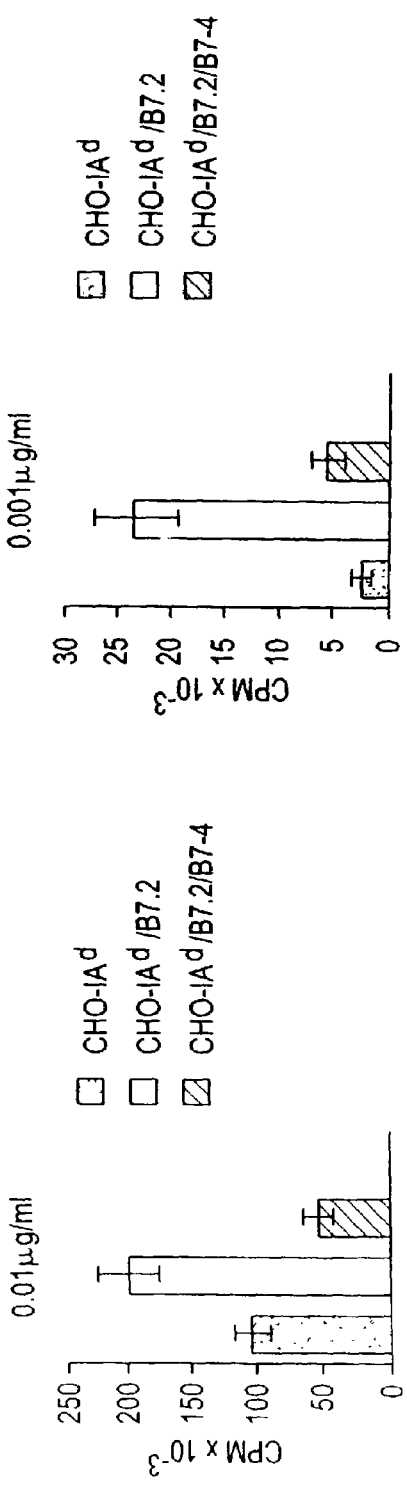

The expression of B7 and IA$^d$ was similar on all CHO transfectants (FIG. 20). As expected, introduction of B7.2 led to an increase in proliferative responses by T cells at all antigen concentrations (FIGS. 21A–21D). However, PD-L1 inhibited responses at lower peptide concentrations (0.01 µg/ml and 0.001 µg/ml) (FIGS. 21C and 21D, respectively).

Figure 23B:
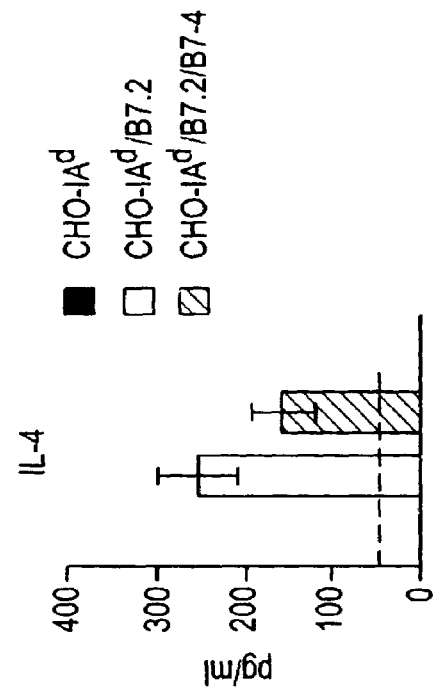
FIGS. 23A–23C illustrate the inhibition of cytokine production by the PD-1:PD-L1 pathway, as measured by cytokine mRNA levels.
Figure 23A:
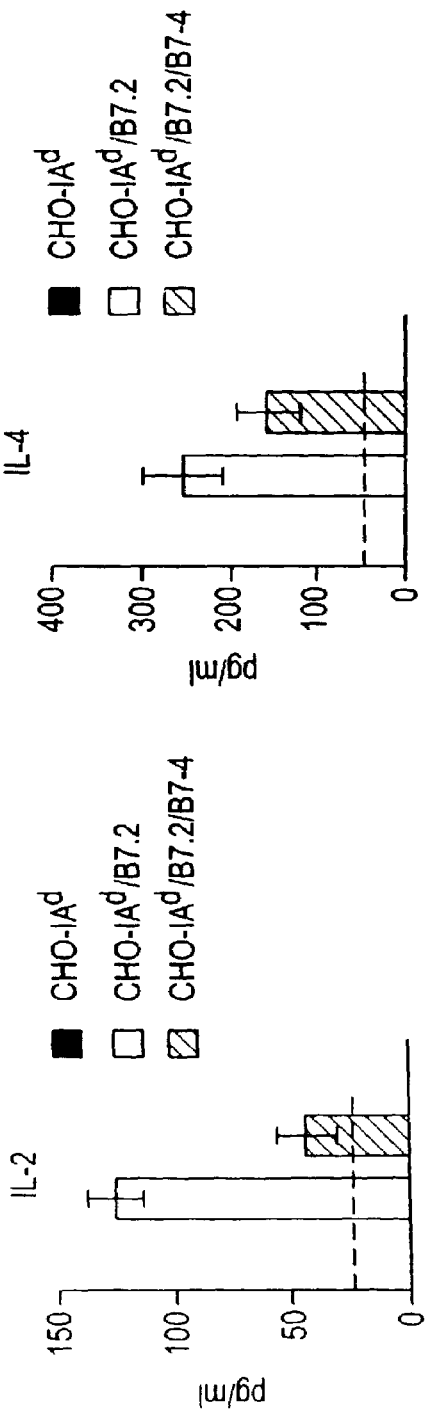
Figure 23C:
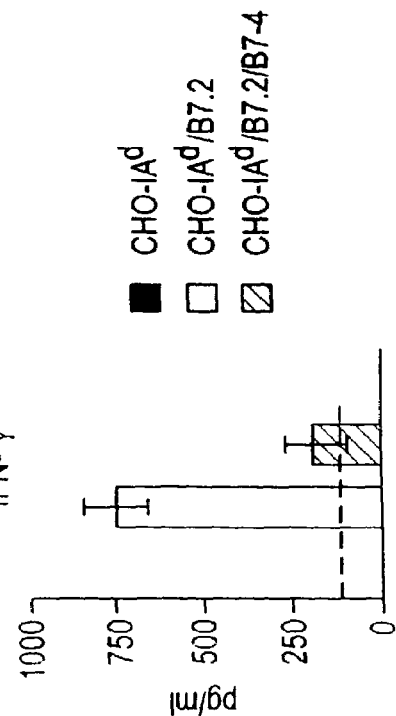

To address the capacity of PD-1:PD-L1 pathway to inhibit cytokine production, supernatants from DO11.10 CD4$^+$T cells activated with OVA peptide presented by CHO cell transfectants were analyzed. Aliquots of supernatants were harvested at various times after initiation of cultures. IL-2, IL-4, IFN-γ and IL-10 levels were analyzed using mAbs and recombinant cytokine standards from Pharmingen. Detection limits were as follows: IL-2, 20 pg/ml, IL-4, 40 pg/ml, IFN-γ, 100 pg/ml and IL-10, 200 pg/ml. Production of IL-2 (FIG. 22A), IL-4 (FIG. 22B), IFN-γ (FIG. 22C), and IL-10 (FIG. 22D) was inhibited significantly when DO11.10 CD4$^+$T cells were cultured with 0.1 µg/ml peptide and PD-L1. At this concentration there was only a weak inhibition of proliferation. However, PD-L1 significantly inhibited cytokine production at 0.01 µg/ml peptide, consistent with the inhibition of proliferation (FIGS. 23A–23C). IL-10 was not detected under these activation conditions. Therefore, PD-1 engagement by PD-L1 can downregulate cytokine production even when T cell proliferation is not affected.

To determine whether the diminished cytokine production was due to reduced mRNA levels, and RNase protection assay was utilized. CD4$^+$ T cells were restimulated with various CHO cell transfectants and 0.01 µg/ml OVA peptide. After 48 hours, cells were harvested and mRNA was isolated using TRIzol® reagent (Life Technologies). 5 µg mRNA was analyzed for cytokine levels by RNase protection assay using RiboQuant multiprobe kit mCK1 according to the manufacturer's instructions (Pharmingen). Transcript levels of IL-4, IL-10, IL-13, IL-2, IL6 and IFN-γ mRNA were detected in pre-activated DO11-10 CD4$^+$T cells after stimulation with 0.01 µg/ml OVA peptide presented by CHO-IA$^d$/ B7.2. However, the introduction of PD-L1 significantly reduced cytokine mRNA levels. There was minimal upregulation of mRNA for cytokines in unstimulated T cell cultures or T cells activated with peptide presented by CHO-IA$^d$. These results further demonstrate the capacity of the PD-1: PD-L1 pathway to antagonize a strong B7/CD28 signal at least when antigenic stimulation is weak or limiting, and the inhibition of at least cytokine production in conditions of strong antigenic stimulation.

Example 17

Mechanism of Action of the PD-1:PD-L1 Pathway

Cross-linking of CTLA-4 has been shown to inhibit cell cycle progression in naïve T cells (Krummel, M. F. and Allison, J. P. (1996) *J. Exp. Med.* 183:2533–2540; Walunas, T. L. et al. (1996) *J. Exp. Med.* 183:2541–2550). As PD-1 was isolated from murine cell lines undergoing apoptosis, a possible mechanism of action of the PD-1:PD-L1 pathway might be to increase programmed cell death. To address this issue, DO11.10 CD4$^+$ T cells were restimulated with 0.01 µg/ml peptide and various CHO transfectants and cell cycle progression was analyzed. CD4$^+$ T cells were restimulated with 0.01 µg/ml peptide as described previously. After 36 hours of culture, cells were recovered and stained with anti CD4-FITC. Cells were washed in PBS, fixed in 70% ethanol for 1 hour on ice and then resuspended in PBS containing 10 µg/ml RNase (Sigma) and 50 µg/ml propidium iodide (Sigma). Analysis was performed within an hour of staining.

Figure 24A:
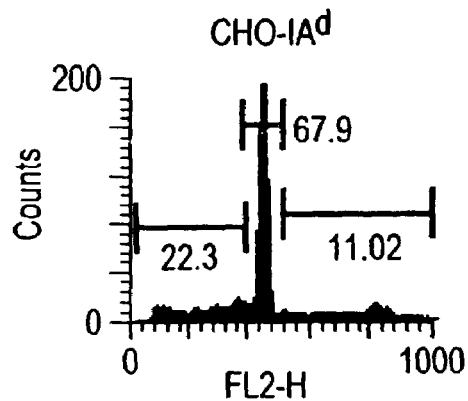
FIGS. 24A–24C illustrate that the mechanism of action of the PD-1:PD-L1 pathway is cell-cycle arrest.
Figure 24B:
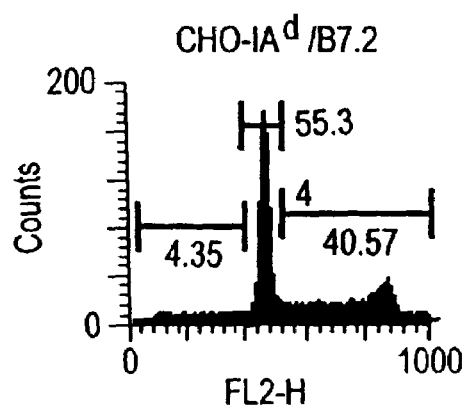
Figure 24C:
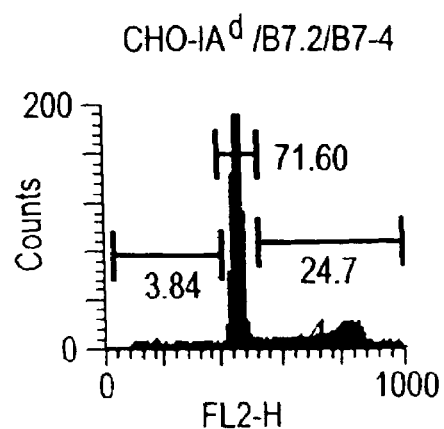

After 48 hours, cells were recovered and stained with CD4-FITC. After permeabilization, cells were incubated with propidium iodide to analyze the $G_0/G_1$, $S/G_2$ and sub-diploid populations. CD4$^+$ T cells restimulated with peptide presented by CHO-IA$^d$ have a large proportion of cells in the sub-diploid population, indicative of apoptosis (FIG. 24A). In cultures where CD4$^+$ T cells were stimulated by peptide presented by CHO-IA$^d$/B7-2, there were increased number of cells in the $S/G_2$ phase, and a decreased number in the sub-diploid population (FIG. 24B), indicating that cells were in cycle and rescued from apoptosis by B7/CD28 costimulation. The introduction of PD-L1 led to an increased number of cells in the G0/G1 phase (FIG. 24C). There were comparable levels of apoptosis in the PD-L1 cultures to the CHO-IA$^d$/B7 cultures. This was confirmed by annexin staining. The inhibition of cell progression by the PD-1:PD-L1 pathway confirms its role in downregulating T cell activation.

Further experiments using PD-L1.Fc confirmed that PD-1:PD-L1 engagement on T cells does not lead to apoptosis. Cells were treated with anti-CD3 or anti-CD3/PD-L1.Fc, or irradiated, stained with propidium iodide and annexin, and analyzed by flow cytometry. Apoptotic cells were identified as those that were positive for both propidium iodide and annexin. Controls done in parallel showed that anti-CD3/B7.4.Fc inhibited proliferation at 48 and 72 hours. There results were as follows:

|  | anti-CD3 | anti-CD3/PD-L1.Fc | Irradiated |
|---|---|---|---|
| % apoptotic |  |  |  |
| 24 hours | 3% | 3% | 18% |
| 48 hours | 5% | 4% | 25% |
| 72 hours | 10% | 12% | 42% |

Still further experiments analyzing DNA content demonstrated that activation of T cells in the presence of PD-L1.Fc results in cell cycle arrest. T cells were stimulated with ctrl.Fc or mPD-L1.Fc beads. On day 4, the percentage of dividing cells was determined by propidium iodide staining. T cells stimulated with mPD-L1.Fc showed half (11% vs. 21% for the control) the number of cells with the increased DNA content indicative of dividing cells. In two other experiments, the percentages were similar: 14% vs. 28% and 11% vs. 24%.

Analysis of mitosis was also examined. T cells were labeled with CSFE and stimulated with ctrl.Fc or mPD-L1.Fc beads as in Example 14. At days 1, 2, 3, and 4, FACS analysis was done. Only live-gated events were analyzed. Percentages are for non-dividing cells. As the following data indicates, treatment with PD-L1 inhibits cell division:

|  | Day 1 | Day 2 | Day 3 | Day 4 |
|---|---|---|---|---|
| % non-dividing |  |  |  |  |
| Ctrl.Fc | 87.4% | 32.4% | 11.9% | 3.8% |
| PD-L1.Fc | 87.7% | 46.7% | 35.1% | 24.5% |

Mitosis was also examined (as above) separately for CD4+ T cells and CD8+ T cells. The results are set forth in FIGS. 28A (CD4+) and 28B (CD8+).

Example 18

IL-2, Induced by Costimulation or Added Exogenously, Can Overcome Proliferative Inhibition Induced by PD-1:PD-L1 Interaction Purified Balb/c LN T cells were stimulated as in Example 14 in the presence or absence of 1 µg/ml soluble anti-CD28 and 10 µg/ml anti-IL-2. Proliferation was measured on day 2. In the presence of costimulation by anti-CD28, addition of anti-IL-2 restores PD-PD-1:PD-L1 mediated inhibition, suggesting that anti-CD28 reverses the inhibitory effect by inducing IL-2 production. Addition of anti-IL-2 also restores PD-1:PD-L1 mediated inhibition in the presence of costimulation by ICOS ligand.

In another example, Balb/c LN T cells were stimulated as in Example 14 with the addition of exogenous IL-2. When proliferation was measured on day 3, exogenous IL-2 reverses PD-1:PD-L1 mediated inhibition of proliferation in a dose-dependent manner (IL-2 concentration range: 3 pg/ml, 10 pg/ml, 30 pg/ml, 100 pg/ml, and 300 pg/ml). Moreover, addition of exogenous IL-2 (at U/ml rhIL-2) reverses PD-1:PD-L1 mediated inhibition of proliferation at all time points (proliferation measured on days 2, 3, 4, and 5).

Example 19

CD8+ T Cells are More Susceptible to Inhibition by PD-L1

This example describes the differences between CD4+ and CD8+ T cell activation in response to PD-L1.

Figure 29A:
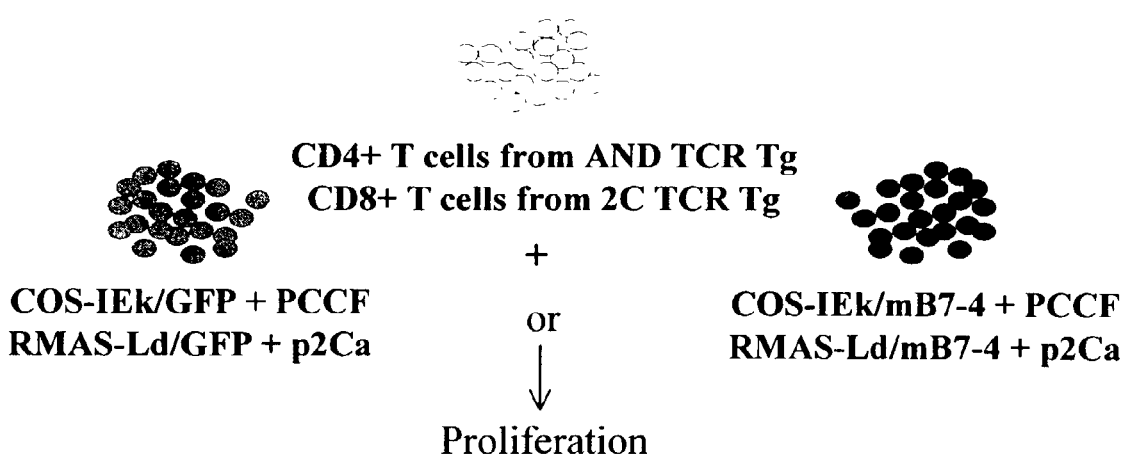
FIGS. 29A–29C illustrate the inhibition of both CD4+ and CD8+ T cells by PD-1:PD-L1 interaction.
Figure 29B:
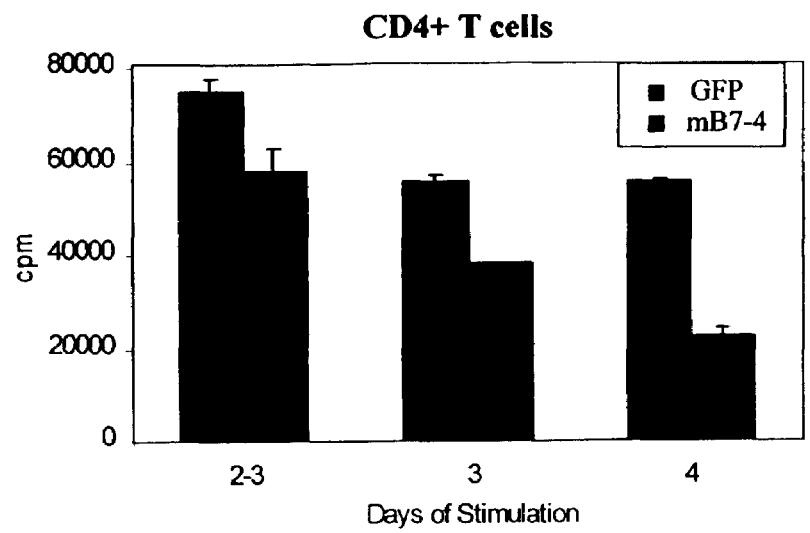
Figure 29C:
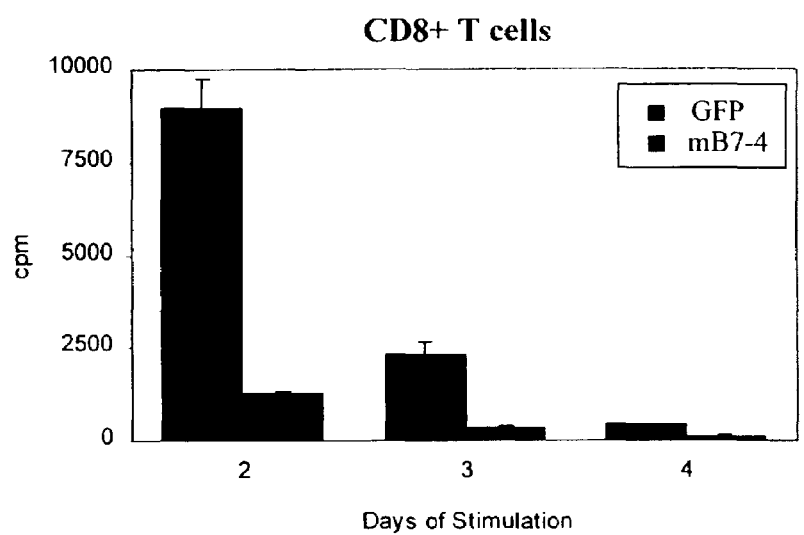

Stable antigen presenting cell (APC) lines were engineered to express GFP or mPD-L1/GFP using retroviral technology. FIG. 29A shows a schematic of the cells used. For CD4+ T cell experiments, the APC:T cell ratio was 1:10 with 10 µM PCCF peptide. For CD8+ T cell experiments, the APC:T cell ratio was 1:1 with 1 mM p2Ca peptide. $5 \times 10^4$ purified LN T cells from TCR transgenic mice were stimulated with irradiated APC plus peptide for 2, 3, or 4 days. As shown in FIGS. 29B and 29C, both CD4+ and CD8+ T cells are inhibited by PD-1:PD-L1 interactions.

Figure 30A:
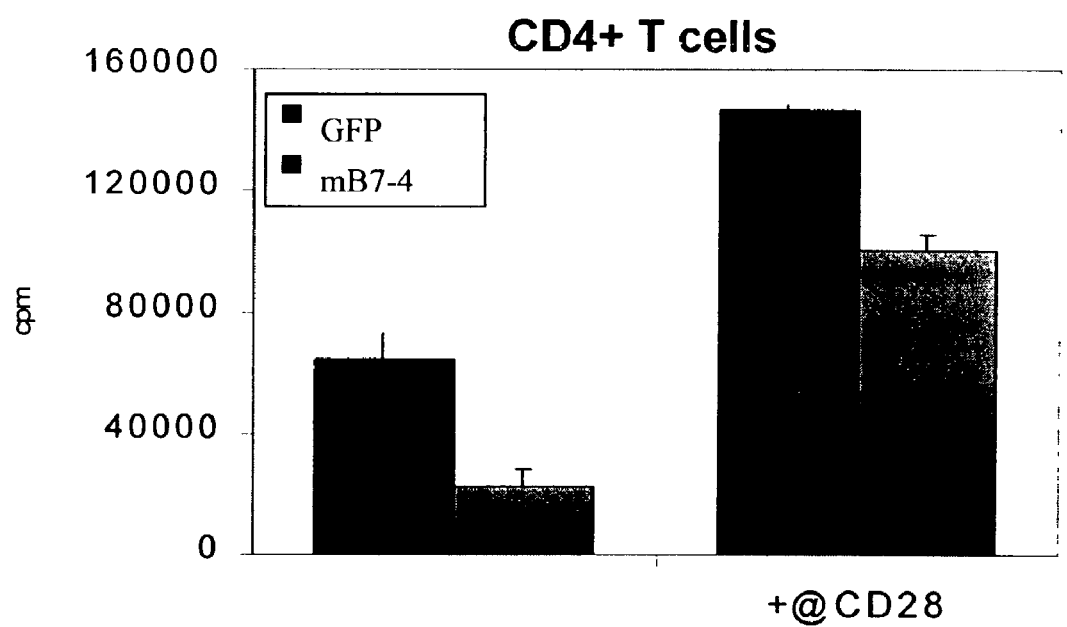
FIGS. 30A–30B illustrate the ability of costimulation to overcome the inhibition of CD4+ but not CD8+ T cell proliferation by PD-1:PD-L1 interaction.
Figure 30B:
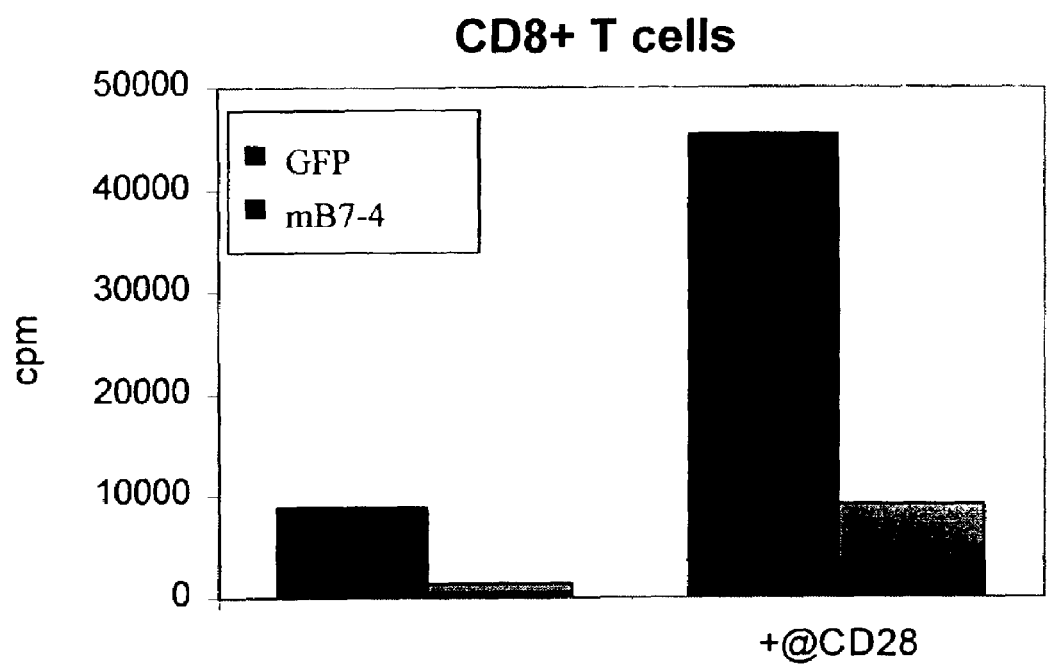

While addition of anti-CD28 can overcome PD-1:PD-L1 mediated inhibition of proliferation of CD4+ T cells (FIG. 30A), it cannot overcome the inhibition of CD8+ T cells (FIG. 30B). Furthermore, either exogenous IL-2 or IL-15 (20 U/ml and 50 ng/ml, respectively, added on day 0) can overcome PD-1:PD-L1 mediated inhibition of CD8+ T cells (proliferation measured on day 2). CD8+ T cells may be more susceptible to inhibition because of their intrinsic inability to produce IL-2.

Example 20

Recruitment of Signaling Molecules through Engagement of the PD-1:PD-L1 Signaling Pathway To further investigate the mechanism of action of the PD-1:PD-L1 pathway in T cells, a Jurkat based system was used. Jurkat cells constitutively express low levels of PD-1. The Jurkat T cells were activated with beads coated with anti-CD3/ctrl.Ig or anti-CD3/hPD-L1.Ig. Ligation of PD-1 plus CD3 leads to inhibition of IL-2 secretion by Jurkat cells, compared to cells stimulated with anti-CD3 alone. Cells were lysed and subjected to anti-SHP-2 immunoprecipitation, run on a gel, and transferred to a membrane. The membrane was immunoblotted with 4G10-HRP (horseradish peroxidase conjugated anti-phosphotyrosine antibody) and subsequently with anti-SHP-2 to confirm SHP-2 expression in the immunoprecipitates. With anti-CD3 and hPD-L1.Ig, ligation of PD-1 plus the TCR rapidly results in the conversion of SHP-2 to the phosphorylated state, compared to TCR activation alone. SHP-1 is not phosphorylated under these conditions. This data suggests that recruitment of SHP-2 is a mechanism for downregulating TCR signaling events via the PD-1:PD-L1 pathway.

Under similar experimental conditions, anti-Zap70 immunoprecipitation results in inhibition of Zap70 associated p23 pTyr upon coligation of CD3 and PD-1 (using anti CD-3 and PD-L1.Ig). CD3ζ immunoprecipitation of Jurkat lysates and anti-pTyr blotting results in inhibition of CD3ζ phosphorylation upon coligation of CD3 and PD-1 (using anti CD-3 and PD-L1.Ig). Inhibition of CD3ζ in this system persists with CD28 stimulation.

Example 21

Inhibition of Binding of Biotinylated Human PD-L1 Fc to Human PD-1Fc

Fc fusion proteins were generated by linking the extracellular region of PD-1 or PD-L1 to the hinge-CH2-CH3 domains of murine Igγ2a. Recombinant proteins were produced in COS cells transiently transfected with LipofectAMINE™ (Gibco-BRL) or stably transfected CHO cell lines and purified from conditioned media using protein A-Sepharose.

Figure 25A:
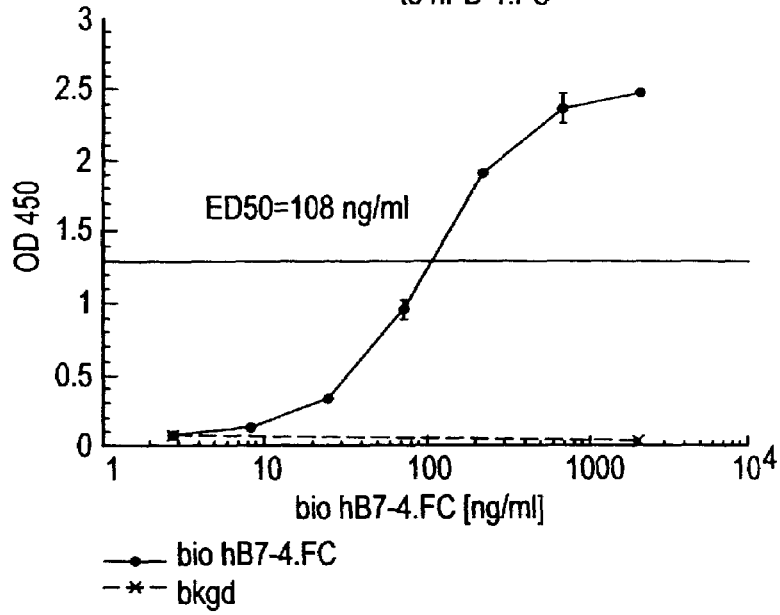
FIGS. 25A–25B illustrate the ability of antibodies to PD-L1 to inhibit the interaction between PD-L1 and PD-1.

The ability of antibodies to PD-L1 or PD-1 to inhibit the interaction of human PD-L1Fc and human PD-1 Fc was tested using standard ELISA methods. Briefly, human PD-1Fc molecules were immobilized in 96-well plates, blocked, and washed. Biotinylated PD-L1Fc molecules (100 ng/ml) were added to wells at concentrations of approximately 2000, 700, 200, 70, 25, 8, and 1.18 ng/ml (FIG. 25A). The wells were incubated with Streptavidin conjugated horse radish peroxidase, washed, and color was developed using standard methods. The ED50 of PD-L1Fc was found to be 108 ng/ml.

Figure 25B:
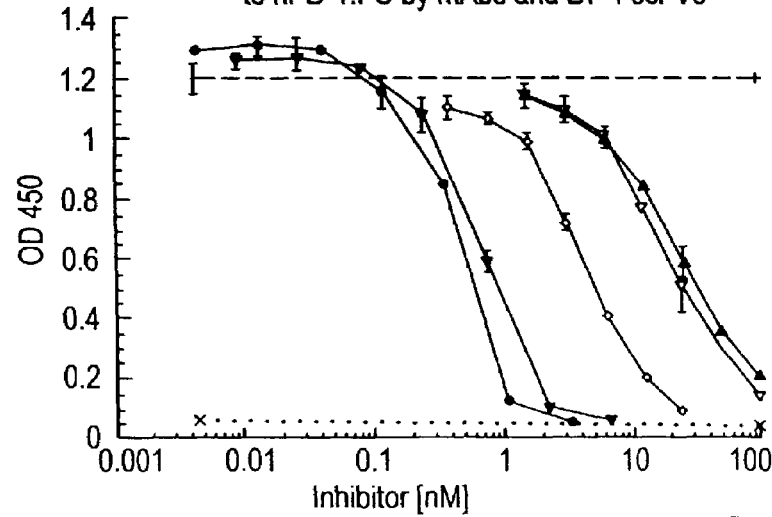

The ability of murine antibodies to human PD-L1 (10D9 and 11D12) or scFv portions of human immunoglobulins (PD-L1-1, PD-L1-6, and PD-L1-12) to inhibit the binding of biotinylated human PD-L1Fc to human PD-1Fc was tested at 7 concentrations of inhibitors. The IC50 was found to range from 0.5 nM to 24 nM and the data are presented in FIG. 25B.

Figure 26:
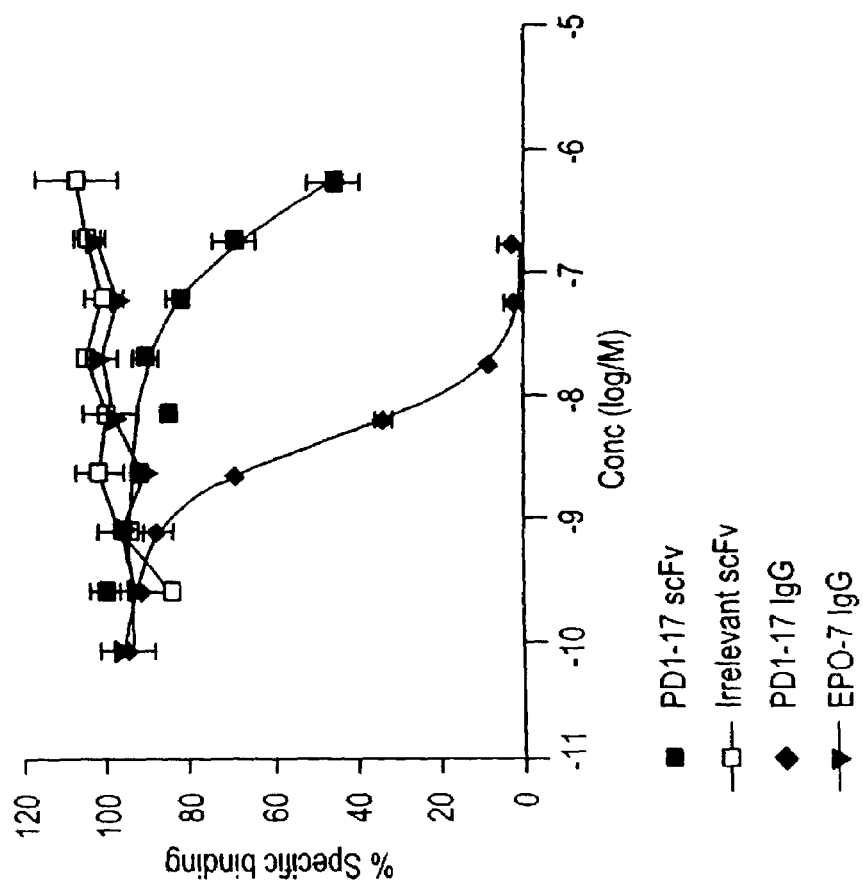
FIG. 26 illustrates the ability of antibodies to PD-1 to inhibit the interaction between PD-L1 and PD-1.

The PD-1 specific scFv were also tested for their ability to inhibit the binding of PD-L1 Fc to PD-1Fc using the same ELISA methods described above. Human scFV reactive with PD-1 (PD1-17 scFv) were found to inhibit specific binding (EC50 between $10^{-7}$ and $10^{-8}$) as shown in FIG. 26. $V_L$ and $V_H$ domains of the PD1-17scFv were used to generate a complete IgG. In brief, the VH and VL coding regions were linked to genomic CH and CL gene sequences in expression vectors. The resulting expression vectors were transiently transfected into human 293 cells and the IgG harvested from the conditioned medium. The potency of the grafted whole IgG molecule was higher than for the scFv antibody (EC 50 between $10^{-8}$M and $10^{-9}$M).

Example 22

Administration of Soluble PD-L1Fc Exacerbates Disease in a Murine Model

To determine if modulation of the PD-L1/PD-1 pathway has immunoregulatory activity in vivo, the protein was evaluated in a murine model of experimental autoimmune encephalomyelitis (EAE) that shares many clinical and pathological features with the human disease multiple sclerosis. Female SJL/J mice were immunized with 100 µg of proteolipid protein (PLP) in complete Freund's adjuvant. Ten days later, spleens were harvested, processed to single cell suspensions and then restimulated in vitro with 5 µg of PLP for 96 hours. Cells were washed three times in PBS and then $15 \times 10^6$ cells transferred to naive SJL/J mice by intraperitoneal injection. The adoptive transfer of autoreactive T cells results in acute paralysis of recipient mice which manifests as loss of tail tone with subsequent progression to full hind limb paralysis. This paralytic episode coincides with marked infiltration of activated T cells and macrophages in the CNS. Under most conditions, this is an acute model of disease with spontaneous recovery occurring after a short period of paralysis. For evaluation of PD-L1Fc, mice were injected subcutaneously with 200 µg of the protein in 100 µl of sterile saline on days 0, 2, 4, 7 and 11 after cell transfer (n=10). Control mice (n=10) received an equal volume of saline only. All animals were monitored regularly for clinical signs of disease which were scored as follows: 1. Loss of tail tone; 2. Hind limb weakness/partial hind limb paralysis; 3. Complete hind limb paralysis; 4. Hind and forelimb paralysis; 5. Moribund.

Figure 27:
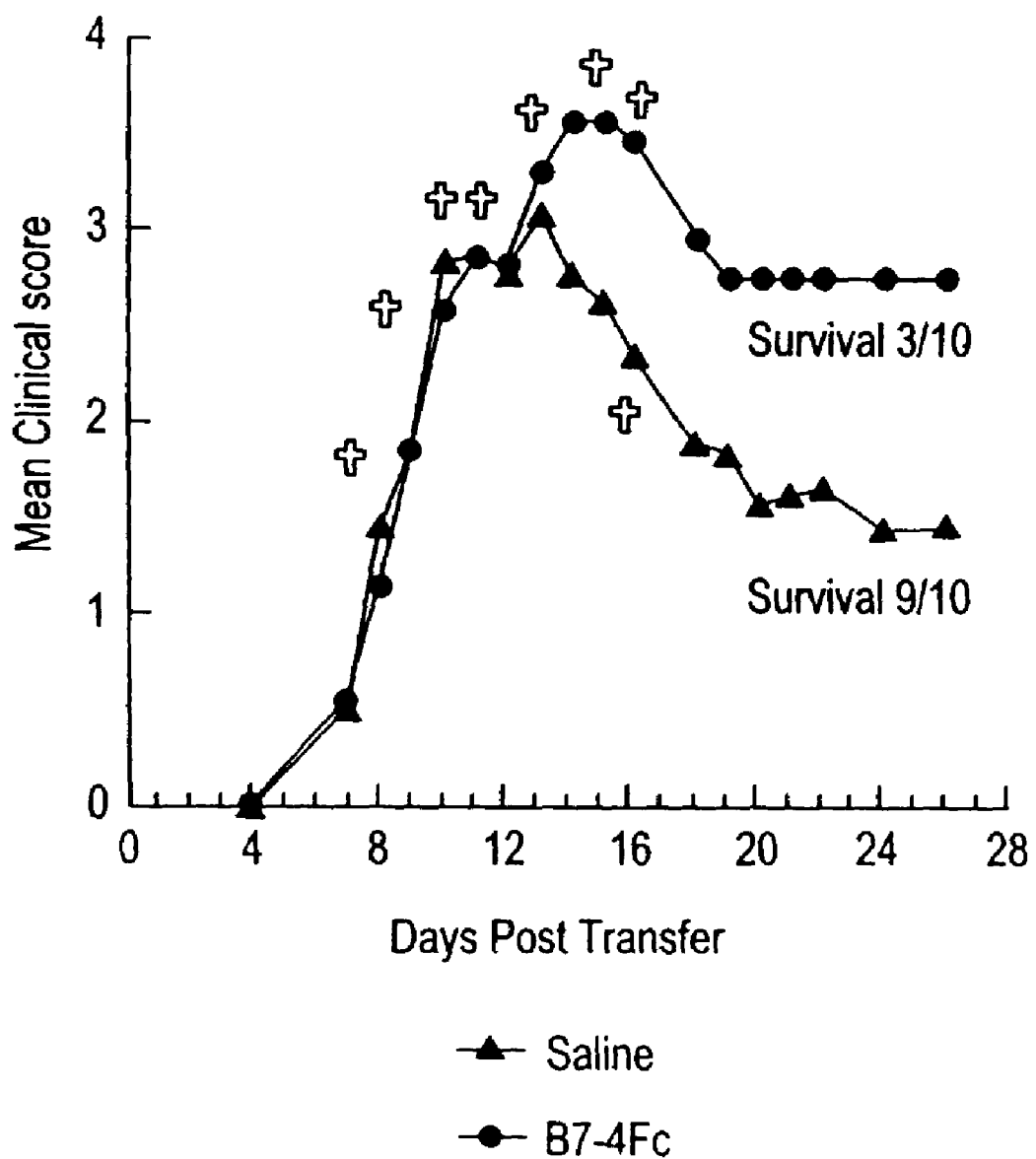
FIG. 27 illustrates the ability of soluble PD-L1Fc to exacerbate disease in a murine model of experimental autoimmune encephalomyelitis.

In the experiment shown in FIG. 27, the incidence and onset of clinical disease were similar in both groups. Mice treated with the PD-L1Fc however, developed severe disease with the majority of animals rapidly progressing to complete hind and forelimb paralysis (9/10 and 1/10 for PD-L1Fc and control mice respectively). Mortality associated with clinical signs of disease was 10% in the control group and 70% in the PD-L1Fc treated mice. In addition, recovery from clinical disease was substantially delayed in the PD-L1Fc treated mice that did survive despite the fact that treatment was discontinued on day 11.

In conclusion, using an adoptive transfer model of T cell mediated autoimmunity, administration of soluble PD-L1Fc exacerbates clinical signs of disease resulting in increased mortality and delayed recovery from paralysis. These findings are consistent with enhanced activation/infiltration of inflammatory cells into the CNS and clearly demonstrate the immunoregulatory potential for the PD-L1Fc protein in vivo.

Example 23

Identification of PD-1 Signaling Molecules

This example describes a screening assay for the identification of proteins which are involved in PD-1 signaling pathways. A schematic of the screening assay is shown in FIG. 31A. $1 \times 10^8$ (experiment 1) or $5 \times 10^8$ (experiment 2) Jurkat T cells were treated in the presence and absence of pervanadate. The cells were then lysed in lysis buffer (1% NP-40, 150 mM NaCl, Tris pH 7.6, protease inhibitors, and phosphatase inhibitors). Proteins were then immunoprecipitated with 100 µg biotinylated peptide for 4 hours at 4° C. The following peptides were used for immunoprecipitation: ITIM peptides Y($PO_4$), F, and Y, and C' (non-ITIM). The sequences of the peptides are shown in FIG. 31B. Streptavidin agarose was added for 30 minutes at 4° C., and samples were then washed 4 times in 1% lysis buffer+0.45 M NaCl, and 2 times with PBS (phosphate buffered saline). Samples were then boiled in SDS-PAGE sample buffer and run on a 4–20% tris-glycine NOVEX gradient gel (reduced). The gel was the silver stained using the Daichi protocol (experiment 1) or the Mann protocol (experiment 2). PD-1 interacting proteins were excised from the gel and analyzed by mass spectrometry analysis.

The following PD-1 interacting proteins were identified:

| Experiment 1 (ITIM peptides): | |
| --- | --- |
| 47 kD Y and pY | −pervanadate |
| 95 kD Y, pY, and F | +pervanadate |

| Experiment 2 (ITIM peptides) | |
| --- | --- |
| 75 kD Y and pY | −pervanadate |
| 70 kD Y and pY | +pervanadate |

| C –peptide | |
|---|---|
| 22 kD | –pervanadate |
| 46 kD | +pervandaate |

Example 24

Inhibition of PD-1 Signaling at Time of Priming Results in Decreased T Cell Responses Peptide specific T cell responses were measured from PD-L1Fc treated mice. SJL/J mice were immunized with proteolipid protein (PLP) in complete Freund's adjuvant (CFA) on the day of immunization. Lymph nodes and spleens were collected on day 10 for in vitro cytokine and proliferation assays. Surprisingly, PLP induced proliferation and cytokine secretion from LNC (FIG. 32A–D), and to a lesser extent spleen cells (FIG. 33A–D), was attenuated in mice treated with the PD-L1Fc. This effect has been observed in two additional experiments. Comparable studies with the PD-1Fc gave similar results with decreased proliferation observed in the PD1FC treated mice. Although cytokines have not been looked at yet, spleen cells from PD1Fc treated donor mice that were reactivated in vitro with peptide failed to transfer EAE to naïve recipients, whereas control IgG and PD-L1Fc treated donor spleen cells did.

Figure 34:
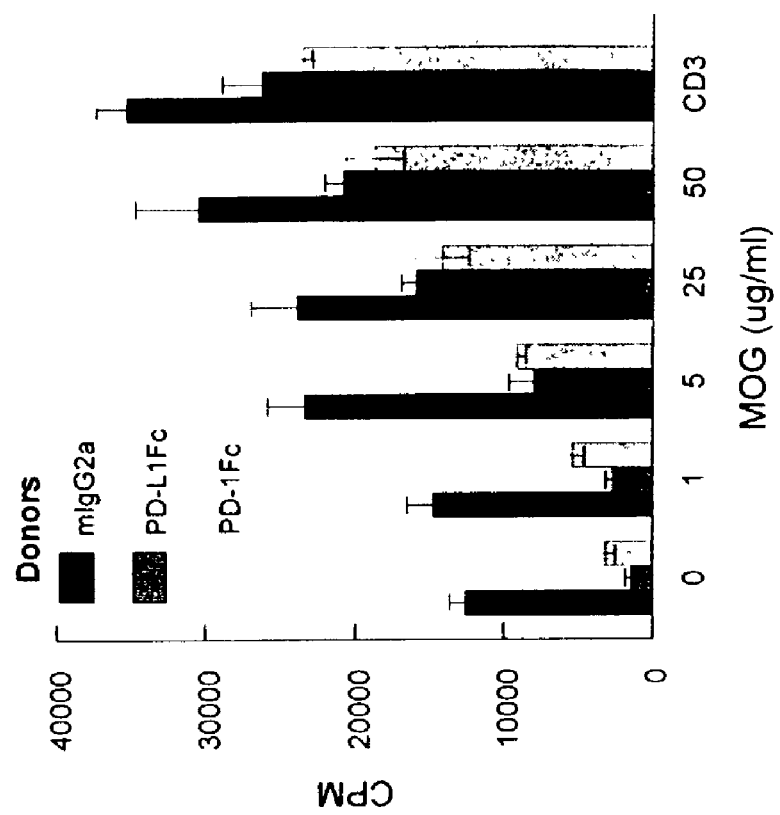
FIG. 34 shows the MOG induced proliferation from spleen cells of MOG immunized C57BL/6 mice was attenuated in mice treated with PD-L1Fc.

Both reagents were being evaluated in another model of EAE: myelin oligodendrocyte glycoprotein (MOG) immunized animals. In this model, PD-L1Fc and PD-1Fc were also found to decrease proliferation of spleen cells from MOG immunized C57BL/6 mice stimulated in vitro in the presence of varying concentrations of MOG (FIG. 34).

Example 25

Modulation of PD-1 Signaling Post-Priming, with an Antibody that Activates PD-1, Attenuates Disease in a Murine Model To further investigate the effect of modulation of the PD-L1/PD-1 pathway on immunoregulatory activity in vivo, the effect of administration of an antibody which binds PD-1 was evaluated in the above described adoptive transfer murine model of experimental autoimmune encephalomyelitis (EAE). Female SJL/J mice were immunized with 100 μg of proteolipid protein (PLP) in complete Freund's adjuvant. Ten days later, spleens were harvested, processed to single cell suspensions and then restimulated in vitro with 5 μg of PLP for 96 hours. Cells were washed three times in PBS and then $10 \times 10^6$ cells were transferred to naive SJL/J mice by intraperitoneal injection. The adoptive transfer of autoreactive T cells results in acute paralysis of recipient mice which manifests as loss of tail tone with subsequent progression to full hind limb paralysis. This paralytic episode coincides with marked infiltration of activated T cells and macrophages in the CNS. Under most conditions, this is an acute model of disease with spontaneous recovery occurring after a short period of paralysis. For evaluation of the effect of administration of an anti-PD-1 monoclonal antibody (J43) mice were injected intraperitoneally with 200 μg of antibody J43 in 100 μl volume, on days 0, 2, 4, 6 and 8 after cell transfer (n=10). Control mice (n=10) received an equal amount of rat IgG on days 0, 2, 4, 6 and 8 after cell transfer. All animals were monitored regularly for clinical signs of disease which were scored as follows: 1. Loss of tail tone; 2. partial hind limb paralysis; 3. Complete hind limb paralysis.

The mean clinical score of the mice which received the anti-PD-1, was compared to the mean clinical score of the control mice. Results indicated that anti-PD-1 antibody reduced the severity of the adoptively transferred experimental autoimmune encephalomyelitis. Administration of the anti-PD-1 antibody attenuated clinical signs of disease in the adoptive transfer model of T cell mediated autoimmunity, resulting in decreased paralysis. These findings are consistent with reduced activation/infiltration of inflammatory cells into the CNS and demonstrate that modulation of PD-1 signaling can be therapeutic in the treatment of an autoimmune disorder. They also demonstrate the immunoregulatory potential for the anti-PD-1 antibody in vivo.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for downmodulating activation of an immune cell, comprising contacting an immune cell, at the time of contact with antigen, with an agent that inhibits signaling via PD-1 to thereby downmodulate activation of an immune cell, wherein the agent is a monovalent antibody that binds to PD-1.

2. The method of claim 1, wherein the immune cell is a T cell.

3. The method of claim 2, wherein the T cell is a naïve T cell.

4. The method of claim 1, wherein anergy is induced in the immune cell.

5. The method of claim 1, further comprising contacting the immune cell with an additional agent that downregulates an immune response.

6. The method of claim 1, wherein the step of contacting occurs in vivo.

7. The method of claim 1, wherein the step of contacting occurs in vitro.

* * * * *

UNITED STATES PATENT AND TRADEMARK OFFICE
CERTIFICATE OF CORRECTION

| | | |
|---|---|---|
| PATENT NO. | : 7,029,674 B2 | |
| APPLICATION NO. | : 10/115609 | |
| DATED | : April 18, 2006 | |
| INVENTOR(S) | : Carreno et al. | |

It is certified that error appears in the above-identified patent and that said Letters Patent is hereby corrected as shown below:

Col. 137, lines 56-57
In Claim 1, replace the phrase "wherein the agent is a monovalent antibody that binds to PD-1" with --wherein the agent is an antibody that binds to PD-1 and inhibits signaling via PD-1--.

Signed and Sealed this
Nineteenth Day of April, 2011

David J. Kappos
*Director of the United States Patent and Trademark Office*